United States Patent
Nesti et al.

(10) Patent No.: US 12,180,255 B2
(45) Date of Patent: Dec. 31, 2024

(54) COMPOSITIONS AND METHODS FOR DEREPRESSING RE1 SILENCING TRANSCRIPTION FACTOR TARGET GENES

(71) Applicant: Alcamena Stem Cell Therapeutics, LLC, Halethorpe, MD (US)

(72) Inventors: Edmund Nesti, Spencerville, MD (US); Alexander Pisarchik, Marriottsville, MD (US)

(73) Assignee: Alcamena Stem Cell Therapeutics, LLC, Halethorpe, MD (US)

( * ) Notice: Subject to any disclaimer, the term of this patent is extended or adjusted under 35 U.S.C. 154(b) by 72 days.

(21) Appl. No.: 17/778,738

(22) PCT Filed: Nov. 20, 2020

(86) PCT No.: PCT/US2020/061632
§ 371 (c)(1),
(2) Date: May 20, 2022

(87) PCT Pub. No.: WO2021/102345
PCT Pub. Date: May 27, 2021

(65) Prior Publication Data
US 2023/0059411 A1 Feb. 23, 2023

Related U.S. Application Data

(60) Provisional application No. 63/086,248, filed on Oct. 1, 2020, provisional application No. 62/939,149, filed on Nov. 22, 2019.

(51) Int. Cl.
*C07K 14/47* (2006.01)
*A61P 25/00* (2006.01)

(52) U.S. Cl.
CPC .......... *C07K 14/4703* (2013.01); *A61P 25/00* (2018.01); *C07K 2319/06* (2013.01)

(58) Field of Classification Search
CPC ............ C07K 14/4703; C07K 2319/06; C07K 14/47; C07K 7/08; C07K 2319/00; A61P 25/00; A61K 38/00; C12N 9/16; C12Y 301/03016
See application file for complete search history.

(56) References Cited

U.S. PATENT DOCUMENTS

| | | |
|---|---|---|
| 2016/0031958 A1 | 2/2016 | Nesti |
| 2016/0280748 A1 | 9/2016 | Liu et al. |

FOREIGN PATENT DOCUMENTS

| | | | |
|---|---|---|---|
| WO | WO/2002/046403 | * | 6/2002 |
| WO | WO2011119507 A2 | | 9/2011 |
| WO | WO2016019315 A2 | | 2/2016 |

OTHER PUBLICATIONS

Martin, D. et al. Functional significance of repressor element 1 silencing transcription factor (REST) target genes in pancreatic beta cells. Diabetologia 51, 1429-1439, doi:10.1007/s00125-008-0984-1 (2008).

Martin, D. et al. REST represses a subset of the pancreatic endocrine differentiation program. Dev Biol 405, 316-327, doi:10.1016/j.ydbio. 2015.07.002 (2015).

Marubini E, V. M. C. Estimation of Survival Probabilities. Analysing survival data from clinical trials and observational studies. 41-81 (John Wiley and Sons, 1995).

McClelland, S. et al. The transcription factor NRSF contributes to epileptogenesis by selective repression of a subset of target genes. Elife 3, e01267 (2014).

Mi, R., Chen, W. & Hoke, A. Pleiotrophin is a neurotrophic factor for spinal motor neurons. Proc Natl Acad Sci U S A 104, 4664-4669, doi:10.1073/pnas.0603243104 (2007).

Monaco, C. M. et al. Environmental enrichment promotes robust functional and histological benefits in female rats after controlled cortical impact injury. Exp Neurol 247, 410-418, doi: 10.1016/j.expneurol.2013.01.007 (2013).

Morrone, L., Scuteri, D., Rombola, L., Mizoguchi, H. & Bagetta, G. Opioids Resistance in Chronic Pain Management. Current Neuropharmacology 15, 444-456, doi: 10.2174/1570159X14666161101092822 (2017).

Mortazavi, A., Leeper Thompson, E. C., Garcia, S. T., Myers, R. M. & Wold, B. Comparative genomics modeling of the NRSF/REST repressor network: from single conserved sites to genome-wide repertoire. Genome Res 16, 1208-1221, doi:gr.4997306 [pii]10. 1101/gr.4997306 (2006).

Mosmann, T. Rapid colorimetric assay for cellular growth and survival: application to proliferation and cytotoxicity assays. J Immunol Methods 65, 55-63, doi:10.1016/0022-1759(83)90303-4 (1983).

Mu, Y. & Gage, F. H. Adult hippocampal neurogenesis and its role in Alzheimer's disease. Mol Neurodegener 6, 85, doi:1750-1326-6-85 [pii]10.1186/1750-1326-6-85 (2011).

Mucha, M. et al. Transcriptional control of KCNQ channel genes and the regulation of neuronal excitability. J Neurosci 30, 13235-13245, doi:10.1523/JNEUROSCI. 1981-10.2010 (2010).

(Continued)

*Primary Examiner* — Kimberly Ballard
*Assistant Examiner* — Stacey N MacFarlane
(74) *Attorney, Agent, or Firm* — CALDERON SAFRAN & WRIGHT P.C.

(57) ABSTRACT

The invention relates to compounds, compositions, and methods for derepressing RE1 silencing transcription factor (REST) target genes are provided. In particular, a peptide having the sequence TEDLEPPEPPLPKEN (SEQ. ID NO: 1) and EDLEPPEPPLPK (SEQ. ID NO: 15), or the reversed sequences made of D-amino acids (retro inverted, RI) nekplppeppeldet (SEQ ID NO: 16) and kplppeppelde (SEQ ID NO: 17), are disclosed for inhibiting REST activity. The peptides are useful to treat, prevent, or ameliorate conditions such as traumatic brain injury, epilepsy, dementia, Huntington's Disease (HD), chronic pain, brain cancer (including glioblastoma multiforme), pancreatic cancer; diabetes, and peripheral nerve injury.

20 Claims, 23 Drawing Sheets
Specification includes a Sequence Listing.

(56) References Cited

OTHER PUBLICATIONS

Nesti, E. Harnessing the master transcriptional repressor REST to reciprocally regulate neurogenesis. Neurogenesis 2, doi:10.1080/23262133.2015.1055419 (2015).

Nesti, E., Corson, G. M., McCleskey, M., Oyer, J. A. & Mandel, G. C-terminal domain small phosphatase 1 and MAP kinase reciprocally control REST stability and neuronal differentiation. Proc Natl Acad Sci U.S.A. 111, E3929-3936, doi:1414770111 [pii]10.1073/pnas.1414770111 (2014).

Nesti, L. J. et al. Differentiation potential of multipotent progenitor cells derived from war-traumatized muscle tissue. J Bone Joint Surg Am 90, 2390-2398, doi:10.2106/JBJS.H.00049 (2008).

Noguchi, H. et al. A new cell-permeable peptide allows successful allogeneic islet transplantation in mice. Nature Medicine 10, 305-309, doi:10.1038/nm994 (2004).

Noh, K. M. et al. Repressor element-1 silencing transcription factor (REST)-dependent epigenetic remodeling is critical to ischemia-induced neuronal death. Proc Natl Acad Sci U.S.A.109, E962-971, doi:1121568109 [pii]10.1073/pnas.1121568109 (2012).

Omura, T. et al. Different expressions of BDNF, NT3, and NT4 in muscle and nerve after various types of peripheral herve injuries. J Peripher Nerv Syst 10, 293-300, doi:10.1111/j.1085-9489.2005.10307.x (2005).

Oomen, C. A., Bekinschtein, P., Kent, B. A., Saksida, L. M. & Bussey, T. J. Adult hippocampal neurogenesis and its role in cognition. Wiley Interdiscip Rev Cogn Sci 5, 573-587, doi: 10.1002/wcs.1304 (2014).

Orta-Salazar, E. et al. REST/NRSF-induced changes of ChAT protein expression in the neocortex and hippocampus of the 3xTg-AD mouse model for Alzheimer's disease. Life sciences 116, 83-89, doi:10.1016/j.lfs.2014.09.013 (2014).

Otto, S. J. et al. A new binding motif for the transcriptional repressor REST uncovers large gene networks devoted to neuronal functions. J Neurosci 27, 6729-6739, doi:27/25/6729 [pii]10.1523/JNEUROSCI.0091-07.2007 (2007).

Papapetrou, E. P. & Schambach, A. Gene Insertion Into Genomic Safe Harbors for Human Gene Therapy. Mol Ther 24, 678-684, doi:10.1038/mt.2016.38 (2016).

Pasquina, P., Kirtley, R. & Ling, G. Moderate-to-severe traumatic brain injury. Semin Neurol 34, 572-583, doi:10.1055/s-0034-1396010 (2014).

Pei, Y. et al. Comparative neurotoxicity screening in human iPSC-derived neural stem cells, neurons and astrocytes. Brain Res 1638, 57-73, doi:10.1016/j.brainres.2015.07.048 (2016).

Persano, L., Rampazzo, E., Basso, G. & Viola, G. Glioblastoma cancer stem cells: role of the microenvironment and therapeutic targeting. Biochem Pharmacol 85, 612-622, doi:10.1016/j.bcp.2012.10.001 (2013).

Phillips, A. G. & LePiane, F. G. Reinforcing effects of morphine microinjection into the ventral tegmental area. Pharmacology, biochemistry, and behavior 12, 965-968 (1980).

Phillips, A. G., LePiane, F. G. & Fibiger, H. C. Dopaminergic mediation of reward produced by direct injection of enkephalin into the ventral tegmental area of the rat. Life sciences 33, 2505-2511 (1983).

Ploj, K., Roman, E. & Nylander, I. Long-term effects of short and long periods of maternal separation on brain opioid peptide levels in male Wistar rats. Neuropeptides 37, 149-156, doi: 10.1016/S0143-4179(03)00043-X (2003).

Pooga, M. et al. Cellular translocation of proteins by transportan. The FASEB journal : official publication of the Federation of American Societies for Experimental Biology 15, 1451-1453, doi:10.1096/fj.00-0780fje (2001).

Prus AJ, J. J., Rosecrans JA. in Methods of Behavior Analysis in Neuroscience (ed Buccafusco JJ) Ch. 4, (CRC Press/Taylor & Francis, 2009).

Pytte, C. L., Gerson, M., Miller, J. & Kirn, J. R. Increasing stereotypy in adult zebra finch song correlates with a declining rate of adult neurogenesis. Dev Neurobiol 67, 1699-1720, doi:10.1002/dneu.20520 (2007).

Ren, Y., Vera, D. L., Hughes, K. A. & Dennis, J. H. Stimulation of the *Drosophila* immune system alters genome-wide nucleosome occupancy. Genom Data 3, 146-147, doi:10.1016/j.gdata.2015.01.001 (2015).

Rigamonti, D. et al. Loss of huntingtin function complemented by small molecules acting as repressor element 1/neuron restrictive silencer element silencer modulators. J Biol Chem 282, 24554-24562, doi: 10.1074/jbc.M609885200 (2007).

Rigaud, M. et al. Species and strain differences in rodent sciatic nerve anatomy: implications for studies of neuropathic pain. Pain 136, 188-201, doi:10.1016/j.pain.2008.01.016 (2008).

River, C. Sergical Services, <https://www.criver.com/sites/default/files/resources/VascularCatheterSurgeryOptionsInformationSheet.pdf> (2018).

Robertson, C. S. et al. Effect of erythropoietin and transfusion threshold on neurological recovery after traumatic brain injury: a randomized clinical trial. JAMA 312, 36-47, doi:1884575 [pii]10.1001/jama.2014.6490 (2014).

Ronchi, G. et al. Discrepancies in quantitative assessment of normal and regenerated peripheral nerve fibers between light and electron microscopy. J Peripher Nerv Syst 19, 224-233, doi:10.1111/jns.12090 (2014).

Roopra, A., Dingledine, R. & Hsieh, J. Epigenetics and epilepsy. Epilepsia 53 Suppl 9, 2-10, doi:10.1111/epi.12030 (2012).

Rose, K. et al. Transcriptional repression of the M channel subunit Kv7.2 in chronic nerve injury. Pain 152, 742-754, doi:10.1016/j.pain.2010.12.028 (2011).

Rothstein, J. D., Jin, L., Dykes-Hoberg, M. & Kuncl, R. W. Chronic inhibition of glutamate uptake produces a model of slow neurotoxicity. Proc Natl Acad Sci U S A 90, 6591-6595 (1993).

Rueden, C. T. et al. ImageJ2: ImageJ for the next generation of scientific image data. BMC Bioinformatics 18, 529-529, doi:10.1186/s12859-017-1934-z (2017).

Salim, A. et al. Role of anemia in traumatic brain injury. J Am Coll Surg 207, 398-406, doi:S1072-7515(08)00322-0 [pii] 10.1016/j.jamcollsurg.2008.03.013 (2008).

Samuels, I. S et al. Deletion of ERK2 mitogen-activated protein kinase identifies its key roles in cortical neurogenesis and cognitive function. J Neurosci 28, 6983-6995, doi:28/27/6983 [pii]10.1523/JNEUROSCI.0679-08.2008 (2008).

Scharff, C., Kirn, J. R., Grossman, M., Macklis, J. D. & Nottebohm, F. Targeted neuronal death affects neuronal replacement and vocal behavior in adult songbirds. Neuron 25, 481-492, doi:S0896-6273(00)80910-1 [pii] (2000).

Schmitz, H. C. & Beer, G. M. The toe-spreading reflex of the rabbit revisited—functional evaluation of complete peroneal nerve lesions. Lab Anim 35, 340-345, doi:10.1258/0023677011911930 (2001).

Schoenherr, C. J. & Anderson, D. J. Silencing is golden: negative regulation in the control of neuronal gene transcription. Curr Opin Neurobiol 5, 566-571, doi:0959-4388(95)80060-3 [pii] (1995).

Schoenherr, C. J., Paquette, A. J. & Anderson, D. J. Identification of potential target genes for the neuron-restrictive silencer factor. Proc Natl Acad Sci U S A 93, 9881-9886 (1996).

Schwartz, A. S. & Marchok, P. L. Depression of morphine-seeking behaviour by dopamine inhibition. Nature 248, 257-258 (1974).

Schwarze, S. R., Ho, A., Vocero-Akbani, A. & Dowdy, S. F. In vivo protein transduction: delivery of a biologically active protein into the mouse. Science (New York, N.Y.) 285, 1569-1572, doi:10.1126/science.285.5433.1569 (1999).

Seib, D. R. et al. Loss of Dickkopf-1 restores neurogenesis in old age and counteracts cognitive decline. Cell Stem Cell 12, 204-214, doi:S1934-5909(12)00644-3 [pii]10.1016/j.stem.2012.11.010 (2013).

Sexton, B. S. et al. Hierarchical regulation of the genome: global changes in nucleosome organization potentiate genome response. Oncotarget 7, 6460-6475, doi:10.18632/oncotarget.6841 (2016).

Sexton, B. S. et al. The spring-loaded genome: nucleosome redistributions are widespread, transient, and DNA-directed. Genome Res 24, 251-259, doi: 10.1101/gr.160150.113 (2014).

(56) References Cited

OTHER PUBLICATIONS

Sharp, D. J., Scott, G. & Leech, R. Network dysfunction after traumatic brain injury. Nat Rev Neurol 10, 156-166, doi:10.1038/nmeurol.2014.15 (2014).
Shear, D. A. et al. Nicotinamide Treatment in Traumatic Brain Injury: Operation Brain Trauma Therapy. J Neurotrauma 33, 523-537, doi:10.1089/neu.2015.4115 (2016).
Shi, T. J. et al. Effect of peripheral nerve injury on dorsal root ganglion neurons in the C57 BL/6J mouse: marked changes both in cell numbers and neuropeptide expression. Neuroscience 105, 249-263 (2001).
Shi, Y. Serine/Threonine Phosphatases: Mechanism through Structure. Cell 139, 468-484, doi: 10.1016/j.cell.2009.10.006 (2009).
Shors, T. J. et al. Neurogenesis in the adult is involved in the formation of trace memories. Nature 410, 372-376, doi:10.1038/35066584 (2001).
Sipione, S. et al. Early transcriptional profiles in huntingtin-inducible striatal cells by microarray analyses. Hum Mol Genet 25, 210, doi:10.1093/hmg/ddv416 (2016).
Sleigh, J. N., Weir, G. A. & Schiavo, G. A simple, step-by-step dissection protocol for the rapid isolation of mouse dorsal root ganglia. BMC Res Notes 9, 82, doi:10.1186/s13104-016-1915-8 (2016).
Spyraki, C., Fibiger, H. C. & Phillips, A. G. Attenuation of heroin reward in rats by disruption of the mesolimbic dopamine system. Psychopharmacology 79, 278-283 (1983).
Susarla, B. T., Villapol, S., Yi, J. H., Geller, H. M. & Symes, A. J. Temporal patterns of cortical proliferation of glial cell populations after traumatic brain injury in mice. ASN Neuro 6, 159-170, doi:10.1042/AN20130034 (2014).
Sussman, F., Villaverde, M. C., L. Dominguez, J. & Danielson, U. H. On the Active Site Protonation State in Aspartic Proteases: Implications for Drug Design. Current Pharmaceutical Design, vol. 19, No. 23 19, 4257-4275, doi:10.1002/(SICI) 1520-667X(1998)10:1<19::AID-MCS3>3.0.CO;2-1 (2013).
Swistowski, A. et al. Xeno-free defined conditions for culture of human embryonic stem cells, neural stem cells and dopaminergic neurons derived from them. PLoS One 4, e6233, doi:10.1371/journal.pone.0006233 (2009).
Symes, A. J. et al. Ciliary neurotrophic factor coordinately activates transcription of neuropeptide genes in a neuroblastoma cell line. Proc Natl Acad Sci U S A 90, 572-576, doi:10.1073/pnas.90.2.572 (1993).
T.J. Shors, G. M., A. Beylin, M. Zhao, T. Rydel, E. Gould. Neurogenesis in the adult is involved in the formation of trace memories. Nature 410, 372-376 (2001).
Taylor, P et al. REST is a novel prognostic factor and therapeutic target for medulloblastoma. Mol Cancer Ther 11, 1713-1723, doi:10.1158/1535-7163.MCT-11-0990 (2012).
Thornton, G. K. & Woods, C. G. Primary microcephaly: do all roads lead to Rome? Trends Genet 25, 501-510, doi:10.1016/j.tig.2009.09.011 (2009).
Tilghman, J. et al. Regulation of Glioblastoma Tumor-Propagating Cells by the Integrin Partner Tetraspanin CD151. Neoplasia 18, 185-198, doi:10.1016/j.neo.2016.02.003 (2016).
Uchida, H., Ma, L. & Ueda, H. Epigenetic Gene Silencing Underlies C-Fiber Dysfunctions in Neuropathic Pain. Journal of Neuroscience 30, 4806-4814, doi:10.1523/JNEUROSCI.5541-09.2010 (2010).
Uchida, H., Sasaki, K., Ma, L. & Ueda, H. Neuron-restrictive silencer factor causes epigenetic silencing of Kv4.3 gene after peripheral nerve injury. Neuroscience 166, 1-4, doi:10.1016/j.neuroscience.2009.12.021 (2010).
Ueda, H. et al. A mimetic of the mSin3-binding helix of NRSF/REST ameliorates abnormal pain behavior in chronic pain models. Bioorg Med Chem Lett 27, 4705-4709, doi:10.1016/j.bmcl.2017.09.006 (2017).
VanElzakker, M., Fevurly, R. D., Breindel, T. & Spencer, R. L. Environmental novelty is associated with a selective increase in Fos expression in the output elements of the hippocampal formation and the perirhinal cortex. Learn Mem 15, 899-908, doi:10.1101/lm.1196508 (2008).
Varejao, A. S. et al. Functional and morphological assessment of a standardized rat sciatic nerve crush injury with a non-serrated clamp. J Neurotrauma 21, 1652-1670, doi:10.1089/neu.2004.21.1652 (2004).
Villeda, S. A. et al. The ageing systemic milieu negatively regulates neurogenesis and cognitive function. Nature 477, 90-94, doi:10.1038/nature10357 (2011).
Vincent, A. S., Roebuck-Spencer, T. M. & Cernich, A. Cognitive changes and dementia risk after traumatic brain injury: implications for aging military personnel. Alzheimers Dement 10, S174-187, doi:10.1016/j.jalz.2014.04.006 (2014).
Wagner, A. K., Postal, B. A., Darrah, S. D., Chen, X. & Khan, A. S. Deficits in novelty exploration after controlled cortical impact. J Neurotrauma 24, 1308-1320, doi:10.1089/neu.2007.0274 (2007).
Wagoner, M. P. & Roopra, A. A REST derived gene signature stratifies glioblastomas into chemotherapy resistant and responsive disease. BMC Genomics 13, 686, doi:10.1186/1471-2164-13-686 (2012).
Weir M. R. Renin inhibitors: novel agents for renoprotection or a better angiotensin receptor blocker for blood pressure lowering? Current opinion in nephrology and hypertension 16, 416-421, doi:10.1097/MNH.0b013e328209fe00 (2007).
Whiteside, G. T., Adedoyin A, Leventhal L. Predictive validity of animal pain models? A comparison of the pharmacokinetic-pharmacodynamic relationship for pain drugs in rats and humans. Neuropharm, 767-775, doi:10.1016/j.neuropharm.2008.01.001 (2008).
Willis, D. E., Wang, M., Brown, E., Fones, L. & Cave, J. W. Selective repression of gene expression in neuropathic pain by the neuron-restrictive silencing factor/repressor element-1 silencing transcription (NRSF/REST). Neuroscience Letters 625, 20-25, doi:10.1016/j.neulet.2015.12.003 (2016).
Woolf, C. J. Phenotypic modification of primary sensory neurons: the role of nerve growth factor in the production of persistent pain. Philos Trans R Soc Lond B Biol Sci 351, 441-448, doi:10.1098/rstb.1996.0040 (1996).
Xiong, Y. et al. Histological and functional outcomes after traumatic brain injury in mice null for the erythropoietin receptor in the central nervous system. Brain Res 1230, 247-257, doi:10.1016/j.brainres.2008.06.127 (2008).
Xiong, Y. et al. Role of gender in outcome after traumatic brain injury and therapeutic effect of erythropoietin in mice. Brain Res 1185, 301-312, doi:10.1016/j.brainres.2007.09.052 (2007).
Xu, Y. et al. Gait Assessment of Pain and Analgesics: Comparison of the DigiGait and CatWalk Gait Imaging Systems. Neurosci Bull 35, 401-418, doi:10.1007/s12264-018-00331-y (2019).
Yan, Y. et al. Efficient and rapid derivation of primitive neural stem cells and generation of brain subtype neurons from human pluripotent stem cells. Stem Cells Transl Med 2, 862-870, doi:10.5966/sctm.2013-0080 (2013).
Yektas, A. et al. Perineural dexmedetomidine effects on sciatic nerve in rat. Brazilian Journal of Anesthesiology (English Edition) 67, 57-66, doi:10.1016/j.bjane.2015.08.012 (2017).
Yeo, M. et al. Small CTD phosphatases function in silencing neuronal gene expression. Science 307, 596-600, doi:307/5709/596 [pii]10.1126/science.1100801 (2005).
Yeo, M., Lin, P. S., Dahmus, M. E. & Gill, G. N. A Novel RNA Polymerase II C-terminal Domain Phosphatase That Preferentially Dephosphorylates Serine 5. Journal of Biological Chemistry 278, 26078-26085, doi:10.1074/jbc.M301791200 (2003).
Zhang, F. et al. Repressor element 1-silencing transcription factor drives the development of chronic pain states. Pain, doi:10.1097/j.pain.0000000000001633 (2019).
Zhang, J. Y., Luo, X. G., Xian, C. J., Liu, Z. H. & Zhou, X. F. Endogenous BDNF is required for myelination and regeneration of injured sciatic nerve in rodents. Eur J Neurosci 12, 4171-4180 (2000).
Zhang, J., Chen, S. R., Chen, H. & Pan, H. L. RE1-silencing transcription factor controls the acute-to-chronic neuropathic pain

(56) References Cited

OTHER PUBLICATIONS transition and Chrm2 receptor gene expression in primary sensory neurons. J Biol Chem 293, 19078-19091, doi:10.1074/jbc.RA118.005846 (2018).
Zhang, J., Groff, R. F. & Dayawansa, S. Imipramine treatment increases cell proliferation following fluid percussion brain injury in rats. Neurol Res 35, 247-254, doi:10.1179/1743132813Y.0000000164 (2013).
Zhao, Y. et al. Brain REST/NRSF Is Not Only a Silent Repressor but Also an Active Protector. Molecular Neurobiology 54, 541-550, doi:10.1007/s12035-015-9658-4 (2017).
Zhu, C. et al. Neuron-restrictive silencer factor-mediated downregulation of µ-opioid receptor contributes to the reduced morphine analgesia in bone cancer pain. Pain 158, 879-890, doi:10.1097/j.pain.0000000000000848 (2017).
Zuccato, C. et al. Huntingtin interacts with REST/NRSF to modulate the transcription of NRSE-controlled neuronal genes. Nat Genet 35, 76-83, doi: 10.1038/ng1219 (2003).
Galli, R. et al. Isolation and characterization of tumorigenic, stem-like neural precursors from human glioblastoma. Cancer Res 64, 7011-7021, doi:10.1158/0008-5472.CAN-04-1364 (2004).
Gao, Z. et al. The master negative regulator REST/NRSF controls adult neurogenesis by restraining the neurogenic program in quiescent stem cells. J Neurosci 31, 9772-9786, doi:31/26/9772 [pii]10.1523/JNEUROSCI.1604-11.2011 (2011).
Garzon-Muvdi, T. et al. Regulation of brain tumor dispersal by NKCC1 through a novel role in focal adhesion regulation. PLoS Biol 10, e1001320, doi:10.1371/journal.pbio.1001320 (2012).
Gervasi NM., D. A., Clark DM., Dingle M,, Pisarchik AV., Nesti LJ. C-terminal domain small phosphatase 1 (CTDSP1) regulates growth factor expression and axonal regeneration. Journal of Translational Medicine Manuscripted submitted for publication. (2020).
Ghaziuddin, M., Zaccagnini, J., Tsai, L. & Elardo, S. Is megalencephaly specific to autism? J Intellect Disabil Res 43 (Pt 4), 279-282 (1999).
Glasby, M. A. & Hems, T. E. Repairing spinal roots after brachial plexus injuries. Paraplegia 33, 359-361, doi: 10.1038/sc.1995.80 (1995).
Goldman, S. A. & Nottebohm, F. Neuronal production, migration, and differentiation in a vocal control nucleus of the adult female canary brain. Proc Natl Acad Sci U.S.A. 80, 2390-2394 (1983).
Gould, E., Beylin, A., Tanapat, P., Reeves, A. & Shors, T. J. Learning enhances adult neurogenesis in the hippocampal formation. Nat Neurosci 2, 260-265, doi:10. 1038/6365 (1999).
Greig, N. H. et al. Incretin mimetics as pharmacologic tools to elucidate and as a new drug strategy to treat traumatic brain injury. Alzheimers Dement 10, S62-75, doi:S1552-5260(13)02925-7 [pii]10.1016/j.jalz.2013.12.011 (2014).
Guerrero-Cazares, H., Chaichana, K. L. & Quinones-Hinojosa, A. Neurosphere culture and human organotypic model to evaluate brain tumor stem cells. Methods Mol Biol 568, 73-83, doi:10.1007/978-1-59745-280-9_6 (2009).
Hall, E. D., Bryant, Y. D., Cho, W. & Sullivan, P. G. Evolution of post-traumatic neurodegeneration after controlled cortical impact traumatic brain injury in mice and rats as assessed by the de Olmos silver and fluorojade staining methods. J Neurotrauma 25, 235-247, doi:10.1089/neu.2007.0383 (2008).
Hammer, P. et al. mRNA-seq with agnostic splice site discovery for nervous system transcriptomics tested in chronic pain. Genome Res 20, 847-860, doi:10.1101/gr.101204.109 (2010).
Hamzeh-Mivehroud, M., Alizadeh, A. A., Morris, M. B., Bret Church, W. & Dastmalchi, S. Phage display as a technology delivering on the promise of peptide drug discovery. Drug Discovery Today 18, 1144-1157, doi:10.1016/j.drudis.2013.09.001 (2013).
Han, D., Lu, J., Xu, L. & Xu, J. Comparison of two electrophysiological methods for the assessment of progress in a rat model of nerve repair. International Journal of Clinical and Experimental Medicine 8, 2392-2398 (2015).

Hargreaves, K., Dubner, R., Brown, F., Flores, C. & Joris, J. A new and sensitive method for measuring thermal nociception in cutaneous hyperalgesia. Pain 32, 77-88, doi:10.1016/0304-3959(88)90026-7 (1988).
Hazari, A., Wiberg, M., Johansson-Ruden, G., Green, C. & Terenghi, G. A resorbable nerve conduit as an alternative to nerve autograft in nerve gap repair. Br J Plast Surg 52, 653-657, doi:10.1054/bjps.1999.3184 (1999).
He, R. et al. Recombinant luciferase-expressing human cytomegalovirus (CMV) for evaluation of CMV inhibitors. Virol J 8, 40, doi:10.1186/1743-422X-8-40 (2011).
Hems, T. E. & Glasby, M. A. The limit of graft length in the experimental use of muscle grafts for nerve repair. J Hand Surg Br 18, 165-170 (1993).
Hoekstra, E., Peppelenbosch, M. P. & Fuhler, G. M. Meeting report europhosphatase 2015: Phosphatases as drug targets in cancer. Cancer Research 76, 193-196, doi:10.1158/0008-5472.CAN-15-2091 (2016).
Hwang, J. Y., Kaneko, N., Noh, K. M., Pontarelli, F. & Zukin, R. S. The gene silencing transcription factor REST represses miR-132 expression in hippocampal neurons destined to die. J Mol Biol 426, 3454-3466, doi:10.1016/j.jmb.2014.07.032 (2014).
Irwin, S. Comprehensive observational assessment: Ia. A systematic, quantitative procedure for assessing the behavioral and physiologic state of the mouse. Psychopharmacologia 13, 222-257 (1968).
Jackson, M., Hassiotou, F. & Nowak, A. Glioblastoma stem-like cells: at the root of tumor recurrence and a therapeutic target. Carcinogenesis 36, 177-185, doi:10.1093/carcin/bgu243 (2015).
Jackson, W. M. et al. Mesenchymal progenitor cells derived from traumatized muscle enhance neurite growth. J Tissue Eng Regen Med 7, 443-451, doi:10.1002/term.539 (2013).
Jacqmain, J., Nudi, E. T., Fluharty, S. & Smith, J. S. Pre and post-injury environmental enrichment effects functional recovery following medial frontal cortical contusion injury in rats. Behav Brain Res 275, 201-211, doi: 10.1016/j.bbr.2014.08.056 (2014).
Jin, H. et al. Identification of RE1-Silencing Transcription Factor as a Promoter of Metastasis in Pancreatic Cancer. Front Oncol 9, 291, doi:10.3389/fonc.2019.00291 (2019).
Jin, J. et al. Functional motor recovery after peripheral nerve repair with an aligned nanofiber tubular conduit in a rat model. Regen Med 7, 799-806, doi:10.2217/rme.12.87 (2012).
Kamal, M. M. et al. REST regulates oncogenic properties of glioblastoma stem cells. Stem Cells 30, 405-414, doi:10.1002/stem.1020 (2012).
Kan Ding, P. K. G., and Ramon Diaz-Arrastia. in Translational Research in Traumatic Brain Injury (ed Grant G Laskowitz D) Ch. 14, (Taylor and Francis, 2016).
Kaneko, N., Hwang, J. Y., Gertner, M., Pontarelli, F. & Zukin, R. S. Casein kinase 1 suppresses activation of REST in insulted hippocampal neurons and halts ischemia-induced neuronal death. J Neurosci 34, 6030-6039, doi:34/17/6030 [pii]10.1523/JNEUROSCI.4045-13.2014 (2014).
Kaplan, E. L. M., P. Nonparametric estimation from incomplete observations. Journal of the American Statistical Association 53, 457-481, doi:10.2307/2281868 (1958).
Kaplan, G. B., Vasterling, J. J. & Vedak, P. C. Brain-derived neurotrophic factor in traumatic brain injury, post-traumatic stress disorder, and their comorbid conditions: role in pathogenesis and treatment. Behav Pharmacol 21, 427-437, doi:10.1097/FBP.0b013e32833d8bc9 (2010).
Kaspar, A. A. & Reichert, J. M. Future directions for peptide therapeutics development. Drug Discov Today 18, 807-817, doi:10.1016/j.drudis.2013.05.011 (2013).
Kirn, J. R. & Nottebohm, F. Direct evidence for loss and replacement of projection neurons in adult canary brain. J Neurosci 13, 1654-1663 (1993).
Kim, J. R. The relationship of neurogenesis and growth of brain regions to song learning. Brain Lang 115, 29-44, doi: S0093-934X(09)00135-7 [pii]10.1016/j.bandl.2009.09.006 (2010).
Knoepfler, P. S. Deconstructing stem cell tumorigenicity: a roadmap to safe regenerative medicine. Stem Cells 27, 1050-1056, doi:10.1002/stem.37 (2009).

(56) References Cited

OTHER PUBLICATIONS

Kobiela Ketz A, B. K., Grunberg NE, Kasper CE, Osborne L, Pryor B, Tosini NL, Wu X, Anders JJ. Characterization of macrophage/microglial activation and effect of photobiomodulation in the spared nerve injury model of neuropathic pain. . Pain Medicine 5, 932-946, doi:10.1093/pm/pnw144 (2016).

Kohyama, J. et al. BMP-induced REST regulates the establishment and maintenance of astrocytic identity. J Cell Biol 189, 159-170, doi:jcb.200908048 [pii]10.1083/jcb.200908048 (2010).

Kuhn, H. G., Cooper-Kuhn, C. M., Boekhoorn, K. & Lucassen, P. J. Changes in neurogenesis in dementia and Alzheimer mouse models: are they functionally relevant? Eur Arch Psychiatry Clin Neurosci 257, 281-289, doi: 10.1007/s00406-007-0732-4 (2007).

LaBuda, C. J. & Fuchs, P. N. A behavioral test paradigm to measure the aversive quality of inflammatory and neuropathic pain in rats. Exp Neurol 163, 490-494, doi:10.1006/exnr.2000.7395 (2000).

Lal, S. et al. An implantable guide-screw system for brain tumor studies in small animals. J Neurosurg 92, 326-333, doi:10.3171/jns.2000.92.2.0326 (2000).

Leung, J. Y. et al. Metallothionein promotes regenerative axonal sprouting of dorsal root ganglion neurons after physical axotomy. Cell Mol Life Sci 69, 809-817, doi:10.1007/s00018-011-0790-7 (2012).

Lischka, F. W. et al. Neonatal mouse cortical but not isogenic human astrocyte feeder layers enhance the functional maturation of induced pluripotent stem cell-derived neurons in culture. Glia 66, 725-748, doi:10.1002/glia.23278 (2018).

Liu, G. et al. Analysis of gene expression and chemoresistance of CD133+ cancer stem cells in glioblastoma. Mol Cancer 5, 67, doi:10.1186/1476-4598-5-67 (2006).

Lu, C. e. et al. Neuron-restrictive silencer factor in periaqueductal gray contributes to remifentanil-induced postoperative hyperalgesia via repression of the mu-opioid receptor. Journal of the Neurological Sciences 352, 48-52, doi:10.1016/j.jns.2015.03.018 (2015).

Lu, T. et al. REST and stress resistance in ageing and Alzheimer's disease. Nature 507, 448-454, doi:nature13163 [pii] 10.1038/nature13163 (2014).

Luca Longhia, , Elisa R. Zaniera, Nicolas Royob, Nino Stocchettia, Tracy K. McIntosha. Stem cell transplantation as a therapeutic strategy for traumatic brain injury. Transplant Immunology 15, 134-148 (2005).

Lunyak, V. V. & Rosenfeld, M. G. No rest for REST: REST/NRSF regulation of neurogenesis. Cell 121, 499-501, doi:10.1016/j.cell.2005.05.003 (2005).

Malik, N. et al. Compounds with species and cell type specific toxicity identified in a 2000 compound drug screen of neural stem cells and rat mixed cortical neurons. Neurotoxicology 45, 192-200, doi:10.1016/j.neuro.2014.10.007 (2014).

Mandel, G. et al. Repressor element 1 silencing transcription factor (REST) controls radial migration and temporal neuronal specification during neocortical development. Proc Natl Acad Sci U S A 108, 16789-16794, doi:1113486108 [pii]10.1073/pnas.1113486108 (2011).

Manton, C. A. et al. Induction of cell death by the novel proteasome inhibitor marizomib in glioblastoma in vitro and in vivo. Sci Rep 6, 18953, doi:10.1038/srep18953 (2016).

Abderrahmani, A. et al. Neuronal traits are required for glucose-induced insulin secretion. FEBS Lett 565, 133-138, doi:10.1016/j.febslet.2004.04.002 (2004).

Abe, K. Therapeutic potential of neurotrophic factors and neural stem cells against ischemic brain injury. J Cereb Blood Flow Metab 20, 1393-1408, doi:10.1097/00004647-200010000-00001 (2000).

Alvarado, S. et al. Peripheral nerve injury is accompanied by chronic transcriptome-wide changes in the mouse prefrontal cortex. Mol Pain 9, 21, doi:10.1186/1744-8069-9-21 (2013).

Anobom, C. D. et al. From structure to catalysis: Recent developments in the biotechnological applications of lipases. BioMed Research International 2014, doi:10.1155/2014/684506 (2014).

Arranz-Gibert, P. et al. Immunosilencing peptides by stereochemical inversion and sequence reversal: retro-D-peptides. Sci Rep 8, 6446, doi:10.1038/s41598-018-24517-6 (2018).

Baastrup, C., Jensen, T. S. & Finnerup, N. B. Pregabalin attenuates place escape/avoidance behavior in a rat model of spinal cord injury. Brain Res 1370, 129-135, doi:10.1016/j.brainres.2010.11.008 (2011).

Baker, M. Tumours spark stem-cell review. Nature 457, 941, doi:10.1038/457941a (2009).

Ballas, N. et al. Regulation of neuronal traits by a novel transcriptional complex. Neuron 31, 353-365, doi:10.1016/60896-6273(01)00371-3 (2001).

Ballas, N., Grunseich, C., Lu, D. D., Speh, J. C. & Mandel, G. REST and its corepressors mediate plasticity of neuronal gene chromatin throughout neurogenesis. Cell 121, 645-657, doi:S0092-8674(05)00285-0 [pii]10.1016/j.cell.2005.03.013 (2005).

Banerjee, P. N., Filippi, D. & Allen Hauser, W. The descriptive epidemiology of epilepsy—a review. Epilepsy Res 85, 31-45, doi:10.1016/j.eplepsyres.2009.03.003 (2009).

Bao, S. et al. Targeting cancer stem cells through L1CAM suppresses glioma growth. Cancer Res 68, 6043-6048, doi:10.1158/0008-5472.CAN-08-1079 (2008).

Beer, S. a. The toe-spreading reflex of the rabbit revisited—functional evaluation of complete peroneal nerve lesions. Laboratory Animals 35, 340-345 (2001).

Bergsland, M., Covacu, R., Perez Estrada, C., Svensson, M. & Brundin, L. Nitric oxide-induced neuronal to glial lineage fate-change depends on NRSF/REST function in neural progenitor cells. Stem Cells 32, 2539-2549, doi:10.1002/stem.1749 (2014).

Bird, C. M. & Burgess, N. The hippocampus supports recognition memory for familiar words but not unfamiliar faces. Curr Biol 18, 1932-1936, doi:10.1016/j.cub.2008.10.046 (2008).

Blundell, T. L., Jhoti, H. & Abell, C. High-Throughput Crystallography for Lead Discovery in Drug Design. Nature Reviews Drug Discovery 1, 45-54, doi:10.1038/nrd706 (2002).

Brederlau, A. et al. Transplantation of human embryonic stem cell-derived cells to a rat model of Parkinson's disease: effect of in vitro differentiation on graft survival and teratoma formation. Stem Cells 24, 1433-1440, doi:2005-0393 [pii] 10.1634/stemcells.2005-0393 (2006).

Bruce, A. W. et al. Genome-wide analysis of repressor element 1 silencing transcription factor/neuron-restrictive silencing factor (REST/NRSF) target genes. Proc Natl Acad Sci U.S.A. 101, 10458-10463, doi:10.1073/pnas.04018271010401827101 [pii] (2004).

Bulken-Hoover, J. D. et al. Inducible expression of neurotrophic factors by mesenchymal progenitor cells derived from traumatically injured human muscle. Mol Biotechnol 51, 128-136, doi:10.1007/s12033-011-9445-z (2012).

Burns, T. C., Verfaillie, C. M. & Low, W. C. Stem cells for ischemic brain injury: a critical review. J Comp Neurol 515, 125-144, doi:10.1002/cne.22038 (2009).

Calderone, A. et al. Ischemic insults derepress the gene silencer REST in neurons destined to die. J Neurosci 23, 2112-2121, doi:23/6/2112 [pii] (2003).

Cargnin, F. et al. An RNA binding protein promotes axonal integrity in peripheral neurons by destabilizing Rest. J Neurosci 34, 16650-16661, doi:10.1523/JNEUROSCI.1650-14.2014 (2014).

Carlson, A. P., Schermer, C. R. & Lu, S. W. Retrospective evaluation of anemia and transfusion in traumatic brain Injury. J Trauma 61, 567-571, doi:10.1097/01.ta.0000231768.44727.a200005373-200609000-00007 [pii] (2006).

Carmeliet, P. & Storkebaum, E. Vascular and neuronal effects of VEGF in the nervous system: implications for neurological disorders. Semin Cell Dev Biol 13, 39-53, doi:10.1006/scdb.2001.0290S1084952101902903 [pii] (2002).

Carr, K. D., Bak, T. H., Simon, E. J. & Portoghese, P. S. Effects of the selective kappa opioid antagonist, nor- binaltorphimine, on electrically-elicited feeding in the rat. Life sciences 45, 1787-1792 (1989).

Carriel, V., Garzon, I., Alaminos, M. & Cornelissen, M. Histological assessment in peripheral nerve tissue engineering. Neural Regen Res 9, 1657-1660, doi:10.4103/1673-5374.141798 (2014).

Chan, J. R., Cosgaya, J. M., Wu, Y. J. & Shooter, E. M. Neurotrophins are key mediators of the myelination program in the peripheral nervous system. Proc Natl Acad Sci U S A 98, 14661-14668, doi:10.1073/pnas.251543398 (2001).

(56) References Cited

OTHER PUBLICATIONS

Charbord, J. et al. High throughput screening for inhibitors of REST in neural derivatives of human embryonic stem cells reveals a chemical compound that promotes expression of neuronal genes. Stem Cells 31, 1816-1828, doi:10.1002/stem.1430 (2013).

Choe, Y., Kozlova, A., Graf, D. & Pleasure, S. J. Bone morphogenic protein signaling is a major determinant of dentate development. J Neurosci 33, 6766-6775, doi:33/16/6766 [pii]10.1523/JNEUROSCI. 0128-13.2013 (2013).

Choi, S. H., Woodlee, M. T., Hong, J. J. & Schallert, T. A simple modification of the water maze test to enhance daily detection of spatial memory in rats and mice. J Neurosci Methods 156, 182-193, doi:10.1016/j.jneumeth.2006.03.002 (2006).

Chong, J. A. et al. REST: a mammalian silencer protein that restricts sodium channel gene expression to neurons. Cell 80, 949-957, doi:0092-8674(95)90298-8 [pii] (1995).

Chou, B. K. et al. Efficient human iPS cell derivation by a non-integrating plasmid from blood cells with unique epigenetic and gene expression signatures. Cell Res 21, 518-529, doi:10.1038/cr.2011.12 (2011).

Cole, L. A., Kurscheid, S., Nekrasov, M., Domaschenz, R., Dennis, J. H., Tremethick, D. J. Redefining the nucleosomal architecture of active and inactive promoters in the context of cellular plasticity and cancer. Nature Communications revision returned (2020).

Conaco, C., Otto, S., Han, J. J. & Mandel, G. Reciprocal actions of REST and a microRNA promote neuronal identity. Proc Natl Acad Sci U S A 103, 2422-2427, doi:0511041103 [pii]10.1073/pnas. 0511041103 (2006).

Conti, L. et al. REST controls self-renewal and tumorigenic competence of human glioblastoma cells. PLoS One 7, e38486, doi:10.1371/journal.pone.0038486 (2012).

Corse, A. M. et al. Preclinical testing of neuroprotective neurotrophic factors in a model of chronic motor neuron degeneration. Neurobiol Dis 6, 335-346, doi:10.1006/nbdi.1999.0253 (1999).

Costigan, M. et al. Multiple chronic pain states are associated with a common amino acid-changing allele in KCNS1. Brain 133, 2519-2527, doi:10.1093/brain/awq195 (2010).

Covey, M. V., Streb, J. W., Spektor, R. & Ballas, N. REST regulates the pool size of the different neural lineages by restricting the generation of neurons and oligodendrocytes from neural stem/progenitor cells. Development 139, 2878-2890, doi:dev.074765 [pii]10.1242/dev.074765 (2012).

Deister, C. & Schmidt, C. E. Optimizing neurotrophic factor combinations for neurite outgrowth. J Neural Eng 3, 172-179, doi:10.1088/1741-2560/3/2/011 (2006).

Deng, W., Aimone, J. B. & Gage, F. H. New neurons and new memories: how does adult hippocampal neurogenesis affect learning and memory? Nat Rev Neurosci 11, 339-350, doi:nrn2822 [pii]10.1038/nrn2822 (2010).

Dirks, P. B. Making a commitment: neurons refuse cancer's advances. Nat Neurosci 22, 507-508, doi:10.1038/s41593-019-0373-8 (2019).

Efthymiou, A. et al. Functional screening assays with neurons generated from pluripotent stem cell-derived neural stem cells. J Biomol Screen 19, 32-43, doi:10.1177/1087057113501869 (2014).

Erdo, F. et al. Host-dependent tumorigenesis of embryonic stem cell transplantation in experimental stroke. J Cereb Blood Flow Metab 23, 780-785, doi:10.1097/01.WCB.0000071886.63724.FB (2003).

Escayg, A. et al. Mutations of SCN1A, encoding a neuronal sodium channel, in two families with GEFS+2. Nat Genet 24, 343-345, doi:10.1038/74159 (2000).

FDA. (ed CDER; CBER) (FDA, https://www.fda.gov/downloads/drugs/guidances/ucm073246.pdf, 2010).

FDA. (ed CDER; CBER) (FDA, https://www.fda.gov/downloads/drugs/guidances/ucm074959.pdf, Jul. 2001).

FDA. Guidance for industry (ed CDER; CBER) (FDA, https://www.fda.gov/downloads/Drugs/GuidanceComplianceRegulatoryInformation/Guidances/UCM074957.pdf, 1997).

FDA. S2B Genotoxicity: A Standard Battery for Genotoxicity Testing of Pharmaceuticals, <https://www.fda.gov/media/71971/download> (1997).

FDA. S7B Nonclinical Evaluation of the Potential for Delayed Ventricular Repolarization (QT Interval Prolongation) by Human Pharmaceuticals, <https://www.fda.gov/media/72043/download> (2005).

Fremin, C. et al. ERK2 but not ERK1 plays a key role in hepatocyte replication: an RNAi-mediated ERK2 knockdown approach in wild-type and ERK1 null hepatocytes. Hepatology 45, 1035-1045, doi:10.1002/hep.21551 (2007).

Fulda, S., Wick, W., Weller, M. & Debatin, K. M. Smac agonists sensitize for Apo2L/TRAIL—or anticancer drug-induced apoptosis and induce regression of malignant glioma in vivo. Nature Medicine 8, 808-815, doi:10.1038/nm735 (2002).

\* cited by examiner

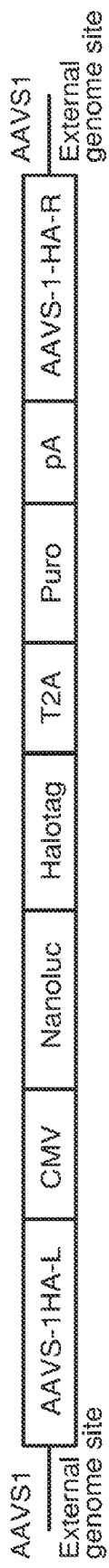
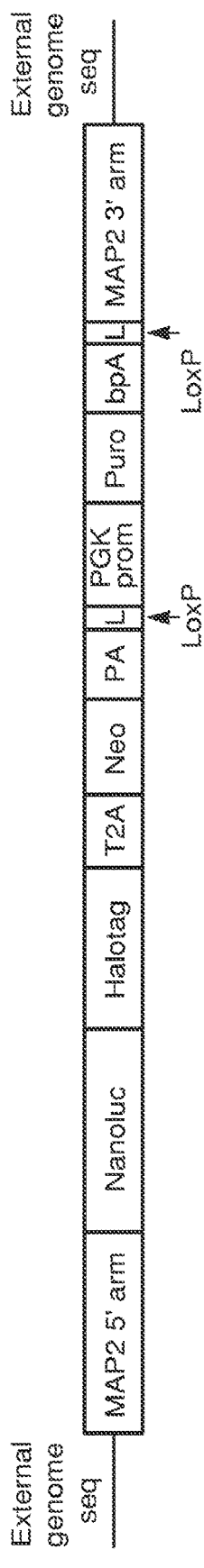
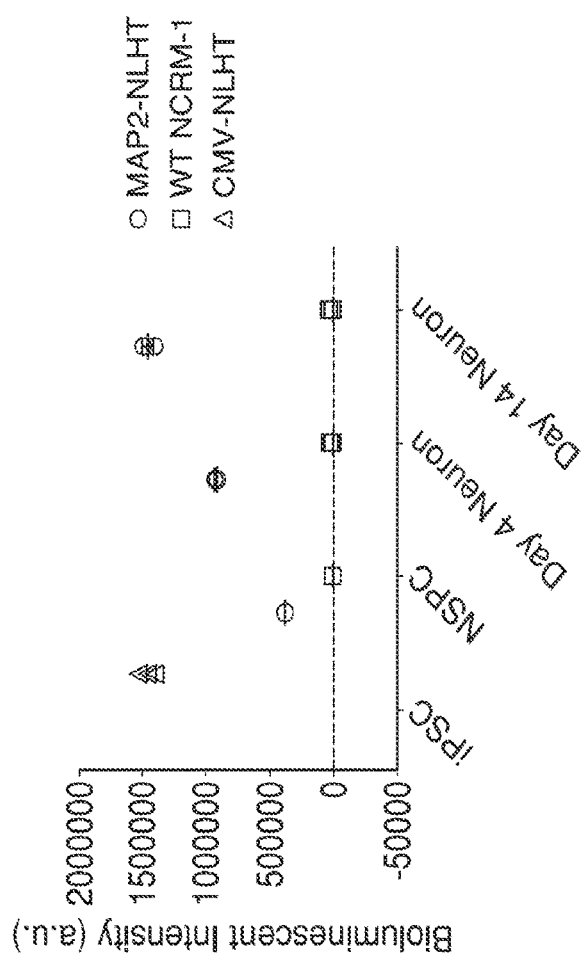
FIG. 20

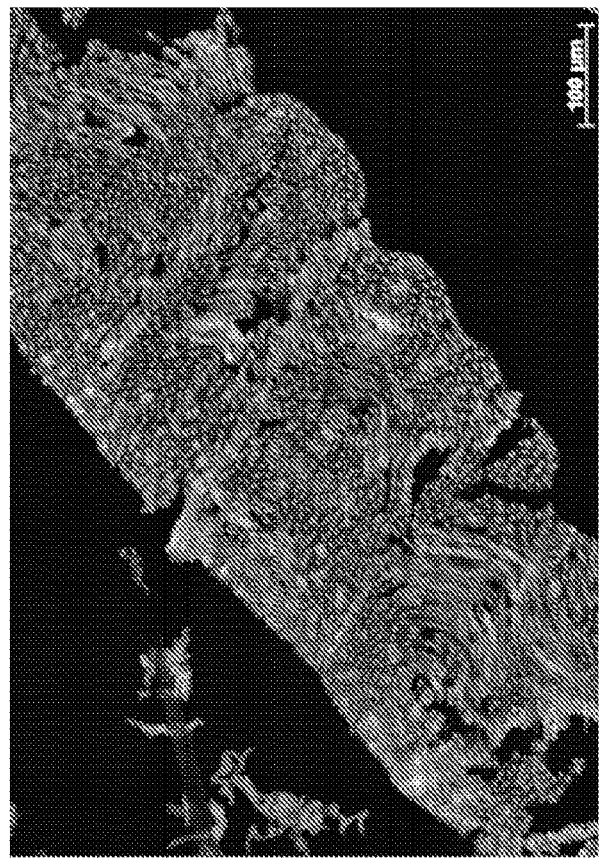
FIG. 21

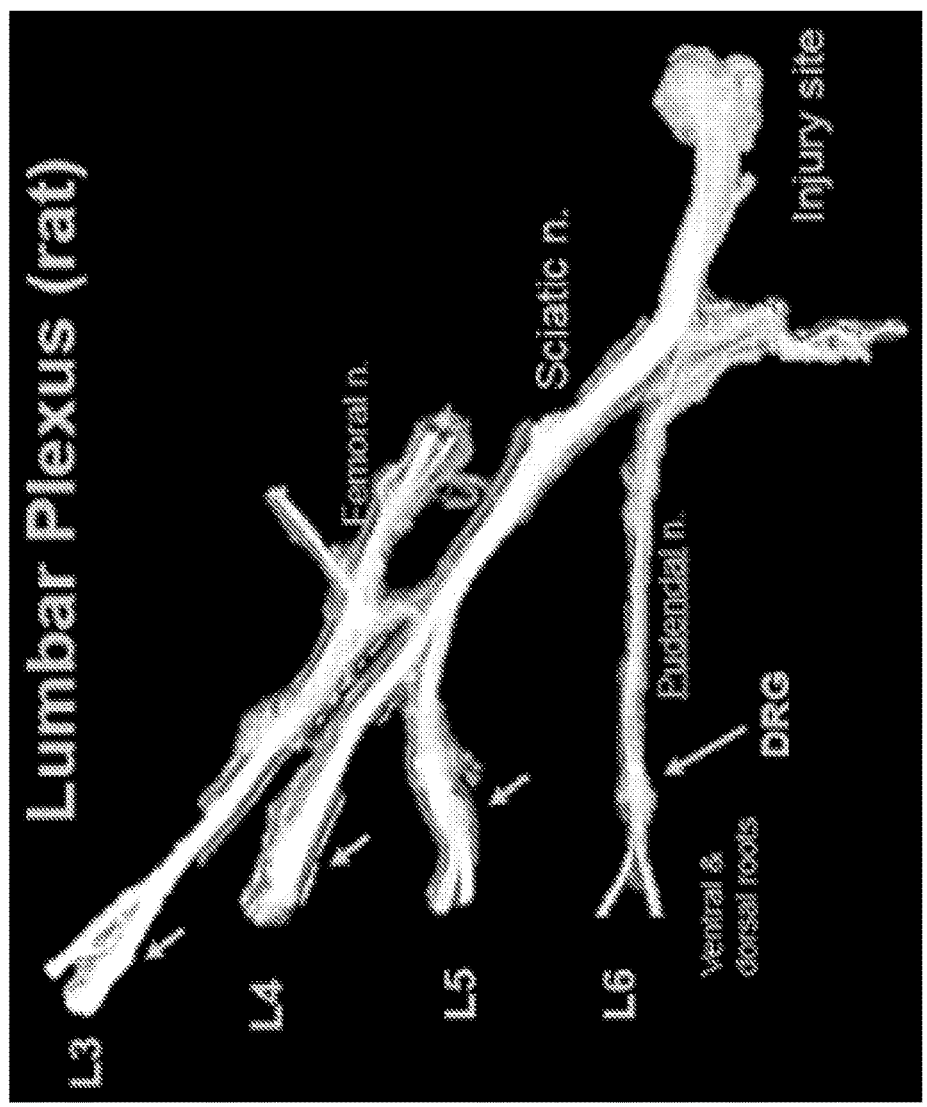
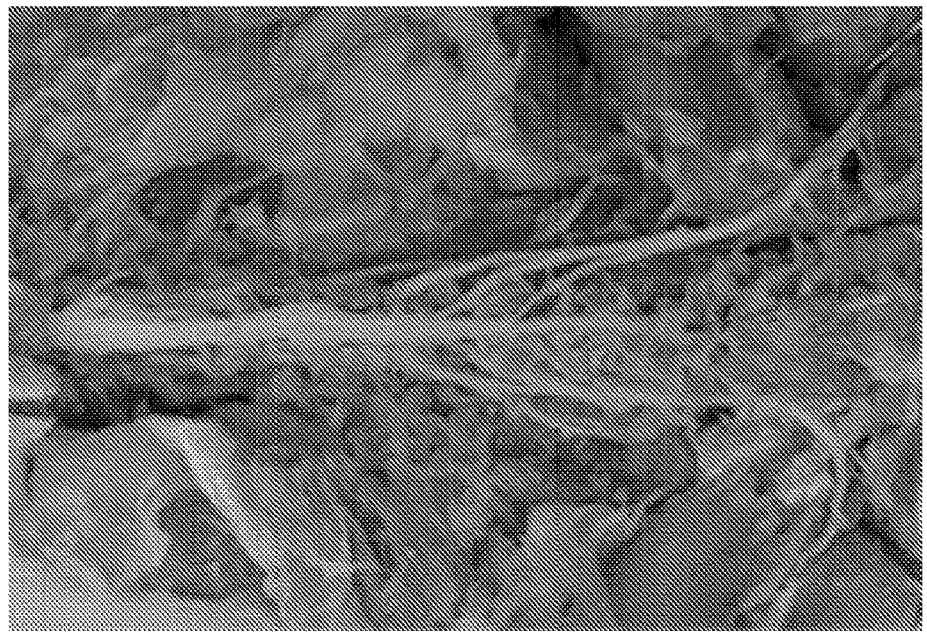
FIG. 22

Amino acids: D-form; Unusual amino acid: recemic $C_{144}H_{257}N_{51}O_{31}$
Mol. Wt.: 3198.91

SEQUENCE LISTING

<160> NUMBER OF SEQ ID NOS: 350

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Thr Glu Asp Leu Glu Pro Pro Glu Pro Pro Leu Pro Lys Glu Asn
1               5                   10                  15

<210> SEQ ID NO 2
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Cys Thr Glu Asp Leu Glu Pro Pro Glu Pro Pro Leu Pro Lys Glu
1               5                   10                  15

Asn Cys Gly Ser Gly Ser Gly Arg Lys Lys Arg Gln Arg Arg
            20                  25                  30

Gly Gly Ser Gly Ser Leu Gly His His His His His Gly Thr Gly
        35                  40                  45

Tyr

<210> SEQ ID NO 3
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Cys Glu Asp Ala Lys Asn Ile Lys Lys Gly Pro Ala Pro Phe Tyr
1               5                   10                  15

Pro Cys Gly Ser Gly Ser Gly Arg Lys Lys Arg Gln Arg Arg
            20                  25                  30

Gly Gly Ser Gly Ser Leu Gly His His His His His Gly Thr Gly
        35                  40                  45

Tyr

<210> SEQ ID NO 4
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Cys Ala Gln Lys Asp Tyr Lys Asp Asp Asp Lys Thr Glu Asp Leu
1               5                   10                  15

Glu Pro Pro Glu Pro Pro Leu Pro Lys Glu Asn Gly Arg Lys Lys Arg
            20                  25                  30

Arg Gln Arg Arg Arg Gly
        35

<210> SEQ ID NO 5
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Cys Thr Glu Asp Leu Glu Pro Pro Glu Pro Pro Leu Pro Lys Glu Asn
1               5                   10                  15

Ser Gly Asp Ile Met Gly Glu Trp Gly Asn Glu Ile Phe Gly Ala Ile

```
                20                  25                  30

Ala Gly Phe Leu Gly Tyr Gly Arg Lys Lys Arg Gln Arg Arg
            35                  40                  45

Gly

<210> SEQ ID NO 6
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: D-amino acid

<400> SEQUENCE: 6

Thr Glu Asp Leu Glu Pro Pro Glu Pro Pro Leu Pro Lys Glu Asn Arg
1               5                   10                  15

Arg Trp Trp Arg Arg Trp Arg Arg Arg Arg Trp Trp Arg Arg
            20                  25                  30

<210> SEQ ID NO 7
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: D-amino acid

<400> SEQUENCE: 7

Glu Asp Leu Glu Pro Pro Glu Pro Pro Leu Pro Lys Arg Trp Trp Arg
1               5                   10                  15

Arg Arg Arg Trp Arg Arg Trp Trp Arg Arg
            20                  25

<210> SEQ ID NO 8
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: D-amino acid

<400> SEQUENCE: 8

Ala Gly Asp Leu Glu Gln Pro Glu Pro Pro Val Ala Lys Lys Lys Lys
1               5                   10                  15

Lys Asn Arg Arg Trp Trp Arg Arg Trp Arg Arg
            20                  25

<210> SEQ ID NO 9
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(29)
<223> OTHER INFORMATION: D-amino acid

<400> SEQUENCE: 9

Arg Arg Arg Arg Trp Arg Arg Trp Trp Arg Arg Trp Arg Arg Asn Glu
1               5                   10                  15

Lys Pro Leu Pro Pro Glu Pro Pro Glu Leu Asp Glu Thr
            20                  25

<210> SEQ ID NO 10
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(29)
<223> OTHER INFORMATION: D-amino acid

<400> SEQUENCE: 10

Thr Glu Asp Leu Glu Pro Pro Glu Pro Pro Leu Pro Lys Glu Asn Arg
1               5                   10                  15

Arg Arg Arg Trp Arg Arg Trp Trp Arg Arg Trp Arg Arg
            20                  25

<210> SEQ ID NO 11
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: 2-amino-tetradecanoic acid
<220> FEATURE:
<221> NAME/KEY: MOD_RES
<222> LOCATION: (29)..(29)
<223> OTHER INFORMATION: D-amino acid

<400> SEQUENCE: 11

Thr Glu Asp Leu Glu Pro Pro Glu Pro Pro Leu Pro Lys Glu Asn Arg
1               5                   10                  15

Arg Arg Arg Arg Arg Xaa Arg Arg Trp Trp Arg Arg Arg
            20                  25

<210> SEQ ID NO 12
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: D-amino acid
<220> FEATURE:
<221> NAME/KEY: MOD_RES
<222> LOCATION: (7)..(7)
<223> OTHER INFORMATION: 2-amino-tetradecanoic acid
<220> FEATURE:
<221> NAME/KEY: MOD_RES
<222> LOCATION: (8)..(24)
<223> OTHER INFORMATION: D-amino acid
```

```
<400> SEQUENCE: 12

Arg Arg Trp Trp Arg Arg Xaa Arg Arg Arg Arg Lys Pro Leu Pro
1               5                   10                  15

Pro Glu Pro Pro Glu Leu Asp Glu
            20

<210> SEQ ID NO 13
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: D-amino acid
<220> FEATURE:
<221> NAME/KEY: MOD_RES
<222> LOCATION: (3)..(3)
<223> OTHER INFORMATION: 2-amino-tetradecanoic acid
<220> FEATURE:
<221> NAME/KEY: MOD_RES
<222> LOCATION: (4)..(5)
<223> OTHER INFORMATION: D-amino acid
<220> FEATURE:
<221> NAME/KEY: MOD_RES
<222> LOCATION: (6)..(6)
<223> OTHER INFORMATION: 2-amino-tetradecanoic acid
<220> FEATURE:
<221> NAME/KEY: MOD_RES
<222> LOCATION: (7)..(23)
<223> OTHER INFORMATION: D-amino acid

<400> SEQUENCE: 13

Arg Arg Xaa Arg Arg Xaa Arg Arg Arg Arg Lys Pro Leu Pro Pro
1               5                   10                  15

Glu Pro Pro Glu Leu Asp Glu
            20

<210> SEQ ID NO 14
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: D-amino acid
<220> FEATURE:
<221> NAME/KEY: MOD_RES
<222> LOCATION: (3)..(3)
<223> OTHER INFORMATION: 2-amino-tetradecanoic acid
<220> FEATURE:
<221> NAME/KEY: MOD_RES
<222> LOCATION: (4)..(18)
<223> OTHER INFORMATION: D-amino acid

<400> SEQUENCE: 14

Arg Arg Xaa Arg Arg Arg Lys Pro Leu Pro Pro Glu Pro Pro Glu Leu
1               5                   10                  15

Asp Glu

<210> SEQ ID NO 15
<211> LENGTH: 12
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 15

Glu Asp Leu Glu Pro Pro Glu Pro Pro Leu Pro Lys
1               5                   10

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(15)
<223> OTHER INFORMATION: D-amino acid

<400> SEQUENCE: 16

Asn Glu Lys Pro Leu Pro Pro Glu Pro Pro Glu Leu Asp Glu Thr
1               5                   10                  15

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(12)
<223> OTHER INFORMATION: D-amino acid

<400> SEQUENCE: 17

Lys Pro Leu Pro Pro Glu Pro Pro Glu Leu Asp Glu
1               5                   10

<210> SEQ ID NO 18
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Met Cys Thr Glu Asp Leu Glu Pro Pro Glu Pro Pro Leu Pro Lys Glu
1               5                   10                  15

Asn Cys

<210> SEQ ID NO 19
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Met Cys Thr Glu Ala Pro Ala Pro Pro Glu Pro Ala Leu Pro Lys Lys
1               5                   10                  15

Lys Lys Lys Asn Cys
            20

<210> SEQ ID NO 20
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Met Cys Thr Glu Asp Leu Gln Pro Pro Thr Ala Val Pro Gln Glu Asn
1               5                   10                  15

Cys

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Met Cys Thr Glu Ala Pro Ala Pro Pro Glu Pro Ala Leu Pro Lys Lys
1               5                   10                  15

Lys Lys Asn Cys
            20

<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Met Cys Thr Ala Asp Leu Glu Pro Pro Glu Pro Arg Met Glu Lys Lys
1               5                   10                  15

Lys Val Asp Cys
            20

<210> SEQ ID NO 23
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Met Cys Thr Gly Asp Leu Gln Pro Pro Lys Thr Thr Val Ser Lys Lys
1               5                   10                  15

Asp Cys

<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Met Cys Thr Glu Asp Leu Gln Ser Pro Lys Thr Thr Met Thr Lys Glu
1               5                   10                  15

Asn Cys
```

```
<210> SEQ ID NO 25
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Met Cys Thr Glu Asp Leu Glu Pro Pro Glu Pro Pro Leu Pro Lys Glu
1               5                   10                  15

Asp Cys

<210> SEQ ID NO 26
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Met Cys Thr Glu Asp Gln Glu Gln Gln Glu Glu Gln Leu Pro Glu Glu
1               5                   10                  15

Asn Cys

<210> SEQ ID NO 27
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Met Cys Thr Ala Asp Leu Lys Pro Pro Lys Thr Thr Met Thr Lys Gln
1               5                   10                  15

Asn Cys

<210> SEQ ID NO 28
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Met Cys Pro Gly Asp Leu Lys Gln Pro Glu Pro Pro Met Pro Lys Glu
1               5                   10                  15

Tyr Cys

<210> SEQ ID NO 29
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Met Cys Thr Glu Asp Leu Glu Pro Pro Lys Ala Thr Met Thr Lys Lys
1               5                   10                  15
```

Asp Cys

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Met Cys Thr Glu Asp Gln Glu Arg Pro Pro Val Thr Lys Glu Asp Cys
1               5                   10                  15

<210> SEQ ID NO 31
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Met Cys Ile Ala Asp Pro Glu Pro Pro Glu Ala Gln Leu Pro Glu Gly
1               5                   10                  15

Asn Cys

<210> SEQ ID NO 32
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Met Cys Thr Gly Val Gln Glu Pro Pro Glu Ala Thr Leu Pro Lys Lys
1               5                   10                  15

Asn Cys

<210> SEQ ID NO 33
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Met Cys Ser Glu Ala Gln Glu Pro Pro Glu Ser Arg Leu Pro Gln Val
1               5                   10                  15

Asn Cys

<210> SEQ ID NO 34
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Met Cys Thr Lys His Leu Glu Pro Pro Gly Pro Pro Leu Pro Gln Glu
1               5                   10                  15

Asn Cys

```
<210> SEQ ID NO 35
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Met Cys Thr Ala Ala Pro Glu Pro Pro Glu Pro Pro Val Ser Lys Glu
1               5                   10                  15

Tyr Cys

<210> SEQ ID NO 36
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Met Cys Thr Glu Asp Leu Gln Leu Pro Lys Thr Thr Met Thr Lys Glu
1               5                   10                  15

Tyr Cys

<210> SEQ ID NO 37
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Met Cys Ser Val Asp Leu Gln Pro Pro Ala Arg Leu Arg Pro Met Val
1               5                   10                  15

Asn Cys

<210> SEQ ID NO 38
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Met Cys Thr Gly Asp Leu Gln Pro Pro Glu Ser Arg Gln Pro Gln Val
1               5                   10                  15

Asn Cys

<210> SEQ ID NO 39
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Met Cys Thr Gly Asp Leu Gln Pro Pro Glu Ala Gln Val Ile Glu Val
1               5                   10                  15
```

Asn Cys

<210> SEQ ID NO 40
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Met Cys Thr Glu Asp Leu Gln Pro Pro Glu Pro Gln Leu Pro Glu Val
1               5                   10                  15

Asn Cys

<210> SEQ ID NO 41
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Met Cys Thr Glu Asp Met Glu Pro Arg Lys Thr Thr Met Thr Lys Lys
1               5                   10                  15

Tyr Cys

<210> SEQ ID NO 42
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Met Cys Thr Glu Ala Pro Ala Pro Pro Glu Pro Ala Leu Pro Lys Lys
1               5                   10                  15

Lys Lys Lys Lys Asn Cys
            20

<210> SEQ ID NO 43
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Met Cys Thr Glu Ala Pro Ala Pro Pro Glu Pro Ala Leu Pro Lys Lys
1               5                   10                  15

Lys Lys Lys Asn Cys
            20

<210> SEQ ID NO 44
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

```
Met Cys Thr Glu Asp Leu Gln Ser Pro Lys Thr Thr Met Thr Lys Glu
1               5                   10                  15

Asn Cys

<210> SEQ ID NO 45
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Met Cys Thr Gly Asp Leu Lys Leu Pro Glu Pro Pro Met Ser Lys Lys
1               5                   10                  15

Lys Lys Lys Asn Cys
            20

<210> SEQ ID NO 46
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Met Cys Thr Glu Asp Leu Gln Pro Pro Lys Thr Thr Met Ala Glu Lys
1               5                   10                  15

Tyr Cys

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Met Cys Ser Glu Asp Pro Glu Pro Pro Lys Thr Thr Met Thr Lys Lys
1               5                   10                  15

Asn Cys

<210> SEQ ID NO 48
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Met Cys Thr Glu Asp Leu Lys Pro Pro Glu Ala Ser Leu Pro Glu Glu
1               5                   10                  15

Asn Cys

<210> SEQ ID NO 49
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 49

Met Cys Ala Gly Asp Leu Glu Gln Pro Glu Pro Pro Val Ala Lys Lys
1               5                   10                  15

Lys Lys Lys Asn Cys
            20

<210> SEQ ID NO 50
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Met Cys Asn Gly Asp Leu Glu Arg Pro Glu Pro Pro Val Ala Lys Glu
1               5                   10                  15

Tyr Cys

<210> SEQ ID NO 51
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Met Cys Thr Glu Asp Leu Lys Pro Pro Glu Pro Pro Leu Pro Lys Glu
1               5                   10                  15

Asn Cys

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Met Cys Asn Glu Ala Leu Glu Pro Pro Pro Leu Arg Lys Glu His Cys
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Met Cys Pro Glu Asp Leu Glu Arg Pro Pro Leu Thr Lys Glu His Cys
1               5                   10                  15

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

```
Met Cys Thr Glu Asp Leu Glu Pro Pro Glu Arg Pro Leu Pro Arg Glu
1               5                   10                  15

Ile Cys

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Met Cys Ala Gly Asp Leu Lys Pro Pro Glu Thr Thr Met Ser Lys Lys
1               5                   10                  15

Asn Cys

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Met Cys Thr Glu Asp Leu Gln Gln Pro Glu Arg Ser Gln Pro Met Glu
1               5                   10                  15

Ser Cys

<210> SEQ ID NO 57
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Cys Pro Glu Asp Leu Gln Pro Pro Glu Pro Ala Leu Pro Glu Lys
1               5                   10                  15

Lys Lys Lys Lys Ile Val Val Leu Ala Leu Val Val Lys Ser Ala Val
            20                  25                  30

Ser Val Gly Val Val
        35

<210> SEQ ID NO 58
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Cys Thr Glu Val Leu Val Pro Arg Thr Thr Ser Gly Lys Gly Arg
1               5                   10                  15

Leu Trp Phe Trp Leu Trp Ser Gln Lys Gly His Pro Ser Ala Ser Ala
            20                  25                  30

Cys Gly Ser
        35

<210> SEQ ID NO 59
```

```
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Met Cys Ala Glu Asp Leu Gln Pro Pro Leu Leu Glu Ala His Cys
1               5                   10                  15

Gly Ser Asp Ser Gly Arg Lys Lys Arg Arg Gln Cys
            20                  25

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Met Cys Thr Ala Ala Pro Glu Pro Pro Glu Pro Gln Leu Pro Gln Ala
1               5                   10                  15

Asn Cys

<210> SEQ ID NO 61
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Met Cys Pro Ala Asp Leu Gln Gln Pro Glu Thr Ser Leu Pro Glu Glu
1               5                   10                  15

Asn Cys

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Met Cys Ser Val Asp Leu Gln Pro Pro Ala Arg Leu Arg Pro Met Val
1               5                   10                  15

Asn Cys

<210> SEQ ID NO 63
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Met Cys Thr Glu Ala Leu Glu Pro Pro Glu Pro Pro Leu Thr Lys Glu
1               5                   10                  15

Asn Cys
```

<210> SEQ ID NO 64
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Met Cys Thr Glu Ala Met Glu Pro Pro Glu Pro Pro Leu Ala Arg Glu
1               5                   10                  15

Ser Cys

<210> SEQ ID NO 65
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Met Cys Thr Ala Asp Leu Gln Pro Pro Glu Ala Ser Leu Pro Gln Gln
1               5                   10                  15

Asn Cys

<210> SEQ ID NO 66
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Met Cys Thr Ala Ala Pro Glu Pro Pro Glu Pro Arg Leu Pro Glu Gly
1               5                   10                  15

Asn Cys

<210> SEQ ID NO 67
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Met Cys Thr Lys Asp Leu Ala Pro Gln Ala Pro Pro Leu Leu Lys Glu
1               5                   10                  15

Asn Cys

<210> SEQ ID NO 68
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 68

Cys Asn Glu Lys Pro Leu Pro Pro Glu Pro Pro Glu Leu Asp Glu Thr
1               5                   10                  15

Cys Met

<210> SEQ ID NO 69
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(21)
<223> OTHER INFORMATION: D-amino acid

<400> SEQUENCE: 69

Cys Asn Lys Lys Lys Lys Pro Leu Ala Pro Glu Pro Pro Ala Pro
1               5                   10                  15

Ala Glu Thr Cys Met
            20

<210> SEQ ID NO 70
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(17)
<223> OTHER INFORMATION: D-amino acid

<400> SEQUENCE: 70

Cys Asn Glu Gln Pro Val Ala Thr Pro Pro Gln Leu Asp Glu Thr Cys
1               5                   10                  15

Met

<210> SEQ ID NO 71
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(20)
<223> OTHER INFORMATION: D-amino acid

<400> SEQUENCE: 71

Cys Asn Lys Lys Lys Lys Pro Leu Ala Pro Glu Pro Pro Ala Pro Ala
1               5                   10                  15

Glu Thr Cys Met
            20

<210> SEQ ID NO 72
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 72

Cys Asp Lys Lys Ser Val Thr Thr Lys Pro Pro Gln Leu Asp Gly Thr
1               5                   10                  15

Cys Met

<210> SEQ ID NO 73
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 73

Cys Asp Lys Lys Ser Val Thr Thr Lys Pro Pro Gln Leu Asp Gly Thr
1               5                   10                  15

Cys Met

<210> SEQ ID NO 74
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 74

Cys Asn Glu Lys Thr Met Thr Thr Lys Pro Ser Gln Leu Asp Glu Thr
1               5                   10                  15

Cys Met

<210> SEQ ID NO 75
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 75

Cys Asp Glu Lys Pro Leu Pro Pro Glu Pro Pro Glu Leu Asp Glu Thr
1               5                   10                  15

Cys Met

<210> SEQ ID NO 76
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)

<223> OTHER INFORMATION: D-amino acid

<400> SEQUENCE: 76

Cys Asn Glu Glu Pro Leu Gln Glu Glu Leu Leu Glu Leu Asp Glu Thr
1               5                   10                  15

Cys Met

<210> SEQ ID NO 77
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 77

Cys Asn Gln Lys Thr Met Thr Thr Lys Pro Pro Lys Leu Asp Gly Pro
1               5                   10                  15

Cys Met

<210> SEQ ID NO 78
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(17)
<223> OTHER INFORMATION: D-amino acid

<400> SEQUENCE: 78

Cys Tyr Glu Lys Pro Met Pro Pro Glu Pro Gln Leu Asp Gly Pro Cys
1               5                   10                  15

Met

<210> SEQ ID NO 79
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(19)
<223> OTHER INFORMATION: D-amino acid

<400> SEQUENCE: 79

Cys Asp Glu Lys Lys Thr Met Thr Ala Lys Pro Pro Glu Leu Asp Glu
1               5                   10                  15

Thr Cys Met

<210> SEQ ID NO 80
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (1)..(16)
<223> OTHER INFORMATION: D-amino acid

<400> SEQUENCE: 80

Cys Asp Glu Lys Thr Val Pro Pro Arg Glu Gln Asp Glu Thr Cys Met
1               5                   10                  15

<210> SEQ ID NO 81
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 81

Cys Asn Gly Glu Pro Leu Gln Ala Glu Pro Pro Glu Pro Asp Ala Ile
1               5                   10                  15

Cys Met

<210> SEQ ID NO 82
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 82

Cys Asn Lys Lys Pro Leu Thr Ala Glu Pro Pro Glu Gln Val Gly Thr
1               5                   10                  15

Cys Met

<210> SEQ ID NO 83
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 83

Cys Asn Val Gln Pro Leu Pro Pro Gly Pro Pro Glu Leu His Lys Thr
1               5                   10                  15

Cys Met

<210> SEQ ID NO 84
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
```

<223> OTHER INFORMATION: D-amino acid

<400> SEQUENCE: 84

Cys Asn Glu Gln Pro Leu Pro Pro Gly Pro Pro Glu Pro Ala Ala Thr
1               5                   10                  15

Cys Met

<210> SEQ ID NO 85
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 85

Cys Tyr Glu Lys Ser Val Pro Pro Glu Pro Pro Glu Pro Ala Ala Thr
1               5                   10                  15

Cys Met

<210> SEQ ID NO 86
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 86

Cys Tyr Glu Lys Thr Met Thr Thr Lys Pro Leu Gln Leu Asp Glu Thr
1               5                   10                  15

Cys Met

<210> SEQ ID NO 87
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 87

Cys Asn Val Met Pro Arg Leu Arg Ala Pro Pro Gln Leu Asp Val Ser
1               5                   10                  15

Cys Met

<210> SEQ ID NO 88
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (1)..(18)
<223> OTHER INFORMATION: D-amino acid

<400> SEQUENCE: 88

Cys Asn Val Gln Pro Gln Arg Ser Glu Pro Pro Gln Leu Asp Gly Thr
1               5                   10                  15

Cys Met

<210> SEQ ID NO 89
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 89

Cys Asn Val Glu Ile Val Gln Ala Glu Pro Pro Gln Leu Asp Gly Thr
1               5                   10                  15

Cys Met

<210> SEQ ID NO 90
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 90

Cys Asn Val Glu Pro Leu Gln Pro Glu Pro Pro Gln Leu Asp Glu Thr
1               5                   10                  15

Cys Met

<210> SEQ ID NO 91
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 91

Cys Tyr Lys Lys Thr Met Thr Thr Lys Pro Pro Glu Met Asp Glu Thr
1               5                   10                  15

Cys Met

<210> SEQ ID NO 92
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(23)
<223> OTHER INFORMATION: D-amino acid

<400> SEQUENCE: 92

Cys Asn Lys Lys Lys Lys Lys Pro Lys Leu Ala Pro Glu Pro Pro
1               5                   10                  15

Ala Pro Ala Glu Thr Cys Met
            20

<210> SEQ ID NO 93
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(21)
<223> OTHER INFORMATION: D-amino acid

<400> SEQUENCE: 93

Cys Asn Lys Lys Lys Lys Lys Pro Leu Ala Pro Glu Pro Pro Ala Pro
1               5                   10                  15

Ala Glu Thr Cys Met
            20

<210> SEQ ID NO 94
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 94

Cys Asn Glu Lys Thr Met Thr Thr Lys Pro Ser Gln Leu Asp Glu Thr
1               5                   10                  15

Cys Met

<210> SEQ ID NO 95
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(22)
<223> OTHER INFORMATION: D-amino acid

<400> SEQUENCE: 95

Cys Asn Lys Lys Lys Lys Lys Ser Met Pro Pro Glu Pro Pro Leu Lys
1               5                   10                  15

Leu Asp Gly Thr Cys Met
            20

<210> SEQ ID NO 96
<211> LENGTH: 18
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 96

Cys Tyr Lys Glu Ala Met Thr Thr Lys Pro Pro Gln Leu Asp Glu Thr
1               5                   10                  15

Cys Met

<210> SEQ ID NO 97
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 97

Cys Asn Lys Lys Thr Met Thr Thr Lys Pro Pro Glu Pro Asp Glu Ser
1               5                   10                  15

Cys Met

<210> SEQ ID NO 98
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 98

Cys Asn Glu Glu Pro Leu Ser Ala Glu Pro Pro Lys Leu Asp Glu Thr
1               5                   10                  15

Cys Met

<210> SEQ ID NO 99
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(21)
<223> OTHER INFORMATION: D-amino acid

<400> SEQUENCE: 99

Cys Asn Lys Lys Lys Lys Lys Ala Val Pro Pro Glu Pro Gln Glu Leu
1               5                   10                  15

Asp Gly Ala Cys Met
            20

<210> SEQ ID NO 100
<211> LENGTH: 18
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 100

Cys Tyr Glu Lys Ala Val Pro Pro Glu Pro Arg Glu Leu Asp Gly Asn
1               5                   10                  15

Cys Met

<210> SEQ ID NO 101
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 101

Cys Asn Glu Lys Pro Leu Pro Pro Glu Pro Lys Leu Asp Glu Thr
1               5                   10                  15

Cys Met

<210> SEQ ID NO 102
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(16)
<223> OTHER INFORMATION: D-amino acid

<400> SEQUENCE: 102

Cys His Glu Lys Arg Leu Pro Pro Glu Leu Ala Glu Asn Cys Met
1               5                   10                  15

<210> SEQ ID NO 103
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(16)
<223> OTHER INFORMATION: D-amino acid

<400> SEQUENCE: 103

Cys His Glu Lys Thr Leu Pro Pro Arg Glu Leu Asp Glu Pro Cys Met
1               5                   10                  15

<210> SEQ ID NO 104
<211> LENGTH: 18
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 104

Cys Ile Glu Arg Pro Leu Pro Arg Glu Pro Pro Glu Leu Asp Glu Thr
1               5                   10                  15

Cys Met

<210> SEQ ID NO 105
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 105

Cys Asn Lys Lys Ser Met Thr Thr Glu Pro Pro Lys Leu Asp Gly Ala
1               5                   10                  15

Cys Met

<210> SEQ ID NO 106
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 106

Cys Ser Met Pro Gln Ser Arg Glu Pro Gln Gln Leu Glu Asp Glu Thr
1               5                   10                  15

Cys Met

<210> SEQ ID NO 107
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(38)
<223> OTHER INFORMATION: D-amino acid

<400> SEQUENCE: 107

Cys Val Val Gly Val Ser Val Ala Ser Lys Val Val Leu Ala Leu Val
1               5                   10                  15

Val Ile Lys Lys Lys Lys Glu Pro Leu Ala Pro Glu Pro Pro Gln
                20                  25                  30

Leu Asp Glu Pro Cys Met
            35
```

```
<210> SEQ ID NO 108
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(36)
<223> OTHER INFORMATION: D-amino acid

<400> SEQUENCE: 108

Cys Ser Gly Cys Ala Ser Ala Ser Pro His Gly Lys Gln Ser Trp Leu
1               5                   10                  15

Trp Phe Trp Leu Arg Gly Lys Gly Ser Thr Thr Arg Pro Val Leu Val
            20                  25                  30

Glu Thr Cys Met
        35

<210> SEQ ID NO 109
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(28)
<223> OTHER INFORMATION: D-amino acid

<400> SEQUENCE: 109

Cys Gln Arg Arg Lys Lys Arg Gly Ser Asp Ser Gly Cys His Ala Glu
1               5                   10                  15

Leu Leu Pro Pro Pro Gln Leu Asp Glu Ala Cys Met
            20                  25

<210> SEQ ID NO 110
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 110

Cys Asn Ala Gln Pro Leu Gln Pro Glu Pro Pro Glu Pro Ala Ala Thr
1               5                   10                  15

Cys Met

<210> SEQ ID NO 111
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 111
```

```
Cys Asn Glu Glu Pro Leu Ser Thr Glu Pro Gln Gln Leu Asp Ala Pro
1               5                   10                  15

Cys Met

<210> SEQ ID NO 112
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 112

Cys Asn Val Met Pro Arg Leu Arg Ala Pro Pro Gln Leu Asp Val Ser
1               5                   10                  15

Cys Met

<210> SEQ ID NO 113
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 113

Cys Asn Glu Lys Thr Leu Pro Pro Glu Pro Pro Glu Leu Ala Glu Thr
1               5                   10                  15

Cys Met

<210> SEQ ID NO 114
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 114

Cys Ser Glu Arg Ala Leu Pro Pro Glu Pro Pro Glu Met Ala Glu Thr
1               5                   10                  15

Cys Met

<210> SEQ ID NO 115
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 115
```

```
Cys Asn Gln Gln Pro Leu Ser Ala Glu Pro Pro Gln Leu Asp Ala Thr
1               5                   10                  15

Cys Met
```

<210> SEQ ID NO 116
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 116

```
Cys Asn Gly Glu Pro Leu Arg Pro Glu Pro Pro Glu Pro Ala Ala Thr
1               5                   10                  15

Cys Met
```

<210> SEQ ID NO 117
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 117

```
Cys Asn Glu Lys Leu Leu Pro Pro Ala Gln Pro Ala Leu Asp Lys Thr
1               5                   10                  15

Cys Met
```

<210> SEQ ID NO 118
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

```
Gly Arg Lys Lys Arg Arg Gln Arg Arg Arg
1               5                   10
```

<210> SEQ ID NO 119
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

```
Gly Asp Ile Met Gly Glu Trp Gly Asn Glu Ile Phe Gly Ala Ile Ala
1               5                   10                  15

Gly Phe Leu Gly Tyr Gly Arg Lys Lys Arg Arg Gln Arg Arg Arg
                20                  25                  30
```

<210> SEQ ID NO 120

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Arg Arg Arg Arg Arg Arg Arg Arg
1               5

<210> SEQ ID NO 121
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Lys Lys Lys Lys Lys Lys Lys Lys
1               5

<210> SEQ ID NO 122
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Asp Ile Met Gly Glu Trp Gly Asn Glu Ile Phe Gly Ala Ile Ala Gly
1               5                   10                  15

Phe Leu Gly

<210> SEQ ID NO 123
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Cys His His His His His Arg Lys Lys Arg Arg Gln Arg Arg Arg Arg
1               5                   10                  15

His His His His His Cys
            20

<210> SEQ ID NO 124
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Cys His His His His His Arg Arg Arg Arg Arg Arg Arg Arg His
1               5                   10                  15

His His His His Cys
            20

<210> SEQ ID NO 125
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Phe Phe Leu Ile Pro Lys Gly Arg Arg Arg Arg Arg Arg Arg Gly
1               5                   10                  15

Cys

<210> SEQ ID NO 126
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: L-2-naphthylalanine

<400> SEQUENCE: 126

Phe Xaa Arg Arg Arg Arg
1               5

<210> SEQ ID NO 127
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: D-amino acid

<400> SEQUENCE: 127

Arg Arg Trp Trp Arg Arg Trp Arg Arg Arg Arg Trp Trp Arg Arg
1               5                   10                  15

<210> SEQ ID NO 128
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: D-amino acid

<400> SEQUENCE: 128

Arg Trp Trp Arg Arg Arg Arg Trp Arg Arg Trp Trp Arg Arg
1               5                   10

<210> SEQ ID NO 129
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: D-amino acid
```

```
<400> SEQUENCE: 129

Arg Arg Trp Trp Arg Arg Trp Arg Arg Arg Trp Trp Arg
1               5                   10

<210> SEQ ID NO 130
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: D-amino acid

<400> SEQUENCE: 130

Arg Arg Trp Trp Arg Arg Trp Arg Arg Arg Arg
1               5                   10

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: D-amino acid

<400> SEQUENCE: 131

Arg Arg Trp Trp Arg Arg Trp Arg Arg
1               5

<210> SEQ ID NO 132
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Arg Arg Trp Trp Arg Arg Trp Arg Arg Arg
1               5                   10

<210> SEQ ID NO 133
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: 2-amino-tetradecanoic acid
<220> FEATURE:
<221> NAME/KEY: MOD_RES
<222> LOCATION: (14)..(14)
<223> OTHER INFORMATION: D-amino acid

<400> SEQUENCE: 133

Arg Arg Arg Arg Arg Arg Xaa Arg Arg Trp Trp Arg Arg Arg
1               5                   10
```

```
<210> SEQ ID NO 134
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Tyr Ala Leu Thr Ser Ala Ile Ser Arg Ile Ile Thr His His His His
1               5                   10                  15

His His

<210> SEQ ID NO 135
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 2-amino-tetradecanoic acid

<400> SEQUENCE: 135

Arg Arg Arg Arg Arg Xaa Arg Arg Trp Trp Arg Arg
1               5                   10

<210> SEQ ID NO 136
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 2-amino-tetradecanoic acid
<220> FEATURE:
<221> NAME/KEY: MOD_RES
<222> LOCATION: (6)..(6)
<223> OTHER INFORMATION: 2-amino-tetradecanoic acid

<400> SEQUENCE: 136

Arg Arg Xaa Arg Arg Xaa Arg Arg Arg Arg Arg
1               5                   10

<210> SEQ ID NO 137
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 2-amino-tetradecanoic acid

<400> SEQUENCE: 137

Arg Arg Xaa Arg Arg Arg
1               5

<210> SEQ ID NO 138
<211> LENGTH: 2
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 138

Gly Ser
1

<210> SEQ ID NO 139
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gly Ser Gly Ser
1

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(10)
<223> OTHER INFORMATION: D-amino acid

<400> SEQUENCE: 140

Arg Arg Arg Gln Arg Arg Lys Lys Arg Gly
1               5                   10

<210> SEQ ID NO 141
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(33)
<223> OTHER INFORMATION: D-amino acid

<400> SEQUENCE: 141

Arg Arg Arg Gln Arg Arg Lys Lys Arg Gly Tyr Gly Leu Phe Gly Ala
1               5                   10                  15

Ile Ala Gly Phe Ile Glu Asn Gly Trp Glu Gly Met Gly Met Ile Asp
            20                  25                  30

Gly

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(8)
<223> OTHER INFORMATION: D-amino acid

<400> SEQUENCE: 142

Arg Arg Arg Arg Arg Arg Arg Arg

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(8)
<223> OTHER INFORMATION: D-amino acid

<400> SEQUENCE: 143

Lys Lys Lys Lys Lys Lys Lys Lys
1               5

<210> SEQ ID NO 144
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(19)
<223> OTHER INFORMATION: D-amino acid

<400> SEQUENCE: 144

Gly Leu Phe Gly Ala Ile Ala Gly Phe Ile Glu Asn Gly Trp Glu Gly
1               5                   10                  15

Met Ile Asp

<210> SEQ ID NO 145
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(22)
<223> OTHER INFORMATION: D-amino acid

<400> SEQUENCE: 145

Cys His His His His His Arg Arg Arg Arg Gln Arg Arg Lys Lys Arg
1               5                   10                  15

His His His His His Cys
            20

<210> SEQ ID NO 146
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(21)
<223> OTHER INFORMATION: D-amino acid

<400> SEQUENCE: 146

Cys His His His His His Arg Arg Arg Arg Arg Arg Arg Arg His
1               5                   10                  15

-continued

His His His His Cys
            20

<210> SEQ ID NO 147
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 147

Cys Gly Arg Arg Arg Arg Arg Arg Arg Gly Lys Pro Ile Leu Phe
1               5                   10                  15

Phe Cys

<210> SEQ ID NO 148
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: D-amino acid
<220> FEATURE:
<221> NAME/KEY: MOD_RES
<222> LOCATION: (5)..(5)
<223> OTHER INFORMATION: L-2-naphthylalanine
<220> FEATURE:
<221> NAME/KEY: MOD_RES
<222> LOCATION: (6)..(6)
<223> OTHER INFORMATION: D-amino acid

<400> SEQUENCE: 148

Arg Arg Arg Arg Xaa Phe
1               5

<210> SEQ ID NO 149
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(15)
<223> OTHER INFORMATION: D-amino acid

<400> SEQUENCE: 149

Arg Arg Trp Trp Arg Arg Arg Arg Trp Arg Arg Trp Trp Arg Arg
1               5                   10                  15

<210> SEQ ID NO 150
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(14)
<223> OTHER INFORMATION: D-amino acid

<400> SEQUENCE: 150

Arg Arg Trp Trp Arg Arg Trp Arg Arg Arg Trp Trp Arg
1               5                   10

<210> SEQ ID NO 151
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(14)
<223> OTHER INFORMATION: D-amino acid

<400> SEQUENCE: 151

Arg Trp Trp Arg Arg Arg Arg Trp Arg Arg Trp Trp Arg Arg
1               5                   10

<210> SEQ ID NO 152
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(11)
<223> OTHER INFORMATION: D-amino acid

<400> SEQUENCE: 152

Arg Arg Arg Arg Trp Arg Arg Trp Trp Arg Arg
1               5                   10

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(9)
<223> OTHER INFORMATION: D-amino acid

<400> SEQUENCE: 153

Arg Arg Trp Arg Arg Trp Trp Arg Arg
1               5

<210> SEQ ID NO 154
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(10)
<223> OTHER INFORMATION: D-amino acid

<400> SEQUENCE: 154

Arg Arg Arg Trp Arg Arg Trp Trp Arg Arg
1               5                   10

```
<210> SEQ ID NO 155
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(7)
<223> OTHER INFORMATION: D-amino acid
<220> FEATURE:
<221> NAME/KEY: MOD_RES
<222> LOCATION: (8)..(8)
<223> OTHER INFORMATION: 2-amino-tetradecanoic acid
<220> FEATURE:
<221> NAME/KEY: MOD_RES
<222> LOCATION: (9)..(14)
<223> OTHER INFORMATION: D-amino acid

<400> SEQUENCE: 155

Arg Arg Arg Trp Trp Arg Arg Xaa Arg Arg Arg Arg Arg Arg
1               5                  10

<210> SEQ ID NO 156
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 156

His His His His His His Thr Ile Ile Arg Ser Ile Ala Ser Thr Leu
1               5                  10                  15

Ala Tyr

<210> SEQ ID NO 157
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: D-amino acid
<220> FEATURE:
<221> NAME/KEY: MOD_RES
<222> LOCATION: (7)..(7)
<223> OTHER INFORMATION: 2-amino-tetradecanoic acid
<220> FEATURE:
<221> NAME/KEY: MOD_RES
<222> LOCATION: (8)..(12)
<223> OTHER INFORMATION: D-amino acid

<400> SEQUENCE: 157

Arg Arg Trp Trp Arg Arg Xaa Arg Arg Arg Arg Arg
1               5                  10

<210> SEQ ID NO 158
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(2)
<223> OTHER INFORMATION: D-amino acid
<220> FEATURE:
<221> NAME/KEY: MOD_RES
<222> LOCATION: (3)..(3)
<223> OTHER INFORMATION: 2-amino-tetradecanoic acid
<220> FEATURE:
<221> NAME/KEY: MOD_RES
<222> LOCATION: (4)..(5)
<223> OTHER INFORMATION: D-amino acid
<220> FEATURE:
<221> NAME/KEY: MOD_RES
<222> LOCATION: (6)..(6)
<223> OTHER INFORMATION: 2-amino-tetradecanoic acid
<220> FEATURE:
<221> NAME/KEY: MOD_RES
<222> LOCATION: (7)..(11)
<223> OTHER INFORMATION: D-amino acid

<400> SEQUENCE: 158

Arg Arg Xaa Arg Arg Xaa Arg Arg Arg Arg
1               5                   10

<210> SEQ ID NO 159
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: D-amino acid
<220> FEATURE:
<221> NAME/KEY: MOD_RES
<222> LOCATION: (3)..(3)
<223> OTHER INFORMATION: 2-amino-tetradecanoic acid
<220> FEATURE:
<221> NAME/KEY: MOD_RES
<222> LOCATION: (4)..(6)
<223> OTHER INFORMATION: D-amino acid

<400> SEQUENCE: 159

Arg Arg Xaa Arg Arg Arg
1               5

<210> SEQ ID NO 160
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: D-amino acid

<400> SEQUENCE: 160

Ser Gly
1

<210> SEQ ID NO 161
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(4)
<223> OTHER INFORMATION: D-amino acid

<400> SEQUENCE: 161

Ser Gly Ser Gly
1

<210> SEQ ID NO 162
<211> LENGTH: 816
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 162
atggatagta gtgcggtgat cacacaaatc tccaaggagg aagcccgtgg gccgctgcgg    60
gggaagggtg atcaaaaatc ggcagctagt caaaaacctc gctctcgtgg gatacttcat   120
tcgctgtttt gctgcgtctg ccgcgatgac ggagaagcat tgcctgcgca ttcaggggcg   180
cctttacttg ttgaggaaaa tggtgcaatt cctaaacaaa ctccagtaca atacttactg   240
ccggaggcaa aggcacaaga cagtgataag atatgtgtag taatagactt agatgaaaca   300
ctggtacatt cgtcattcaa acctgttaat aatgcggatt tcatcatacc tgtagaaatc   360 gacgggggttg tccatcaggt ttacgtcctg aagcggcctc atgtagatga ttttttacag   420
cggatgggcg agttatttga atgtgtgctg tttacagcta gtcttgccaa gtacgcggat   480
cctgtcgcgg atttgcttga taagtggggt gcgtttcggg cgagattatt tcgcgaatct   540
tgcgtttttc acagaggtaa ctacgtgaag gaccttagtc gtctgggtag agatcttaga   600
agagtgctga tccttgacaa cagcccagcc agctatgtct ttcatccgga taacgcagta   660
cccgtggcgt cttggttcga caatatgtcg gacacggagc tgcatgacct gttgccgttc   720
tttgagcagt tgagtcgcgt tgatgacgtt tactcggttt tgcgtcaacc ccgtccggga   780
tctggttctg gctctcacca tcaccatcac cactag                              816

<210> SEQ ID NO 163
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Met Asp Ser Ser Ala Val Ile Thr Gln Ile Ser Lys Glu Glu Ala Arg
1               5                   10                  15

Gly Pro Leu Arg Gly Lys Gly Asp Gln Lys Ser Ala Ala Ser Gln Lys
            20                  25                  30

Pro Arg Ser Arg Gly Ile Leu His Ser Leu Phe Cys Cys Val Cys Arg
        35                  40                  45

Asp Asp Gly Glu Ala Leu Pro Ala His Ser Gly Ala Pro Leu Leu Val
    50                  55                  60

Glu Glu Asn Gly Ala Ile Pro Lys Gln Thr Pro Val Gln Tyr Leu Leu
65                  70                  75                  80

Pro Glu Ala Lys Ala Gln Asp Ser Asp Lys Ile Cys Val Val Ile Asp
                85                  90                  95

Leu Asp Glu Thr Leu Val His Ser Ser Phe Lys Pro Val Asn Asn Ala
            100                 105                 110
```

Asp Phe Ile Ile Pro Val Glu Ile Asp Gly Val Val His Gln Val Tyr
            115                 120                 125

Val Leu Lys Arg Pro His Val Asp Glu Phe Leu Gln Arg Met Gly Glu
        130                 135                 140

Leu Phe Glu Cys Val Leu Phe Thr Ala Ser Leu Ala Lys Tyr Ala Asp
145                 150                 155                 160

Pro Val Ala Asp Leu Leu Asp Lys Trp Gly Ala Phe Arg Ala Arg Leu
                165                 170                 175

Phe Arg Glu Ser Cys Val Phe His Arg Gly Asn Tyr Val Lys Asp Leu
            180                 185                 190

Ser Arg Leu Gly Arg Asp Leu Arg Val Leu Ile Leu Asp Asn Ser
        195                 200                 205

Pro Ala Ser Tyr Val Phe His Pro Asn Ala Val Pro Val Ala Ser
    210                 215                 220

Trp Phe Asp Asn Met Ser Asp Thr Glu Leu His Asp Leu Leu Pro Phe
225                 230                 235                 240

Phe Glu Gln Leu Ser Arg Val Asp Asp Val Tyr Ser Val Leu Arg Gln
                245                 250                 255

Pro Arg Pro Gly Ser Gly Ser Gly Ser His His His His His His
                260                 265                 270

<210> SEQ ID NO 164
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 164
atgtgtaccg aagatctgga accaccagaa ccaccactgc aaaggaaaaa ttgtggatcc      60
ggttctggct caggttcttc ccctatacta ggttattgga aaattaaggg ccttgtgcaa     120
cccactcgac ttcttttgga atatcttgaa gaaaaatatg aagagcattt gtatgagcgc     180
gatgaaggtg ataaatggcg aaacaaaaag tttgaattgg gtttggagtt tcccaatctt     240
ccttattata ttgatggtga tgttaaatta acacagtcta tggccatcat acgttatata     300
gctgacaagc acaacatgtt gggtggttgt ccaaaagagc gtgcagagat tcaatgcttt     360
gaaggagcgg ttttggatat tagatacggt gtttcgagaa ttgcatatag taaagacttt     420
gaaactctca agttgatttt cttagcaag ctacctgaaa tgctgaaaat gttcgaagat     480
cgtttatgtc ataaaacata tttaaatggt gatcatgtaa cccatcctga cttcatgttg     540
tatgacgctc ttgatgttgt tttatacatg gacccaatgt gcctggatgc gttcccaaaa     600
ttagtttgtt ttaaaaacg tattgaagct atcccacaa ttgataagta cttgaaatcc     660
agcaagtata tagcatggcc tttgcagggc tggcaagcca cgtttggtgg tggcgaccat     720
cctccaaaat aa                                                         732

<210> SEQ ID NO 165
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

```
Met Cys Thr Glu Asp Leu Glu Pro Pro Glu Pro Pro Leu Pro Lys Glu
1               5                   10                  15

Asn Cys Gly Ser Gly Ser Gly Ser Gly Ser Ser Pro Ile Leu Gly Tyr
            20                  25                  30

Trp Lys Ile Lys Gly Leu Val Gln Pro Thr Arg Leu Leu Leu Glu Tyr
        35                  40                  45

Leu Glu Glu Lys Tyr Glu Glu His Leu Tyr Glu Arg Asp Glu Gly Asp
    50                  55                  60

Lys Trp Arg Asn Lys Lys Phe Glu Leu Gly Leu Glu Phe Pro Asn Leu
65                  70                  75                  80

Pro Tyr Tyr Ile Asp Gly Asp Val Lys Leu Thr Gln Ser Met Ala Ile
                85                  90                  95

Ile Arg Tyr Ile Ala Asp Lys His Asn Met Leu Gly Gly Cys Pro Lys
            100                 105                 110

Glu Arg Ala Glu Ile Ser Met Leu Glu Gly Ala Val Leu Asp Ile Arg
        115                 120                 125

Tyr Gly Val Ser Arg Ile Ala Tyr Ser Lys Asp Phe Glu Thr Leu Lys
    130                 135                 140

Val Asp Phe Leu Ser Lys Leu Pro Glu Met Leu Lys Met Phe Glu Asp
145                 150                 155                 160

Arg Leu Cys His Lys Thr Tyr Leu Asn Gly Asp His Val Thr His Pro
                165                 170                 175

Asp Phe Met Leu Tyr Asp Ala Leu Asp Val Val Leu Tyr Met Asp Pro
            180                 185                 190

Met Cys Leu Asp Ala Phe Pro Lys Leu Val Cys Phe Lys Lys Arg Ile
        195                 200                 205

Glu Ala Ile Pro Gln Ile Asp Lys Tyr Leu Lys Ser Ser Lys Tyr Ile
    210                 215                 220

Ala Trp Pro Leu Gln Gly Trp Gln Ala Thr Phe Gly Gly Gly Asp His
225                 230                 235                 240

Pro Pro Lys

<210> SEQ ID NO 166
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
aataaagctt atgtgtaccg aagatctgga accaccagaa ccaccactgc caa          53

<210> SEQ ID NO 167
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
aataggatcc acaatttttcc tttggcagtg gtggttctgg tggttcca                48

<210> SEQ ID NO 168
<211> LENGTH: 55
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 168
aataaagctt atgtgtaccg aagctccggc accaccagaa ccagcactgc caaag          55

<210> SEQ ID NO 169
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
aataggatcc acaattttt tttttttct ttggcagtgc tggttctggt ggtgc            55

<210> SEQ ID NO 170
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
aataaagctt atgtgtaccg aagatctgca accaccaaca gcagtgccac                50

<210> SEQ ID NO 171
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
aataggatcc acaattttcc tgtggcactg ctgttggtgg ttgcagatct tc             52

<210> SEQ ID NO 172
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
aataaagctt atgtgtaccg aagctccggc accaccagaa ccagcactgc caaag          55

<210> SEQ ID NO 173
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
aataggatcc acaattttt ttttctttg gcagtgctgg ttctggtggt gc               52

<210> SEQ ID NO 174
<211> LENGTH: 42
<212> TYPE: DNA
<213> ORGANISM: Artificial Sequence
<220> FEATURE:
<223> OTHER INFORMATION: Description of Artificial Sequence: Synthetic
```

```
                                    primer

<400> SEQUENCE: 174
atgtgtaccg cagatctgga accaccagaa ccacgaatgg aa                       42

<210> SEQ ID NO 175
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
aataggatcc acaatctacc tttttttttt ccattcgtgg ttctggtggt tcca          54

<210> SEQ ID NO 176
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
aataaagctt atgtgtaccg gagatctgca accaccaaaa acaacagtgt caa           53

<210> SEQ ID NO 177
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
aataggatcc acaatctttc tttgacactg ttgtttttgg tggttgcaga              50

<210> SEQ ID NO 178
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
aataaagctt atgtgtaccg aagatctgca atcaccaaaa acaacaatga caa           53

<210> SEQ ID NO 179
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
aataggatcc acaattttcc tttgtcattg ttgttttttgg tgattgcaga             50

<210> SEQ ID NO 180
<211> LENGTH: 53
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 180
aataaagctt atgtgtaccg aagatctgga accaccagaa ccaccactgc caa    53

<210> SEQ ID NO 181
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
aataggatcc cacaatcttc ctttggcagt ggtggttctg gtggttccag a    51

<210> SEQ ID NO 182
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
aataaagctt atgtgtaccg aagatcagga acaacaagaa gaacaactg    49

<210> SEQ ID NO 183
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
aataggatcc acaattttcc tctggcagtt gttcttcttg ttgttcctga tc    52

<210> SEQ ID NO 184
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
aataaagctt atgtgtaccg cagatctgaa accaccaaaa acaacaatga caa    53

<210> SEQ ID NO 185
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
aataggatcc acaattttgc tttgtcattg ttgttttttgg tggtttcaga    50

<210> SEQ ID NO 186
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 186
aataaagctt atgtgtcccg gagatctgaa acaaccagaa ccaccaatgc caa         53

<210> SEQ ID NO 187
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
aataggatcc acaatattcc tttggcattg gtggttctgg ttgtttcaga             50

<210> SEQ ID NO 188
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
aataaagctt atgtgtaccg aagatctgga accaccaaaa gcaacaatga caa         53

<210> SEQ ID NO 189
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
aataggatcc acaatctttc tttgtcattg ttgcttttgg tggttccaga             50

<210> SEQ ID NO 190
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
aataaagctt atgtgtaccg aagatcagga acgaccacca gtgacaaag              49

<210> SEQ ID NO 191
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
aataggatcc acaatcttcc tttgtcactg gtggtcgttc ctgatcttc              49

<210> SEQ ID NO 192
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
```

```
aataaagctt atgtgtatcg cagatccgga accaccagaa gcacaactg          49
```

<210> SEQ ID NO 193
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193

```
aataggatcc acaatttccc tctggcagtt gtgcttctgg tggttccgga tctg    54
```

<210> SEQ ID NO 194
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194

```
aataaagctt atgtgtaccg gagttcagga accaccagaa gcaacactg          49
```

<210> SEQ ID NO 195
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195

```
aataggatcc acaattttc tttggcagtg ttgcttctgg tggttcctga ac       52
```

<210> SEQ ID NO 196
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196

```
aataaagctt atgtgtagcg aagctcagga accaccagaa tcacgactg          49
```

<210> SEQ ID NO 197
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197

```
aataggatcc acaatttacc tgtggcagtc gtgattctgg tggttcctga g       51
```

<210> SEQ ID NO 198
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
aataaagctt atgtgtacca aacatctgga accaccagga ccaccattgc        50

<210> SEQ ID NO 199
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
aataggatcc acaattttcc tgtggcaatg gtggtcctgg tggttccaga tg        52

<210> SEQ ID NO 200
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
aataaagctt atgtgtaccg cagctccgga accaccagaa ccaccagtgt        50

<210> SEQ ID NO 201
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
aataggatcc acaatattcc tttgacactg gtggttctgg tggttccgga g        51

<210> SEQ ID NO 202
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
aataaagctt atgtgtaccg aagatctgca actaccaaaa acaacaatga ca        52

<210> SEQ ID NO 203
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
aataggatcc acaatattcc tttgtcattg ttgttttttgg tagttgcaga        50

<210> SEQ ID NO 204
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
aataaagctt atgtgttccg tagatctgca accaccagca cgactacggc caa        53

<210> SEQ ID NO 205
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
aataggatcc acaatttacc attggccgta gtcgtgctgg tggttgcaga t          51

<210> SEQ ID NO 206
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
aataaagctt atgtgtaccg gagatctgca accaccagaa tcacgacagc ca         52

<210> SEQ ID NO 207
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
aataggatcc acaatttacc tgtggctgtc gtgattctgg tggttgcaga t          51

<210> SEQ ID NO 208
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
aataaagctt atgtgtaccg gagatctgca accaccagaa gcacaagtga            50

<210> SEQ ID NO 209
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
aataggatcc acaatttacc tctatcactt gtgcttctgg tggttgcaga t          51

<210> SEQ ID NO 210
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
aataaagctt atgtgtaccg aagatctgca accaccagaa ccacaactgc ca         52

<210> SEQ ID NO 211
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211 ataggatcc acaatttacc tctggcagtt gtggttctgg tggttgcaga t        51

<210> SEQ ID NO 212
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
aataaagctt atgtgtaccg aagatatgga accacgaaaa acaacaatga           50

<210> SEQ ID NO 213
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
aataggatcc acaatatttc tttgtcattg ttgttttcg tggttccata t          51

<210> SEQ ID NO 214
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
aataaagctt atgtgtaccg aagctccggc accaccagaa ccagcactgc caaag     55

<210> SEQ ID NO 215
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
aataggatcc acaatttttt tttttttttt tctttggcag tgctggttct ggtggt    56

<210> SEQ ID NO 216
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
aataaagctt atgtgtaccg aagctccggc accaccagaa ccagcactgc caaag     55

```
<210> SEQ ID NO 217
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
aataggatcc acaatttttt ttttttttct ttggcagtgc tggttctggt ggtg            54

<210> SEQ ID NO 218
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
aataaagctt atgtgtaccg aagatctgca atcaccaaaa acaacaatg                 49

<210> SEQ ID NO 219
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
aataggatcc acaattttcc tttgtcattg ttgttttggg tgattgcaga                50

<210> SEQ ID NO 220
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
aataaagctt atgtgtaccg gagatctgaa actaccagaa ccaccaatgt caaag          55

<210> SEQ ID NO 221
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
aataggatcc acaatttttt ttttttttct ttgacattgg tggttctggt ag             52

<210> SEQ ID NO 222
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
aataaagctt atgtgtaccg aagatctgca accaccaaaa acaacaatg                 49

<210> SEQ ID NO 223
```

<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 223
aataggatcc acaatatttc tctgccattg ttgtttttgg tggttgcaga t        51

<210> SEQ ID NO 224
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 224
aataaagctt atgtgtagcg aagatccgga accaccaaaa acaacaatga c        51

<210> SEQ ID NO 225
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 225
aataggatcc acaattttc tttgtcattg ttgtttttgg tggttccgga t        51

<210> SEQ ID NO 226
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 226
aataaagctt atgtgtaccg aagatctgaa accaccagaa gcatcactgc          50

<210> SEQ ID NO 227
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 227
aataggatcc acaattttcc tctggcagtg atgcttctgg tggtttcaga t        51

<210> SEQ ID NO 228
<211> LENGTH: 54
<212> TYPE: DNA
<213> ORGANISM: Artificial Sequence
<220> FEATURE:
<223> OTHER INFORMATION: Description of Artificial Sequence: Synthetic primer

<400> SEQUENCE: 228
aataaagctt atgtgtgccg gagatctgga acaaccagaa ccaccagtgg caaa     54

<210> SEQ ID NO 229
<211> LENGTH: 55

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
aataggatcc acaatttttt ttttttttct tgccactgg tggttctggt tgttc         55

<210> SEQ ID NO 230
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
aataaagctt atgtgtaacg gagatctgga acgaccagaa ccaccagtg               49

<210> SEQ ID NO 231
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
aataggatcc acaatattcc tttgccactg gtggttctgg tcgttccaga t            51

<210> SEQ ID NO 232
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
aataaagctt atgtgtaccg aagatctgaa accaccagaa ccaccactgc              50

<210> SEQ ID NO 233
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
aataggatcc acaattttcc tttggcagtg gtggttctgg tggtttcaga t            51

<210> SEQ ID NO 234
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
aataaagctt atgtgtaacg aagctctgga accaccacca ctgcgaaag               49

<210> SEQ ID NO 235
<211> LENGTH: 49
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 235
aataggatcc acaatgttcc tttcgcagtg gtggtggttc cagagcttc                49

<210> SEQ ID NO 236
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
aataaagctt atgtgtcccg aagatctgga acgaccacca ttgacaaag                49

<210> SEQ ID NO 237
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
aataggatcc acaatgttcc tttgtcaatg gtggtcgttc cagat                    45

<210> SEQ ID NO 238
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
aataaagctt atgtgtaccg aagatctgga accaccagaa cgaccactgc               50

<210> SEQ ID NO 239
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
aataggatcc acaaatttcc cttggcagtg gtcgttctgg tggttccaga               50

<210> SEQ ID NO 240
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
aataaagctt atgtgtgccg gagatctgaa accaccagaa caacaatgt c              51

<210> SEQ ID NO 241
<211> LENGTH: 50
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 241 ataggatcc acaattttc tttgacattg ttgtttctgg tggtttcaga          50

<210> SEQ ID NO 242
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
aataaagctt atgtgcaccg aagatctgca acaaccagaa cgatcacagc          50

<210> SEQ ID NO 243
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
aataggatcc acaactttcc attggctgtg atcgttctgg ttgttgcaga          50

<210> SEQ ID NO 244
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
aataaagctt atgtgtcccg aagatctgca accaccagaa ccagcactgc cagagaaaaa          60

<210> SEQ ID NO 245
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
aataggatcc gaccacgccg acgctgacgg cgcttttac gaccagagcc agaaccacaa          60

<210> SEQ ID NO 246
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
accagaacca gcactgccag agaaaaaaaa aaaaaaatt gtggttctgg ctctggtcgt          60

<210> SEQ ID NO 247
<211> LENGTH: 57
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 247
aataaagctt atgtgtaccg aagttctggt accacgaacc accagtggca aaggaag      57

<210> SEQ ID NO 248
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
aataggatcc ggagccacac gccgatgctg acggatggcc tttttgcgac cagagccaga      60
a      61

<210> SEQ ID NO 249
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
accacgaacc accagtggca aaggaagatt gtggttctgg ctctggtcgc aaaaaggcca      60

<210> SEQ ID NO 250
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
aataaagctt atgtgtgccg aagatctgca accaccacca ctgctagagg ca      52

<210> SEQ ID NO 251
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
aataggatcc acactgacgg cgcttttac gaccagagtc agaaccacaa tgtgcctct      59

<210> SEQ ID NO 252
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
atctgcaacc accaccactg ctagaggcac attgtggttc tgactctggt cgtaaaaag      59

<210> SEQ ID NO 253
<211> LENGTH: 49
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 253
aataaagctt atgtgtaccg cagctccgga accaccagaa ccacaactg           49

<210> SEQ ID NO 254
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
aataggatcc acaatttgcc tgtggcagtt gtggttctgg tggttccgga g         51

<210> SEQ ID NO 255
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
aataaagctt atgtgtcccg cagatctgca acaaccagaa acatcactg           49

<210> SEQ ID NO 256
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
aataggatcc acaattttcc tctggcagtg atgtttctgg ttgttgcaga t         51

<210> SEQ ID NO 257
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
aataaagctt atgtgttccg tagatctgca accaccagca cgactacg            48

<210> SEQ ID NO 258
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
aataggatcc acaatttacc attggccgta gtcgtgctgg tggttgcaga t         51

<210> SEQ ID NO 259
<211> LENGTH: 49
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 259
aataaagctt atgtgcaccg aggctttgga accaccagaa ccaccactg                49

<210> SEQ ID NO 260
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
aataggatcc acaattttcc tttgtcagtg gtggttctgg tggttccaaa g              51

<210> SEQ ID NO 261
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261
aataaagctt atgtgtaccg aagctatgga accaccagaa ccaccactg                49

<210> SEQ ID NO 262
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262
aataggatcc acaactttcc cttgccagtg gtggttctgg tggttccata g              51

<210> SEQ ID NO 263
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
aataaagctt atgtgtaccg cagatctgca accaccagaa gcatcactg                49

<210> SEQ ID NO 264
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264
aataggatcc acaattttgc tgtggcagtg atgcttctgg tggttgcaga t              51

<210> SEQ ID NO 265
<211> LENGTH: 52
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 265
aataaagctt atgtgtaccg cagctccgga accaccagaa ccacgactgc ca         52

<210> SEQ ID NO 266
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
aataggatcc acaatttccc tctggcagtc gtggttctgg tggttcc              47

<210> SEQ ID NO 267
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
aataaagctt atgtgtacca aagatttggc accacaagca ccaccattgc t          51

<210> SEQ ID NO 268
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
aataggatcc acaattttcc tttagcaatg gtggtgcttg tggtgccaaa             50

<210> SEQ ID NO 269
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
aaataagctt gtatatctcc ttcttaaagt taaaca                           36

<210> SEQ ID NO 270
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
aataactcga gagatccggc tgctaacaaa gc                               32

<210> SEQ ID NO 271
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
ataagcttta atacgactca ctatagggtt aactttagta aggaggacag ctaa                54

<210> SEQ ID NO 272
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
gtggtgatgg tgatggtgac cta                                                  23

<210> SEQ ID NO 273
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
attattctcg agttaatagc cggtgccgtg gtgatggtga tggtgaccta                     50

<210> SEQ ID NO 274
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
aaatactcga gtcgttttat ctgttgtttg tcggt                                     35

<210> SEQ ID NO 275
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
aaataaagct tctctgaatg gcgggagtat gaaaa                                     35

<210> SEQ ID NO 276
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
ccgcgaatgg tgagattgag aa                                                   22

<210> SEQ ID NO 277
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
acgcaaaaag gccatccgtc ag                                           22

<210> SEQ ID NO 278
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
attattctcg agttaatagc cggtgcctaa gccgctacca ccacgccgac gctgacgg    58

<210> SEQ ID NO 279
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
aaataagctt atggatagta gtgcggtgat ca                                32

<210> SEQ ID NO 280
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
attattctcg agctagtggt gatggtgatg gt                                32

<210> SEQ ID NO 281
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
aactaagctt ttcctcctgt tagcccaaaa aac                               33

<210> SEQ ID NO 282
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
aatactcgag gctgttttgg cggatgagag aa                                32

<210> SEQ ID NO 283
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
aaatccatgg atagtagtgc ggtgatca                                          28

<210> SEQ ID NO 284
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
aaatcatatg gatagtagtg cggtgatca                                         29

<210> SEQ ID NO 285
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
aatactcgag ctagtggtga tggtgatggt gag                                    33

<210> SEQ ID NO 286
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
aatactcgag agagccagaa ccagatcccg ga                                     32

<210> SEQ ID NO 287
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 287
taagccgcta ccaccacgcc gac                                               23

<210> SEQ ID NO 288
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
ggtgcaattc ctaaaactcc agtacaatac ttactgc                                37

<210> SEQ ID NO 289
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 289

```
gtattgtact ggagttttag gaattgcacc attttcctc                        39
```

<210> SEQ ID NO 290
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 290

```
aatactcgag ttattttgga ggatggtcgc cacca                            35
```

<210> SEQ ID NO 291
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 291

```
aataaagctt atgggatccg gttctggctc aggttcttcc                       40
```

<210> SEQ ID NO 292
<211> LENGTH: 49
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other

<400> SEQUENCE: 292

```
naancancan tgncanagna anattgtggt tctggctctg gtcgtaaaa             49
```

<210> SEQ ID NO 293
<211> LENGTH: 49
<212> TYPE: DNA
<213> ORGANISM: Artificial Sequence
<220> FEATURE:

```
<223> OTHER INFORMATION: Description of Artificial Sequence: Synthetic
      primer
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other
<220> FEATURE:
<221> NAME/KEY: modified_base
<222> LOCATION: (23)..(23)
<223> OTHER INFORMATION: a, c, t, g, unknown or other

<400> SEQUENCE: 293
gnacnacnac ngcnaanggn aanttgtggt tctggctctg gtcgtaaaa                49

<210> SEQ ID NO 294
<211> LENGTH: 49
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other
```

<400> SEQUENCE: 294
gnancacnan tgcnanaggn anattgtggt tctggctctg gtcgtaaaa                49

<210> SEQ ID NO 295
<211> LENGTH: 49
<212> TYPE: DNA
<213> ORGANISM: Artificial Sequence
<220> FEATURE:
<223> OTHER INFORMATION: Description of Artificial Sequence: Synthetic
      primer
<220> FEATURE
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (23)..(23)
<223> OTHER INFORMATION: a, c, t, g, unknown or other

<400> SEQUENCE: 295
naacnancac ngncaangna aanttgtggt tctggctctg gtcgtaaaa                49

<210> SEQ ID NO 296
<211> LENGTH: 49
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other
<220> FEATURE:

<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other

<400> SEQUENCE: 296
gaancancan tgncanagna anattgtggt tctggctctg gtcgtaaaa         49

<210> SEQ ID NO 297
<211> LENGTH: 49
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other
<220> FEATURE:
<221> NAME/KEY: modified_base
<222> LOCATION: (23)..(23)
<223> OTHER INFORMATION: a, c, t, g, unknown or other

<400> SEQUENCE: 297
gaacnacnac ngcnaanggn aanttgtggt tctggctctg gtcgtaaaa         49

<210> SEQ ID NO 298
<211> LENGTH: 49
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base

```
<222> LOCATION: (16)..(16)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other

<400> SEQUENCE: 298
gaancacnan tgcnanaggn anattgtggt tctggctctg gtcgtaaaa        49

<210> SEQ ID NO 299
<211> LENGTH: 49
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (23)..(23)
<223> OTHER INFORMATION: a, c, t, g, unknown or other

<400> SEQUENCE: 299
gaacnancac ngncaangna aanttgtggt tctggctctg gtcgtaaaa        49

<210> SEQ ID NO 300
<211> LENGTH: 49
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: modified_base
<222> LOCATION: (19)..(19)
```

<223> OTHER INFORMATION: a, c, t, g, unknown or other

<400> SEQUENCE: 300
gaancancac tgccanagna aaattgtggt tctggctctg gtcgtaaaa            49

<210> SEQ ID NO 301
<211> LENGTH: 49
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other

<400> SEQUENCE: 301
naaccaccan tgncaaagga anattgtggt tctggctctg gtcgtaaaa            49

<210> SEQ ID NO 302
<211> LENGTH: 49
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other

<400> SEQUENCE: 302
gaancacnac tgccanaggn aaattgtggt tctggctctg gtcgtaaaa            49

<210> SEQ ID NO 303
<211> LENGTH: 49
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (10)..(10)

```
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other

<400> SEQUENCE: 303
gnaccaccan tgcnaaagga anattgtggt tctggctctg gtcgtaaaa        49

<210> SEQ ID NO 304
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (18)..(18)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other

<400> SEQUENCE: 304
tgntgnttnc anatnttngg nacacattta gctgtcctcc ttactaaagt t      51

<210> SEQ ID NO 305
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
```

-continued

```
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other

<400> SEQUENCE: 305
tngtngtncc nganctncgn tacacattta gctgtcctcc ttactaaagt t          51

<210> SEQ ID NO 306
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other

<400> SEQUENCE: 306
tgntngttnc ngatntncgg nacacattta gctgtcctcc ttactaaagt t          51

<210> SEQ ID NO 307
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other
<220> FEATURE:
```

```
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (18)..(18)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other

<400> SEQUENCE: 307
tngtgntncc anancttngn tacacattta gctgtcctcc ttactaaagt t          51

<210> SEQ ID NO 308
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (18)..(18)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other

<400> SEQUENCE: 308
tgntgnttcc anatnttngg nacacattta gctgtcctcc ttactaaagt t          51

<210> SEQ ID NO 309
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
```

<222> LOCATION: (14)..(14)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other

<400> SEQUENCE: 309
tngtngttcc nganctncgn tacacattta gctgtcctcc ttactaaagt t            51

<210> SEQ ID NO 310
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other

<400> SEQUENCE: 310
tgntngttcc ngatntncgg nacacattta gctgtcctcc ttactaaagt t            51

<210> SEQ ID NO 311
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (18)..(18)

<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other

<400> SEQUENCE: 311
tngtgnttcc anancttngn tacacattta gctgtcctcc ttactaaagt t        51

<210> SEQ ID NO 312
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (18)..(18)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other

<400> SEQUENCE: 312
tggtgnttnc agatcttngg nacacattta gctgtcctcc ttactaaagt t        51

<210> SEQ ID NO 313
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 313
tgntggttcc anatnttcgg tacacattta gctgtcctcc ttactaaagt t        51

<210> SEQ ID NO 314
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (9)..(9)

<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other

<400> SEQUENCE: 314
tggtngttnc agatctncgg nacacattta gctgtcctcc ttactaaagt t          51

<210> SEQ ID NO 315
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 315
tgntggttcc ngatnttcgg tacacattta gctgtcctcc ttactaaagt t          51

<210> SEQ ID NO 316
<211> LENGTH: 216
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 316
cctgcaggta atacgactca ctatagggtt aactttagta aggaggacag ctaaaagctt    60
atgtgtaccg aagatctgga accaccagaa ccaccactgc caaaggaaaa ttgtggatcc   120
ggctctggtc gtaaaaagcg ccgtcagcgt cggcgtggtg gctccggtag cttaggtcac   180
catcaccatc accacggcac cggctattaa ctcgag                            216

<210> SEQ ID NO 317
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 317
atgtgtaccg aagatctgga accaccagaa ccaccactgc caaaggaaaa ttgtggatcc    60
ggctctggtc gtaaaaagcg ccgtcagcgt cggcgtggtg gctccggtag cttaggtcac   120
catcaccatc accacggcac cggctattaa                                   150

<210> SEQ ID NO 318
<211> LENGTH: 37
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 318
aaatcctgca ggtaatacga ctcactatag ggttaac                              37

<210> SEQ ID NO 319
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319
attattctcg agttaatagc cggtgccgtg gtgatggtga tggtgaccta               50

<210> SEQ ID NO 320
<211> LENGTH: 226
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 320
tataccctgc aggtaatacg actcactata gggttaactt tagtaaggag acagctaaa     60 agcttatgtg tgaagacgcc aaaaacataa agaaaggccc ggcgccattc tatccgtgtg   120
gatccggctc tggtcgtaaa aagcgccgtc agcgtcggcg tggtggctcc ggtagcttag   180
gtcaccatca ccatcaccac ggcaccggct attaactcga gagatc                  226

<210> SEQ ID NO 321
<211> LENGTH: 216
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 321
cctgcaggta atacgactca ctatagggtt aactttagta aggaggacag ctaaagctt     60 atgtgtgaag acgccaaaaa cataaagaaa ggcccggcgc cattctatcc gtgtggatcc   120
ggctctggtc gtaaaaagcg ccgtcagcgt cggcgtggtg gctccggtag cttaggtcac   180
catcaccatc accacggcac cggctattaa ctcgag                             216

<210> SEQ ID NO 322
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 322
atgtgtgaag acgccaaaaa cataaagaaa ggcccggcgc cattctatcc gtgtggatcc    60
ggctctggtc gtaaaaagcg ccgtcagcgt cggcgtggtg gctccggtag cttaggtcac   120
catcaccatc accacggcac cggctattaa                                    150

<210> SEQ ID NO 323
```

```
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 323
aaatcctgca ggtaatacga ctcactatag ggttaac                              37

<210> SEQ ID NO 324
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324
attattctcg agttaatagc cggtgccgtg gtgatggtga tggtgaccta               50

<210> SEQ ID NO 325
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 325
aataggatcc acaatttacc tgtggctgtc gtgattctgg tggttgcaga t             51

<210> SEQ ID NO 326
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 326
acaatttacc attggccgta gtcgtgctgg tggttgcaga t                        41

<210> SEQ ID NO 327
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 327
aataaagctt atgtgcaccg agctttggaa ccaccagaac caccactg                 48

<210> SEQ ID NO 328
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 328
aataggatcc acaatttgc tgtggcagtg atgcttctgg tggttgcaga                50

<210> SEQ ID NO 329
<211> LENGTH: 14
```

-continued

```
<212> TYPE: PRT
<213> ORGANISM: Unknown
<220> FEATURE:
<223> OTHER INFORMATION: Description of Unknown:
      REST peptide
<220> FEATURE:
<221> NAME/KEY: MOD_RES
<222> LOCATION: (4)..(4)
<223> OTHER INFORMATION: Phosphorylated Ser
<220> FEATURE:
<221> NAME/KEY: MOD_RES
<222> LOCATION: (7)..(7)
<223> OTHER INFORMATION: Phosphorylated Ser

<400> SEQUENCE: 329

Thr Glu Asp Ser Pro Pro Ser Pro Pro Leu Pro Lys Glu Asn
1               5                   10

<210> SEQ ID NO 330
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 330
uagccgguga aaaaaaaaaa aaaa                                          24

<210> SEQ ID NO 331
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
tttttttttt tttttttttt ttttt                                         25

<210> SEQ ID NO 332
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 332
agagcacgag ctgcctgac                                                19

<210> SEQ ID NO 333
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 333
ggatgccaca ggactcca                                                 18

<210> SEQ ID NO 334
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 334
tattagtgag tgggtaacgg cg                                          22

<210> SEQ ID NO 335
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 335
gaagtattgc ttcagttggc ctt                                         23

<210> SEQ ID NO 336
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 336
ctcactacca cctgctgctc                                             20

<210> SEQ ID NO 337
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 337
tcagtccgtc gtctgctttc                                             20

<210> SEQ ID NO 338
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 338
tatcctggcc acactgaggt                                             20

<210> SEQ ID NO 339
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 339
tcctgcaggg acattgctc                                              19

<210> SEQ ID NO 340
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 340
agagctatga gctgcctgac                                           20

<210> SEQ ID NO 341
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 341
agctgtgcct cagaactagg cttt                                      24

<210> SEQ ID NO 342
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 342
taccagaaag acgcagggat gctt                                      24

<210> SEQ ID NO 343
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 343
ccggcagaac tcagaagaag                                           20

<210> SEQ ID NO 344
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 344
tttgaggcca ggggtaagat                                           20

<210> SEQ ID NO 345
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 345
ttcctggtca tgtatgtgat tgta                                      24

<210> SEQ ID NO 346
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 346

```
gggcagtgta ctggtcgcta a                                              21
```

<210> SEQ ID NO 347
<211> LENGTH: 5
<212> TYPE: PRT
<213> ORGANISM: Unknown
<220> FEATURE:
<223> OTHER INFORMATION: Description of Unknown:
      REST peptide

<400> SEQUENCE: 347

Ser Pro Pro Ser Pro
1               5

<210> SEQ ID NO 348
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: D-amino acid

<400> SEQUENCE: 348

Pro Glu Pro Pro Glu
1               5

<210> SEQ ID NO 349
<211> LENGTH: 223
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 349

```
aataataagc tttaatacga ctcactatag ggttaacttt agtaaggagg acagctaaat      60
gtgtaccgaa gatctggaac caccagaacc accactgcca aaggaaaatt gtggttctgg     120
ctctggtcgt aaaaagcgcc gtcagcgtcg gcgtggtggc tccggtagcg gcttaggtca    180
ccatcaccat caccgacgca ccggctatta actcgagaat aat                      223
```

<210> SEQ ID NO 350
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 350

Met Cys Thr Glu Asp Leu Glu Pro Pro Glu Pro Leu Pro Lys Glu
1               5                   10                  15

Asn Cys Gly Ser Gly Ser Gly Arg Lys Lys Arg Arg Gln Arg Arg
                20                  25                  30

Gly Gly Ser Gly Ser Gly Leu Gly His His His His His Gly Thr
                35                  40                  45

Gly Tyr
    50

COMPOSITIONS AND METHODS FOR DEREPRESSING RE1 SILENCING TRANSCRIPTION FACTOR TARGET GENES

CROSS-REFERENCE TO RELATED APPLICATIONS AND CLAIM TO PRIORITY

This application is a national stage application of International Application No. PCT/US2020/061632 filed Nov. 20, 2020, which claims the priority of U.S. Provisional Patent Application Nos. 62/939,149, filed Nov. 22, 2019, and 63/086,248, filed Oct. 1, 2020, the disclosures of which are incorporated herein by reference and to which priority is claimed.

SEQUENCE LISTING

The instant application contains a Sequence Listing which has been submitted electronically in ASCII format and is hereby incorporated by reference in its entirety. Said ASCII copy, created on Jan. 8, 2021, is named 09097_001_PCT_SL.txt and is 120,717 bytes in size.

FIELD OF THE INVENTION

Methods, compounds, and compositions for derepressing RE1 silencing transcription factor (REST) target genes are provided. In particular, a peptide having the sequence TEDLEPPEPPLPKEN (SEQ. ID NO: 1) and EDLEPPEPPLPK (SEQ. ID NO: 15), or the reversed sequences made of D-amino acids (retro inverted, RI) nekplppeppeldet (SEQ ID NO: 16) and kplppeppelde (SEQ ID NO: 17), are disclosed for inhibiting REST activity. The peptides are useful to treat, prevent, or ameliorate conditions such as traumatic brain injury, epilepsy, dementia, Huntington's Disease (HD), chronic pain, brain cancer (including glioblastoma multiforme), pancreatic cancer; diabetes, and peripheral nerve injury.

BACKGROUND

The repressor element 1 (RE1) silencing transcription factor (REST) is a repressor of hundreds of neuronal genes[1]. Its targets represent genes required for the terminally differentiated neuronal cell phenotype, including genes encoding voltage and ligand dependent ion channels, their receptors, growth factors, and axonal-guidance proteins (Bruce A W et al, Proc Natl Acad Sci USA 101, 10458-10463 (2004); Conaco C et al, Proc Natl Acad Sci USA 103, 2422-2427 (2006); Mortazavi A et al, Genome Res 16, 1208-1221 (2006); and Otto S J et al, J Neurosci 27, 6729-6739 (2007); all of which are incorporated by reference herein). Thus, during neurogenesis, REST is progressively down regulated to allow elaboration of the mature neuronal phenotype (Ballas et al, 2005 supra). The importance of this event is demonstrated by gain-of-function studies that indicate the persistence of REST impedes terminal neuronal differentiation (Mandel G et al, Proc Natl Acad Sci USA 108, 16789-16794 (2011) and Gao Z ei a I, J Neurosci 31, 9772-9786 (2011); both of which are incorporated by reference herein).

Relatively little is known either about the transcriptional or post-transcriptional regulation of REST (Ballas N et al 2005 supra; Ballas N et al, Neuron 31, 353-365 (2001); and Kojima T et al, Brain Res Mol Brain Res 90, 174-186 (2001); all of which are incorporated by reference herein). However, two phosphorylation sites on REST (serines 861 and 864) regulate neuronal differentiation by their interaction with C-terminal domain small phosphatase-1 (CTDSP1)[2]. When CTDSP1 removes phosphates from serine 861 and 864, REST protein is stabilized and neuronal differentiation is inhibited[2-4].

SUMMARY OF THE INVENTION

Disclosed herein are methods, compounds, and compositions for developing peptides with high affinity to CTDSP1.

Disclosed herein are methods, compounds, and compositions for binding C-terminal domain small phosphatase 1 (CTDSP1).

Disclosed herein are REST phosphomimetic peptides, TEDLEPPEPPLPKEN (SEQ ID NO: 1), EDLEPPEPPLPK (SEQ. ID NO: 15), nekplppeppeldet (SEQ ID NO: 16) and kplppeppelde (SEQ ID NO: 17), which bind CTDSP1 to inhibit REST activity. The lowercase letters represent D-amino acids, which are resistant to degradation and therefore increase peptide half-life, without compromising binding affinity[5].

Disclosed herein are ninety eight (98) REST phosphomimetic peptide variants (RPPv) (SEQ IDS: 18 through 117), which inhibit CTDSP1 activity on REST to varying degrees (FIG. 25).

Disclosed herein are intracellular transport peptides, such as cell penetrating peptides (CPP) and/or endosomal release sequences, (SEQ ID NOS: 118 through 137 and 140 through 159) that may be fussed to an RPP (SEQ ID NOS: 1 and 15 through 17) or an RPP$_V$ (SEQ ID NOS: 18 through 117) at the N- or C-terminus to improve intracellular transport. Also disclosed are linkers (SEQ ID NOS: 138, 139, 160 and 161) that may be inserted between an RPP or RPPv and one of the peptides listed in Table 7, to further improve intracellular transport.

Disclosed herein is that RPP (SEQ ID NO: 1 and 15 through 17) or RPP$_V$ (SEQ ID NOS: 18 through 117) fused at the N- or C-terminus to an intracellular transport peptide (SEQ ID NOS: 118 through 137 and 140 through 159) and cyclized to further improve binding affinity and stability (increase peptide half-life). Examples of cyclized fusion proteins are SEQ ID NOS: 2, 5, 12, 13, and 14.

Disclosed herein is that RPP (SEQ ID NO: 1 and 15 through 17) or RPP$_V$ (SEQ ID NOS: 18 through 137 and 140 through 159) fused at the N- or C-terminus to an intracellular transport peptide (SEQ ID NOS: 118 through 137 and 140 through 159), promotes degradation of REST protein. Examples of the fusion protein are SEQ ID NOS: 2, and 4 through 14.

Disclosed herein is that REST phosphomimetic peptide of SEQ ID NO: 1 and 15-17 or RPP$_V$ SEQ ID NOS: 18 through 117 fused at the N- or C-terminus to an intracellular transport sequence (SEQ ID NOS: 118 through 137 and 140 through 159), promotes expression of REST target genes. Examples of the fusion protein are SEQ ID NOS: 2, 4 through 14.

Disclosed herein are RPP SEQ ID NOS: 1 and 15 through 17 or RPP$_V$ (SEQ ID NOS: 18 through 117) fused at the N- or C-terminus to an intracellular transport peptide (SEQ ID NOS: 118 through 137 and 140 through 159), is useful for treating animals having a disease or condition associated with REST or CTDSP1 by administering to the animal a therapeutically effective amount of the compound so that expression of REST target genes are increased or that expression of BDNF is increased. Examples of the fusion protein are SEQ ID NOS: 2 and 4 through 14.

Disclosed herein are RPP SEQ ID NOS: 1 and 15 through 17 or RPP$_V$ (SEQ ID NOS: 18 through 117) fused to an intracellular transport peptide (SEQ ID NOS: 118 through 137 and 140 through 159), is useful for treating traumatic brain injury, chronic pain, peripheral nerve injury, epilepsy, diabetes, Alzheimer's disease, Huntington's disease, brain tumors (including glioblastoma multiforme), or pancreatic cancer in an animal. Examples of the fusion protein are SEQ ID NOS: 2 and 4 through 14.

BRIEF DESCRIPTION OF THE DRAWINGS

The accompanying drawings are incorporated in and constitute a part of the specification. The drawings, together with the general description given above and the detailed description of the exemplary embodiments and methods given below, serve to explain the principles of the invention. In such drawings.

| Sequence ID number (SEQ ID NO) | Peptide |
|---|---|
| Control | Water |
| 5 | CTEDLEPPEPPLPKENSGDIMGEWGNEIFGAIAGFLGYGR KKRRQRRRG$^{cyclic}$ |
| 6 | TEDLEPPEPPLPKENRRWWRRWRRRRWWRr |
| 7 | EDLEPPEPPLPKRWWRRRRWRRWWRr |
| 8 | AGDLEQPEPPVAKKKKKNRRWWRRWRr |
| 9 | rrrrwrrwwrrwrrnekplppeppeldet |
| 10 | TEDLEPPEPPLPKENrrrrwrrwwrrwrr |
| 11 | TEDLEPPEPPLPKENRRRRRRC$_{14}$RRWWRRr |

Lowercase = D-amino acids
$C_{14}$ = 2-amino-tetradecanoic acid

Figure 12:
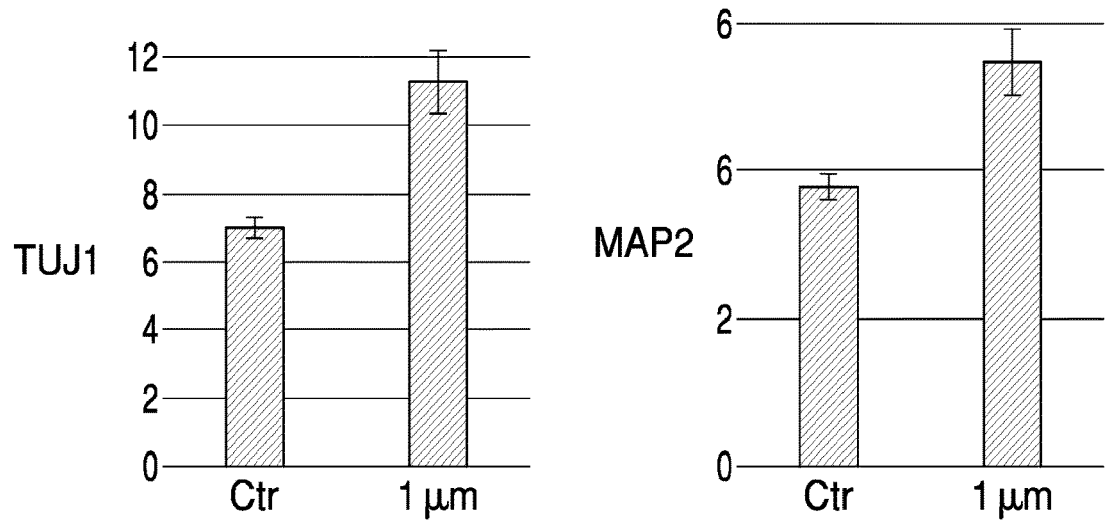

FIG. 12. iPSCs (neural stem cells (NSC)-NL5) were with 1 μM RPP (SEQ ID NO. 9) or water control. After 7 days in culture, cells were assessed for neuronal differentiation using neuronal markers TUJ1 (class III beta-tubulin) and MAP2 (both normalized to DAPI). Media and RPP were replaced on Day 3. (standard deviation, n=6).

Figure 13:
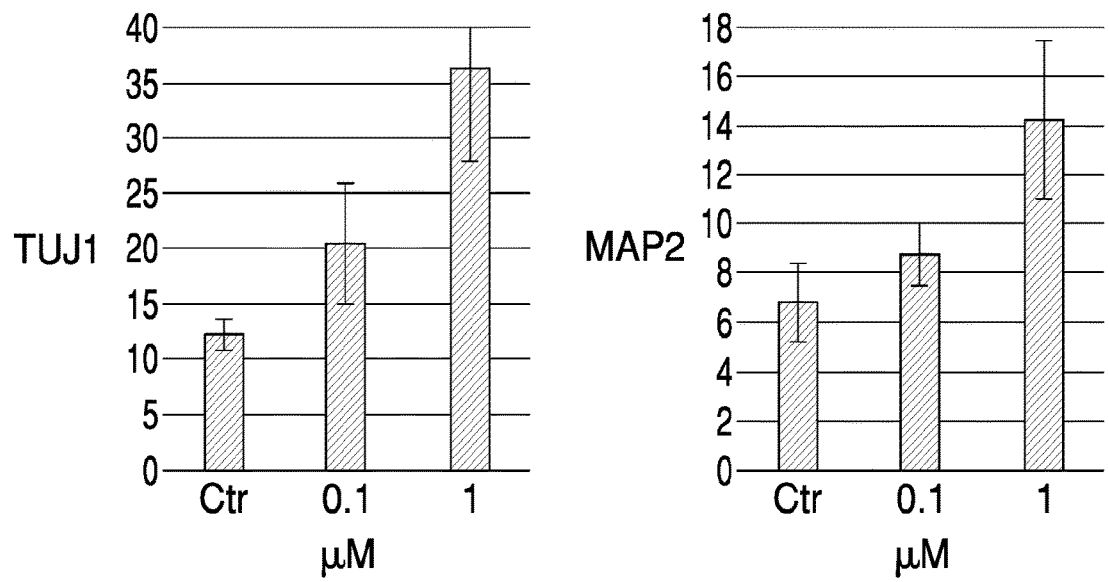

FIG. 13. iPSCs (neural stem cells (NSC)-NL5) were with 1 μM RPP (SEQ ID NO. 13) or water control. After 7 days in culture, cells were assessed for neuronal differentiation using neuronal markers TUJ1 and MAP2 (both normalized to DAPI). Media and RPP were replaced on Day 3. (standard deviation, n=6).

Figure 14:
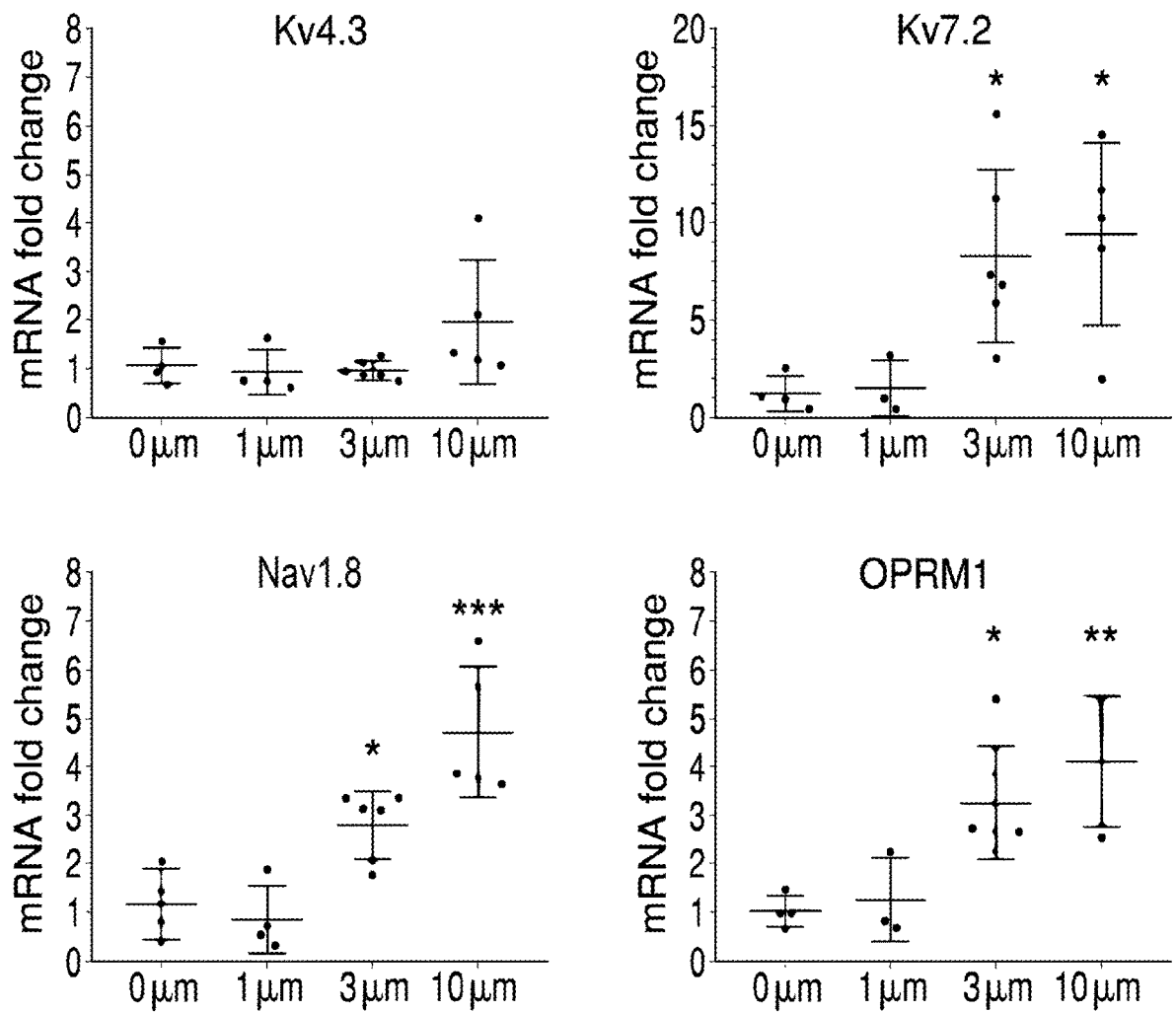

FIG. 14. RPP (SEQ. ID NO: 12) increases expression of $K_V4.3$, $K_V7.2$, Nav1.8 and OPRM1. qRT-PCR analysis of mRNA expression (normalized to β-actin), relative to water control, after incubation of adult Sprague Dawley (SD) rat L5 DRGs with various concentrations of rpp for 48 h. *= $p<0.05$, =$p<0.01$, *=$p<0.001$, one-way ANOVA and Dunnett's test, error bars=standard error of the mean.

Figure 15:
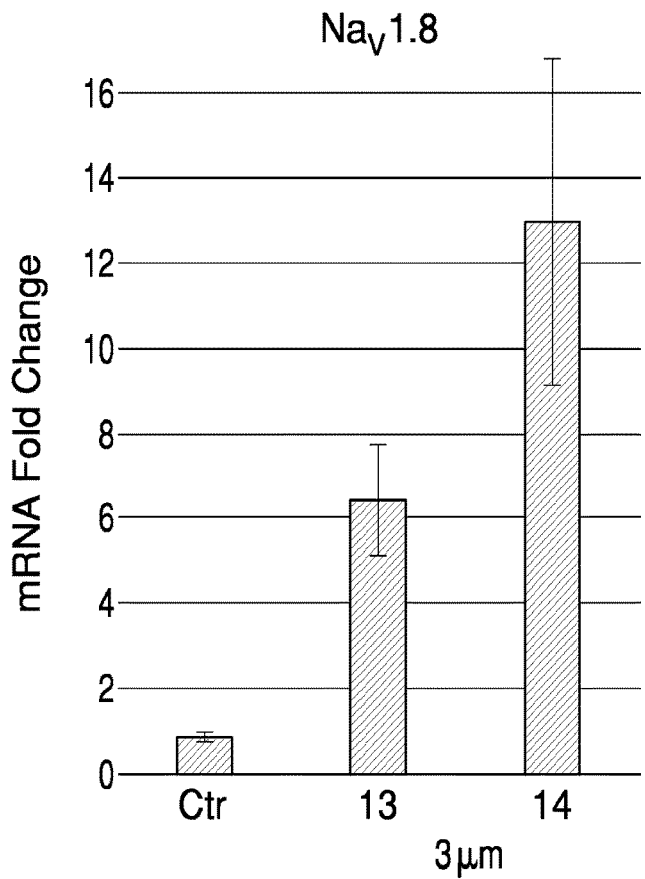

FIG. 15. 3 μM RPP for 48 hours (SEQ ID NOS: 13 and 14) increased expression of Nav1.8. qRT-PCR analysis of mRNA expression (normalized to β-actin), relative to water control, after incubation of RPP with adult Sprague Dawley (SD) rat L5 DRGs. Error bars =standard error of the mean.

Figure 16:
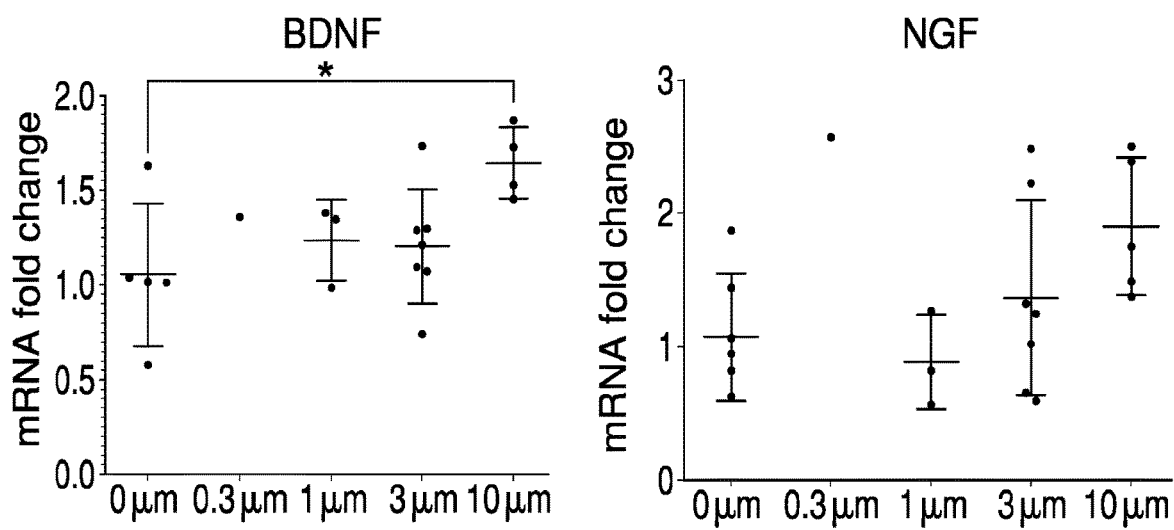

FIG. 16. RPP (SEQ. ID NO: 12) increases expression of BDNF and NGF. qRT-PCR analysis of mRNA expression (normalized to β-actin), relative to water control, after incubation of adult Sprague Dawley (SD) rat L5 DRG neurons with various concentrations of RPP for 48 h. *=p<0.05, one-way ANOVA and Dunnett's test, error bars=SEM.

Figure 17:
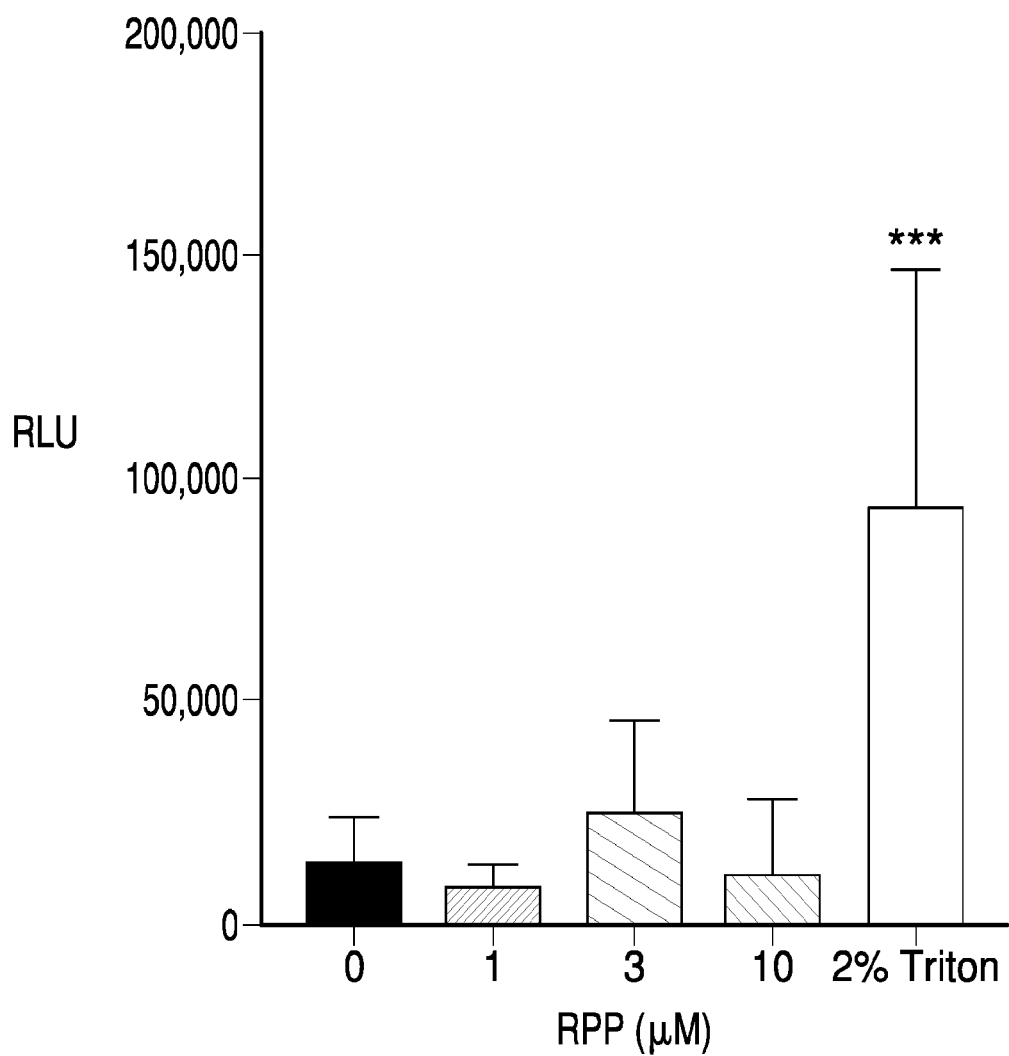

FIG. 17. RPP (SEQ. ID NO: 12) does not cause necrosis in DRG neurons. LDH toxicity assay in SD rat incubated with water, RPP (1, 3, or 10 PM), or triton for 48 hours. ***=p<0.001, one-way ANOVA and Dunnett's test, error bars=SD.

Figure 18:
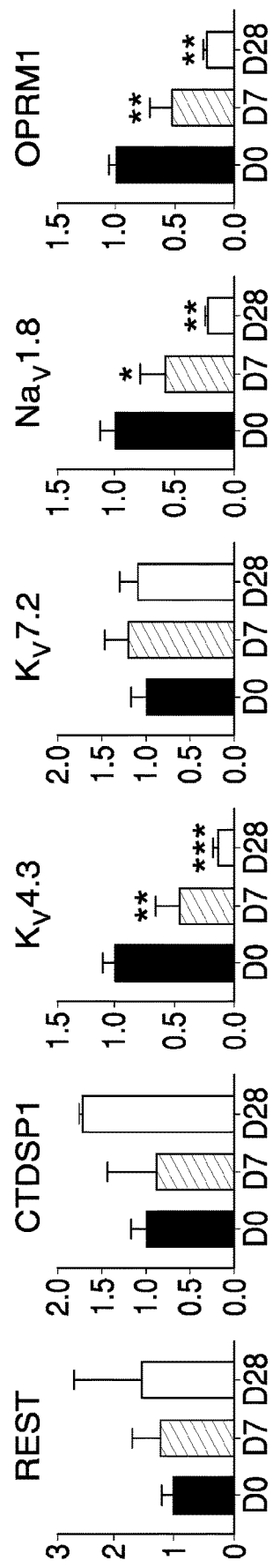

FIG. 18, RNA Levels of Chronic Pain Genes After SNI. RNA fold change relative to β-actin on Day 0 (sham, n=3), 7 (n=5), or 28 (n=2) after SNI (mean±SD, p<0.01, *p<0.001, one-way ANOVA with Dunnett's multiple comparison test. RNA was isolated from sciatic nerve DRG (L5).

Figure 19:
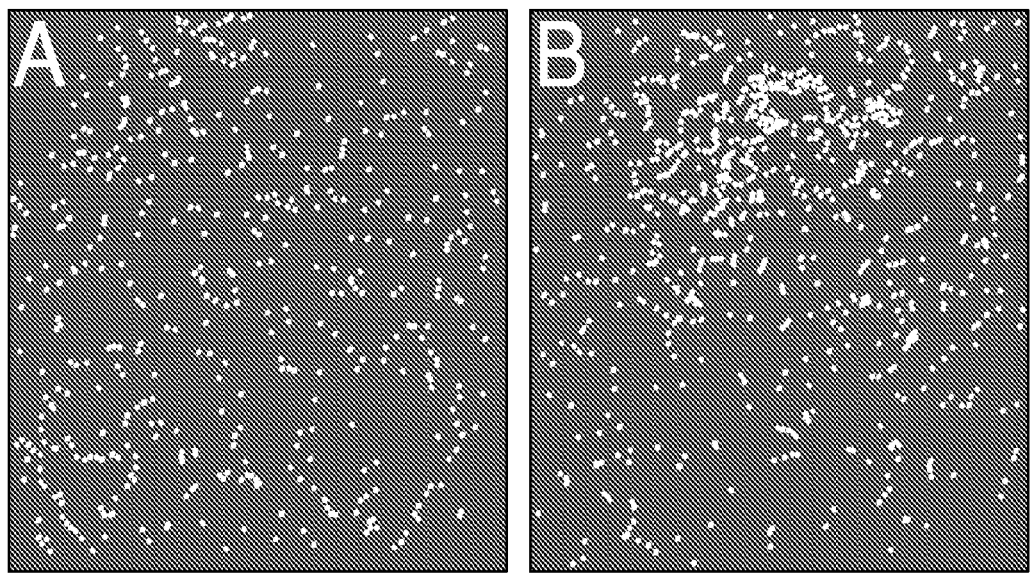

FIG. 19. REST mRNA levels increase after TBI. (A) Normal levels of REST mRNA expression in the ipsilateral cortex of uninjured mouse. (B) REST levels increase dramatically in the mouse ipsilateral cortex 7 days after cortical controlled impact injury[6]. mRNA visualized by RNAscope with DAPI counterstain.

FIG. 20. (a) Schematic of AAVS1-Nanoluc-Halotag Knock-in (KI) construct used to engineer NCRM-1 iPSCs. The CMV-driven construct was inserted into the safe harbor AAVS1 locus of Chr. 19q by transcription activator-like effector nucleases (TALENS). AAVS1 KI was confirmed by sequencing and junction PCR (not shown). (b) Schematic of MAP2-Nanoluc-Halotag Knock-in (KI) construct used to engineer NCRM-1 iPSCs. Nanoluciferase-Halotag was knocked-in to the MAP2 transcriptional start site (TSS) (Chr. 2) using zinc finger nucleases (ZFN) and MAP2-in frame KI confirmed by sequencing and junction PCR (not shown). CMV-NLHT and MAP2-NLHT iPSCs express pluripotency markers OCT4/NANOG/TRA 1-81/TRA 1-60 (not shown). (c) Luciferase assay of CMV-NLHT iPSCs and MAP2-NLHT neural stem progenitor cells (NSPC) and neurons. Note the increasing luciferase activity with neuronal differentiation of MAP2-NLHT cells consistent with increased MAP2 expression with differentiation.

FIG. 21. Rat sciatic nerve injury model: (Left) Surgical approach of sciatic nerve transection. (Right) Immunohistochemistry-Immunofluorescence staining from section of sciatic nerve. Tissues were stained for PIII Tubulin, Laminin I, and DAPI. The scale bars=100 μm.

Figure 23:
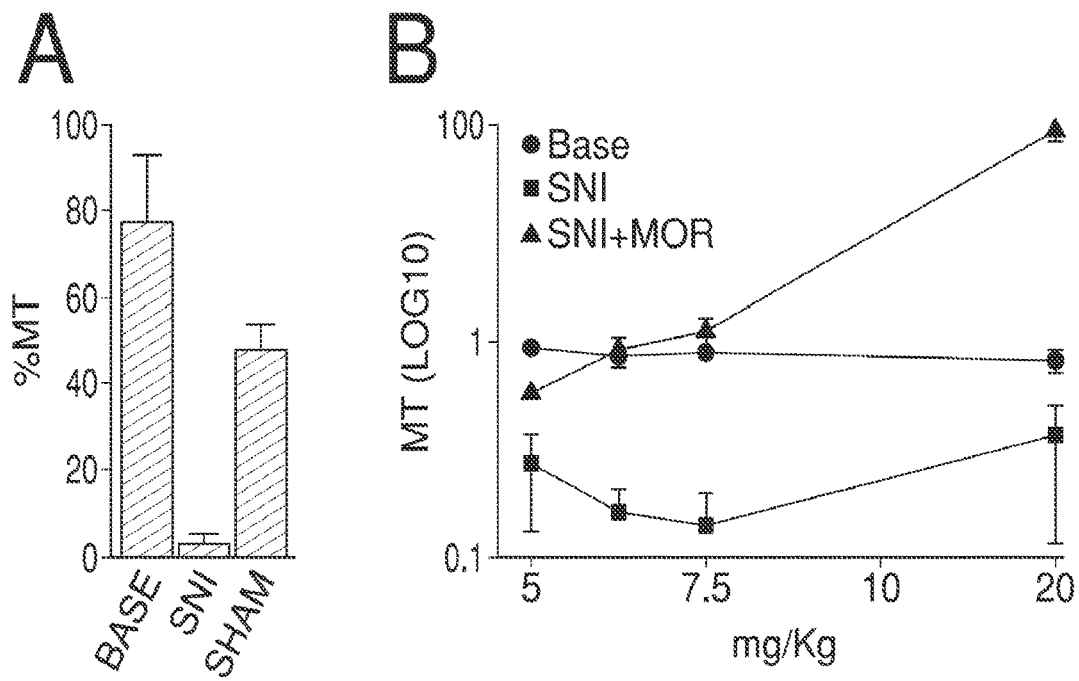

FIG. 22. Rat sciatic nerve harvest: (Left) En Bloc section of rat spinal column and associated peripheral nerves. (Right) Image of sciatic nerve injury site with associated lumbar nerve roots FIG. 23. A. Compared to baseline (BASE), SNI induces sensitization of mechanical pain threshold (MT) 4-days post-injury (n=16); paired t-test, *p<0.05, SHAM shows no significant difference in mechanical threshold 4-days post-surgery. B. Analgesic effect of single S.C. injection of morphine on MT post-injury (SNI+MOR, n=4). Mean±SEM; F=4.62, *p<0.05 by one-way ANOVA before and after treatment; mean difference and 95% CI=−7.3, −14.5 to −0.135, p<0.05 by Bonferroni's Multiple Comparison test. 20 mg/Kg of MOR (n=4; F=19.03, **p<0.001 by one-way ANOVA).

Figure 24:
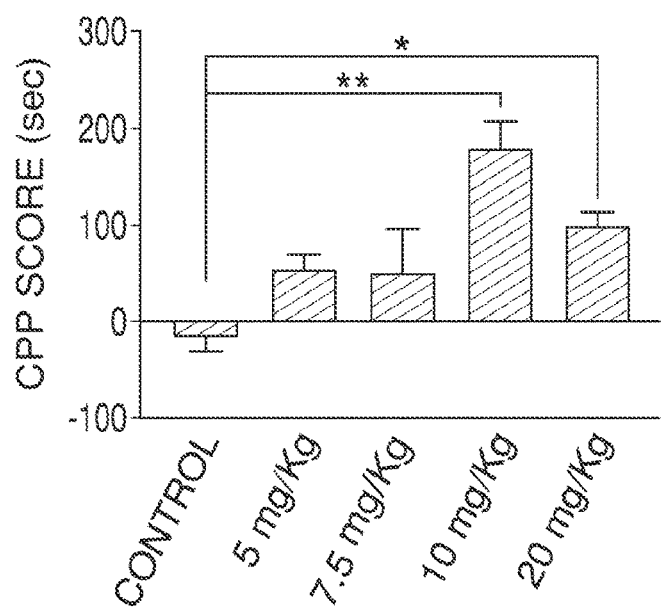

FIG. 24. Conditioned Place Preference (CPP) after conditioning with saline (control) and 4 doses of morphine (MOR) in SNI mice. MOR induced CPP in a dose-dependent manner (one-way ANOVA, F=4.167, p<0.05); 10 mg vs control (p<0.001) and 20 mg (p<0.05) by Tukey's multiple comparisons test.

Figure 25:
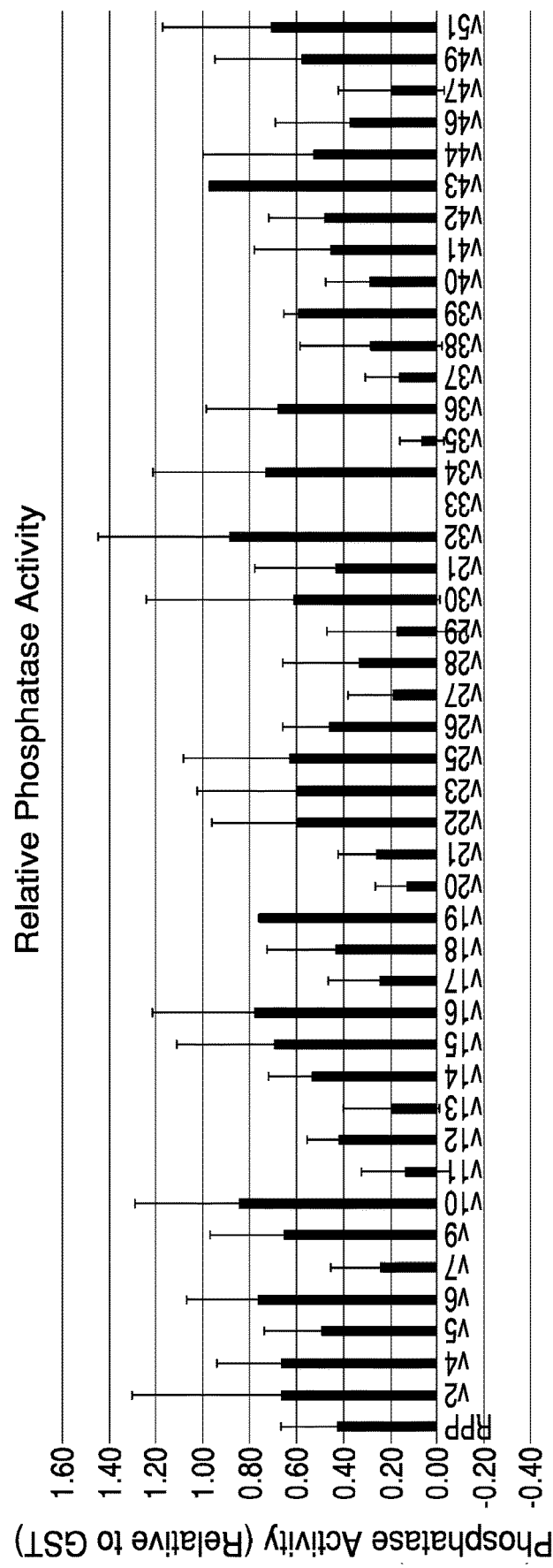

FIG. 25. In vitro CTDSP1 phosphatase activity (relative to GST control) on the REST peptide (TEDpSPPpSP-PLPKEN (SEQ ID NO: 329)) as a substrate after exposure to 1 μM of RPP (SEQ ID NO: 1) or one of its variants (Table 3).

Figure 26:
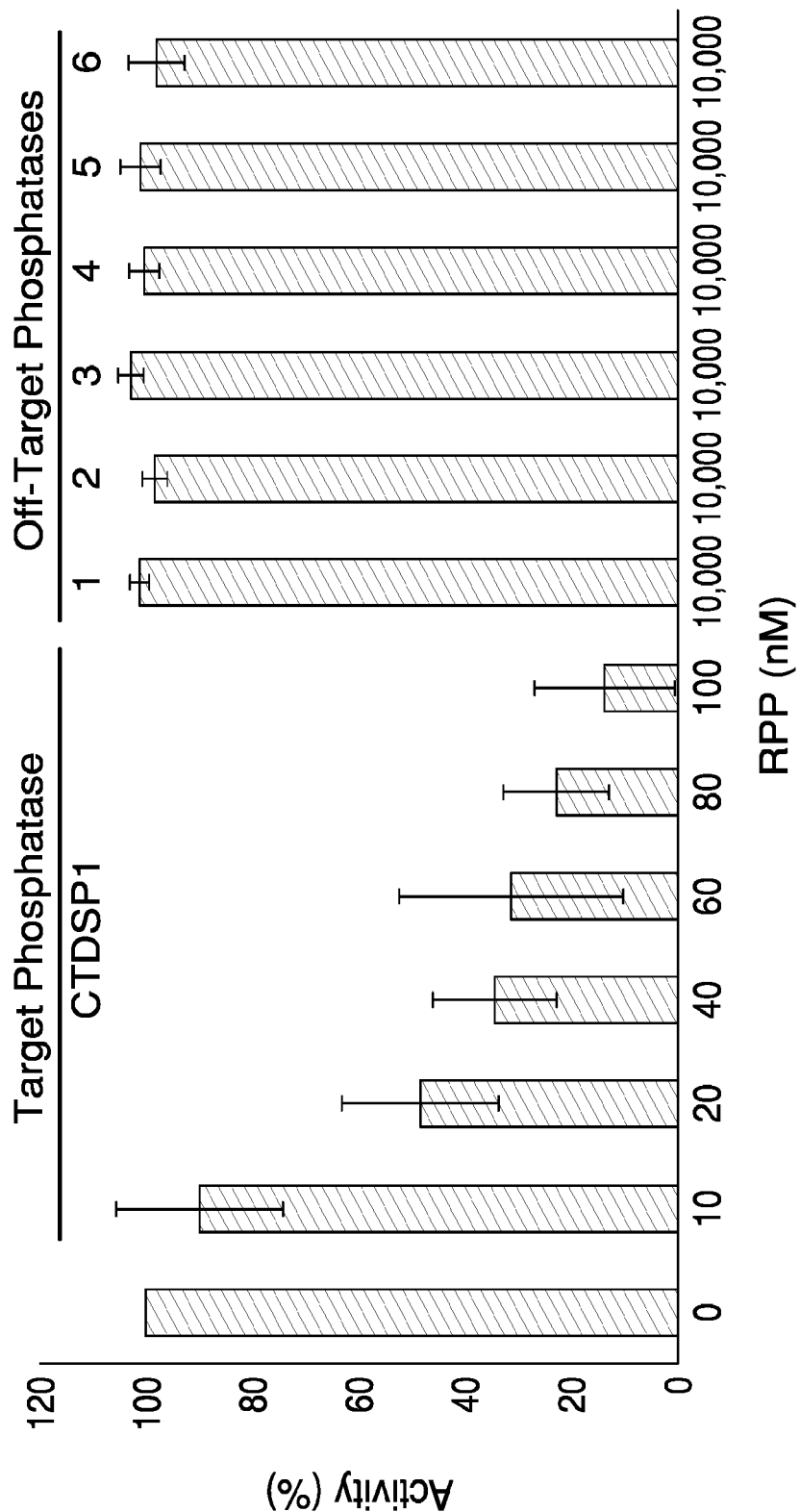

FIG. 26. In vitro on target (CTDSP1) and off target phosphatase activity (1=PPA1, 2=PPM1H, 3=PPM1A, 4=PP3CA, 5=PPP1CA, 6=PP5CA), relative to water control, on the phosphorylated REST peptide (TEDpSPPpSP-PLPKEN (SEQ ID NO: 329)) as a substrate after exposure to RPP (SEQ ID NO: 12). N=5, error bars are standard deviation.

Figure 27:
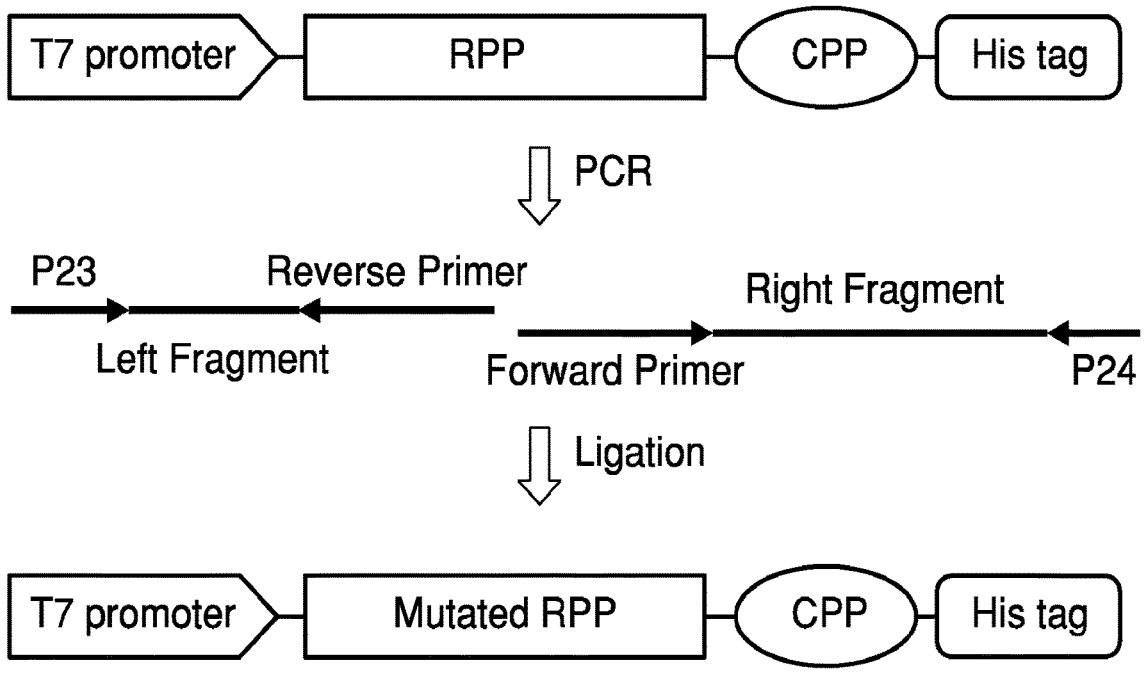

FIG. 27. Building RPP libraries. A) Scheme of the experiment; B) Nucleotide Sequence of the REST construct (before mutagenesis) (SEQ ID NO: 349); C) Protein Sequence of the REST construct (before mutagenesis) (SEQ ID NO: 350). RPP, CPP and His tag are underlined.

Figure 28:
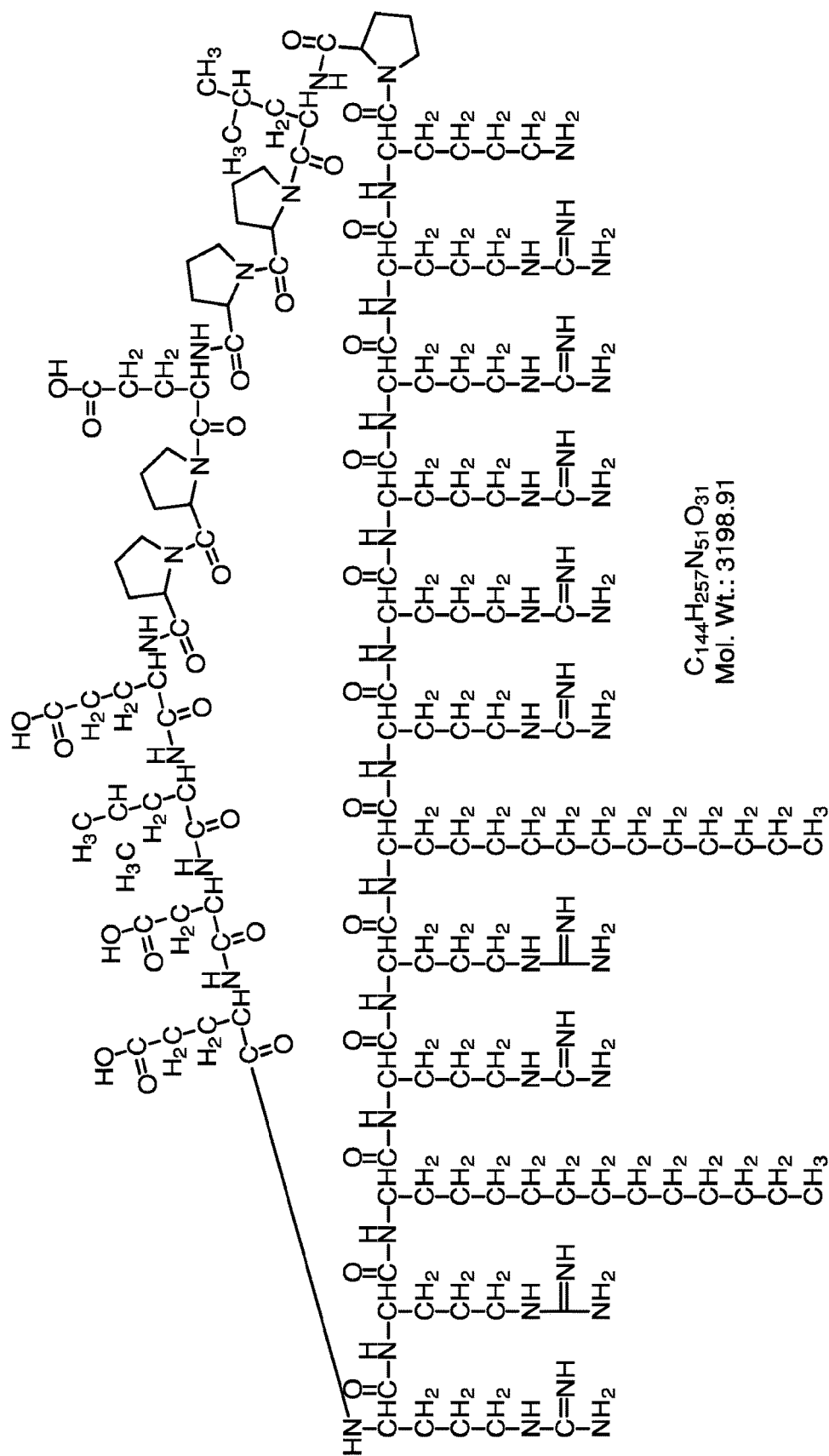

FIG. 28. RPP (SEQ ID NO: 13) structure. Along the bottom of the structure is the CPP containing a poly arginine sequence with two 2-aminotetradecanoic acids that are integrated with the REST RI phosphomimetic (starting with the lysine at the bottom right of the structure).

DETAILED DESCRIPTION OF THE EMBODIMENTS

In an embodiment, the present invention provides the methods (described in examples 1 through 3) for developing peptides with high affinity to CTDSP1. Importantly, the method uses peptide evolution techniques to generate peptides with high affinity to CTDSP1.

In an embodiment, the present invention provides a peptide of SEQ ID NOS: 1 and 15 through 17 or a peptide having at least 50%, more preferably at least 60%, yet more preferably at least 70%, still more preferably at least 80%, even more preferably at least 90%, or even yet more preferably at least 95% similarity to SEQ ID NO: 1 and 15 through 17. These peptides or similar peptides thereof are referred to herein as REST phosphomimetic peptides (RPP). Importantly, however, the glutamic acids in the RPP must be maintained, particularly the glutamic acid at positions 5 and 8 of SEQ ID NO: 1, positions 4 and 7 of SEQ ID NO: 15, positions 8 and 11 of SEQ ID NO: 16, and positions 6 and 9 of SEQ ID NO: 17.

In an embodiment, the present invention provides $RPP_V$ (SEQ ID NOS: 18 through 117), or a peptide having at least 50%, more preferably at least 60%, yet more preferably at least 70%, still more preferably at least 80%, even more preferably at least 90%, or even yet more preferably at least 95% similarity to an $RPP_V$ (SEQ ID NOS: 18 through 117). The peptide or similar peptide thereof is referred to herein as the REST phosphomimetic peptide variant (RPPv) (SEQ ID NOS: 18 through 117). Importantly, however, the glutamic acids in SEQ ID NOS: 18 through 67 must be maintained, particularly the glutamic acid at positions equivalent to 5 and 8 of SEQ ID NO: 1. For the retro inverted sequences ($RPPv^{RI}$) (SEQ ID NOS: 68 through 117), positions 8 and 11 of SEQ ID NO: 16 must be maintained.

In an embodiment, the present invention a fusion protein between RPP (SEQ ID NOS: 1 and 15 through 17) or $RPP_V$ (SEQ ID NOS: 18 through 117) and an intracellular transport peptide (SEQ ID NOS: 118 through 137 and 140 through 159) or a peptide having at least 50%, more preferably at least 60%, yet more preferably at least 70%, still more preferably at least 80%, even more preferably at least 90%, or even yet more preferably at least 95% similarity.

The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237-44, 1988; Higgins & Sharp, CABIOS 5:151-3, 1989; Corpet et al., Nuc. Acids Res. 16:10881-90, 1988; Huang et al. Computer Appls. in the Biosciences 8, 155-65, 1992; and Pearson et al., Meth. Mol. Bio. 24:307-31, 1994. Altschul et al., J. Mol. Biol. 215:403-10, 1990, presents a detailed consideration of sequence alignment methods and homology calculations.

The NCBI Basic Local Alignment Search Tool (BLAST) (Altschul et al., J. Mol. Biol. 215:403-10, 1990) is available from several sources, including the National Center for Biological Information (NCBI, National Library of Medicine, Building 38A, Room 8N805, Bethesda, MD 20894) and on the Internet, for use in connection with the sequence analysis programs BLASTP, BLASTN, BLASTX, TBLASTN AND TBLASTX. Additional information can be found at the NCBI web site (www.ncbi.nlm.nih.gov).

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166/1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 15-nucleotide region that aligns with 20 consecutive nucleotides from an identified sequence as follows contains a region that shares 75 percent sequence identity to that identified sequence (that is, 15/20*100=75).

For comparisons of amino acid sequences of greater than about 30 amino acids, the Blast 2 sequences function is employed using the default BLOSUM62 matrix set to default parameters, (gap existence cost of 11, and a per residue gap cost 5 of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, Comput. Appl. Biosci. 10:67-70). Other programs use SEG. In addition, a manual alignment can be performed. Proteins with even greater similarity will show increasing percentage identities when assessed by this method, such as at least about 75%, 80%, 85%, 90%, 95%, 98%, or 99% sequence identity to a protein. When aligning short peptides (fewer than around 30 amino acids), the alignment is performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least about 60%, 70%, 75%, 80%, 85%, 90%, 95%, 98%, or 99% sequence identity to a protein. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. An alternative (and not necessarily cumulative) indication that two nucleic acid sequences are substantially identical is that the polypeptide which the first nucleic acid encodes is immunologically cross reactive with the polypeptide encoded by the second nucleic acid.

In certain embodiments, the RPP (SEQ ID NOS: 1 and 15 through 17) or RPPv (SEQ ID NOS: 18 through 117) may be fused to another peptide, e.g., to allow for cell penetration. Preferably, the RPP (SEQ ID NOS: 1 and 15 through 17) or $RPP_V$ (SEQ ID NOS: 18 through 117) is fused to a peptide sequence that allows cell penetration and escape from endosomes. More preferably, the cell penetration and escape peptide sequence is one SEQ ID NOS: 118 through 137 and 140 through 159. RPP (SEQ ID NOS: 1 and 15 through 17) or $RPP_V$ (SEQ ID NOS: 18 through 117) and cell penetration peptide (CPP) (SEQ ID NOS: 118 through 137 and 140 through 159) may be fused directly or contain a linker (e.g., SEQ ID NOS: 138, 139, 160, or 161) sequence connecting them. It has been shown that when cells or tissues are dosed with RPP (SEQ ID NOS: 1 and 15 through 17) or $RPP_V$ (SEQ ID NOS: 18 through 117) peptide fused to a CPP (SEQ ID NOS: 118 through 137 and 140 through 159), it localizes in the nucleus (FIG. 3, SEQ ID NO: 4 and FIG. 4 SEQ ID NO: 4), causes REST degradation (FIG. 5, SEQ ID NO: 4), increases the expression of genes targeted by REST (FIG. 7, SEQ. ID NO: 4, FIG. 8, SEQ ID NO: 1, FIG. 9, linear SEQ ID NO: 4 and cyclic SEQ ID NO: 2, FIG. 10, SEQ ID NO: 9, FIG. 14, SEQ ID NO: 12, FIG. 15, SEQ ID NOS: 13 & 14, and FIG. 16, SEQ ID NO: 12), and causes neural differentiation (FIG. 11, SEQ ID NOS: 5 through 11, FIG. 12, SEQ ID NO: 9, and FIG. 13, SEQ ID NO: 13).

The present inventor has discovered that the RPP (SEQ ID NOS:1 and 15 through 17) binds CTDSP1 to inhibit REST activity. The RPP has low pM affinity for CTDSP1, as demonstrated by the binding curves shown in FIGS. 2 and 3. In cells and animals, the RPP binds to CTDSP1, which prevents CTDSP1 from binding to REST.

Increased REST and associated neural gene repression underlie the pathology of the following diseases or disorders:

Traumatic Brain Injury—Traumatic brain injury (TBI) results in loss of cognitive ability due to neuronal death. Two issues should be addressed to improve cognitive recovery after TBI, 1) reduce the neuronal death that continues after injury and 2) regenerate lost neurons.

REST levels increase dramatically in the brain after TBI (FIG. 19). Consistently, several studies have shown that brain injury caused by acute ischemia induces REST expression in neurons resulting in their death[7-9]. These studies demonstrate that neuron survival improves when REST is removed[7-9]. The clinical implications are profound. For example, elevated levels of REST are correlated with an increased frequency of seizures, which commonly occur after brain injury[10-12]. In animal models of brain injury, the rate of seizure decreases significantly when REST is inhibited[13,14]. Also, chronically elevated levels of REST after TBI are likely to play a role in neurodegenerative diseases attributed to a history of brain injury[15-17]. Both in vitro and in vivo studies show that removing REST improves neuronal survival[7-9], function[14-18], and regeneration[2,19-24]. Therefore, targeting REST after TBI should mitigate the effects of brain damage and offset the risks of developing associated age-related neurodegenerative diseases, such as Alzheimer's[17,25].

The basis for neurogenesis improving cognitive function in TBI patients are studies associating increased neurogenesis with improved learning, memory, and other cognitive functions[26-30] and studies showing the converse, that inhibition of neurogenesis via antimitotic agents, radiation, or genetic manipulations impairs hippocampal dependent forms of memory[29-33]. Defects in neurogenesis are also linked with many diseases with cognitive etiologies including developmental disorders (e.g., microcephaly[34], megalencephaly[35], and autism[35]) and neurodegenerative diseases (e.g., dementia and Alzheimer disease)[36]. Experimental treatments (including blood transfusions, growth and neurotrophic factors, and stem cell transplantation[10,37-49]) have focused on regenerating neurons. These attempts have failed to stimulate the neurogenesis required to restore cognitive function, at least in part because they are not capable of terminal differentiation of neural progenitor cells in the context of TBI[26,28,50-57]. Terminal differentiation of neural progenitors into neurons is blocked at a single checkpoint by the RE1 silencing transcription factor known as REST.

Peripheral Nerve Injury—Neuronal regeneration in peripheral nerve injury (PNI) patients is inhibited in at least two ways. First, there is a reduction in neurotrophic factors (NTFs) that support the growth, survival, and differentiation of both developing and mature neurons[58]. Second, there is a decrease in the expression of genes required for synaptic plasticity including axonal growth, vesicular transport, and ionic conductance[59]. Both phenomena occur coincident with injury-induced expression of REST[60]. Therefore, eliminating REST accelerates recovery from a PNI by reversing a block on nerve regeneration. Inhibition of CTDSP1 with the RPP promotes REST degradation (FIG. 6), increases neuronal differentiation (FIGS. 11, 12, and 13), and increases NTF expression (FIGS. 7, 9, 10, and 16), which demonstrates the potential of RPP (SEQ ID NOS: 1 and 15 through 17) or $RPP_V$ (SEQ ID NOS: 18 through 117) fused to a CPP (SEQ ID NOS: 118 through 137 and 140 through 159) to stimulate nerve regeneration.

Chronic Pain—Many of the genes that are repressed in the central and peripheral circuits during chronic pain are either direct or indirect targets of the repressor element-1 (RE1)-silencing transcription factor (REST), an inhibitor of neuronal gene expression in stem cells, neural progenitors, and non-neuronal cells[61-63]. REST levels are normally kept low in healthy neurons through active degradation to keep the chromatin clear of this powerful neuronal gene repressor[64-69]. Before the transition to neuropathic pain, REST levels significantly increase in the neurons of the peripheral nerves of mice and rats after peripheral nerve injury followed by a spike in neurons in the central nervous system where pain stimuli are processed and experienced[60,70,71]. The activation of REST after nerve injury results in decreased expression of several genes required for normal excitability of sensory neurons, including the potassium channels $K_V4.3$ (Kcnd3) and $K_V7.2$ (Kcnq2), the sodium channel Nav1.8 (Scn10a), and the mu opioid receptor Oprm1 (FIG. 18)[60,72-74] The basis for blocking REST to alleviate chronic pain are published studies using mouse and rat peripheral nerve injury (PNI) models[60,72-74]. In mice, genetic knockdown of REST in sensory neurons after PNI restores gene expression of the mu opioid receptor[60,72,73], Nav1.8[60,72,73], $K_V4.3$[72,73,75], and $K_V7.2$[72,73] in the dorsal root ganglion, restores normal K+M-type current in C nerve fibers[60], reduces hyperalgesia and allodynia[72-74], and restores morphine analgesia[60,74] in chronic pain models (Table 12). Disruption of the REST repressor complex, using an optimized REST mimetic of the mSin3 binding site, an adaptor protein which contributes to transcriptional repression of many genes including REST targets, restored C-fiber function, reduced hyperalgesia and allodynia, and restored morphine analgesia in mouse models of chronic pain (Table 12)[74]. In rats, knockdown of REST controls the transition from acute to chronic pain, demonstrated by a reduction in hyperalgesia and allodynia, and restored muscarine analgesia (Table 12)[72,73].

TABLE 12

Summary of chronic pain studies using REST blocking methods

| REST block | Day post injury | PNI | Assessment | Result | Species | Number | Ref. |
|---|---|---|---|---|---|---|---|
| Antisense Oligo | 1, 3, 5, & 6 | pSNL | Kv4.3 | Recovered [+2x (mRNA) compared to vehicle control on Day 7] | Mouse | 5 M | 75 |

TABLE 12-continued

Summary of chronic pain studies using REST blocking methods

| REST block | Day post injury | PNI | Assessment | Result | Species | Number | Ref. |
|---|---|---|---|---|---|---|---|
| Antisense Oligo | 1, 3, 5, & 6 | pSNL | Oprm1 | Recovered [+3x (mRNA) compared to Vehicle control on Day 7] | Mouse | 3 M | 60 |
| | | | Nav1.8 | 85% recovered [+2x (mRNA) compared to control on Day 7] | | | |
| | | | C-fiber | Recovery of function, compared to sham [PWTonDay 7] | | | |
| | | | Morphine analgesia | 85% recovery, compared to sham [PWTonDay 7] | | | |
| mSin3 decoy | 5-11 | pSNL | C-fiber | 75% reversal of hyposensitivity, compared to Sham [PWT on Day 12] | Mouse | 2-6/sex | 74 |
| | | | Morphine analgesia | Reversal of loss [PWT (ICS, IPS) on Day 12 & 19] | | | |
| | | Fibromyalgia (IPS, ICS) | Hyperalgesia/allodynia | Reverse (Day 12 & 19) | | | |
| Over expression AAV-REST (DRG) | — | — | Hyperalgesia (mechanical, hot, & cold) | Induction (PWT) on Day 20, 25, 30 | Mouse | 3-5/sex | 72,73 |
| cKO | Pre | CFA, SNI, pSNL-SNI | Hyperalgesia (mechanical, hot, & cold) | None (PWT, Day 5, 10, 15) | | | |
| | | | Kv7.2, Navi.8, Oprm1, Kv4.3 | Prevent down regulation | | | |
| siRNA | 21-26 | SNL | Allodynia (tactile) | Reduce (up to 45%, Day 21 to 26) | Rat | 6-9 M | 72,73 |
| | | | Hyperalgesia (mechanical) | Reduce (up to 65%, Day 21 to 26) | | | |
| | | | Chrm2 | Restores mRNA [2x compared to control siRNA on Day 5] | | | |
| | | | Muscarine analgesia (tactile & mechanical) | Restores (PWT) | | | |

Intermediate psycological stress (IPS); Intermittent cold stress (ICS); Paw withdrawal threshold (PWT)

We recognize the studies presented in Table 12 reveal a discrepancy in the reduction in hypersensitivity between the mouse conditional knockout (cKO) study (complete knockout), which showed no hypersensitivity and no downregulation of REST target genes after injury (Table 12), and the rat siRNA knockdown study, which only partially reduced allodynia (up to 45%) and hyperalgesia (up to 65%) after injury. We believe the knockout effect is more potent than siRNA knockdown, because the bioavailability of siRNAs is limited by their size (>13,000 kD) and poor cellular trafficking, due to endosomal entrapment.

We are aware that the studies in Table 12 lack rigor in that power analysis was not done to establish the number of animals per group and the animal numbers were low which makes statistical analysis questionable. Some of the studies used the less predictive partial sciatic nerve ligation (pSNL) model, versus the preferred spared nerve injury (SNI) chronic pain model. The majority of these studies only assess males. However, despite these shortcomings, the outcomes of the studies are consistent and, therefore, support our proposed in vivo efficacy assessment of drug for the treatment of chronic pain. Furthermore, because REST activity is highly conserved in mammals, we believe these studies provide strong proof-of-concept support to test modulation of REST in humans.

We discovered that REST is targeted for degradation through phosphorylation of its serines 861 and 864. REST is stabilized by dephosphorylation of these sites by the C-terminal domain small phosphatase 1 (CTDSP1)[2-4]. Like REST, CTDSP1 is expressed in nonneuronal tissues where it contributes to neural gene silencing via its interaction with REST. We concluded that inhibition of CTDSP1 would be sufficient to promote REST degradation and stimulate gene expression. In support of this conclusion, we have demonstrated that knockdown of CTDSP1 in mesenchymal progenitor cells (MPCs) and nerves causes expression of REST target genes and axonal regeneration[76]. We leveraged our mechanistic understanding of the REST-CTDSP1 interaction to develop a cyclic phosphomimetic peptide encompassing the relevant regulatory region of REST[77]. The REST phosphomimetic peptide (RPP) has several pharmacologic attributes. It is highly stable due to its cyclic structure and D-amino acid composition (e.g., SEQ ID NO: 9, 12, 13, 14, 16, 17, and 68-117). It has low pM binding affinity exceeding that of most antibodies (FIGS. 2 & 3), suggesting a low risk of off-target effects. Its small size (<3.5 kD) indicates it should have bioavailability approaching that of a small molecule drug. Our preliminary data shows that our mimetic inhibits the activity of CTDSP1, reduces REST protein levels, and results in the expression of neural genes needed for proper neuronal activity[77].

Figure 11:
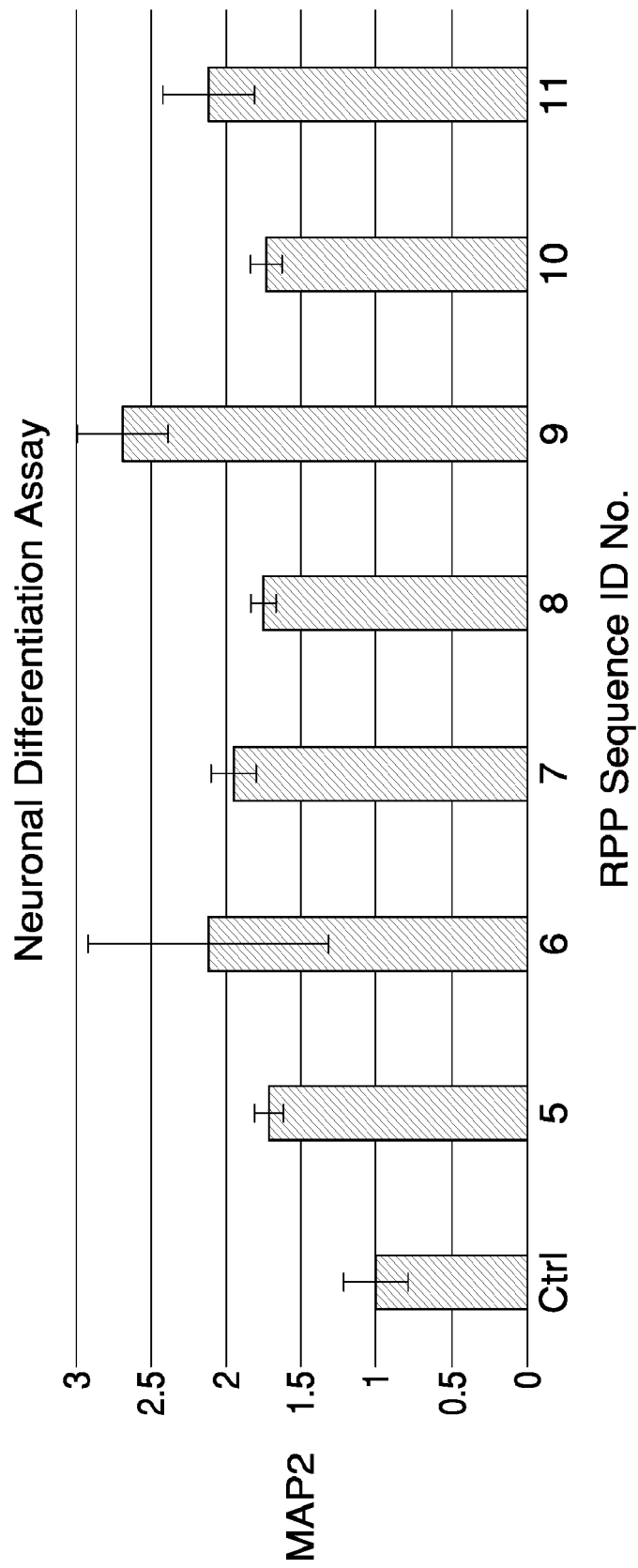
FIG. 11. iPSCs (neural stem cells (NSC)-NL5) were dosed with one of the RPP sequences (3 μM) or water control shown below. After 7 days in culture, cells were assessed for neuronal differentiation using the Microtubule Associated Protein 2 (MAP2) neuronal marker (normalized to DAPI). Media and variants were replaced on Day 3. MAP2 levels are relative to control in the bar graph (standard deviation n=4).

Most importantly, our approach is predicted to be safe and effective for the following reasons: 1) Our drug is selective for nuclear targets primed for regenerative response, such as after nerve injury. The basal organization of chromatin does not permit the epigenetic "writing" of a new set of instructions; nerve injury however, triggers a concerted, widespread, and transient nucleosome reorganization, a Genomic Transient Intermediate State (GTIS): a temporary nucleosomal architecture favorable for epigenetic reprograming for the necessary response[78-81]. 2) Our drug has very high binding affinity (low pM) and therefor will not have off target affects (FIGS. 2 & 3). 3) We are proposing a brief treatment period of less than 1 month duration. The basis for our short treatment period is that REST is the gate keeper for terminal differentiation of neurons[64,82], a process which irreversibly commits a cell to that lineage[83]. Neural progenitors, which have epigenetic similarities to neurons in a chronic pain state[63], because they are also in a GTIS, terminally differentiate after a few days of induction. Consistently, we have shown the RPP can induce neuronal differentiation (measured by MAP2 positive cells, a marker of neuronal differentiation) within 7 days (FIGS. 11, 12, and 13). Once the process has been started and the cell has been committed, there is no need for further treatment. Therefore, we expect the pain relief achieved through this early treatment period to be durable. 4) We have shown our drug is not toxic to neurons in an ex vivo DRG neuron toxicity assay measuring necrosis (FIG. 17). 5) REST and CTDSP1 are primarily involved in neurodevelopment, therefore, we predict inhibiting their activity in injured, adult cells will be well tolerated. 6) The safety of peptide drugs has made them an attractive therapeutic strategy. Currently, there are more than 68 marketed peptide drugs with global sales exceeding $14.7 billion, and 140 are in clinical development[84,85].

Innovation

First-in-class drug candidate. We have developed the first drug to target a transcriptional repressor of neuronal genes, REST. The published literature show that REST expression contributes to chronic pain (Table 12). After PNI, REST and CTDSP1 expression is increased in both the peripheral (FIG. 18) and central nervous systems resulting in dysfunction[7-9]. Several published studies in rodents have shown that blocking REST alleviates chronic pain[60,72-74].

Innovative drug design. We have developed a cyclic phosphomimetic cell penetrating peptide that destabilizes REST by inhibiting CTDSP1[3], the phosphatase that protects REST from degradation, allowing for the expression of neural-specific genes. Like REST, expression of CTDSP1 is restricted to nonneuronal cell types, except after neuronal injury. Our inhibitor is novel in that it directly targets a transcriptional checkpoint that immediately regulates the genes necessary to induce regeneration. It overcomes challenges to targeting transcription factors and to creating therapeutics against serine phosphatases. Regarding the latter, other approaches have focused on phosphoprotein phosphatases (PPPs), and the metal-dependent protein phosphatases (PPMs)[86]. However, CTDSP1 is a haloacid dehalogenase (HAD) which uses two catalytic aspartic acids instead of relying solely on a metal ion for activity[87]. This catalytic site is amenable to specific inhibition as demonstrated by the success in developing therapeutics against similar enzymes, such as HIV-1 protease[88-91]. Finally, CTDSP1 has a proline dependent substrate preference, not found in other serine phosphatases, which we have exploited to improve the binding and stability of our drug.

PRELIMINARY DATA. REST represses gene expression by binding to the chromatin at repressor element-1 (RE-1) sites near the regulatory regions of neuronal genes, including ion channels, growth factors, and axonal-guidance proteins[1]. Therefore, before stem cells, such as neural progenitor cells (NPCs), can terminally differentiate, they must first target REST for degradation to express the required neuronal genes[64]. REST is protected from degradation by CTDSP1, which is both necessary and sufficient to prevent neuronal gene expression[2]. Dominant-negative CTDSP1, which can bind phosphorylated targets but cannot catalyze dephosphorylation, induces terminal differentiation of P19 stem cells[92].

We have previously shown that the interaction between CTDSP1 and REST is dependent on phosphorylation of REST serines 861 and 864 by the MAP kinase, ERK2, and that mutation of these serines to alanine increases REST stability[2-4]. We surmised that a non-hydrolysable phosphomimetic of this REST regulatory region could slow down CTDSP1 activity and promote REST degradation. To test our hypothesis, we developed a REST Phosphomimetic Peptide or RPP[77] to assess dose-dependent effects on REST and REST-targets. The RPP contains amino acids 858 to 870 from REST with serine 861 and 864 mutated to glutamates, which can mimic both the shape and overall charge of phosphoserine. To the C-terminus, we fused an arginine-rich cell-penetrating peptide and endosomal exit sequence derived from HIV-Tat and HA2, respectively, which are used to deliver peptides and proteins into cultured mammalian cells and live organisms and facilitate crossing of the blood-brain barrier (BBB)[93-96].

Figure 6:
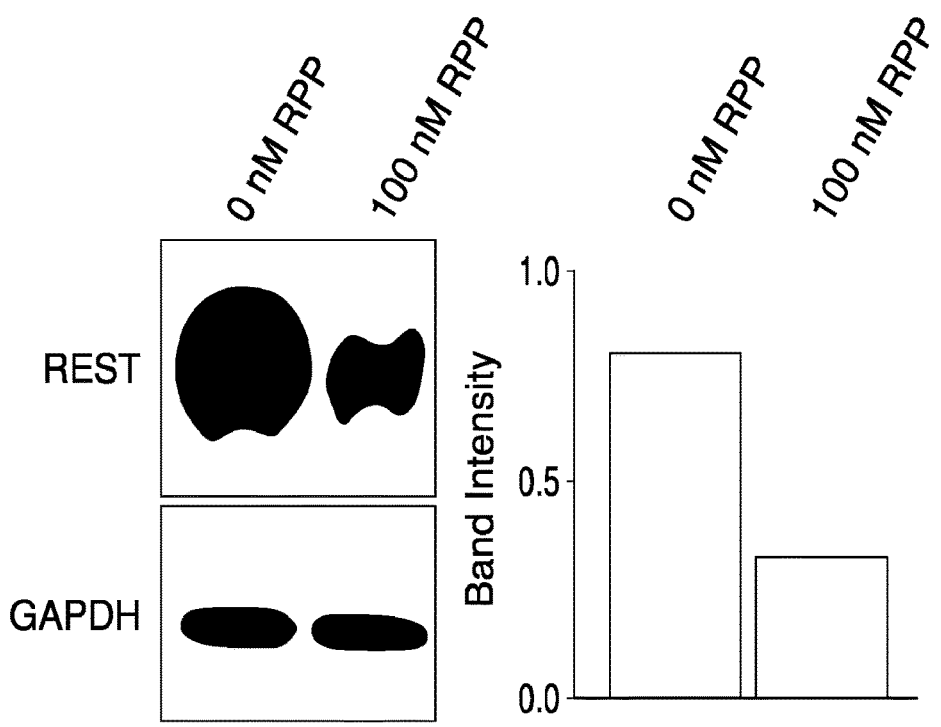
FIG. 6. RPP reduces REST protein levels. (Left) Western blot showing exogenously expressed REST protein levels in HEK293 cells after treatment with vehicle or 100 nM FLAG-RPP-CPP (SEQ ID NO: 4) for 4 hours. The blot was probed with anti-REST (Millipore-Sigma, 07-579) and anti-GAPDH. (Right) Bar graph showing 100 nM FLAG-RPP-CPP decreased REST protein levels 58%. Band intensity was calculated by measuring the area of gel peaks using ImageJ.

We investigated if RPP could decrease REST protein (FIG. 6). In the left panel, the Western blot (WB) shows that RPP decreased REST (exogenous+endogenous) levels in HEK cells. In the right panel, quantification of total REST protein (exogenous+endogenous) levels by WB analysis shows an overall decrease of 58.3% in the RPP dosed HEK cells (FIG. 6).

Figure 1:
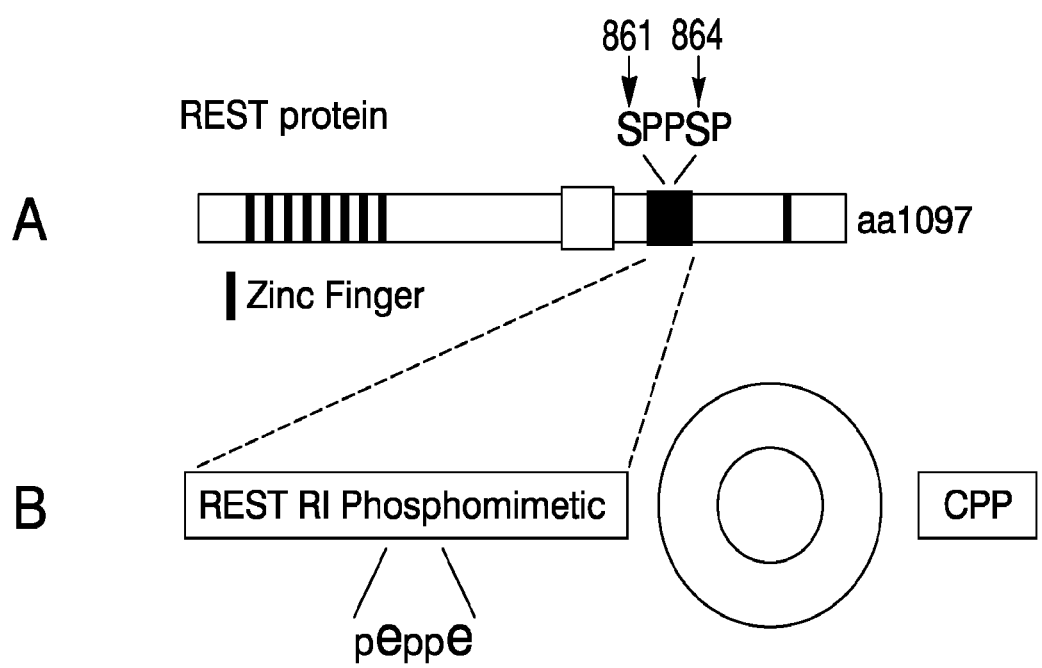
FIG. 1. (A) Full length REST protein showing the location of the CTDSP1 binding site. Figure discloses SEQ ID NO: 347. (B) The retro inverted (RI) REST phosphomimetic peptide integrated with a cell penetrating peptide in a cyclic format. Figure discloses SEQ ID NO: 348.
Figure 2:
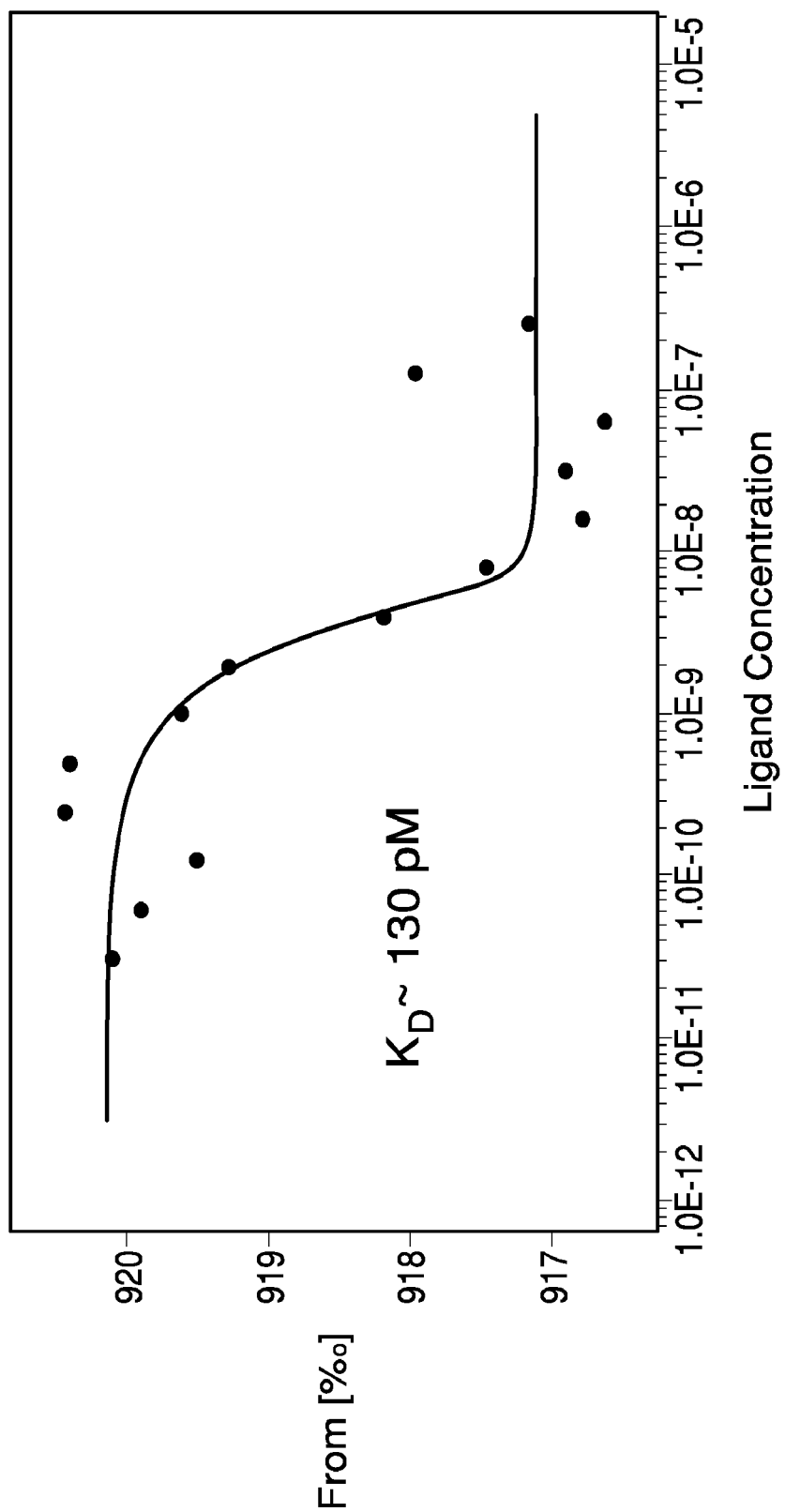
FIG. 2. Binding affinity of the REST phosphomimetic peptide (RPP) for CTDSP1 was measured using the Monolith (NanoTemper). The affinity of RPP (Table 4; SEQ ID NO: 165) for CTDSP1 (Table 2; SEQ ID NO:163) is approximately 130 pM. Binding was assessed by fluorescently labelling the His tag on CTDSP1 (40 nM) with RED-tris NTA dye (20 nM) and measuring the change in fluorescents when RPP (up to 0.5 pM) is bound.
Figure 3:
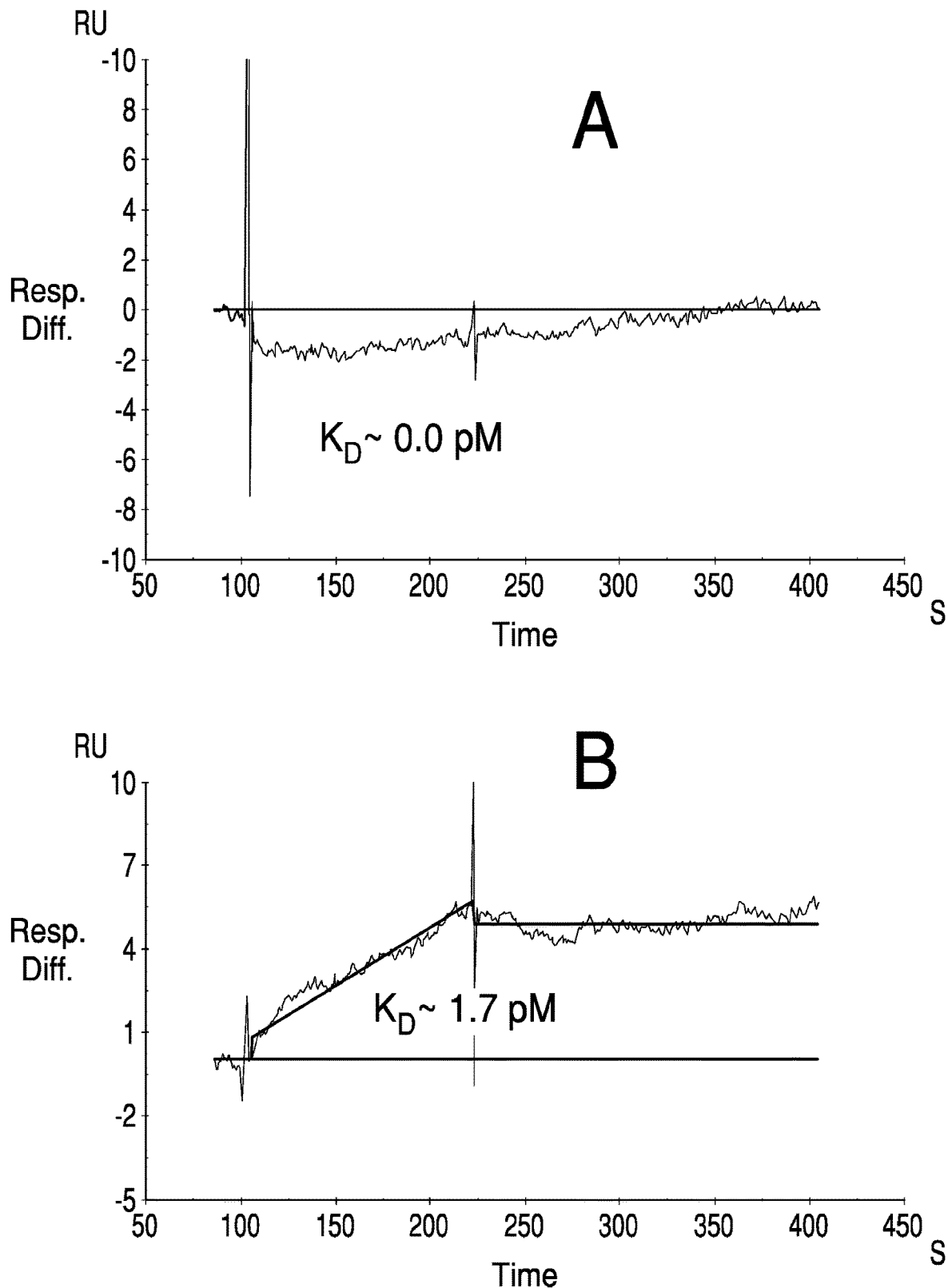
FIG. 3. Binding affinity of the RPP for CTDSP1 was measured using the Biacore (GE Heathcare Life Sciences). CTDSP1 (Table 2; SEQ ID NOS: 163) was immobilized on a CM5 sensor chip (GE Healthcare Life Sciences) and binding affinity of (A) GST control or (B) RPP (Table 4; SEQ ID NO: 165) was measured.

In an in vitro binding assay, RPP had low pM affinity for CTDSP1, with a slow off rate (FIGS. 2 & 3). In an in vitro assay of phosphatase inhibition, RPP inhibited its target, CTDSP1, at low nM concentrations, but did not inhibit off target PP5, PP1, PPM1H, PPM1A, or PP3CA activity at 10 μM (FIG. 26). In a cell permeability and stability assay in MPCs, RPP translocated into the nucleus (FIG. 4 and FIG. 5), which is consistent with the localization profile of both REST and CTDSP1[92,97]. RPP levels remained stable after 6 days in culture.

Figure 8:
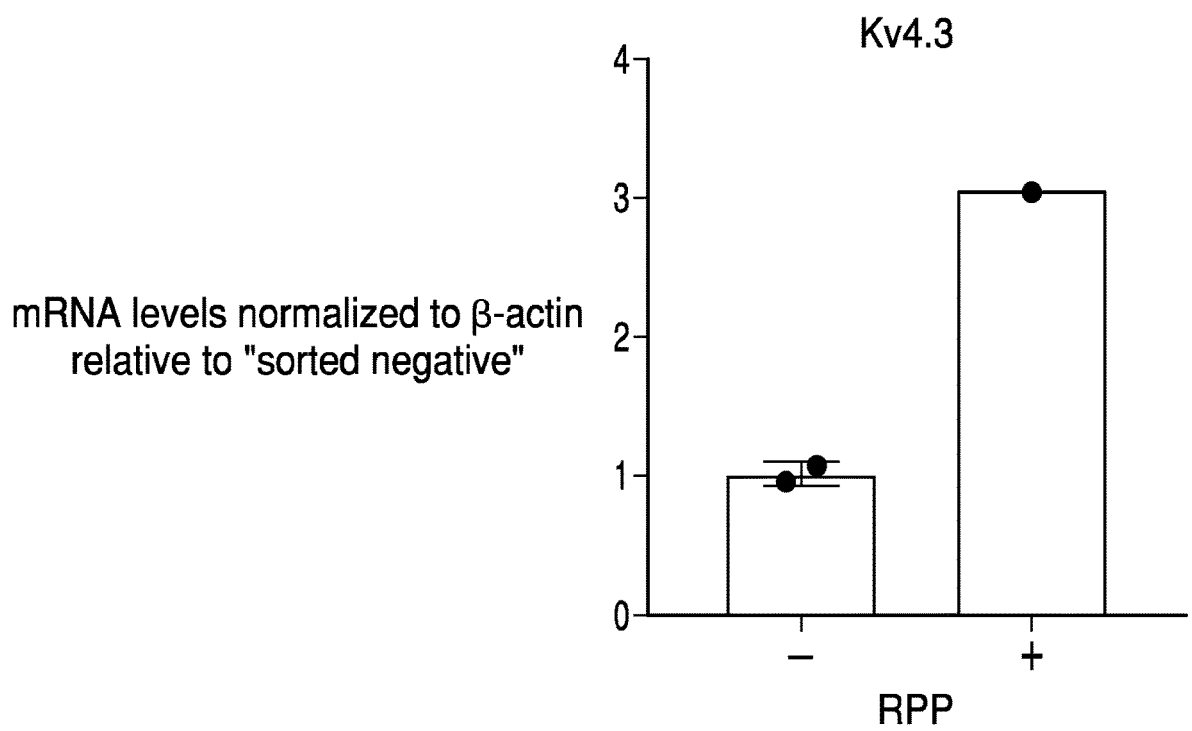
FIG. 8. mRNA levels of $K_V4.3$ in NBFL cells 48 h after CTDSP1 inhibition. Cells were transfected with a plasmid expressing RPP (SEQ ID NO: 1) with GFP (+) or a control peptide with GFP (−). 24 hours after transfection, cells were sorted based on fluorescence intensity. Error bars represent standard deviation, n=2.

It has been established by that blocking REST in rodent chronic pain models, prevents downregulation of Nav1.8, $K_V4.3$, $K_V7.2$, and Oprm1 which are implicated as the cause of hyperalgesia and allodynia (Table 12). Based on these studies, we tested whether blocking CTDSP1 could stimulate the expression of REST target genes associated with chronic pain. We have also shown that NBFL cells transfected with RPP (without HIVTAT-HA2) or dosed with linear or cyclic RPP evoke an increase (2-fold and up to 4-fold, respectively) in $K_V4.3$ mRNA (FIGS. 8 & 9c).

We found that 3 μM RPP (SEQ ID NOS: 5-11) increased human neural progenitor cell (iPSC) differentiation by 2- to 2.7-times as measured by MAP2 (mature neuron marker) expression normalized to DAPI (nucleus), compared to control (FIG. 11), and 1 μM RPP (SEQ ID NO: 9 and 13) increased human neural progenitor cell (iPSC) differentiation as measured by TUJ1 (up to 36% and 3-times respectively) and MAP2 (up to 33% and 2-times respectively) (neuronal markers) expression normalized to DAPI (nucleus) (FIGS. 12 and 13). There was no increase in cell death compared to control (data not shown). The basis for using this screen is that eliminating REST in neural progenitor cells has been shown to induce neuronal differentiation[22], which is a readout for ensemble derepression of neuronal genes.

In a preliminary assessment of efficacy and toxicity, RPP was assessed at 0, 1, 3, or 10 μM for 48 hours in an ex vivo culture of whole DRG neurons for its potential to induce expression of $K_V4.3$ (FIG. 14), $K_V7.2$ (FIG. 14), Nav1.8 (FIGS. 14 and 15) and OPRM1 (FIG. 14) and cause neurotoxicity (FIG. 17). At 3 μM SEQ ID NO: 12 induced $K_V4.3$, $K_V7.2$, Nav1.8, and OPRM1 approximately 0-, 6-, 3-, and 3-times, respectively, compared to control (FIG. 14). At 3 μM SEQ ID NOS: 13 and 14 induced Nav1.8 approximately 6- and 13-times, respectively (FIG. 15). At 10 μM SEQ ID NO: 12 induced $K_V4.3$, $K_V7.2$, Nav1.8, and OPRM1 approximately 2-, 7-, 5-, and 4-times, respectively (FIG. 14). In a lactate dehydrogenase LDH cytotoxicity assay, RPP sequence ID NO: 12 showed no toxicity at 0, 1, 3, or 10 μM (FIG. 16). As expected, the positive control (triton, n=6)) was toxic (FIG. 17).

Epilepsy—Epilepsy is uncontrolled electrical activity in the brain which causes confusion, loss of consciousness, and uncontrolled movements[98]. It is the result of dysregulation of ion channels and receptors including SCN1A (Nav1.1), SCN2A (Nav1.2), SCN1B (Nav beta subunit 1), KCNQ2 ($K_V7.2$), and KCNQ3 ($K_V7.3$), which are targets of REST repression[14,99]. The underlying cause of epilepsy is an increase in REST levels in the nucleus of neurons[1000].

Diabetes—Pancreatic beta cells and neurons share similar transcriptional pathways during their differentiation program, which involve the elimination of REST[101]. Down regulation of REST target genes by over expression of REST in beta cells decreases insulin secretion[102-103].

Alzheimer's disease—In Alzheimer's disease, acetylcholine and choline acetyltransferase (ChAT), a transferase enzyme necessary for the synthesis of acetylcholine, are very low. The decrease in concentration of this enzymes contributes to the memory and cognition deficits associated with Alzheimer's. Increased REST levels in the brain suppress ChAT[16].

Huntington's disease—In Huntington's disease, the translocation of REST from the cytoplasm to the nucleus of neurons is thought to be the cause of neuronal degeneration associated with the disease[104-106].

Brain cancers, including glioblastoma multiforme—Brain cancers, including glioblastoma multiforme (GBM), originate from brain tumor initiating cells (BTICs), which are cancerous stem cells that display a robust capacity for self-renewal and can become cancerous tumors. These cells are resistant to radiation and chemotherapy and become proliferative months after treatment[107-109]. The RPP (SEQ ID NOS: 1 and 15 through 17) or $RPP_V$ (SEQ ID NOS: 18 through 117) peptide fused to a CPP (SEQ ID NOS: 118 through 137 and 140 through 159) has the potential to prevent tumors from forming by terminally differentiating BTICs. Once cells have terminally differentiated they can no longer proliferate and seed new tumors[110]. It is important to state that terminal differentiation is not the same as the differentiation achieved by other methods, such as by targeting chromatin remodeling with inhibitors of histone deacetylases (HDACs). Inhibition of these enzymes alters gene expression indiscriminately and cannot achieve the permanent terminal differentiation that is required to prevent recurrent GBM. Terminal differentiation of BTIC into neurons is blocked at a single checkpoint by REST. The importance of this repressor in maintaining oncogenicity is highlighted by the observation that increased levels of REST correlate with both recurrence of GBM[111-113] and shorter periods of disease free survival[122,114]. The reliance of BTICs on REST to maintain their oncogenicity creates an opportunity for therapeutic intervention. REST is targeted for degradation through phosphorylation of serines 861 and 864, and that these serines are kept in a dephosphorylated state by the C-terminal domain small phosphatase, CTDSP1[2]. Therefore, inhibition of CTDSP1 with the RPP (SEQ ID NOS: 1 and 15-17) or $RPP_V$ (SEQ ID NOS: 18 through 117) that is fused to a CPP (SEQ ID NOS: 118 through 137 and 140 through 159) should release the REST-brake on terminal differentiation and prevent the recurrence of GBM and other brain tumors.

Pancreatic cancer—REST levels are high in advance stage, metastatic positive pancreatic cancer cells[115]. Pancreatic cancer patients with high REST levels in their tumors have worse survival rates[115]. In vitro functional experiments show that knockdown of REST suppressed proliferation, migration, invasion and epithelial-mesenchymal transition of pancreatic cancer cells (AsPC-1 and PANC-1)[115]. In vivo experiments (a subcutaneous BALB/c nude mouse model and a superior mesenteric vein injection BALB/c nude mouse model) show that knockdown of REST suppressed growth and metastasis of xenografted tumors[115]. Therefore, inhibiting REST improves patient outcomes for those disorders. Accordingly, the present invention also relates to methods for inhibiting REST in a cell. In general, the method comprises contacting a cell with the RPP (SEQ ID NOS: 1 and 15 through 17) or $RPP_V$ (SEQ ID NOS: 18 through 117) peptide fused to a CPP (SEQ ID NOS: 118 through 137 and 140 through 159). For example, it can be exposing a cell for a sufficient amount of time for the RPP-(SEQ ID NOS: 1 and 15 through 17) or $RPP_V$ (SEQ ID NOS: 18 through 117) fused to a CPP (SEQ ID NOS: 118 through 137 and 140 through 159) to enter the cell and have an effect on REST activity. The method can be practiced either in vitro or in vivo. Where practiced in vitro, the method can be used to study the activity of REST, to test other compounds for the ability to supplement or antagonize the effects of the RPP- (SEQ ID NOS: 1 and 15 through 17) or $RPP_V$ (SEQ ID NOS: 18 through 117) fused to a CPP (SEQ ID NOS: 118 through 137 and 140 through 159) on REST, or for any other reason of importance to a researcher. When practiced in vivo, the method can be used as a method of treating a subject for one or more diseases or disorders associated with REST. According to the method of this aspect of the invention, preferably, activity of REST is decreased. The step of contacting a cell can be any action that causes the agent to physically contact one or more target cells. Thus, it can be by way of adding the agent directly to an in vitro culture of cells to be contacted, and allowing the agent sufficient time to diffuse through the media and contact at least one cell. Likewise, it can be through addition of the agent to cells in an aqueous environment. Alternatively, it can be by way of administering the agent to a subject via any acceptable administration route, and allowing the body of the subject to distribute the agent to the target cell through natural processes. Thus, the in vivo methods can be methods of localized or systemic delivery of the agent to a cell in animals, including all mammals and humans in particular. According to this aspect, the RPP (SEQ ID NOS: 1 and 15 through 17) or $RPP_V$ (SEQ ID NOS: 18 through 117) fused to a CPP (SEQ ID NOS: 118 through 137 and 140 through 159) can be used to treat a subject therapeutically or prophylactically, and to prepare a composition for use in treating.

In yet another embodiment, the invention provides a method of treating a subject suffering from or at risk of suffering from a disease or disorder involving REST. In general, the method comprises administering the RPP (SEQ ID NOS: 1 and 15 through 17) or RPP$_V$ (SEQ ID NOS: 18 through 117) fused to a CPP (SEQ ID NOS: 118 through 137 and 140 through 159), in an amount sufficient to affect the amount or activity of REST in the subject. In certain aspects, the binding of the RPP (SEQ ID NOS: 1 and 15 through 17) or RPP$_V$ (SEQ ID NOS: 18 through 117) fused to a CPP (SEQ ID NOS: 118 through 137 and 140 through 159) to CTDSP1 results in inhibition of REST activity in a cell. In general, the method comprises administering a sufficient amount of the RPP (SEQ ID NOS: 1 and 15 through 17) or RPP$_V$ (SEQ ID NOS: 18 through 117) fused to a CPP (SEQ ID NOS: 118 through 137 and 140 through 159) for a sufficient time to inhibit REST activity. Often, the amount administered and the amount of time is adequate to see a change in one or more clinical symptoms of a disease or disorder, or to stop progression of a disease or disorder from reaching a stage where one or more clinical symptoms are seen. According to this aspect, agent can be used to treat a subject therapeutically or prophylactically, and to prepare a composition for use in treating.

In one embodiment, the present invention provides methods for treating, alleviating, or ameliorating traumatic brain injury, chronic pain, peripheral nerve injury, epilepsy, diabetes, Alzheimer's disease, Huntington's disease, brain tumors (including glioblastoma multiforme), or pancreatic cancer in a subject. The terms "treating" or "alleviating" or "ameliorating" and similar terms used herein, include prophylaxis and full or partial treatment. The terms may also include reducing symptoms, ameliorating symptoms, reducing the severity of symptoms, reducing the incidence of the disease, or any other change in the condition of the patient, which improves the therapeutic outcome. The methods involve administering to a subject suffering from traumatic brain injury, chronic pain, peripheral nerve injury, epilepsy, diabetes, Alzheimer's disease, Huntington's disease, brain tumors (including glioblastoma multiforme), or pancreatic cancer in an animal, or a subject in need of treatment for traumatic brain injury, chronic pain, peripheral nerve injury, epilepsy, diabetes, Alzheimer's disease, Huntington's disease, brain tumors (including glioblastoma multiforme), or pancreatic cancer in an animal, the RPP (SEQ ID NOS: 1 and 15 through 17) or RPP$_V$ (SEQ ID NOS: 18 through 117) fused to a CPP (SEQ ID NOS: 118 through 137 and 140 through 159).

The administration of the RPP (SEQ ID NOS: 1 and 15 through 17) or RPP$_V$ (SEQ ID NOS: 18 through 117) fused to a CPP (SEQ ID NOS: 118 through 137 and 140 through 159) to the subject can be through any known and acceptable route. Such routes include, but are not necessarily limited to, oral, via a mucosal membrane (e.g., nasally, via inhalation, rectally, intrauterally or intravaginally, sublingually), intravenously (e.g., intravenous bolus injection, intravenous infusion), intraperitoneally, and subcutaneously. Administering can likewise be by direct injection to a site (e.g., organ, tissue) containing a target cell (i.e., a cell to be treated). Furthermore, administering can follow any number of regimens. It thus can comprise a single dose or dosing of the drug, or multiple doses or dosings over a period of time. Accordingly, treatment can involve repeating the administering step one or more times until a desired result is achieved. In embodiments, treating can continue for extended periods of time, such as weeks, months, or years. Those of skill in the art are fully capable of easily developing suitable dosing regimens for individuals based on known parameters in the art. The methods thus also contemplate controlling, but not necessarily eliminating, the disease or disorder. The preferred routes of administration in accordance with the present invention are oral and via a mucosal membrane.

The amount to be administered varies depending on the subject, stage of the disease, age of the subject, general health of the subject, and various other parameters known and routinely taken into consideration by those of skill in the medical arts. As a general matter, a sufficient amount of the agent will be administered in order to make a detectable change in the symptom of the subject. Suitable amounts are disclosed herein, and additional suitable amounts can be identified by those of skill in the art without undue or excessive experimentation.

The RPP (SEQ ID NOS: 1 and 15 through 17) or RPP$_V$ (SEQ ID NOS: 18 through 117) fused to a CPP (SEQ ID NOS: 118 through 137 and 140 through 159) is administered in a form that is acceptable, tolerable, and effective for the subject. Numerous pharmaceutical forms and formulations for biologically active agents are known in the art, and any and all of these are contemplated by the present invention. Thus, for example, the agent can be formulated in oral solution, a caplet, a capsule, an injectable, an infusible, a suppository, a lozenge, a tablet, a cream or salve, an inhalant, and the like.

Those of ordinary skill in the art will readily optimize effective dosages and administration regimens as determined by good medical practice and the clinical condition of the individual subject.

The frequency of dosing will depend on the pharmacokinetic parameters of the compounds and the routes of administration. The optimal pharmaceutical formulation will be determined by one of skill in the art depending on the route of administration and the desired dosage. Such formulations may influence the physical state, stability, rate of in vivo release and rate of in vivo clearance of the administered agents. Depending on the route of administration, a suitable dose is calculated according to body weight, body surface areas or organ size. The availability of animal models is particularly useful in facilitating a determination of appropriate dosages of a given therapeutic. Further refinement of the calculations necessary to determine the appropriate treatment dose is routinely made by those of ordinary skill in the art without undue experimentation, especially in light of the dosage information and assays disclosed herein as well as the pharmacokinetic data observed in animals or human clinical trials.

Typically, appropriate dosages are ascertained through the use of established assays for determining blood levels in conjunction with relevant dose response data. The final dosage regimen will be determined by the attending physician, considering factors which modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment for specific diseases and conditions. Those studies, however, are routine and within the level of skilled persons in the art. Typical dosage may be about 0.6 mg (0.01 mg/kg) to about 60 g (1 g/kg) weekly (in human), more preferably monthly.

It will be appreciated that the peptides, compositions and treatment methods of the invention are useful in fields of human medicine and veterinary medicine. Thus, the subject to be treated is a mammal, such as a human or other mammalian animal. For veterinary purposes, subjects include for example, farm animals including cows, sheep, pigs, horses and goats, companion animals such as dogs and cats, exotic and/or zoo animals, and laboratory animals including mice, rats, rabbits, guinea pigs and hamsters.

The RPP (SEQ ID NOS: 1 and 15 through 17) or $RPP_V$ (SEQ ID NOS: 18 through 117) fused to a CPP (SEQ ID NOS: 118 through 137 and 140 through 159) may be administered to a subject animal, preferably mammals, such as humans, in need thereof as a pharmaceutical or veterinary composition, such as tablets, capsules, solutions, or emulsions. The RPP (SEQ ID NOS: 1 and 15 through 17) or $RPP_V$ (SEQ ID NOS: 18 through 117) fused to a CPP (SEQ ID NOS: 118 through 137 and 140 through 159) can be present in compositions containing other ingredients. Non-limiting examples of compositions appropriate for the present invention are pharmaceutical compositions, such as in the form of tablets, pills, capsules, caplets, multiparticulates (including granules, beads, pellets and micro-encapsulated particles); powders, elixirs, syrups, suspensions, and solutions. Pharmaceutical compositions will typically comprise a pharmaceutically acceptable diluent or carrier. Pharmaceutical compositions are preferably adapted for administration parenterally (e.g., orally). Orally administrable compositions may be in solid or liquid form and may take the form of tablets, powders, suspensions, and syrups, among other things. Optionally, the compositions comprise one or more flavoring and/or coloring agents. In general, therapeutic and nutritional compositions may comprise any substance that does not significantly interfere with the action of the agent on the subject.

Pharmaceutically acceptable excipients or carriers suitable for use in such compositions are well known in the art of pharmacy. The compositions of the invention may contain 0.01-99% by weight of the agent. The compositions of the invention are generally prepared in unit dosage form. The excipients used in the preparation of these compositions are well-known in the art.

Further examples of product forms for the composition are food supplements, such as in the form of a soft gel or a hard capsule comprising an encapsulating material selected from the group consisting of gelatin, starch, modified starch, starch derivatives such as glucose, sucrose, lactose, and fructose. The encapsulating material may optionally contain cross-linking or polymerizing agents, stabilizers, antioxidants, light absorbing agents for protecting light-sensitive fills, preservatives, and the like.

In general, the term carrier may be used throughout this application to represent a composition with which the agent may be mixed, be it a pharmaceutical carrier, foodstuff, nutritional supplement or dietary aid. The materials described above may be considered carriers of the agent for the purposes of the invention. In certain embodiments of the invention, the carrier has little to no biological activity, particularly on REST.

Without further description, it is believed that one of ordinary skill in the art can, using the preceding description and the following illustrative examples, make and utilize the compounds of the present invention and practice the claimed methods. The following examples are given to illustrate the present invention. It should be understood that the invention is not to be limited to the specific conditions or details described in the examples.

Example 1—his-CTDSP1 Plasmid Construction

The codon optimized (using IDT codon optimization tool) CTDSP1 gene was cloned into the pBAD-HisA plasmid (Thermo Fisher Scientific). First, pBAD-HisA plasmid was amplified with primers P33 and P34 (Table 1) introducing HindIII and XhoI restriction sites. The PCR reaction (20 µL) was initially heated at 95° C. for 2.5 min followed by 30 cycles of denaturation at 94° C. for 15 sec., annealing at 55° C. for 15 sec. and extension at 72° C. for 6 min. Following amplification, the PCR fragment was gel-purified by the QIAGEN gel-band purification kit and digested with HindIII and XhoI restriction enzymes. All digested fragments were purified with a QIAGEN kit and ligated in appropriate combination using T4 DNA ligase (NEB) according to recommendations of the manufacturer.

TABLE 1

Primers used for plasmid construction

| Name | Sequence | SEQ ID NO: |
|---|---|---|
| Primers | | |
| P12 | AAATAAGCTTGTATATCTCCTTCTTAAAGTTAAACA | 269 |
| P14 | AATAACTCGAGAGATCCGGCTGCTAACAAAGC | 270 |
| P17 | ATAAGCTTTAATACGACTCACTATAGGGTTAACTTTAGTAAGGAGGACAGCTAA | 271 |
| P19 | GTGGTGATGGTGATGGTGACCTA | 272 |
| P20 | ATTATTCTCGAGTTAATAGCCGGTGCCGTGGTGATGGTGATGGTGACCTA | 273 |
| P21 | AAATACTCGAGTCGTTTTATCTGTTGTTTGTCGGT | 274 |
| P22 | AAATAAGCTTCTCTGAATGGCGGGAGTATGAAAA | 275 |
| P23 | CCGCGAATGGTGAGATTGAGAA | 276 |
| P24 | ACGCAAAAAGGCCATCCGTCAG | 277 |
| P28 | ATTATTCTCGAGTTAATAGCCGGTGCCTAAGCCGCTACCACCACGCCGACGCTGACGG | 278 |
| P31 | AAATAAGCTTATGGATAGTAGTGCGGTGATCA | 279 |

TABLE 1-continued

Primers used for plasmid construction

| Name | Sequence | SEQ ID NO: |
|---|---|---|
| P32 | ATTATTCTCGAGCTAGTGGTGATGGTGATGGT | 280 |
| P33 | AACTAAGCTTTTCCTCCTGTTAGCCCAAAAAAC | 281 |
| P34 | AATACTCGAGGCTGTTTTGGCGGATGAGAGAA | 282 |
| P35 | AAATCCATGGATAGTAGTGCGGTGATCA | 283 |
| P36 | AAATCATATGGATAGTAGTGCGGTGATCA | 284 |
| P37 | AATACTCGAGCTAGTGGTGATGGTGATGGTGAG | 285 |
| P38 | AATACTCGAGAGAGCCAGAACCAGATCCCGGA | 286 |
| P39 | TAAGCCGCTACCACCACGCCGAC | 287 |
| P40 | GGTGCAATTCCTAAAACTCCAGTACAATACTTACTGC | 288 |
| P41 | GTATTGTACTGGAGTTTTAGGAATTGCACCATTTTCCTC | 289 |
| P108 | AATACTCGAGTTATTTTGGAGGATGGTCGCCACCA | 290 |
| P109 | AATAAAGCTTATGGGATCCGGTTCTGGCTCAGGTTCTTCC | 291 |

Degenerate Primers

| | | |
|---|---|---|
| 11F | NAANCANCANTGNCANAGNAANATTGTGGTTCTGGCTCTGGTCGTAAAA | 292 |
| 12F | GNACNACNACNGCNAANGGNAANTTGTGGTTCTGGCTCTGGTCGTAAAA | 293 |
| 13F | GNANCACNANTGCNANAGGNANATTGTGGTTCTGGCTCTGGTCGTAAAA | 294 |
| 14F | NAACNANCACNGCNAANGNAAANTTGTGGTTCTGGCTCTGGTCGTAAAA | 295 |
| 15F | GAANCANCANTGNCANAGNAANATTGTGGTTCTGGCTCTGGTCGTAAAA | 296 |
| 16F | GAACNACNACNGCNAANGGNAANTTGTGGTTCTGGCTCTGGTCGTAAAA | 297 |
| 17F | GAANCACNANTGCNANAGGNANATTGTGGTTCTGGCTCTGGTCGTAAAA | 298 |
| 18F | GAACNANCACNGCNAANGNAAANTTGTGGTTCTGGCTCTGGTCGTAAAA | 299 |
| 19F | GAANCANCACTGCCANAGNAAAATTGTGGTTCTGGCTCTGGTCGTAAAA | 300 |
| 20F | NAACCACCANTGNCAAAGGAANATTGTGGTTCTGGCTCTGGTCGTAAAA | 301 |
| 21F | GAANCACNACTGCCANAGGNAAATTGTGGTTCTGGCTCTGGTCGTAAAA | 302 |
| 22F | GNACCACCANTGCNAAAGGAANATTGTGGTTCTGGCTCTGGTCGTAAAA | 303 |
| 11R | TGNTGNTTNCANATNTTNGGNACACATTTAGCTGTCCTCCTTACTAAAGTT | 304 |
| 12R | TNGTNGTNCCNGANCTNCGNTACACATTTAGCTGTCCTCCTTACTAAAGTT | 305 |
| 13R | TGNTNGTTNCNGATNTNCGGNACACATTTAGCTGTCCTCCTTACTAAAGTT | 306 |
| 14R | TNGTGNTNCCANANCTTNGNTACACATTTAGCTGTCCTCCTTACTAAAGTT | 307 |
| 15R | TGNTGNTTCCANATNTTNGGNACACATTTAGCTGTCCTCCTTACTAAAGTT | 308 |
| 16R | TNGTNGTTCCNGANCTNCGNTACACATTTAGCTGTCCTCCTTACTAAAGTT | 309 |
| 17R | TGNTNGTTCCNGATNTNCGGNACACATTTAGCTGTCCTCCTTACTAAAGTT | 310 |
| 18R | TNGTGNTTCCANANCTTNGNTACACATTTAGCTGTCCTCCTTACTAAAGTT | 311 |
| 19R | TGGTGNTTNCAGATCTTNGGNACACATTTAGCTGTCCTCCTTACTAAAGTT | 312 |
| 20R | TGNTGGTTCCANATNTTCGGTACACATTTAGCTGTCCTCCTTACTAAAGTT | 313 |
| 21R | TGGTNGTTNCAGATCTNCGGNACACATTTAGCTGTCCTCCTTACTAAAGTT | 314 |
| 22R | TGNTGGTTCCNGATNTTCGGTACACATTTAGCTGTCCTCCTTACTAAAGTT | 315 |

N = any nucleotide

Ligated fragments were transformed in 10G chemically competent cells (Lucigen) according to manufacturer's protocol. Transformed cells were plated on LB plates containing 50 µg/mL ampicillin and incubated overnight at 37° C. Colonies were tested for the presence of the insert by colony PCR. Colonies were picked and resuspended in 20 µl of sterile 0.9% sodium chloride solution. One µl of this solution was transferred to the PCR tube and amplified with Taq polymerase (New England Biolabs, cat #M0482S) and 30 µM of the flanking primers. Each PCR reaction (20 µL) was initially heated to 95° C. for 2.5 min followed by 30 cycles of denaturation at 94° C. for 15 sec., annealed at 55° C. for 15 sec., and extended at 72° C. for 1 min. Amplification products were visualized by agarose electrophoresis. Clones with the correct inserts were inoculated into the culture tubes containing 5 mL of LB with the appropriate antibiotic and incubated overnight at 37° C. Constructs were then purified using the Monarch Plasmid miniprep kit (NEB).

Example 2—Expression and Purification Methods for his-CTDSP1

His-CTDSP1 (Table 2; SEQ ID NO: 162): E. coli (10G strain Lucigen) with pBAD-CTDSP1 construct were incubated overnight at 37° C. with vigorous shaking. Then 4 mL of the night culture was added to 500 mL of LB media with 50 µg/mL ampicillin in a 1 L flask and incubated at 37° C. with shaking. When the culture's OD600 reached 0.4, we added arabinose to the final concentration of 0.02% and incubated 16 hours at 30° C. with shaking. Next morning, cells were spun down (Eppendorf centrifuge 5810R) at maximum speed and frozen at −80° C. When needed, cell pellets were removed from the freezer, incubated at room temperature, lysed with 4 mL of BPER protein lysis reagent (ThermoFischer) and purified protein with HisPur Cobalt Purification kit (ThermoFischer, Cat #90091) as described by the manufacturer.

TABLE 2

CTDSP1 Nucleotide and Protein Sequences

Nucleotide Sequence (SEQ ID NO: 162)
ATGGATAGTAGTGCGGTGATCACACAAATCTCCAAGGAGGAAGCCCGTGG
GCCGCTGCGGGGAAGGGTGATCAAAAATCGGCAGCTAGTCAAAAACCTC
GCTCTCGTGGGATACTTCATTCGCTGTTTTGCTGCGTCTGCCGCGATGAC
GGAGAAGCATTGCCTGCGCATTCAGGGGCGCCTTTACTTGTTGAGGAAAA
TGGTGCAATTCCTAAACAAACTCCAGTACAATACTTACTGCCGGAGGCAA
AGGCACAAGACAGTGATAAGATATGTGTAGTAATAGACTTAGATGAAACA
CTGGTACATTCGTCATTCAAACCTGTTAATAATGCGGATTTCATCATACC
TGTAGAAATCGACGGGGTTGTCCATCAGGTTTACGTCCTGAAGCGGCCTC
ATGTAGATGAATTTTTACAGCGGATGGGCGAGTTATTTGAATGTGTGCTG
TTTACAGCTAGTCTTGCCAAGTACGCGGATCCTGTCGCGGATTTGCTTGA
TAAGTGGGGTGCGTTTCGGGCGAGATTATTTCGCGAATCTTGCGTTTTTC
ACAGAGGTAACTACGTGAAGGACCTTAGTCGTCTGGGTAGAGATCTTAGA
AGAGTGCTGATCCTTGACAACAGCCCAGCCAGCTATGTCTTTCATCCGGA
TAACGCGATACCCGTGGCGTCTTGGTTCGACAATATGTCGGACACGGAGC
TGCATGACCTGTTGCCGTTCTTTGAGCAGTTGAGTCGCGTTGATGACGTT
TACTCGGTTTTGCGTCAACCCCGTCCGGGATCTGGTTCTGGCTCTCACCA
TCACCATCACCACTAG Protein Sequence (SEQ ID NO: 163)
MDSSAVITQISKEEARGPLRGKGDQKSAASQKPRSRGILHSLFCCVCRDD
GEALPAHSGAPLLVEENGAIPKQTPVQYLLPEAKAQDSDKICVVIDLDET
LVHSSFKPVNNADFIIPVEIDGVVHQVYVLKRPHVDEFLQRMGELFECVL
FTASLAKYADPVADLLDKWGAFRARLFRESCVFHRGNYVKDLSRLGRDLR
RVLILDNSPASYVFHPDNAVPVASWFDNMSDTELHDLLPFFEQLSRVDDV
YSVLRQPRPGSGSGSHHHHHH Linker and His tag are underlined Example 3—Developing Peptides with High Affinity to CTDSP1

Peptide candidates were generated using RNA display and protein evolution methods.

Construction of RNA display libraries. We've built 3 different libraries of RPP variants. In all libraries serines 861 and 864 were replaced by glutamates. Library 1 was built using primers P11 through P14 (Table 1). In library 1 each position of the REST peptide was mutated. It was estimated to have $1 \times 10^9$ variants. In library 2 (primers P14 through P18, Table 1), glutamates were not touched by the degenerate oligos. This library was expected to have $65 \times 10^6$ variants. In library 3, only one of the glutamates and every second codon was mutated. This library was expected to generate only 65000 variants.

In all 3 libraries, the RPP sequence (SEQ. ID NO: 1) was diversified by synthetic degenerate oligoes. Only one degenerate base was introduced per codon: either first or the second position which gave a choice or 4 amino acids. REST cassettes were amplified from pBAD constructs as two fragments: left and right, which were reunited by ligation (FIG. 27). The left fragment was amplified with flanking forward primer P23 (Table 1) and one of the reverse primers (11R trough 22R, Table 1).

The right fragment was amplified with one of the forward primers (1 IF through 22F, Table 1) and the reverse primer P24 (Table 1). The PCR reaction (20 µL) was initially heated at 95° C. for 2.5 min followed by 30 cycles of denaturation at 94° C. for 15 sec., annealing at 55° C. for 15 sec. and extension at 72° C. for 40 sec. Following amplification, PCR fragments were gel-purified by the QIAGEN gel-band purification kit, mixed and ligated with T4 DNA ligase. The ligation reaction contained 20 µl of 10× ligation buffer, 100 ng of fragment mix, 0.5 µl of 100 mM ATP, 1 µl of T4 DNA ligase (NEB cat #M0202S) and 1 µl of T4 polynucleotide kinase. The reaction mix was incubated at room temperature and used as a template for PCR with flanking primers P17 and P20 (Table 1) using program described above. PCR fragment was gel-purified by the QIAGEN gel-band purification kit and used as a template in the mRNA display experiments.

For quality control purposes, we cloned and sequenced a fraction of this library. An aliquot of this library was digested by HindIII and XhoI restriction enzymes, purified by QIAGEN kit and cloned in pBAD vector as described above for CTDSP1 gene. Individual clones were sequenced by GeneWiz to confirm that REST cassettes were successfully mutated and that majority of clones were ligated without frame-shift mutations.

In vitro transcription. RNA was translated from amplified libraries using RiboMAX Large Scale RNA Production System T7 (Promega, Cat #P1300) according to the manufacturers protocol and purified by RNeasy Mini Kit (Qiagen, Cat #74104)

Ligation of mRNA to DNA linker with puromycin. XL-PSO oligonucleotide was synthesized by IDT. The sequence of the oligonucleotide was: 5'-PsoC6-(uagccggug)$_{2'-OMe}$-AAAAAAAAAAAAAAAA-Spacer9-Spaser9-ACC-Puro-3' (SEQ ID NO: 330). For ligating this oligonucleotide to mRNA we mixed the following reagents in a PCR tube: 29.5 µl of RNAse-free water. 1 µl of 1 M HEPES-KOH, pH 7.6, 5 µl of 1 M KCl, 2 µl of 25 mM spermidine, 0.5 µl of 125 mM EDTA, 8 µl of mRNA from previous step and 4 µl of 100 mM of XL-PSO oligonucleotide. PCR tube was placed in the PCR machine, heated to 70° C. for 5 min and cooled to 25° C. at 0.1° C./s speed. Then we transferred the mixture to the 96-well plate on ice, put the 365-nm handheld UV lamp on top and irradiated the plate for 20 min. After that cross-linked RNA was purified by RNeasy Mini Kit (Qiagen, Cat #74104).

In vitro translation. Translation was performed using PUREexpress in vitro Protein Synthesis Kit (NEB, Cat #E6800S). We mixed the following reagents in a 1.5 ml tube: 20 µl of Solution A, 15 µl of solution B, 0.5 µl of RNAsin Plus, 4.5 µl of water and 10 µl of cross-lined RNA (1 µg/µl). The mixture was incubated at 37° C. for 2 h.

Purification of Peptides with His-tag. We purified RNA-peptide complexes using Ni-NTA magnetic beads (Qiagen, Cat #36111). 100 µl of beads was washed with 300 µl of wash buffer (50 mM NaH$_2$PO$_4$, 300 mM NaCl, 10 mM imidazole, 0.005% Tween 20), separated on the magnetic stand and suspended in 300 µl of wash buffer. 25 µl of RNA-peptide complexes from previous step was added to the washed beads and incubated on the end-over-end shaker for 30 min at room temperature. Beads were washed 3 times with the wash buffer followed by separation on the magnetic stand and eluted with 50 µl of the elution buffer (50 mM NaH$_2$PO$_4$, 300 mM NaCl, 500 mM imidazole, 0.005% Tween 20).

Purification with Oligo-d(T)25 (SEQ ID NO: 331) magnetic beads. Oligo-d(T)$_{25}$ (SEQ ID NO: 331) magnetic beads were purchased from New England Biolabs (Cat #S1419S). 100 µl of the bead suspension was washed with 500 µl of wash buffer I (20 mM Tris-HCl, pH 7.5, 500 mM NaCl, 1 mM EDTA) by spending them in the buffer and separating on the magnetic stand followed by suspension in 50 µl of wash buffer I. 50 µl of the RNA-peptide complexes from the previous step were mixed with 50 µl of binding buffer (100 mM Tris-HCl, pH 7.5, 1 M NaCl, 2 mM EDTA), heated at 65° C. for 2 min, placed on ice for 1 min and mixed with the washed beads. This mixture was incubated at room temperature for 5 min, then washed twice with 500 µl of wash buffer I (20 mM Tris-HCl, pH 7.8, 500 mM NaCl, 1 mM EDTA) and once with 500 µl of wash buffer 1 (20 mM Tris-HCl, pH 7.8, 200 mM NaCl, 1 mM EDTA).

Peptide Cyclization. RNA-peptide complexes bound by the Oligo-d(T)$_{25}$ (SEQ ID NO: 331) magnetic beads were incubated for 30 min in the cyclization buffer (20 mM Tris-HCl, pH 7.8, 0.00 M NaCl, 3 mM α,α"-dibromo-m-xylene (Sigma-Aldrich), 33% acetonitrile) with periodic shaking. Following incubation, beads were washed with the washing buffer III (20 mM Tris-HCl, pH 7.8, 0.3 M NaCl, 5 mM 2-mercaptoethanol), then with washing buffer IV (20 mM Tris-HCl, pH 7.8, 0.3 M NaCl, 0.5 mM TCEP) followed by washes with wash buffer I (20 mM Tris-HCl, pH 7.8, 500 mM NaCl, 1 mM EDTA) and wash buffer 11 (20 mM Tris-HCl, pH 7.8, 200 mM NaCl, 1 mM EDTA). Purified products were eluted from the beads by adding 30 ul of elution buffer (20 mM Tris-HCl, pH 7.8) and incubating at 65° C. for 2 min followed by immediate separation on the magnetic bead stand.

Affinity Selection. Affinity selection was performed in NUNC Maxisorp plates (Thermo Fischer Scientific). His-CTDSP1 (Table 2; SEQ ID NOS: 163) was dissolved in 100 µl of PBS, transferred to Maxisorp plate well and incubated on orbital shaker for 2 h at room temperature. Plate wells were washed twice with PBS and blocked with casein (PBSC buffer or PBS with 1% casein) at room temperature for 1 h with shaking and then washed 3 times with PBS. Negative selection wells were coated with casein only by incubating with 300 µl of the PBSC solution and washed 3 times with PBS. Purified RNA-peptide complexes were first added to these negative selection wells containing 100 µl of PBS and incubated with shaking at room temperature for 20 min. Next, this solution was transferred to the positive selection wells (covered by His-CTDSP1) containing 125 µl of PBSC and incubated with shaking at room temperature for 1 h. Off-target selection was performed by adding 25 µl of purified His-CTDSP1 to each well and incubating for 3 min. Following incubation wells were washed 3 times with PBS and used for cDNA synthesis.

cDNA Synthesis and PCR. We used SuperScript III First-Strand Synthesis System (Invitrogen, Cat #18080-051) for the cDNA synthesis. First, 16 µl of water was mixed with 2 ul of 50 mM primer P19 (Table 1) and 1 µl of the dNTP solution and added this mix to the well in the Maxisorp plate. Next, this plate was incubated at 65° C. for 5 min followed by cooling down at 4° C. for 1 min. Then we transferred 20 µl mixture from the plate to the PCR tube and added 20 µl of the reaction mixture containing 4 µl of 10× buffer, 8 µl of 25 mM MgCl$_2$, 4 µl of 0.1M DTT, 2 µl of RNaseOUT and 2 µl of Superscript III reverse transcriptase. This mixture was incubated at 50° C. for 50 min. Then we added 2 µl of RNAse H and incubated tubes at 37° C. for 20 min.

DNA corresponding to the strong binders surviving the selection was amplified with primers P17 and P20 (Table 1). Amplifications was carried out using Vent DNA polymerase. The PCR reaction (20 µL) was initially heated at 95° C. for 2.5 min followed by 20 or 25 cycles of denaturation at 94° C. for 15 sec., annealing at 55° C. for 15 sec. and extension at 72° C. for 30 sec. Following amplification, PCR fragment was run on the agarose gel, purified by the QIAGEN gel-band purification kit according to manufacturer's protocol.

Analysis of the NGS Data. PCR reactions from each cycle were submitted for Next Generation Sequencing. We used Amplicon-EZ service GeneWiz. Unique sequences were quantified and the most abundant sequences were selected for further testing (Tables 3 and 3a)

TABLE 3

Protein and Nucleotide Sequences of RPP Variants
(SEQ ID NOS are identified in Table 19)

| RPP Variant | Protein Sequence | SEQ ID NO: |
|---|---|---|
| v1 | MCTEDLEPPEPPLPKENC | 18 |
| v2 | MCTEAPAPPEPALPKKKKKNC | 19 |
| v3 | MCTEDLQPPTAVPQENC | 20 |
| v4 | MCTEAPAPPEPALPKKKKNC | 21 |
| v5 | MCTADLEPPEPRMEKKKVDC | 22 |
| v6 | MCTGDLQPPKTTVSKKDC | 23 |
| v7 | MCTEDLQSPKTTMTKENC | 24 |
| v8 | MCTEDLEPPEPPLPKEDC | 25 |
| v9 | MCTEDQEQQEEQLPEENC | 26 |
| v10 | MCTADLKPPKTTMTKQNC | 27 |
| v11 | MCPGDLKQPEPPMPKEYC | 28 |
| v12 | MCTEDLEPPKATMTKKDC | 29 |
| v13 | MCTEDQERPPVTKEDC | 30 |
| v14 | MCIADPEPPEAQLPEGNC | 31 |

TABLE 3-continued

Protein and Nucleotide Sequences of RPP Variants
(SEQ ID NOS are identified in Table 19)

| RPP Variant | Protein Sequence | SEQ ID NO: |
|---|---|---|
| v15 | MCTGVQEPPEATLPKKNC | 32 |
| v16 | MCSEAQEPPESRLPQVNC | 33 |
| v17 | MCTKHLEPPGPPLPQENC | 34 |
| v18 | MCTAAPEPPEPPVSKEYC | 35 |
| v19 | MCTEDLQLPKTTMTKEYC | 36 |
| v20 | MCSVDLQPPARLRPMVNC | 37 |
| v21 | MCTGDLQPPESRQPQVNC | 38 |
| v22 | MCTGDLQPPEAQVIEVNC | 39 |
| v23 | MCTEDLQPPEPQLPEVNC | 40 |
| v25 | MCTEDMEPRKTTMTKKYC | 41 |
| v26 | MCTEAPAPPEPALPKKKKKNC | 42 |
| v27 | MCTEAPAPPEPALPKKKKKNC | 19 |
| v28 | MCTEDLQSPKTTMTKENC | 24 |
| v29 | MCTGDLKLPEPPMSKKKKKNC | 45 |
| v30 | MCTEDLQPPKTTMAEKYC | 46 |
| v31 | MCSEDPEPPKTTMTKKNC | 47 |
| v32 | MCTEDLKPPEASLPEENC | 48 |
| v33 | MCAGDLEQPEPPVAKKKKKNC | 49 |
| v34 | MCNGDLERPEPPVAKEYC | 50 |
| v35 | MCTEDLKPPEPPLPKENC | 51 |
| v36 | MCNEALEPPPLRKEHC | 52 |
| v37 | MCPEDLERPPLTKEHC | 53 |
| v38 | MCTEDLEPPERPLPREIC | 54 |
| v39 | MCAGDLKPPETTMSKKNC | 55 |
| v40 | MCTEDLQQPERSQPMESC | 56 |
| v41 | MCPEDLQPPEPALPEKKKKKIVVLALVVKSAVSVGVV | 57 |
| v42 | MCTEVLVPRTTSGKGRLWFWLWSQKGHPSASACGS | 58 |
| v43 | MCAEDLQPPPLLEAHCGSDSGRKKRRQC | 59 |
| v44 | MCTAAPEPPEPQLPQANC | 60 |
| v45 | MCPADLQQPETSLPEENC | 61 |
| v46 | MCSVDLQPPARLRPMVNC | 37 |
| v47 | MCTEALEPPEPPLTKENC | 63 |
| v48 | MCTEAMEPPEPPLARESC | 64 |
| v49 | MCTADLQPPEASLPQQNC | 65 |
| v50 | MCTAAPEPPEPRLPEGNC | 66 |
| v51 | MCTKDLAPQAPPLLKENC | 67 |

TABLE 3b

Protein Sequences of RPP$^{RI}$ Variants* (SEQ ID NOS are identified in Table 19)

| RPP$^{RI}$ Variant | Retroverted (RI) Protein Sequence | SEQ ID NO: |
|---|---|---|
| v1 | cnekplppeppeldetcm | 68 |
| v2 | cnkkkkkplapeppapaetcm | 69 |
| v3 | cneqpvatppqldetcm | 70 |
| v4 | cnkkkkplapeppapaetcm | 71 |
| v5 | cdkksvttkppqldgtcm | 72 |
| v6 | cdkksvttkppqldgtcm | 73 |
| v7 | cnektmttkpsqldetcm | 74 |
| v8 | cdekplppeppeldetcm | 75 |
| v9 | cneeplqeellleldetcm | 76 |
| v10 | cnqktmttkppkldgpcm | 77 |
| v11 | cyekpmppepqldgpcm | 78 |
| v12 | cdekktmtakppeldetcm | 79 |
| v13 | cdektvppreqdetcm | 80 |
| v14 | cngeplqaeppepdaicm | 81 |
| v15 | cnkkpltaeppeqvgtcm | 82 |
| v16 | cnvqplppgppelhktcm | 83 |
| v17 | cneqplppgppepaatcm | 84 |
| v18 | cyeksvppeppepaatcm | 85 |
| v19 | cyektmttkplqldetem | 86 |
| v20 | cnvmprlrappqldvscm | 87 |
| v21 | cnvqpqrseppqldgtcm | 88 |
| v22 | cnveivqaeppqldgtcm | 89 |
| v23 | cnveplqpeppqldetcm | 90 |
| v25 | cykktmttkppemdetcm | 91 |
| v26 | cnkkkkkkpklapeppapaetcm | 92 |
| v27 | cnkkkkkplapeppapaetcm | 69 |
| v28 | cnektmttkpsqldetcm | 74 |
| v29 | cnkkkkksmppeppplkldgtcm | 95 |
| v30 | cykeamttkppqldetcm | 96 |
| v31 | cnkktmttkppepdescm | 97 |

TABLE 3b-continued

Protein Sequences of RPP$^{RI}$ Variants* (SEQ ID NOS are identified in Table 19)

| RPP$^{RI}$ Variant | Retroverted (RI) Protein Sequence | SEQ ID NO: |
|---|---|---|
| v32 | cneeplsaepppkldetcm | 98 |
| v33 | cnkkkkkavppepqeldgacm | 99 |
| v34 | cyekavppepreldgncm | 100 |
| v35 | cnekplppeppkldetcm | 101 |
| v36 | chekrlpppelaencm | 102 |
| v37 | chektlppreldepcm | 103 |
| v38 | cierplpreppeldetcm | 104 |
| v39 | cnkksmtteppkldgacm | 105 |
| v40 | csmpqsrepqqledetcm | 106 |
| v41 | cvvgvsvaskvvlalvvikkkkkepla-peppqldepcm | 107 |
| v42 | csgcasasphgkqswlwfwlrgkgstt-rpvlvetcm | 108 |
| v43 | cqrrkkrgsdsgchaellpppqldeacm | 109 |
| v44 | cnaqplqpeppepaatcm | 110 |
| v45 | cneeplstepqqldapcm | 111 |
| v46 | cnvmprlrappqldvscm | 87 |
| v47 | cnektlppeppelaetcm | 113 |
| v48 | cseralppeppemaetcm | 114 |
| v49 | cnqqplsaeppqldatcm | 115 |
| v50 | cngeplrpeppepaatcm | 116 |
| v51 | cnekllppaqpaldktcm | 117 |

*the lowercase letter depicts D-amino acids.

Example 4—Construction of the Peptide-GST Fusions and their Expression

As a first step we cloned GST protein in pET29 vector. GST was codon optimized, flanked by HindII and XhoI sites and synthesized by IDT. It was amplified by Phusion DNA polymerase (NEB, cat #M0530S) with primers P109 and P108 (Table 1). The PCR reaction (20 μL) was initially heated at 95° C. for 2.5 min followed by 30 cycles of denaturation at 94° C. for 15 sec., annealing at 55° C. for 15 sec. and extension at 72° C. for 1 min. Following amplification, PCR fragment was gel-purified by the QIAGEN gel-band purification kit according to manufacturer's protocol.

pET29 plasmid was amplified with primers P12 and P14 (Table 1) introducing HindII and XhoI restriction sites. The PCR reaction (20 μL) was initially heated at 95° C. for 2.5 min followed by 30 cycles of denaturation at 94° C. for 15 sec., annealing at 55° C. for 15 sec. and extension at 72° C. for 6 min. Following amplification, PCR fragment was gel-purified by the QIAGEN gel-band purification kit and digested with HindII and XhoI restriction enzymes All digested fragments were purified with QUIAGEN kit and ligated in appropriate combination using T4 DNA ligase (NEB) according to recommendations of the manufacturer. Ligated fragments were transformed in 10G chemically competent and sequenced as described above. Expression construct for GST-RPP is shown in Table 4 (SEQ ID NO: 164)

TABLE 4

Nucleotide and Protein Sequences of RPP-GST fusion

Nucleotide Sequence (SEQ ID NO: 164)
ATGTGTACCGAAGATCTGGAACCACCAGAACCACCACTGCCAAAGGAAAA
TTGTggatccGGTTCTGGCTCAGGTTCTTCCCCTATACTAGGTTATTGGA
AAATTAAGGGCCTTGTGCAACCCACTCGACTTCTTTTGGAATATCTTGAA
GAAAAATATGAAGAGCATTTGTATGAGCGCGATGAAGGTGATAAATGGCG
AAACAAAAAGTTTGAATTGGGTTTGGAGTTTCCCAATCTTCCTTATTATA
TTGATGGTGATGTTAAATTAACACAGTCTATGGCCATCATACGTTATATA
GCTGACAAGCACAACATGTTGGGTGGTTGTCCAAAAGAGCGTGCAGAGAT
TTCAATGCTTGAAGGAGCGGTTTTGGATATTAGATACGGTGTTTCGAGAA
TTGCATATAGTAAAGACTTTGAAACTCTCAAAGTTGATTTTCTTAGCAAG
CTACCTGAAATGCTGAAAATGTTCGAAGATCGTTTATGTCATAAAACATA
TTTAAATGGTGATCATGTAACCCATCCTGACTTCATGTTGTATGACGCTC
TTGATGTTGTTTTATACATGGACCCAATGTGCCTGGATGCGTTCCCAAAA
TTAGTTTGTTTTAAAAAACGTATTGAAGCTATCCCACAAATTGATAAGTA
CTTGAAATCCAGCAAGTATATAGCATGGCCTTTGCAGGGCTGGCAAGCCA
CGTTTGGTGGTGGCGACCATCCTCCAAAATAA Protein Sequence (SEQ ID NO: 165)
MCTEDLEPPEPPLPKENCGSGSGSGSSPILGYWKIKGLVQPTRLLLEYLE
EKYEEHLYERDEGDKWRNKKFELGLEFPNLPYYIDGDVKLTQSMAIIRYI
ADKHNMLGGCPKERAEISMLEGAVLDIRYGVSRIAYSKDFETLKVDFLSK
LPEMLKMFEDRLCHKTYLNGDHVTHPDFMLYDALDVVLYMDPMCLDAFPK
LVCFKKRIEAIPQIDKYLKSSKYIAWPLQGWQATFGGGDHPPK RPP Sequence is underlined Selected sequences were re-created by PCR using primers shown in Table 5, gel-purified by the QIAGEN gel-band purification kit, digested by HindIII and BamHI restriction enzymes and cloned in pET vector described above in-frame with the GST tag. Ligated fragments were transformed in 10G chemically competent cells (Lucigen) according to manufacturer's protocol. Transformed cells were plated on LB plates containing 25 μg/mL kanamycin and incubated overnight at 37° C. Next morning colonies were tested for the presence of the insert by colony PCR. Colonies were picked and resuspended in 20 μl of sterile 0.9% sodium chloride solution. One μl of this solution was transferred to the PCR tube and amplified with Taq polymerase (New England Biolabs, cat #M0482S) and 30 pmoles of the flanking primers Each PCR reaction (20 μL) was initially heated at 95° C. for 2.5 min followed by 30 cycles of denaturation at 94° C. for 15 sec., annealing at 55° C. for 15 sec. and extension at 72° C. for 1 min. Amplification products were visualized by agarose electrophoresis. Clones with the correct inserts were inoculated into the culture tubes containing 25 μg/mL kanamycin and incubated overnight at 37° C. Next morning constructs were purified by Monarch Plasmid miniprep kit (NEB). Constructs were transformed into BL21(DE3) competent cells (Lucigen) as described above.

Purification for Peptide-GST fusions. E. coli cells (BL21 strain) with the selected constructs were incubated overnight at 37° C. with vigorous shaking. Next morning, we added 1 ml of the night culture to 100 ml of LB media with 25 μg/mL kanamycin in 1 L flask and incubated it at 37° C. with shaking. When culture's OD600 reached 0.4 we added IPTG to the final concentration of 1 mM and incubated 16 h at 30° C. with shaking. Next morning, cells were spun down in the Eppendorf centrifuge 5810R at maximum speed and frozen at −80° C. When needed, cell pellets were removed from the freezer, incubated at room temperature and lysed with 3 ml of BPER protein lysis reagent (ThermoFischer). Peptide-GST fusions were purified using glutathione agarose (ThermoScientific cat #16100) as described by the manufacturer.

TABLE 5

Primers used for cloning RPP variants in-frame with GST

| RPP Variant | Primer | Primer Sequence | SEQ ID NO: |
|---|---|---|---|
| v1 (RPP) | forward primer | AATAAAGCTTATGTGTACCGAAGATCTGGAACCACCAGAACCACCACTGCCAA | 166 |
| | reverse primer | AATAGGATCCACAATTTTCCTTTGGCAGTGGTGGTTCTGGTGGTTCCA | 167 |
| v2 | forward primer | AATAAAGCTTATGTGTACCGAAGCTCCGGCACCACCAGAACCAGCACTGCCAAAG | 168 |
| | reverse primer | AATAGGATCCACAATTTTTTTTTTTTCTTTGGCAGTGCTGGTTCTGGTGGTGC | 169 |
| v3 | forward primer | AATAAAGCTTATGTGTACCGAAGATCTGCAACCACCAACAGCAGTGCCAC | 170 |
| | reverse primer | AATAGGATCCACAATTTTCCTGTGGCACTGCTGTTGGTGGTTGCAGATCTTC | 171 |
| v4 | forward primer | AATAAAGCTTATGTGTACCGAAGCTCCGGCACCACCAGAACCAGCACTGCCAAAG | 172 |
| | reverse primer | AATAGGATCCACAATTTTTTTTTCTTTGGCAGTGCTGGTTCTGGTGGTGC | 173 |
| v5 | forward primer | ATGTGTACCGCAGATCTGGAACCACCAGAACCACGAATGGAA | 174 |
| | reverse primer | AATAGGATCCACAATCTACCTTTTTTTTTTCCATTCGTGGTTCTGGTGGTTCCA | 175 |
| v6 | forward primer | AATAAAGCTTATGTGTACCGGAGATCTGCAACCACCAAAAACAACAGTGTCAA | 176 |
| | reverse primer | AATAGGATCCACAATCTTTCTTTGACACTGTTGTTTTGGTGGTTGCAGA | 177 |
| v7 | forward primer | AATAAAGCTTATGTGTACCGAAGATCTGCAATCACCAAAAACAACAATGACAA | 178 |
| | reverse primer | AATAGGATCCACAATTTTCCTTTGTCATTGTTGTTTTGGTGATTGCAGA | 179 |
| v8 | forward primer | AATAAAGCTTATGTGTACCGAAGATCTGGAACCACCAGAACCACCACTGCCAA | 180 |
| | reverse primer | AATAGGATCCCACAATCTTCCTTTGGCAGTGGTGGTTCTGGTGGTTCCAGA | 181 |
| v9 | forward primer | AATAAAGCTTATGTGTACCGAAGATCAGGAACAACAAGAAGACAACTG | 182 |
| | reverse primer | AATAGGATCCACAATTTTCCTCTGGCAGTTGTTCTTCTTGTTGTTCCTGATC | 183 |
| v10 | forward primer | AATAAAGCTTATGTGTACCGCAGATCTGAAACCACCAAAAACAACAATGACAA | 184 |
| | reverse primer | AATAGGATCCACAATTTTGCTTTGTCATTGTTGTTTTGGTGGTTCAGA | 185 |
| V11 | forward primer | AATAAAGCTTATGTGTCCCGGAGATCTGAAACAACCAGAACCACCAATGCCAA | 186 |
| | reverse primer | AATAGGATCCACAATATTCCTTTGGCATTGGTGGTTCTGGTTGTTTCAGA | 187 |
| V12 | forward primer | AATAAAGCTTATGTGTACCGAAGATCTGGAACCACCAAAAGCAACAATGACAA | 188 |
| | reverse primer | AATAGGATCCACAATCTTTCTTTGTCATTGTTGCTTTTGGTGGTTCCAGA | 189 |
| V13 | forward primer | AATAAAGCTTATGTGTACCGAAGATCAGGAACGACCACCAGTGACAAAG | 190 |
| | reverse primer | AATAGGATCCACAATCTTCCTTTGTCACTGGTGGTCGTTCCTGATCTTC | 191 |
| V14 | forward primer | AATAAAGCTTATGTGTATCGCAGATCCGGAACCACCAGAAGCACAACTG | 192 |
| | reverse primer | AATAGGATCCACAATTTCCCTCTGGCAGTTGTGCTTCTGGTGGTTCCGGATCTG | 193 |
| V15 | forward primer | AATAAAGCTTATGTGTACCGGAGTTCAGGAACCACCAGAAGCAACACTG | 194 |
| | reverse primer | AATAGGATCCACAATTTTTCTTTGGCAGTGTTGCTTCTGGTGGTTCCTGAAC | 195 |

TABLE 5-continued

Primers used for cloning RPP variants in-frame with GST

| RPP Variant | Primer | Primer Sequence | SEQ ID NO: |
|---|---|---|---|
| v16 | forward primer | AATAAAGCTTATGTGTAGCGAAGCTCAGGAACCACCAGAATCACGACTG | 196 |
|  | reverse primer | AATAGGATCCACAATTTACCTGTGGCAGTCGTGATTCTGGTGGTTCCTGAG | 197 |
| V17 | forward primer | AATAAAGCTTATGTGTACCAAACATCTGGAACCACCAGGACCACCATTGC | 198 |
|  | reverse primer | AATAGGATCCACAATTTTCCTGTGGCAATGGTGGTCCTGGTGGTTCCAGATG | 199 |
| v18 | forward primer | AATAAAGCTTATGTGTACCGCAGCTCCGGAACCACCAGAACCACCAGTGT | 200 |
|  | reverse primer | AATAGGATCCACAATATTCCTTTGACACTGGTGGTTCTGGTGGTTCCGGAG | 201 |
| v19 | forward primer | AATAAAGCTTATGTGTACCGAAGATCTGCAACTACCAAAAACAACAATGACA | 202 |
|  | reverse primer | AATAGGATCCACAATATTCCTTTGTCATTGTTGTTTTTGGTAGTTGCAGA | 203 |
| v20 | forward primer | AATAAAGCTTATGTGTTCCGTAGATCTGCAACCACCAGCACGACTACGGCCAA | 204 |
|  | reverse primer | AATAGGATCCACAATTTACCATTGGCCGTAGTCGTGCTGGTGGTTGCAGAT | 205 |
| v21 | forward primer | AATAAAGCTTATGTGTACCGGAGATCTGCAACCACCAGAATCACGACAGCCA | 206 |
|  | reverse primer | AATAGGATCCACAATTTACCTGTGGCTGTCGTGATTCTGGTGGTTGCAGAT | 207 |
| v22 | forward primer | AATAAAGCTTATGTGTACCGGAGATCTGCAACCACCAGAAGCACAAGTGA | 208 |
|  | reverse primer | AATAGGATCCACAATTTACCTCTATCACTTGTGCTTCTGGTGGTTGCAGAT | 209 |
| v23 | forward primer | AATAAAGCTTATGTGTACCGAAGATCTGCAACCACCAGAACCACAACTGCCA | 210 |
|  | reverse primer | AATAGGATCCACAATTTACCTCTGGCAGTTGTGGTTCTGGTGGTTGCAGAT | 211 |
| v25 | forward primer | AATAAAGCTTATGTGTACCGAAGATATGGAACCACGAAAAACAACAATGA | 212 |
|  | reverse primer | AATAGGATCCACAATATTTCTTTGTCATTGTTGTTTTTCGTGGTTCCATAT | 213 |
| v26 | forward primer | AATAAAGCTTATGTGTACCGAAGCTCCGGCACCACCAGAACCAGCACTGCCAAAG | 214 |
|  | reverse primer | AATAGGATCCACAATTTTTTTTTTTTTCTTTGGCAGTGCTGGTTCTGGTGGT | 215 |
| v27 | forward primer | AATAAAGCTTATGTGTACCGAAGCTCCGGCACCACCAGAACCAGCACTGCCAAAG | 216 |
|  | reverse primer | AATAGGATCCACAATTTTTTTTTTTTCTTTGGCAGTGCTGGTTCTGGTGGTG | 217 |
| v28 | forward primer | AATAAAGCTTATGTGTACCGAAGATCTGCAATCACCAAAAACAACAATG | 218 |
|  | reverse primer | AATAGGATCCACAATTTTCCTTTGTCATTGTTGTTTTTGGTGATTGCAGA | 219 |
| v29 | forward primer | AATAAAGCTTATGTGTACCGGAGATCTGAAACTACCAGAACCACCAATGTCAAAG | 220 |
|  | reverse primer | AATAGGATCCACAATTTTTTTTTTTTCTTTGACATTGGTGGTTCTGGTAG | 221 |
| v30 | forward primer | AATAAAGCTTATGTGTACCGAAGATCTGCAACCACCAAAAACAACAATG | 222 |
|  | reverse primer | AATAGGATCCACAATATTTCTCTGCCATTGTTGTTTTTGGTGGTTGCAGAT | 223 |
| v31 | forward primer | AATAAAGCTTATGTGTAGCGAAGATCCGGAACCACCAAAAACAACAATGAC | 224 |
|  | reverse primer | AATAGGATCCACAATTTTCTTTGTCATTGTTGTTTTTGGTGGTTCCGGAT | 225 |

TABLE 5-continued

Primers used for cloning RPP variants in-frame with GST

| RPP Variant | Primer | Primer Sequence | SEQ ID NO: |
|---|---|---|---|
| v32 | forward primer | AATAAAGCTTATGTGTACCGAAGATCTGAAACCACCAGAAGCATCACTGC | 226 |
|  | reverse primer | AATAGGATCCACAATTTTCCTCTGGCAGTGATGCTTCTGGTGGTTTCAGAT | 227 |
| v33 | forward primer | AATAAAGCTTATGTGTGCCGGAGATCTGGAACAACCAGAACCACCAGTGGCAAA | 228 |
|  | reverse primer | AATAGGATCCACAATTTTTTTTTTTTTCTTTGCCACTGGTGGTTCTGGTTGTTC | 229 |
| v34 | forward primer | AATAAAGCTTATGTGTAACGGAGATCTGGAACGACCAGAACCACCAGTG | 230 |
|  | reverse primer | AATAGGATCCACAATATTCCTTTGCCACTGGTGGTTCTGGTCGTTCCAGAT | 231 |
| v35 | forward primer | AATAAAGCTTATGTGTACCGAAGATCTGAAACCACCAGAACCACCACTGC | 232 |
|  | reverse primer | AATAGGATCCACAATTTTCCTTTGGCAGTGGTGGTTCTGGTGGTTTCAGAT | 233 |
| v36 | forward primer | AATAAAGCTTATGTGTAACGAAGCTCTGGAACCACCACCACTGCGAAAG | 234 |
|  | reverse primer | AATAGGATCCACAATGTTCCTTTCGCAGTGGTGGTGGTTCCAGAGCTTC | 235 |
| v37 | forward primer | AATAAAGCTTATGTGTCCCGAAGATCTGGAACGACCACCATTGACAAAG | 236 |
|  | reverse primer | AATAGGATCCACAATGTTCCTTTGTCAATGGTGGTCGTTCCAGAT | 237 |
| v38 | forward primer | AATAAAGCTTATGTGTACCGAAGATCTGGAACCACCAGAACGACCACTGC | 238 |
|  | reverse primer | AATAGGATCCACAAATTTCCCTTGGCAGTGGTCGTTCTGGTGGTTCCAGA | 239 |
| v39 | forward primer | AATAAAGCTTATGTGTGCCGGAGATCTGAAACCACCAGAAACAACAATGTC | 240 |
|  | reverse primer | AATAGGATCCACAATTTTTCTTTGACATTGTTGTTTCTGGTGGTTTCAGA | 241 |
| v40 | forward primer | AATAAAGCTTATGTGCACCGAAGATCTGCAACAACCAGAACGATCACAGC | 242 |
|  | reverse primer | AATAGGATCCACAACTTTCCATTGGCTGTGATCGTTCTGGTTGTTGCAGA | 243 |
| v41 | forward primer | AATAAAGCTTATGTGTCCCGAAGATCTGCAACCACCAGAACCAGCACTGCCAGAGAAAAA | 244 |
|  | reverse primer | AATAGGATCCGACCACGCCGACGCTGACGGCGCTTTTTACGACCAGAGCCAGAACCACAA | 245 |
|  | additional primer | ACCAGAACCAGCACTGCCAGAGAAAAAAAAAAAAAAATTGTGGTTCTGGCTCTGGTCGT | 246 |
| v42 | forward primer | AATAAAGCTTATGTGTACCGAAGTTCTGGTACCACGAACCACCAGTGGCAAAGGAAG | 247 |
|  | reverse primer | AATAGGATCCGGAGCCACACGCCGATGCTGACGGATGGCCTTTTTGCGACCAGAGCCAGAA | 248 |
|  | additional primer | ACCACGAACCACCAGTGGCAAAGGAAGATTGTGGTTCTGGCTCTGGTCGCAAAAAGGCCA | 249 |
| v43 | forward primer | AATAAAGCTTATGTGTGCCGAAGATCTGCAACCACCACCACTGCTAGAGGCA | 250 |
|  | reverse primer | AATAGGATCCACACTGACGGCGCTTTTTACGACCAGAGTCAGAACCACAATGTGCCTCT | 251 |
|  | additional primer | ATCTGCAACCACCACCACTGCTAGAGGCACATTGTGGTTCTGACTCTGGTCGTAAAAAG | 252 |
| v44 | forward primer | AATAAAGCTTATGTGTACCGCAGCTCCGGAACCACCAGAACCACAACTG | 253 |
|  | reverse primer | AATAGGATCCACAATTTGCCTGTGGCAGTTGTGGTTCTGGTGGTTCCGGAG | 254 |
| v45 | forward primer | AATAAAGCTTATGTGTCCCGCAGATCTGCAACAACCAGAAACATCACTG | 255 |
|  | reverse primer | AATAGGATCCACAATTTTCCTCTGGCAGTGATGTTTCTGGTTGTTGCAGAT | 256 |

TABLE 5-continued

Primers used for cloning RPP variants in-frame with GST

| RPP Variant | Primer | Primer Sequence | SEQ ID NO: |
|---|---|---|---|
| v46 | forward primer | AATAAAGCTTATGTGTTCCGTAGATCTGCAACCACCAGCACGACTACG | 257 |
|  | reverse primer | ACAATTTACCATTGGCCGTAGTCGTGCTGGTGGTTGCAGAT | 326 |
| v47 | forward primer | AATAAAGCTTATGTGCACCGAGCTTTGGAACCACCAGAACCACCACTG | 327 |
|  | reverse primer | AATAGGATCCACAATTTTCCTTTGTCAGTGGTGGTTCTGGTGGTTCCAAAG | 260 |
| v48 | forward primer | AATAAAGCTTATGTGTACCGAAGCTATGGAACCACCAGAACCACCACTG | 261 |
|  | reverse primer | AATAGGATCCACAACTTTCCCTTGCCAGTGGTGGTTCTGGTGGTTCCATAG | 262 |
| v49 | forward primer | AATAAAGCTTATGTGTACCGCAGATCTGCAACCACCAGAAGCATCACTG | 263 |
|  | reverse primer | AATAGGATCCACAATTTTGCTGTGGCAGTGATGCTTCTGGTGGTTGCAGA | 328 |
| v50 | forward primer | AATAAAGCTTATGTGTACCGCAGCTCCGGAACCACCAGAACCACGACTGCCA | 265 |
|  | reverse primer | AATAGGATCCACAATTTCCCTCTGGCAGTCGTGGTTCTGGTGGTTCC | 266 |
| v51 | forward primer | AATAAAGCTTATGTGTACCAAAGATTTGGCACCACAAGCACCACCATTGCT | 267 |
|  | reverse primer | AATAGGATCCACAATTTTCCTTTAGCAATGGTGGTGCTTGTGGTGCCAAA | 268 |

Example 5—Inhibition of the CTDSP1 Phosphatase Activity by RPP and RPP Variants Results: FIG. 25—The top 51 most abundant RPP variants identified in the RNA display/protein evolution screen are listed in Table 3 in the order of most (V1) to least (V51) abundant peptides. The primers used to make these peptides are listed in Table 5. A phosphatase activity screen (Table 6, FIG. 25) was used to assess the ability of the top 51 RPP$_V$ to inhibit CTDSP1 phosphatase activity at amino acids 861 and 864 on the endogenous phosphorylated REST peptide (TEDpSPPpSPPLPKEN (SEQ ID NO: 329)).

The phosphorylated REST peptide (TEDpSPPpSPPLPKEN (SEQ ID NO: 329)) was synthesized by GeneScript. Phosphatase reactions were performed with 10 mM Tris pH 8, 10 mM $MgCl_2$, 100 nM CTDSP1, 0.5 μM phosphate sensor (Thermo Fischer), 50 μM of REST peptide and various concentrations of peptide-GST fusions at room temperature for 10 min. All assays were performed in 96-well pates (Corning P/N 3686) rinsed with water 10 times. Fluorescence was measured by BioTek Synergy HTX using kinetic read with excitation at 420/27 nm and emission at 485/20 nm.

The screen showed RPP (V1) inhibited phosphatase activity by approximately 60%, relative to control (GST), at 1 μM (Table 6, FIG. 25). Several variants inhibited phosphatase activity better than RPP (Table 6, FIG. 25). The most potent inhibitors were v33, with 100% inhibition, and v35, with approximately 90% inhibition of phosphatase activity (Table 6, FIG. 25).

TABLE 6

Inhibition of CTDSP1 phosphatase acclivity by RPP variants

| RPP variant | Relative Phosphatase activity | Standard deviation, $P < 0.05$ | Number of replicas |
|---|---|---|---|
| RPP | 0.42 | 0.25 | 5 |
| v2 | 0.66 | 0.64 | 6 |
| v4 | 0.67 | 0.28 | 3 |
| v5 | 0.49 | 0.25 | 6 |
| v6 | 0.77 | 0.30 | 4 |
| v7 | 0.24 | 0.21 | 5 |
| v9 | 0.65 | 0.32 | 4 |
| v10 | 0.84 | 0.45 | 4 |
| v11 | 0.13 | 0.19 | 3 |
| v12 | 0.41 | 0.14 | 4 |
| v13 | 0.20 | 0.20 | 4 |
| v14 | 0.54 | 0.19 | 2 |
| v15 | 0.70 | 0.41 | 4 |
| v16 | 0.79 | 0.43 | 4 |
| v17 | 0.24 | 0.22 | 6 |
| v18 | 0.43 | 0.30 | 4 |
| v19 | 0.76 | 0.00 | 1 |
| v20 | 0.13 | 0.13 | 2 |
| v21 | 0.26 | 0.17 | 4 |
| v22 | 0.59 | 0.37 | 2 |
| v23 | 0.60 | 0.42 | 4 |
| v25 | 0.63 | 0.45 | 4 |
| v26 | 0.46 | 0.20 | 2 |
| v27 | 0.19 | 0.19 | 2 |
| v28 | 0.33 | 0.33 | 2 |
| v29 | 0.17 | 0.30 | 4 |
| v30 | 0.62 | 0.63 | 4 |
| v31 | 0.43 | 0.35 | 3 |
| v32 | 0.89 | 0.56 | 4 |
| v33 | 0.00 | 0.00 | 3 |
| v34 | 0.74 | 0.48 | 4 |
| v35 | 0.07 | 0.09 | 4 |
| v36 | 0.68 | 0.31 | 3 |

TABLE 6-continued

Inhibition of CTDSP1 phosphatase
acclivity by RPP variants

| RPP variant | Relative Phosphatase activity | Standard deviation, P < 0.05 | Number of replicas |
|---|---|---|---|
| v37 | 0.16 | 0.15 | 5 |
| v38 | 0.28 | 0.30 | 3 |
| v39 | 0.59 | 0.07 | 3 |
| v40 | 0.29 | 0.19 | 3 |
| v41 | 0.46 | 0.33 | 6 |
| v42 | 0.48 | 0.24 | 7 |
| v43 | 0.97 | 0.00 | 1 |
| v44 | 0.53 | 0.47 | 3 |
| v46 | 0.37 | 0.32 | 7 |
| v47 | 0.20 | 0.22 | 3 |
| v49 | 0.58 | 0.37 | 4 |
| v51 | 0.71 | 0.46 | 3 |

FIG. 26, Table 13—RPP, SEQ ID NO: 12, inhibited CTDSP1 activity with an $EC_{50}$ of approximately 20 nM, but did not affect the activity of several other phosphatases. Assay: The ability of RPP SEQ ID NO: 12 to inhibit CTDSP1 activity at amino acids 861 and 864 on the endogenous phosphorylated REST peptide (TEDpSPPpSP-PLPKEN (SEQ ID NO: 329)) was assessed as described for FIG. 26 above.

TABLE 13

CTDSP1 and off target phosphatase acclivity
after RPP (SEQ ID NO: 12) dosing

| Phosphatase | RPP SEQ ID NO: 12 nM | Average N = 5 % Activity | Standard Deviation |
|---|---|---|---|
| CTDSP1 | 0 | 100 | 0 |
| CTDSP1 | 10 | 89.97 | 15.64 |
| CTDSP1 | 20 | 48.7 | 14.65 |
| CTDSP1 | 40 | 34.46 | 11.58 |
| CTDSP1 | 60 | 31.17 | 21.23 |
| CTDSP1 | 80 | 22.67 | 10.2 |
| CTDSP1 | 100 | 13.72 | 13.35 |
| PPA1 | 10000 | 101.125 | 1.611 |
| PPM1H | 10000 | 98.279 | 2.406 |
| PPM1A | 10000 | 102.786 | 2.559 |
| PP3CA | 10000 | 100.222 | 2.897 |
| PPP1CA | 10000 | 101.136 | 3.711 |
| PP5CA | 10000 | 97.902 | 5.245 |

Example 6—Binding Affinity of RPP Assessed Using Monolith (NanoTemper) and Biacore (GE Heathcare Life Sciences)

Expression constructs for His-CTDSPL (Table 2; SEQ ID NO: 162) and GST-RPP (Table 4; SEQ ID NO: 164) were constructed and purified as described in Example 2. The His tag on CTDSP1 (40 nM) was labelled with RED-tris NTA dye (20 nM), with a 3:1 dye to CTDSP1 ratio, and unbound dye was removed by gravity-flow size exclusion. Binding affinity of the linear GST-RPP (Table 4; SEQ ID NO: 165) to His-CTDSP1 (Table 2; SEQ ID NO:163) was determined using Monolith (NanoTemper), following manufacturer recommendations. Results of the binding assay are presented in FIG. 2: The RPP (Table 4; SEQ ID NO: 165) was assessed for binding to His-CTDSP1 at several concentrations ranging from low pM up to 0.5 µM. $K_D$ corresponding to the binding of linear RPP to CTDSP1 was calculated at 130 µM.

Binding affinity of the linear GST-RPP (Table 4; SEQ ID NO: 165) to His-CTDSP1 (Table 2; SEQ ID NO: 163) was measured using Biacore by GE Heathcare Life Sciences. 20 µL (5 µg/mL) of His-tagged CTDSP1 in 10 mM sodium acetate, pH 5.0 was immobilized on a CM5 chip (GE Healthcare Life Science) using an amine coupling following a protocol recommended by Biacore (cat #BR-1000-50, GE Healthcare Life Science). This purification yielded approximately 1300 RU of protein bound to the CM5 chip. The CM5 chip was then washed with HBS-EP buffer (pH 7.4), 120 µL of the analyte: GST-RPP or GST alone (negative control) was injected at a concentration of 500 nM in HBS-EP buffer (pH 7.4) at flow rate of 30 µL/min. The association time was 2 minutes and dissociation time is 3 minutes. Finally, bound protein was washed with 10 mM glycine-HCl, pH1.5 (BR-1003-54, GE Health science) for 25 second at 50 µL/min flow rate. The binding of linear RPP to CTDSP1 resulted in: $K_D$=1.7 µM (FIG. 3B, the negative control is shown in FIG. 3A).

Example 7—RPP and $RPP_V$ Fused with the Cell-Penetrating Peptides (CPPs) and/or Peptides Facilitating Endosome Escape Several RPP and $RPP_V$ were synthesized with attachments of the cell-penetrating peptides (CPPs) and/or peptides facilitating endosome escape. The list of CPPs and linkers we used is shown in Table 7.

TABLE 7

| Additional peptide allowing cell penetration and escape from endosomes | | | | |
|---|---|---|---|---|
| Name | Protein Sequence (a) | SEQ ID NO: | RI sequence (b) | SEQ ID NO: |
| CPP | GRKKRRQRRR | 118 | rrrqrrkkrg | 140 |
| CPP | GDIMGEWGNEIFGAIAGFLGYGRKKRRQRRR | 119 | rrrqrrkkrgyglfgaiagfiengwegmgmidg | 141 |
| CPP | RRRRRRRR | 120 | rrrrrrrr | 142 |
| CPP | KKKKKKKK | 121 | kkkkkkkk | 143 |
| CPP | DIMGEWGNEIFGAIAGFLG | 122 | glfgaiagfiengwegmid | 144 |
| CPP | CHHHHHRKKRRQRRRRHHHHHC | 123 | chhhhhrrrrqrrkkrhhhhhc | 145 |
| CPP | CHHHHHRRRRRRRRRHHHHHC | 124 | chhhhhrrrrrrrrrhhhhhc | 146 |

TABLE 7-continued

Additional peptide allowing cell penetration and escape from endosomes

| Name | Protein Sequence (a) | SEQ ID NO: | RI sequence (b) | SEQ ID NO: |
|---|---|---|---|---|
| CPP | FFLIPKGRRRRRRRGC | 125 | cgrrrrrrrgkpilffc | 147 |
| CPP | FΦRRRR | 126 | rrrrΦf | 148 |
| CPP | RRWWRRWRRRRWWRr | 127 | rrwwrrrrwrrwwrr | 149 |
| CPP | RWWRRRRWRRWWRr | 128 | rrwwrrwrrrrwwr | 150 |
| CPP | RRWWRRWRRRRWWr | 129 | rwwrrrrwrrwwrr | 151 |
| CPP | RRWWRRWRRRr | 130 | rrrrwrrwwrr | 152 |
| CPP | RRWWRRWRr | 131 | rrwrrwwrr | 153 |
| CPP | RRWWRRWRRR | 132 | rrrwrrwwrr | 154 |
| CPP | RRRRRC$_{14}$RRWWRRr | 133 | rrrwwrrC$_{14}$rrrrrr | 155 |
| CPP | YALTSAISRIITHHHHHH | 134 | hhhhhhtiirsiastlay | 156 |
| CPP | RRRRRC$_{14}$RRWWRR- | 135 | rrwwrrC$_{14}$rrrrr | 157 |
| CPP | RRC$_{14}$RRC$_{14}$RRRRR | 136 | rrC$_{14}$rrC$_{14}$rrrrr | 158 |
| CPP | RRC$_{14}$RRR | 137 | rrC$_{14}$rrr | 159 |
| Linker 1 | GS | 138 | sg | 160 |
| Linker 2 | GSGS | 139 | sgsg | 161 |

Φ is L-2-naphthylalanine
Lower case = D-amino acids
C$_{14}$ = 2-amino-tetradecanoic acid

Example 8—RPP is Internalizalized by Mesenchymal Progenitor Cells and Sciatic Nerve. Mesenchymal Progenitor Cells (MPCs)

Figure 4:
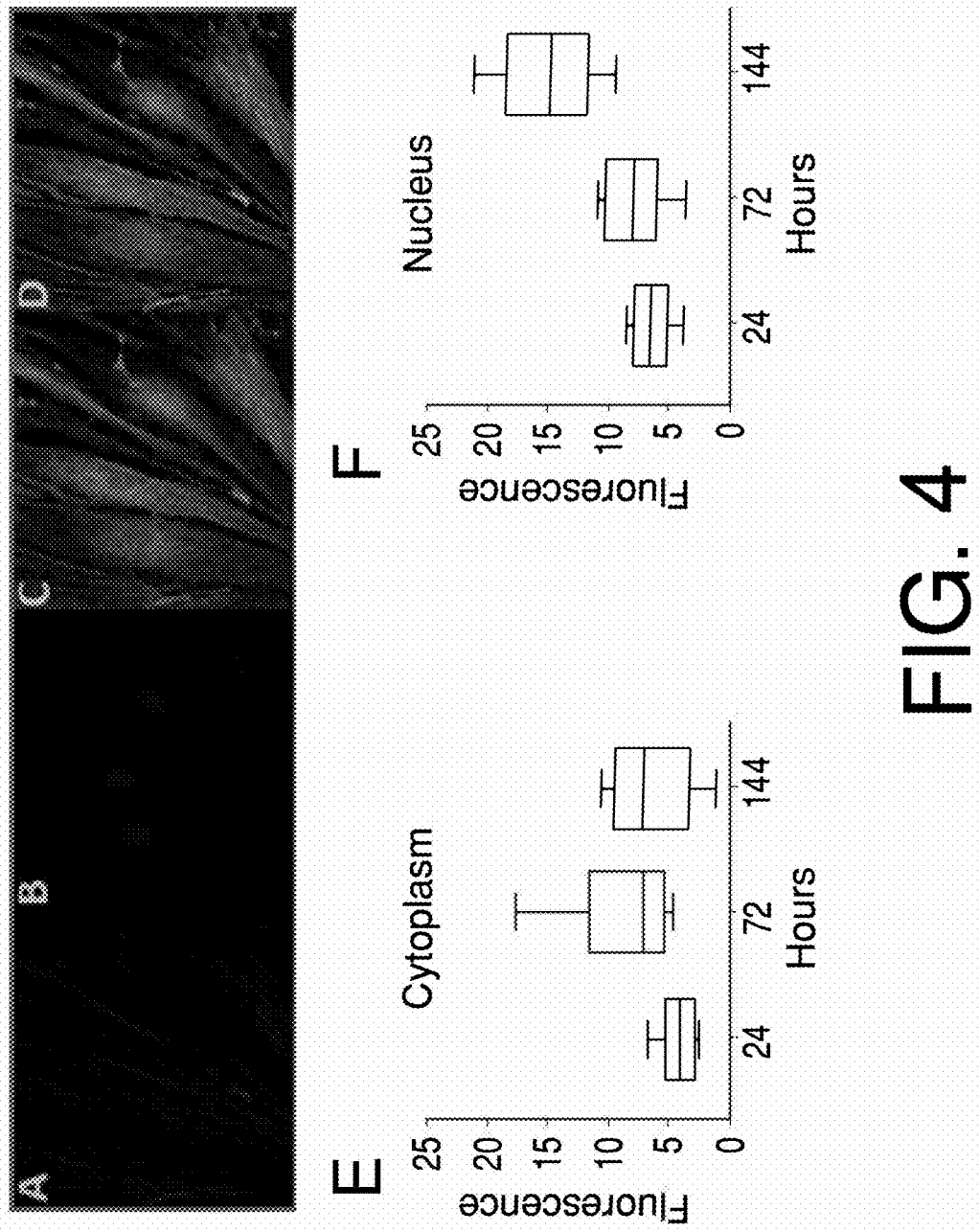
FIG. 4. RPP is cell permeable and accumulates in the nucleus. (A-D) 100 nM FLAG-RPP-CPP (CAQKDYKD-DDDKTEDLEPPEPPLPKENGRKKRRQRRRG (SEQ. ID NO: 4)) was added to mesenchymal progenitor cells (MPCs) and incubated for 4 hours. After 6 days in culture, the RPP concentrated in the nucleus. (E, F). Over a 6-day period, the peptide translocates from the cytoplasm to the nucleus (standard deviation, n=3). (A) cytoskeleton (phalloidin); (B) nucleus (hoechst dye); (C) RPP (FLAG Ab); (D) composite image.

Result. After a 4 hour incubation with RPP (SEQ ID NO.: 4), followed by 6 days in culture, RPP remains internalized in mesenchymal progenitor cells (MPCs) (FIGS. 4, C and D) and localizes in the nucleus over the 6 day culture period (FIGS. 4, E and F).

Materials and Methods

Dosing and Cell Culture. MPCs were cultured as previously described[116], plated at $1.0 \times 10^4$ cells/cm$^2$ onto glass coverslips in a 24-well plate, incubated overnight at 37° C., dosed with 100 nM RPP (SEQ ID NO: 4) for 4 hours, followed by a change in media. Cell were cultured for 6 days with a media change every two days. Interim MPC harvesting occurred at 24 and 72 hours to assess intracellular RPP localization.

Immunohistochemistry. Phalloidin (Invitrogen) was used for cytoskeletal staining, Hoechst 333429 (Calbiochem) dye was used to visualize the nucleus, and FLAG antibody (Sigma-Aldrich) was used to visualize the RPP. Images were taken with a confocal laser scanning microscope.

Sciatic Nerve

Figure 5:
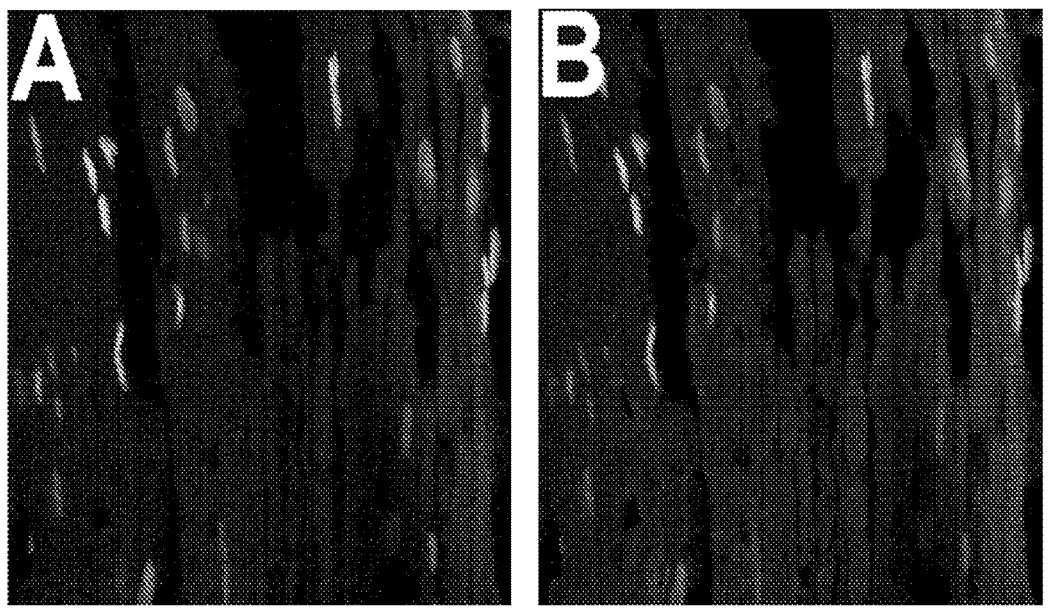
FIG. 5. RPP accumulates in the nuclei of the sciatic nerve in spinal cord. A 0.7 cm coronal spinal cord section from the L3 and L4 region of a Sprague Dawley (SD) male rat showing the surrounding nuclei of the sciatic nerve, harvested 48 hours after 1 mg (1 mg/mL) of peptide was injected into the sight of a mid-thigh sciatic nerve defect injury. A. Hoechst stain shows nuclei. B. FLAG antibody shows FLAG-RPP-CPP (SEQ. ID NO: 4) localization.

Result. Linear RPP accumulates in the nucleus of sciatic nerve tissue (FIGS. 5, A and B).

Materials and Methods

Dosing and Procedure. FIG. 5: The sciatic nerve of a Sprague Dawley rat (L3 and L4 region) was exposed (Schmitz and Beer, 2001)[117] and a 0.7 cm section remove to create an approximately 1 cm segmental defect following retraction of the nerve stumps (Hems and Glasby, 1993)[118] 1 mg of RPP (SEQ ID NO: 4) in PBS was injected into the site of injury and the surgical incision was closed. After 48 hours, the animal was sacrificed and the spinal cord from the L4 to L6 region was sectioned coronally.

Rational for dose levels. Maximum feasible dose.
Test Article Identification. RPP (SEQ ID NO: 4)
Purity. ≥95%

Immunohistochemistry. Hoechst 333429 (Calbiochem) dye was used to visualize the nucleus, and FLAG antibody (Sigma-Aldrich) was used to visualize the RPP. Images were taken with a light microscope.

Example 9—RPP Induced Degradation of REST Protein

Result. RPP (SEQ ID NO: 4) decreased REST protein levels by 58% compared to vehicle control (FIG. 6).

Materials and Methods

Test Article Identification. RPP (SEQ ID NO: 4)
Purity. ≥95%

Dosing and Cell Culture. HEK 293 cells were grown in Dulbecco's Modified Eagle's Medium (DMEM) supplemented with 10% bovine calf serum. Transfection of HEK 293 cells, with 100 nM of full-length human REST protein[2], was performed in 80 to 90% confluent cultures in 35 mm dishes using lipofectamine2000 (Life Technologies), following manufacturer recommendations. 24 hours post transfection, cells were dosed with 100 nM RPP (SEQ ID NO: 4) or vehicle control (PBS) overnight.

Western Blot Analysis. Whole-cell lysates were prepared following the procedures in Ballas et. al., 2001[119]. Western blots were performed by standard procedures using anti-REST-C[64], anti-GAPDH (abeam [6C5]), and anti-IgG conjugated to infrared dyes (Thermo Fisher), and analyzed on an Odyssey infrared fluorescence imager (LiCor). The bar graph is a quantification of the Western Blot using ImageJ (https://imagei.nih.gov/ii).

Example 10—RPP can be Used to Induce Expression of BDNF, NGF, $K_V4.3$, $K_V7.2$, Nav1.8, and OPRM1 mRNR and is not Neurotoxic Result. RPP increases expression of BDNF, NGF, $K_V4.3$, $K_V7.2$, Nav1.8, and OPRM1 (FIGS. 7, 8, 9, 10, 14, 15, and 16; Table 15). RPP (SEQ ID NO: 12) does not cause necrosis in DRG neurons (FIG. 17), as demonstrated by an LDH cytoxicity assay in DRG neurons incubated with various concentrations of RPP for 48 h. ***=p<0.001, n=4, one-way ANOVA and Dunnett's test, error bars=SD.

Drop 2000 (ThermoFIsher), and reverse transcription was run using High Capacity cDNA Reverse Transcription Kit (Applied Biosystems) and 2 ng/μL RNA per reaction. For qRT-PCR, 5 μL of cDNA (corresponding to 10 ng of RNA) were mixed with to 10 μL SsoAdvanced™ Universal SYBR® Green Supermix (BioRad) and 1 μL of each primer (final primer concentration 500 nM each). Reactions were run in triplicates in a QuantStudio™ 7 Flex Real-Time PCR system (Applied Biosystems). Amplification data were analyzed using the comparative cycle threshold ($\Delta DC_t$) method and β-actin as calibrator. The primers used were as follows: β-actin forward: 5'-AGAGCACGAGCTGCCTGAC-3' (SEQ ID NO: 332), β-actin reverse: 5'-GGATGCCACA-GGACTCCA-3' (SEQ ID NO: 333), BDNF forward: 5'TATTAGTGAGTGGGTAACGGCG3' (SEQ ID NO: 334), and BDNF reverse: 5'GAAGTATTGCTTCAGTTGGC-CTT3' (SEQ ID NO: 335).

FIG. 8 Material and Methods

Transient Transfections and Cell Culture. NBFL cells were grown as previously described[120]. 0.5 M NFBL cells were seeded on a 35 mm dish, incubated at 37° C. overnight, and transfected with 2 μg of REST (SEQ. ID NO: 1)-IRES-

TABLE 15

RPP induced expression of BDNF, NGF, Kv4.3, Kv7.2, Navi.8, and OPRM1 mRNA

| Target | Figure | Increase | Cell Type | RPP SEQ ID NO | Dose | Duration |
|---|---|---|---|---|---|---|
| BDNF | 7 | 2.4x | HEK 293 | 4 | 100 nM | 24 h |
| BDNF | 9 | 5x | NBFL | 2 | 1 μM | 16 h |
| BDNF | 9 | 2.3x | NBFL | 2 | 1 μM | 48 h |
| BDNF | 9 | 2.3x | NBFL | 4 | 1 μM | 48 h |
| BDNF | 10 | 2x | MPC | 9 | 3 μM | 48 h |
| BDNF | 16 | 1.4x | DRG | 12 | 0.3 μM | 48 h |
| BDNF | 16 | 1.3x | DRG | 12 | 1 μM | 48 h |
| BDNF | 16 | 1.3x | DRG | 12 | 3 μM | 48 h |
| BDNF | 16 | 1.7 | DRG | 12 | 10 μM | 48 h |
| NGF | 9 | 3.2x | NBFL | 2 | 1 μM | 16 h |
| NGF | 9 | 1.7x | NBFL | 2 | 1 μM | 48 h |
| NGF | 9 | 1.9x | NBFL | 4 | 1 μM | 48 h |
| NGF | 10 | 2.9x | MPC | 9 | 3 μM | 48 h |
| NGF | 16 | — | DRG | 12 | 0.3 μM | 48 h |
| NGF | 16 | 0.9x | DRG | 12 | 1 μM | 48 h |
| NGF | 16 | 1.25 | DRG | 12 | 3 μM | 48 h |
| NGF | 16 | 1.9 | DRG | 12 | 10 μM | 48 h |
| $K_V4.3$ | 8 | 3x | NBFL | 1 | 2 μg (transfected) | 48 h |
| $K_V4.3$ | 9 | 5x | NBFL | 2 | 1 μM | 16 h |
| $K_V4.3$ | 9 | 5x | NBFL | 2 | 1 μM | 48 h |
| $K_V4.3$ | 9 | 19.5x | NBFL | 4 | 1 μM | 48 h |
| $K_V4.3$ | 14 | 0x | DRG | 12 | 1 μM | 48 h |
| $K_V4.3$ | 14 | 0x | DRG | 12 | 3 μM | 48 h |
| $K_V4.3$ | 14 | 1.9x | DRG | 12 | 10 μM | 48 h |
| $K_V7.2$ | 14 | 0 | DRG | 12 | 1 μM | 48 h |
| $K_V7.2$ | 14 | 6.7x | DRG | 12 | 3 μM | 48 h |
| $K_V7.2$ | 14 | 7.5x | DRG | 12 | 10 μM | 48 h |
| Nav1.8 | 13 | 0.8x | DRG | 12 | 1 μM | 48 h |
| Nav1.8 | 14 | 2.6x | DRG | 12 | 3 μM | 48 h |
| Nav1.8 | 14 | 4x | DRG | 12 | 10 μM | 48 h |
| Nav1.8 | 15 | 6x | DRG | 13 | 1 μM | 48 h |
| Nav1.8 | 15 | 13x | DRG | 14 | 1 μM | 48 h |
| OPRM1 | 14 | 1.2x | DRG | 12 | 1 μM | 48 h |
| OPRM1 | 14 | 3x | DRG | 12 | 3 μM | 48 h |
| OPRM1 | 14 | 3.9x | DRG | 12 | 10 μM | 48 h |

Figure 7:
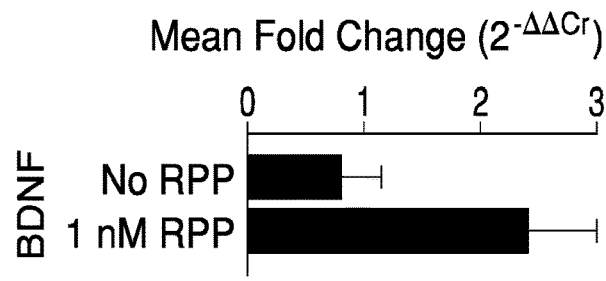
FIG. 7. RPP increases BDNF expression. mRNA levels in HEK 293 cells measured with qPCR after a 4-hour incubation with FLAG-RPP-CPP (SEQ ID NO: 4, 100 nM) or vehicle (PBS) 24 hours in culture. The mean fold change in expression of BDNF ($2^{-DDC_T}$) was 2.401 10.885 (standard deviation, n=3). A mean fold change of 1=no change. $2^{-DDCT}$ calculated as described by Livak et al., 2001.

FIG. 7 Materials and Methods

Test Article Identification. RPP (SEQ ID NO: 4), purity. ≥95%

Dosing and Cell Culture. 100 nM RPP; HEK 293 cells, mRNA extraction and quantification protocol. Cells were lysed in QiAzol (Qiagen) and total RNA was extracted using RNeasy Midi Kit (Qiagen) according to manufacturer's instructions. Purified RNA was quantified with the Nano- GFP cDNA[2] using lipofectamine2000 (Life Technologies), following manufacturer recommendations. After a 48 hour incubation period, cell were sorted by fluorescence activated cell sorting (FACS), mRNA extraction and quantification. mRNA was extracted, as described in Example 10, from GFP+ and – cells; mRNA levels of $K_V4.3$ were determined using real-time RT-PCR[116]. Gene expression was normalized using β-actin (ACTB) as an internal housekeeping control. The β-actin primers used are the same as Example 10. The K$_V$4.3 primers were: forward: CTCACTACCACCTGCTGCTC (SEQ ID NO: 336) and reverse: TCAGTCCGTCGTC-TGCTTTC (SEQ ID NO: 337).

Figure 9:
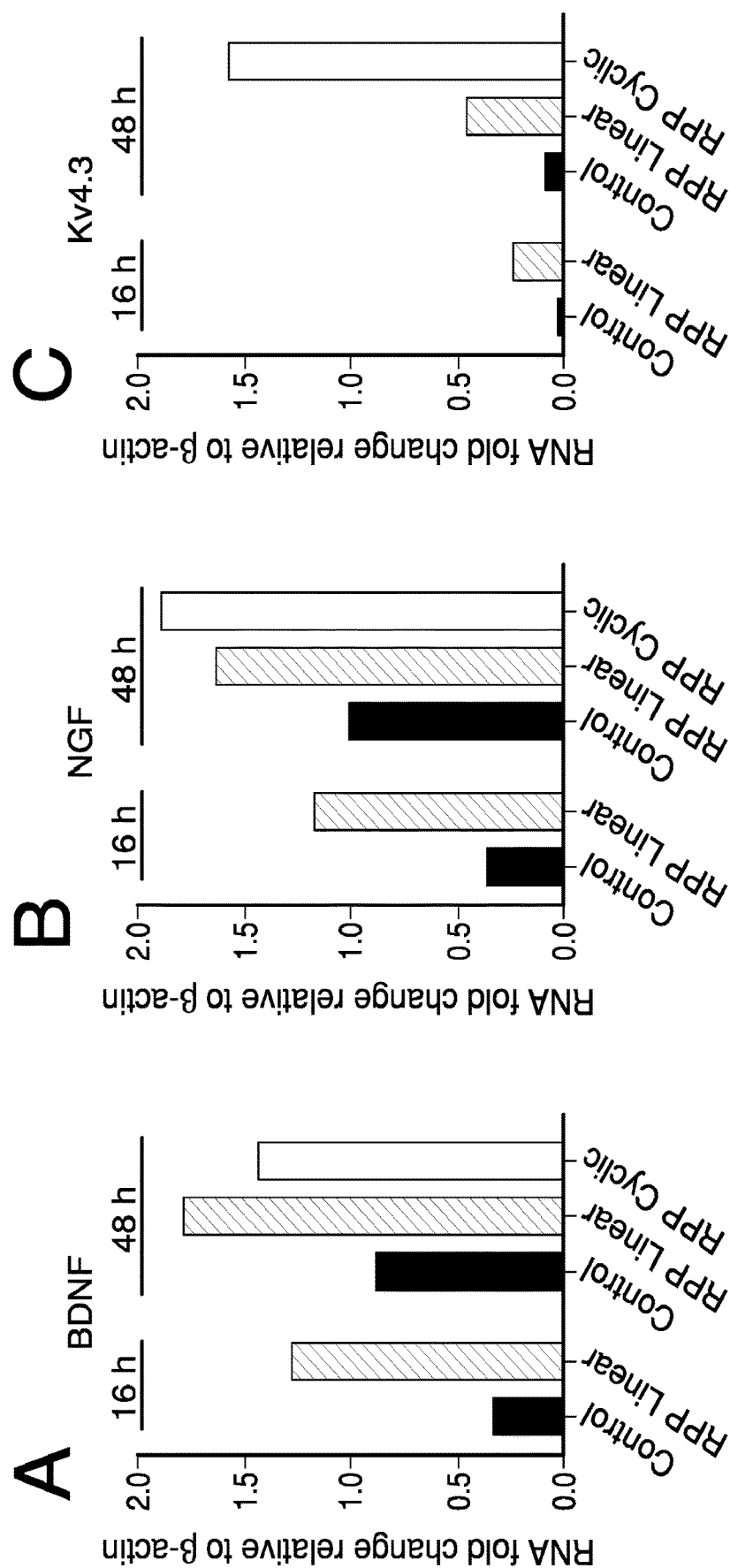
FIG. 9. Comparison of linear and cyclic RPP. NBFL cells were dosed with (1 pM) RPP (linear: SEQ ID NO: 4; cyclic: SEQ ID NO: 2, Table 8) or control peptide (SEQ ID NO:3, Table 9) for 24 or 48 hours. Efficacy on was assessed by measuring changes in (A) BDNF, (B) NGF, and (C) $K_V4.3$ transcript levels. N=1

FIG. 9: Material and Methods

Plasmids. RPP (SEQ ID NOS: 2 and 4): One segment of this construct containing T7 promoter, CPP, and His tag was synthesized as a gBlock (Table 8) by IDT and amplified with primers described in Table 8. The PCR reaction (20 µL) was initially heated at 95° C. for 2.5 min followed by 30 cycles of denaturation at 94° C. for 15 sec., annealing at 55° C. for 15 sec., and extension at 72° C. for 30 seconds. Following amplification, PCR fragment was gel-purified by the QIAGEN gel-band purification kit according to manufacturer's protocol.

pET29 plasmid was amplified with primers: forward: P12 and P14 (Table 1) introducing SbfI and XhoI restriction sites. The PCR reaction (20 µL) was initially heated at 95° C. for 2.5 min followed by 30 cycles of denaturation at 94° C. for 15 sec., annealing at 55° C. for 15 sec. and extension at 72° C. for 6 min. Following amplification, PCR fragment was gel-purified by the QIAGEN gel-band purification kit and digested with SbfI and XhoI restriction enzymes. All digested fragments were purified with a QIAGEN kit and ligated in appropriate combination using T4 DNA ligase (NEB) according to the manufacturer's recommendations. Ligated fragments were transformed in 10G chemically competent cells and sequenced.

The nucleotide sequence of RPP (Table 8) was assembled and digested by HindIII and BamHI restriction enzymes. This fragment was cloned in pET vector described above in-frame with the CPP and His tag.

Control peptide: The control peptide (CP) was incorporated into the gBlock sequence shown in Table 9 and then cloned into the pET vector. The CP sequences are shown in Table 9.

In vitro Expression. RPP (Table 8) or CP (Table 9) were expressed in vitro using the PURE Express In Vitro Protein Synthesis Kit (New England Biolabs). The RPP (SEQ ID NOS: 2 and 4) or CP sequence was amplified from the RPP (SEQ ID NOS: 2 and 4) or CP expression constructs (Table 8 and 9) with primers listed in Table 8, and gel-purified by the QIAGEN gel-band purification kit. The PCR reaction (20 µL) was initially heated at 95° C. for 2.5 min followed by 30 cycles of denaturation at 94° C. for 15 sec., annealing at 55° C. for 15 sec., and extension at 72° C. for 30 sec. Then, 15 µL of the purified PCR fragment was mixed with 10 µL of Solution A and 7.5 µL of Solution B of the PURE Express In Vitro Protein Synthesis Kit (New England Biolabs) and incubated 2 hours at 37° C. Next, 2 µL of DNAse I was added and incubated for 20 min at 37° C.

TABLE 8

RPP-CPP-His_pET cassette

Nucleotide Sequence (SEQ ID NO: 316)
cctgcaggTAATACGACTCACTATAGGGTTAACTTTAGTAAGGAGGACAG
CTAAaagcttATGTGTACCGAAGATCTGGAACCACCAGAACCACCACTGC
CAAAGGAAAATTGTggatccGGCTCTGGTCGTAAAAAGCGCCGTCAGCGT
CGGCGTGGTGGCTCCGGTAGCTTAGGTCACCATCACCATCACCACGGCAC
CGGCTATTAActcgag Coding Sequence (SEQ ID NO: 317)
ATGTGTACCGAAGATCTGGAACCACCAGAACCACCACTGCCAAAGGAAAA
TTGTggatccGGCTCTGGTCGTAAAAAGCGCCGTCAGCGTCGGCGTGGTG
GCTCCGGTAGCTTAGGTCACCATCACCATCACCACGGCACCGGCTATTAA TABLE 8-continued RPP-CPP-His_pET cassette Protein Sequence (SEQ ID NO: 2)
MCTEDLEPPEPPLPKENCGSGSGRKKRRQRRRGGSGSLGHHHHHHGTGY Amplification Primers
Forward: aaatcctgcaggTAATACGACTCACTATAGGGTTAAC
(SEQ ID NO: 318)
Reverse: ATTATTctcgagTTAATAGCCGGTGCCGTGGTGATGGTGAT
GGTGACCTA (SEQ ID NO: 319)

gBlock (SEQ ID NO: 320)
tataccctgcaggTAATACGACTCACTATAGGGTTAACTTTAGTAAGGAG
GACAGCTAAaagcttATGTGTGAAGACGCCAAAAACATAAAGAAAGGCCC
GGCGCCATTCTATCCGTGTggatccGGCTCTGGTCGTAAAAAGCGCCGTC
AGCGTCGGCGTGGTGGCTCCGGTAGCTTAGGTCACCATCACCATCACCAC
GGCACCGGCTATTAActcgagagatc The restriction sites: small font
RPP, CPP and His tag: underlined

TABLE 9

Control-CPP-His pET cassette

Nucleotide Sequence (SEQ ID NO: 321)
cctgcaggTAATACGACTCACTATAGGGTTAACTTTAGTAAGGAGGACAG
CTAAaagcttATGTGTGAAGACGCCAAAAACATAAAGAAAGGCCCGGCGC
CATTCTATCCGTGTggatccGGCTCTGGTCGTAAAAAGCGCCGTCAGCGT
CGGCGTGGTGGCTCCGGTAGCTTAGGTCACCATCACCATCACCACGGCAC
CGGCTATTAActcgag Coding Sequence (SEQ ID NO: 322)
ATGTGTGAAGACGCCAAAAACATAAAGAAAGGCCCGGCGCCATTCTATCC
GTGTggatccGGCTCTGGTCGTAAAAAGCGCCGTCAGCGTCGGCGTGGTG
GCTCCGGTAGCTTAGGTCACCATCACCATCACCACGGCACCGGCTATTAA Protein Sequence (SEQ ID NO: 3)
MCEDAKNIKKGPAPFYPCGSGSGRKKRRQRRRGGSGSLGHHHHHHGTGY Amplification Primers
Forward: aaatcctgcaggTAATACGACTCACTATAGGGTTAAC
(SEQ ID NO: 323)
Reverse: ATTATTctcgagTTAATAGCCGGTGCCGTGGTGATGGTGAT
GGTGACCTA (SEQ ID NO: 324)

The restriction sites: small font
Control peptide, CPP and His tag: underlined

Purification. RPP (SEQ ID NOS: 2 and 4) and CP: The final solution from the in vitro expression step was diluted to 100 µL and filtered through the Amicon Ultracel 0.5 mL-100K columns (Sigma) to remove ribosomes. The flow through was added to 100 µL of washed Ni-NTA Magnetic Agarose Beads (Qiagen) and was washed with wash buffer as described by the manufacturer.

Cyclization. The RPP (SEQ ID NO: 2) or was cyclized by mixing the beads with 500 µL of the cyclization solution which was made by mixing 2.65 mL of the 1.33×PBS (66.5 mM phosphate buffer, 400 mM NaCl) with 1.32 mL of dibromo-m-xylene solution in acetonitrile (2.5 mg/mL). Following incubation with the cyclization solution beads were washed once with wash buffer I (PBS with 25 mM imidazole, 0.5 µL/mL of mercaptoethanol), once with wash buffer II (PBS with 25 mM imidazole, 0.5 mM TCEP), twice with wash buffer III (PBS with 25 mM imidazole) and eluted with 50 µL of the elution buffer (PBS with 500 mM imidazole). Imidazole was removed using Bio-Rad Micro Bio-Spin Chromatography columns.

Dosing and Cell Culture. NBFL cells (FIG. 9) grown in 6 well were dosed with 1 µM of linear (SEQ ID NO: 2) or cyclic (SEQ ID NO: 2) RPP (Table 8) or control peptide (Table 9) for 16 or 48 hours.

Mesenchymal progenitor cells (MPCs) (FIG. 10) from two patients were plated on 12 well plates and cultured in general medium (GM) (DMEM, 10% FBS, PSF). Lyophilized RPP (SEQ ID NO: 9) was dissolved in water at a concentration of 5 mM (1 mg/34.89, diluted in medium to 3 µM, and then incubated with the cell for 48 hours. The control was water.

mRNA Extraction and Quantification.

After dosing, cells were lysed and assessed for BDNF, NGF, and $K_V4.3$ mRNA levels (FIG. 9). All of the primers used have been described except for NGF: forward: 5'TATCCTGGCCACACTGAGGT3' (SEQ ID NO: 338) and reverse 5'TCCTGCAGGGACATTGCTC3' (SEQ ID NO: 339).

Figure 10:
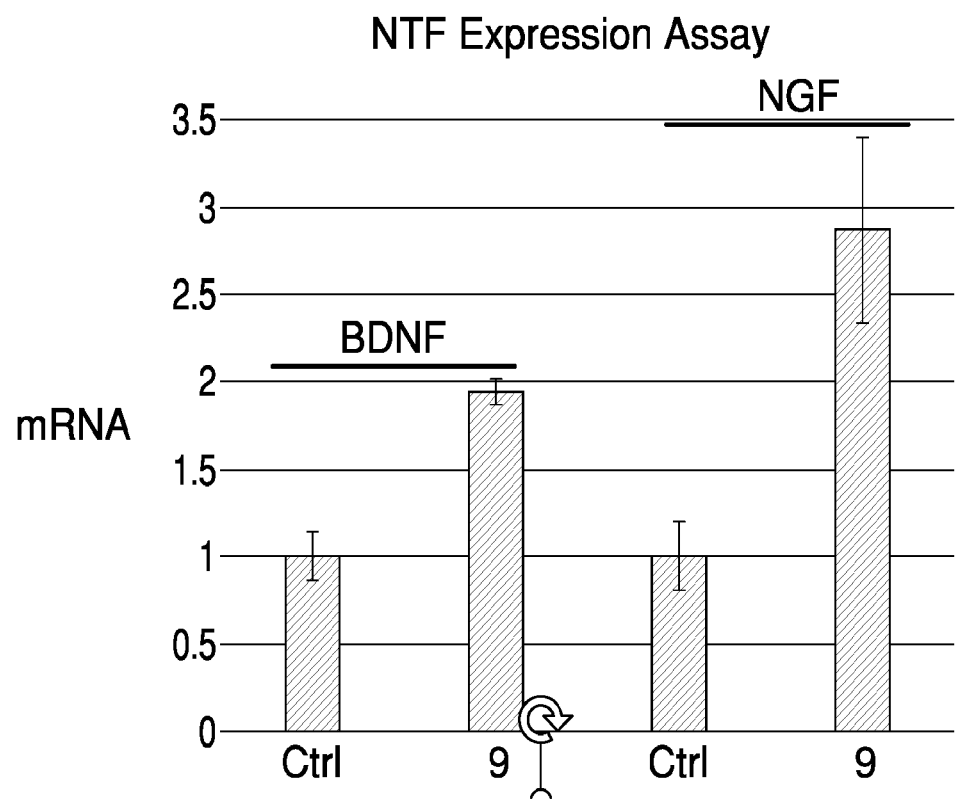
FIG. 10. BDNF and NGF mRNA expression (normalized to actin) in mesenchymal progenitor cells (MPCs), from two patients, after a 48 hour incubation with water (Ctrl) or 3 pM RPP (SEQ. ID NO: 9). mRNA levels are shown relative to control (standard deviation, n=2).

FIG. 10 Materials and Methods

MPCs were cultured as described in Gervasi et al., 2020[76].

FIGS. 14, 15, and 16 Material and Methods.

L5 DRGs were dissected from adult male rats and plated in 12-well plates pre-coated with poly-D-Lysine (PDL) and laminin in a minimal volume of medium (250 ul Neurobasal™-A medium (GIBCO) supplemented with B27 (GIBCO), 50 ng/ml NGF (Sigma-Aldrich) and penicillin streptomycin) to allow attachment to the culture plate. One day after plating, DRGs were incubated with RPP (SEQ. ID NO: 12: 1 µM, 3 µM or 10 µM in culture medium, FIGS. 14 and 16; SEQ ID NOS: 13 and 14: 3 µM, FIG. 15) for 48 h. For RNA expression analysis, DRGs were lysed in 300 µl of Qiazol in a 1.5 ml tube containing Bullet Blender Pink Beads using a Bullet Blender Tissue Homogenizer (NextAdvance). Total RNA was extracted using RNeasy Midi Kit (Qiagen) according to manufacturer's instructions. Purified RNA was quantified with NanoDrop 2000 (ThermoFIsher), and reverse transcription was run using High Capacity cDNA Reverse Transcription Kit (Applied Biosystems) and 2 ng/ul RNA per reaction. For qRT-PCR, 5 ul of cDNA (corresponding to 10 ng of RNA) were mixed with to 10 ul SsoAdvanced™ Universal SYBR® Green Supermix (Bio-Rad) and 1 ul of each primer (final primer concentration 500 nM each). Reactions were run in triplicates in a QuantStudio™ 7 Flex Real-Time PCR system (Applied Biosystems). Amplification data were analyzed using the comparative cycle threshold (ΔΔCt) method and β-actin as calibrator. Primers were as follows: β-actin: F-AGAGCTATGAGCTGCCTGAC (SEQ ID NO: 340), R-GGATGCCACAGGACTCCA (SEQ ID NO: 333); $K_V4.3$: F-AGCTGTGCCTCAGAACTAGGCTTT (SEQ ID NO: 341), R-TACCAGAAAGACGCAGGGATGCTT (SEQ ID NO: 342); $K_V7.2$ F-CCGGCAGAACTCAGAAGA AG (SEQ ID NO: 343), R-TTTGAGGCCAGGGGTAAGAT (SEQ ID NO: 344); OPRM1: F-TTCCTGGTCATGTATGTGATTGTA (SEQ ID NO: 345), R-GGGCAGTGTACTGGTCGCTAA (SEQ ID NO: 346).

FIG. 17 Materials and Methods

Cytotoxicity Assay: Cytotoxicity of RPP (SEQ. ID NO: 12) was assessed with LDH-Glo™ Cytotoxicity Assay (Promega) according to the manufacturer's instructions. Medium was collected 48 h after treatment with RPP or 15 min incubation with 2% triton X-100 (which induces necrosis). Medium was diluted 1:50 in LDH storage buffer (200 mM Tris-HCl (pH 7.3), 10% Glycerol, 1% BSA). To verify the linear range of the assay, LDH titration curve was also run together with the experimental samples. 50 µl of diluted medium or LDH serial dilutions were incubated with 50 µl of LDH Detection Reagent (50 µl LDH Detection Enzyme Mix, 0.25 µl Reductase Substrate) for 40 min. Luminescence was recorded with an Infinite M200 Pro (Tecan) instrument.

Example 11—RPP (SEQ ID NOS: 1 and 15 Through 17) or $RPP_V$ (SEQ ID NOS: 18 Through 117) Peptide Fused to a CPP (SEQ ID NOS: 118 Through 137 and 140 Through 159) can be Used to Induce Neurodifferentiation Approach 1. To determine if RPP (SEQ ID NOS: 1 and 15 through 17) or $RPP_V$ (SEQ ID NOS: 18 through 117) peptide fused to a CPP (SEQ ID NOS: 118 through 137 and 140 through 159) are the most effective in promoting human neurogenesis and differentiation, an in vitro screening assay using neural stem progenitor cells (NSPCs) from the NCRM-1/XCL-1 iPS cell line will be used. NCRM-1/XCL-1 iPS cells were generated from CD34+ human cord blood cells by episomal plasmid reprogramming[121] and differentiated to neural stem progenitor cells (NSPCs) through an embryoid body (EB) method[122]. NCRM-1/XCL-1 NSPCs are positionally naïve NSPCs that can be rapidly differentiated to neurons[123] making them ideal for broad-based toxicology and phenotypic screening platforms[124-126]

We will use two engineered NCRM-1/XCL-1 lines for high-throughput screening in 96-well plate assays. To determine if the RPP (SEQ ID NOS: 1 and 15 through 17) or RPPv (SEQ ID NOS: 18 through 117) peptide fused to a CPP (SEQ ID NOS: 118 through 137 and 140 through 159) is cytotoxic, we will use an NCRM-1/XCL-1 line that constitutively expresses NanoLuc® luciferase under the control the CMV promoter. In this line, a CMV-Nanoluciferase-Halotag (CMV-NLHT) construct was inserted into the safe harbor AAVS1 locus of Chr. 19q by transcription activator-like effector nucleases (TALENS) (FIG. 20a). We will use luciferase activity as a rapid surrogate readout of CMV-NLHT cell number. Using this approach, we will collect time-course data to measure toxicity over prolonged exposures to the drug. If the RPP (SEQ ID NOS: 1 and 15 through 17) or $RPP_V$ (SEQ ID NOS: 18 through 117) peptide fused to a CPP (SEQ ID NOS: 118 through 137 and 140 through 159) shows toxicity levels resulting in ≥10% loss of luciferase signal, this will be confirmed using CellTox™ Green Cytotoxicity Assay.

To assess the pro-neuronal differentiation effect of RPP (SEQ ID NOS: 1 and 15 through 17) or $RPP_V$ (SEQ ID NOS: 18 through 117) peptide fused to a CPP (SEQ ID NOS: 118 through 137 and 140 through 159), we will use a second engineered NCRM-1/XCL-1 line. In this line, Nanoluciferase-Halotag (NLHT) is knocked-into the MAP2 transcriptional start site (TSS) (Chr. 2) using zinc finger nucleases (ZFN) (FIG. 20b). MAP2 expression increases with neuronal differentiation in NCRM-1/XCL-1 cultures[127] and this is replicated by increasing luciferase activity in MAP2-NHLT culture media (FIG. 20c). We will use luciferase activity in media as a surrogate readout of MAP2-NLHT neurodifferentiation and collect time-course data to track RPP (SEQ ID NOS: 1 and 15 through 17) or $RPP_V$ (SEQ ID NOS: 18 through 117) peptide fused to a CPP (SEQ ID NOS: 118 through 137 and 140 through 159) differentiation effects over real-time. This approach will allow us to rapidly compare the neurodifferentiation rates in cultures treated with RPP (SEQ ID NOS: 1 and 15 through 17) or $RPP_V$ (SEQ ID NOS: 18 through 117) peptide fused to a CPP (SEQ ID NOS: 118 through 137 and 140 through 159) or control peptide. Positive neurodifferentiation effects will be independently validated by qRT-PCR expression screening of two cohorts of cell fate marker genes[121]; a cohort of NSPC and multipotency marker genes of LIN28A, RPS27L, IFITM2, IGFBP3, ANXA1; and neuronal marker genes C10RF61, IGLON5, IGSF11, CHL1, SOX9. Luciferase activity and qRT-PCR values will be reported as mean±standard error of the mean (SEM). Statistically significant drug effects on the rate of neuronal differentiation will be determined by one-way analysis of variance (ANOVA) with Tukey's multiple comparison test.

PREDICTED RESULT & ALTERNATIVE STRATEGY. We predict that dosing of human NSPCs with RPP (SEQ ID NOS: 1 and 15 through 17) or RPP$_V$ (SEQ ID NOS: 18 through 117) peptide fused to a CPP (SEQ ID NOS: 118 through 137 and 140 through 159) will accelerate neuronal differentiation as measured by increased MAP2-luiferase activity, decreased expression of NSPC/multipotency markers and increased expression of neuronal markers when compared to vehicle controls.

If the RPP (SEQ ID NOS: 1 and 15 through 17) or RPP$_V$ (SEQ ID NOS: 18 through 117) peptide fused to a CPP (SEQ ID NOS: 118 through 137 and 140 through 159) effects shift the temporal profile NCRM-1/XCLs marker expression, this may necessitate data collection at alternate time-points. If the luciferase screen lacks the sensitivity to assess the pro-differentiation effects of the RPP (SEQ ID NOS: 1 and 15 through 17) or RPP$_V$ (SEQ ID NOS: 18 through 117) peptide fused to a CPP (SEQ ID NOS: 118 through 137 and 140 through 159), qRT-PCR data can be used to assess neural differentiation.

Material and Methods

Plasmids. CMV-Nanoluciferase-Halotag (CMV-NLHT) is commercially available from Promaga.

Cell lines and cell culture. NCRM-1/XCL-1 iPS cells were generated from CD34+ human cord blood cells by episomal plasmid reprogramming[121] and differentiated to neural stem progenitor cells (NSPCs) through an embryoid body (EB) method[122] and neurons[123] as previously described. The method for inserting a CMV-Nanoluciferase-Halotag (CMV-NLHT) construct into the safe harbor AAVS1 locus of Chr. 19q (NCRM-1/XCL-1 cell line) by transcription activator-like effector nucleases (TALENS) was previously described by Papapetrou et all., 2016[128]. The method for knocking in Nanoluciferase-Halotag (NLHT) into the MAP2 transcriptional start site (TSS) (Chr.2, of the NCRM-1/XCL-1 cell line) using zinc finger nuclease (ZFN) has been previously described[127].

Luciferase assay. The methods for determining CMV-NLHT cell number and neurodifferentiation (MAP2-NLHT) have been previously described by Fritz et al., 2017[127] and He et al., 2011[129].

qRT-PCR screen. The qRT-PCR methods for screening cell fate marker genes has been previously described by Chou et al., 2011[121].

Approach 2: Induced pluripotent stem cells (neural stem cells (NSC)-NL5) differentiate after 7 Days of RPP dosing (FIG. 11 (SEQ ID NOS: 5-11, 3 μM); FIG. 12 (SEQ ID NO: 9, 1 μM) FIG. 13 (SEQ ID NO: 13 (FIG. 27), 1 μM)) using the following "Neuron to Blank" protocol:
1. 24 well culture plates (Black Visiplate) were coated with Matrigel (12 mL/well for 30 minutes at 37° C.).
2. NSCs-NLS (see media below) were plated at 0.5×10$^5$ per well.

| Component | Final Concentration | Amount |
|---|---|---|
| DMEM/12 Medium | 1× | 97 mL |
| N2 (100×) | 1× | 1 mL |
| B27 Supplement | 2% | 2 mL |
| bFGF (prepared as 100 ug/mL stock) | 10 ng/mL | 10 μL |

3. After 24 hours (cells should be >70% confluent), the media was changed to neuronal differentiation medium (below) with various concentrations of test peptides or water control added (FIGS. 11, 12, and 13, Table 14). The neuronal differentiation medium, with new test peptides and control, was changed every 2 days for 5 days.

| Component | Final Concentration | Amount |
|---|---|---|
| D-MEM/F-12 | 1× | 88.6 mL |
| GlutaMAX™ -I Supplement | 2 mM | 1 mL |
| Bovine Serum Albumin (at 25%) | 1.8% | 7.2 mL |
| hESC Supplement | 2% | 2 mL |
| BDNF (prepared as 25 ug/mL stock) | 10 ng/mL | 40 μL |
| GDNF (prepared as 100 ug/mL stock) | 10 ng/mL | 10 μL |

4. On Day 7 cells were fixed 4% formaldehyde in 1×PBS for 30 minutes.
5. Cells were immunolabeled with mouse anti-TUJ1 (1:1000) and rabbit anti-Map2 (1:500) overnight. Then label with $2^{nd}$ antibody (anti-mouse488, anti-rabbit568 and DAPi) for 1 hour.
6. Data was collected on a BioTek plate reader
   a. Dapi: Excitation 360/40; Emission 460/20, Gain 35;
   b. Alexa 488: Excitation 485/20; Emission 528/20, Gain 50;
   c. Alexa 568: Excitation 560/20; Emission 620/10, Gain 75).

Results: In FIG. 11, RPPs SEQ ID NOS: 5 through 11 at 3 μM increased (1.7- to 2.7-times)NSC-NL5 differentiation after 7 days, as measured by MAP2 (mature neuron marker) expression normalized to DAPI (nucleus) and relative to control. In FIG. 12, RPP SEQ ID NO: 9 at 1 μM increased NSC-NL5 differentiation approximately 35% after 7 days, as measured by TUJ1 and MAP2 neuronal markers (normalized to DAPI (nucleus)) and relative to control. In FIG. 13, RPP SEQ ID NO: 13 at 0.1 and 1 μM increased NSC-NL5 differentiation after 7 days, as measured by TUJ1 (increased 60% and 3-times, respectively) and MAP2 (increased 27% and 2-times, respectively) neuronal markers (normalized to DAPI (nucleus) and relative to control). The basis for using this screen is that eliminating REST in neural progenitors cells has been shown to induce neuronal differentiation[22], which is a readout for ensemble derepression of neuronal genes.

Example 12—RPP (SEQ ID NOS: 1 and 15 Through 17) or RPP$_V$ (SEQ ID NOS: 18 Through 117) Peptide Fused to a CPP (SEQ ID NOS: 118 Through 137 and 140 Through 159) can be Used to Improve Motor and Cognitive Function after Traumatic Brain Injury Approach. We will determine whether treatment with the RPP (SEQ ID NOS: 1 and 15 through 17) or RPP$_V$ (SEQ ID NOS: 18 through 117) peptide fused to a CPP (SEQ ID NOS: 118 through 137 and 140 through 159), in a rat model of TBI alters neuronal survival and the amount of neurogenesis. We will correlate these measures with histopathological and functional recovery outcomes to determine the effectiveness of the REST peptide after TBI. We have shown that REST mRNA increases around the lesion after injury (FIG. 19). We will use a well-characterized rat model of controlled cortical impact injury (CCI)[6,130-134].

Male and female Sprague-Dawley rats (approximately 250-300 g males, 150-200 g females) will be injured by CCI unilaterally over the right parietal cortex (5 mm diameter, 4 m/s, 2 mm depth). Sham animals will undergo identical procedures without impact. Six hours after CCI, rats will have a cannula implanted in their right ventricle that will attach to an osmotic minipump for intraventricular catheter (ICV) delivery of the control or RPP (SEQ ID NOS: 1 and 15 through 17) or $RPP_V$ (SEQ ID NOS: 18 through 117) peptide fused to a CPP (SEQ ID NOS: 118 through 137 and 140 through 159) (0.17 µg/h). Six hours is a realistic initial therapeutic window with translational relevance to determine the efficacy of the RPP (SEQ ID NOS: 1 and 15 through 17) or $RPP_V$ (SEQ ID NOS: 18 through 117) peptide fused to a CPP (SEQ ID NOS: 118 through 137 and 140 through 159) will be infused until sacrifice. We will sacrifice rats at two different time points—the first cohort at 3 dpi to examine acute effects of the RPP (SEQ ID NOS: 1 and 15 through 17) or $RPP_V$ (SEQ ID NOS: 18 through 117) peptide fused to a CPP (SEQ ID NOS: 118 through 137 and 140 through 159) on neuronal death and proliferation, and the second cohort at 30 dpi to determine effects of the RPP (SEQ ID NOS: 1 and 15 through 17) or $RPP_V$ (SEQ ID NOS: 18 through 117) peptide fused to a CPP (SEQ ID NOS: 118 through 137 and 140 through 159) on functional and morphological recovery and neurogenesis. For each cohort, there will be 12 groups in a 3 (control peptide, two doses of RPP (SEQ ID NOS: 1 and 15 through 17) or $RPP_V$ (SEQ ID NOS: 18 through 117) peptide fused to a CPP (SEQ ID NOS: 118 through 137 and 159 through 143)×2 (sham, CCI)×2 (male/female) design. Male and female rats will be run on different days to enable identification of any sex-specific differences in injury, behavior or response to the RPP (SEQ ID NOS: 1 and 15 through 17) or $RPP_V$ (SEQ ID NOS: 18 through 117) peptide fused to a CPP (SEQ ID NOS: 118 through 137 and 140 through 159). Rats will be injected intraperitoneal (i.p.) with BrdU (50 mg/kg) daily during the first week to determine proliferation and maturational cell fate ($1^{st}$ cohort—daily injections 1-3 dpi, sacrifice 2 h after final injection; 2nd cohort—daily 1-7 dpi). Our prior experience suggests that we will need 16 rats/group for significant behavioral data (2nd cohort), 8 rats/group for immunohistochemistry (1st cohort).

In the second cohort, to determine the functional consequence of treatment with the RPP (SEQ ID NOS: 1 and 15 through 17) or $RPP_V$ (SEQ ID NOS: 18 through 117) peptide fused to a CPP (SEQ ID NOS: 118 through 137 and 140 through 159) compared to controls, we will examine motor and cognitive behavior at different time points post-CCI or sham injury. We will train rats before injury to obtain baseline readings for motor function on the beamwalk, rotorod, and open field tests. Rats will be tested for recovery of motor function on both beamwalk and rotorod on days 1, 3, 7, and 10 days post-injury (dpi). Open field testing will be conducted on days 4, 12, and 22 dpi. Recognition memory will be assessed with a novel object recognition test performed at 20 dpi. Data will be analyzed by repeated measure two-way ANOVA with Dunnets post hoc correction. Spatial memory and learning will be determined by the Morris Water Maze (MWM) assay starting at 25 dpi. Swim speed and latency to find a hidden platform will be recorded for all trials. The probe trial, conducted on the fifth day of training, will determine the time the rat spends in the quadrant that previously contained the hidden platform. A visible platform test will also be performed on each rat to ensure that there is little difference in visual acuity between the animals. A two-way ANOVA with Tukey's multiple comparison correction will determine if the RPP (SEQ ID NOS: 1 and 15 through 17) or $RPP_V$ (SEQ ID NOS: 18 through 117) peptide fused to a CPP (SEQ ID NOS: 118 through 137 and 140 through 159) significantly alters cognitive function in the MWM in either the sham or injured rats in comparison with control peptide[135].

After the functional assessments, 8 rats/group will be sacrificed by transcardial perfusion, and the brains removed and processed. We will determine lesion size at both 3 and 30 dpi by staining sections with cresyl violet and measuring 12 sections spaced at 500 µm intervals through the lesion. Lesion volume will be expressed as a percentage of the volume of the ipsilateral hemisphere. Serial coronal brain sections through the frontoparietal cortex and dorsal hippocampus containing the subventricular zone (SVZ) and the dentate gyrus (DG) will be examined. The total number of BrdU positive cells (detected with anti-BrdU) in different hippocampal regions and the SVZ will be counted using stereology to determine whether the RPP (SEQ ID NOS: 1 and 15 through 17) or $RPP_V$ (SEQ ID NOS: 18 through 117) peptide fused to a CPP (SEQ ID NOS: 118 through 137 and 140 through 159) alters the survival of newly proliferated cells after injury. Sections will be co-stained with different cell-specific markers to determine the identity of the proliferated cells at 3 dpi and their maturational fate at 30 dpi. Cell specific markers include NeuN (mature neurons), SOX2 (neural stem cells), doublecortin (DCX) (neuronal progenitors), GFAP or ALDHIL1 (astrocytes), Iba1 (microglia), NG2 (oligodendrocyte precursor cells, OPCs), and APC or GSTpi (mature oligodendrocytes). The number of BrdU/NeuN double positive cells in the DG and olfactory bulb at 30 dpi will be compared between the different treatment groups to determine whether the RPP (SEQ ID NOS: 1 and 15 through 17) or $RPP_V$ (SEQ ID NOS: 18 through 117) peptide fused to a CPP (SEQ ID NOS: 118 through 137 and 140 through 159) increases post injury neurogenesis. We will also determine whether there is migration of BrdU+ neuronal progenitors or mature neurons to different regions of the hippocampus—away from the DG, or from the SVZ towards the lesion area or in the rostral migratory stream (RMS). Examination of the total number of each BrdU+ cell type within the perilesional area in addition to the neurogenic niches will determine whether the RPP (SEQ ID NOS: 1 and 15 through 17) or $RPP_V$ (SEQ ID NOS: 18 through 117) peptide fused to a CPP (SEQ ID NOS: 118 through 137 and 140 through 159) alters pathology after injury. As we expect that the RPP (SEQ ID NOS: 1 and 15 through 17) or RPPv (SEQ ID NOS: 18 through 117) peptide fused to a CPP (SEQ ID NOS: 118 through 137 and 140 through 159) will increase neuronal survival, we will quantify the number of degenerating neurons (Fluorojade C), and the number of surviving neurons (NeuN) in the peri-lesional area at both time points. We will examine the corpus callosum with Luxol fast blue to indicate any differences in the amount of myelin. The unbiased optical fractionator method will be used to count cells in the neurogenic areas, peri-lesional area, and the rostromigratory stream and olfactory bulb to obtain accurate cell specific and proliferating cell counts. All data will be analyzed by two-way ANOVA with Dunnetts post hoc correction. The distribution of RPP (SEQ ID NOS: 1 and 15 through 17) or RPP$_V$ (SEQ ID NOS: 18 through 117) peptide fused to a CPP (SEQ ID NOS: 118 through 137 and 140 through 159) will be examined in sections by staining with the FLAG antiserum. The remaining 8 rats per group (2nd cohort) will be sacrificed and their brains quickly removed. Brain regions that are both ipsilateral and contralateral to the lesion will be punched out and snap frozen for RNA and protein isolation. We will determine REST levels by western blot and BDNF expression by qRT-PCR around the lesion or in neurogenic niches in comparison to control treated rat brains.

PREDICTED RESULT & ALTERNATIVE STRATEGY. We expect the RPP (SEQ ID NOS: 1 and 15 through 17) or RPP$_V$ (SEQ ID NOS: 18 through 117) peptide fused to a CPP (SEQ ID NOS: 118 through 137 and 140 through 159) will reduce the lesion volume after CCI at both 3 dpi and 30 dpi by enhancing neuronal survival. Degenerating and surviving neurons will be examined at both time points to directly assess the effect of RPP (SEQ ID NOS: 1 and 15 through 17) or RPP$_V$ (SEQ ID NOS: 18 through 117) peptide fused to a CPP (SEQ ID NOS: 118 through 137 and 140 through 159) treatment on neuronal survival. A significant early neuroprotective effect of the RPP (SEQ ID NOS: 1 and 15 through 17) or RPP$_V$ (SEQ ID NOS: 18 through 117) peptide fused to a CPP (SEQ ID NOS: 118 through 137 and 140 through 159) in the perilesional area may result in improved motor function in the first week. Although we have previously found that the greatest neuronal death was at 3 dpi after CCI in the mouse[136], it is possible that we may need to examine a different time point in the rat. We also expect that animals treated with the RPP (SEQ ID NOS: 1 and 15 through 17) or RPP$_V$ (SEQ ID NOS: 18 through 117) peptide fused to a CPP (SEQ ID NOS: 118 through 137 and 140 through 159) will show increased neurogenesis in comparison to those treated with control peptide. Our data will show whether treatment with RPP (SEQ ID NOS: 1 and 15 through 17) or RPP$_V$ (SEQ ID NOS: 18 through 117) peptide fused to a CPP (SEQ ID NOS: 118 through 137 and 140 through 159) results in an increase in DCX+ precursors in different brain regions at 3 dpi or an increase in BrdU+/NeuN+ mature neurons in the hippocampus, olfactory bulb or around the lesion at 30 dpi. We will be able to correlate these data will behavioral outcomes, to see whether treatment with the RPP (SEQ ID NOS: 1 and 15 through 17) or RPPv (SEQ ID NOS: 18 through 117) peptide fused to a CPP (SEQ ID NOS: 118 through 137 and 140 through 159) will result in improved performance in the MWM assay or novel object recognition assay[135]. In this way, we will be able to determine whether the RPP (SEQ ID NOS: 1 and 15 through 17) or RPP$_V$ (SEQ ID NOS: 18 through 117) peptide fused to a CPP (SEQ ID NOS: 118 through 137 and 140 through 159) has any negative effect on inflammation or cell proliferation.

Materials and Methods

Test System.
  Species. Male and female Sprague-Dawley rat.
  Age at Study start. Approximately 22 to 29 weeks
  Weight at study start. Approximately 250 to 300 g for males and 150 to 200 g for females.
  Study Design. For each cohort (1 and 2), there will be 12 groups in a 3 (control peptide, two doses of RPP (SEQ ID NOS: 1 and 15 through 17) or RPP$_V$ (SEQ ID NOS: 18 through 117) peptide fused to a CPP (SEQ ID NOS: 118 through 137 and 140 through 159)×2 (sham, CCI)×2 (male/female) design. In cohort 1 (immunohistochemistry), there will be 8 rats/group and in cohort 2 (behavior), there will be 16 rats/group.

Rational for dose levels. The high dose will be the maximum feasible dose (approximately 0.17 μg/h) and the lower dose will be the estimated efficacious dose based on cerebral spinal fluid (CSF) drug levels that approximate the efficacious dose determined in Example 13.

Route of Administration. A cannula implanted in the right ventricle attach to an osmotic minipump for intraventricular catheter (ICV) delivery.

Frequency of Administration. Continuous infusion until sacrifice.

Period of Dosing. Cohort 1: 3 dpi; Cohort 2: 30 dpi.

Environmental Conditions. 2 Rats/cage, with food and water provided ad libitum.

Test Article Identification. RPP (SEQ ID NOS: 1 and 15 through 17) or RPP$_V$ (SEQ ID NOS: 18 through 117) peptide fused to a CPP (SEQ ID NOS: 118 through 137 and 140 through 159)

Purity. ≥95%

Preparation of Dose Formulation. In bulk every 4 days.

Dose Formulation Assay and Stability. Dose formulations will be assessed for stability and concentration on Day 1 and 7 in the first week of the study. The acceptable concentration range is ±10% of nominal.

Controlled Cortical Impact (CCI) Model. The CCI model has been previously described[6,130-134]. RPP (SEQ ID NOS: 1 and 15 through 17) or RPP$_V$ (SEQ ID NOS: 18 through 117) peptide fused to a CPP (SEQ ID NOS: 118 through 137 and 140 through 159) or control (vehicle only) administration will initiate 6 h after CCI.

Immunohistochemistry. Methods have been previously described by Xiong, Y et al., 2007 and 2008[135,137].

Morris Water Maze. Methods have been previously described by Choi et al., 2006[138].

Example 13—RPP (SEQ ID NOS: 1 and 15 Through 17) or RPP$_V$ (SEQ ID NOS: 18 Through 117) Peptide Fused to a CPP (SEQ ID NOS: 118 Through 137 and 140 Through 159) can be Used to Improve Regeneration after Peripheral Nerve Injury Approach. Nuerotrophic factors (NTFs) are needed for functional recovery after a peripheral nerve injury (PNI) and their presence, or lack thereof, are biomarkers of the strength of the regenerative response[139,140]. Several NTF genes, including brain-derived neurotrophic factor (BDNF), nerve growth factor (NGF), pleitrophin (PTN), and neurotrophin-3 (NTF-3), are known to be repressed by injury-induced expression of REST and we have demonstrated that RPP (SEQ ID NO: 2) can reverse this transcriptional repression, at least in the case of BDNF and NGF (FIGS. 7, 9, 10, and 16)[141,142].

1) Real-time quantitative reverse transcription PCR (qRT-PCR) analysis showed that NBFL cells dosed with 1 μM linear (SEQ ID NO: 4) or cyclic (SEQ ID NO: 2) RPP for 16 or 48 hours, evoke an increase in BDNF and NGF mRNA expression (FIGS. 9, A and B and table below).

| NTF response to 1 μM RPP in FIG. 9 | | | |
|---|---|---|---|
| | | Increase | |
| NTF | RPP | 16 h | 48 h |
| BDNF | Linear | 5× | 2.25× |
| BDNF | Cyclic | NA | 1.75× |

-continued

NTF response to 1 µM RPP in FIG. 9

| NTF | RPP | Increase | |
|---|---|---|---|
| | | 16 h | 48 h |
| NGF | Linear | 3.2× | 1.66× |
| NGF | Cyclic | NA | 1.87 |

NA = Not assessed

2) RPP (SEQ ID NO: 9, 3 µM) increased NTFs BDNF and NGF approximately 2- and 3-times, respectively, relative to water control, after 48 hours. This finding confirmed that RPP is active in MPCs (FIG. 10). MPCs were cultured in general medium as previously described by Gerevasi et al., 2020[76].

3) We will quantify the effect of RPP (SEQ ID NOS: 1 and 15 through 17) or RPP$_V$ (SEQ ID NOS: 18 through 117) peptide fused to a CPP (SEQ ID NOS: 118 through 137 and 140 through 159) on the expression of NGF, BDNF, PTN, and NTF-3 in mesenchymal progenitor cells (MPCs) isolated from male and female patients with musculoskeletal trauma. MPCs are present at the site of peripheral nerve injury and are extensively characterized[143]. MPCs will be harvested during the course of normal and pre-planned surgical treatments using a standard isolation protocol developed by Dr. Leon Nesti[116,143]. MPCs from 3 different subjects will be expanded in culture. First, we will passage cells four times without neuronal induction to establish a baseline for the expression of REST and NTFs transcript and protein levels by qRT-PCR and Western Blot (WB). Next, we will repeat expansion with neuronal induction as described by Bulken-Hoover, et al.[144]. Briefly, MPCs are plated in pre-induction media, for 2 days, then augmented with all-trans-retinoic acid (RA) for 1 day, followed by 7 days in the neuroinductive media. The neuroinductive media will be changed every third day. On day 7-post induction, REST and NTFs levels will be assessed. We expect that neuronal induction should result in decreased REST expression with a corresponding increase in expression of NTFs.

To assess the potency of RPP (SEQ ID NOS: 1 and 15 through 17) or RPPv (SEQ ID NOS: 18 through 117) peptide fused to a CPP (SEQ ID NOS: 118 through 137 and 159 through 143) induction of NTFs expression in MPCs, we will first need to establish dosing by assessing RPP (SEQ ID NOS: 1 and 15 through 17) or RPP$_V$ (SEQ ID NOS: 18 through 117) peptide fused to a CPP (SEQ ID NOS: 118 through 137 and 140 through 159) cytotoxicity. Briefly, MPCs will be plated in a modified pre-induction media substituting RA with RPP (SEQ ID NOS: 1 and 15 through 17) or RPP$_V$ (SEQ ID NOS: 18 through 117) peptide fused to a CPP (SEQ ID NOS: 118 through 137 and 140 through 159) at 4 dose levels up to 10 µM or pre-induction media (with RA) for 1-day. There will be three technical and three biological replicates for each dosing group and cytotoxicity will be determined using the MTT assay[145]. To determine the optimal concentration of RPP (SEQ ID NOS: 1 and 15 through 17) or RPP$_V$ (SEQ ID NOS: 18 through 117) peptide fused to a CPP (SEQ ID NOS: 118 through 137 and 140 through 159) for decreasing levels of REST and increasing levels of NTFs, we will perform a dose-response (3 dose levels) in neuroinductive media with RPP (SEQ ID NOS: 1 and 15 through 17) or RPP$_V$ (SEQ ID NOS: 18 through 117) peptide fused to a CPP (SEQ ID NOS: 118 through 137 and 140 through 159) replacing RA at 1, 3, and 6-days post-treatment (dpt). RPP (SEQ ID NOS: 1 and 15 through 17) or RPP$_V$ (SEQ ID NOS: 18 through 117) peptide fused to a CPP (SEQ ID NOS: 118 through 137 and 140 through 159) doses will be based on the findings of the MTT assay[145]. Our negative and positive controls will be neuroinductive media − or +RA, respectively. We will quantify the gene expression and protein levels of REST and NTFs with qRT-PCR and WB[139,146]. Cells will be harvested at 1, 4, and 7-dpt and RNA and protein will be isolated from the cell lysates. A two-way ANOVA analysis, followed by a Tukey's post hoc test, will be performed to make comparisons between − and + controls and RPP (SEQ ID NOS: 1 and 15 through 17) or RPP$_V$ (SEQ ID NOS: 18 through 117) peptide fused to a CPP (SEQ ID NOS: 118 through 137 and 140 through 159) dosing groups for indicated time points. Means of populations will be reported as mean±SD, with a p-value of 0.05 or less considered statistically significant. Statistical analysis will be performed using the SAS statistical package (SAS Institute, Cary NC).

4) RPP (SEQ ID NO: 12) was assessed at 0, 0.3, 1, 3, 10 µM in an ex vivo culture of whole DRG neurons (L5, from male SD rats) for its potential to induce expression of BDNF and NGF (FIG. 16). RPP increased BDNF expression approximately 25% at 0.3, 1, and 3 µM and 75% at 10 µM. RPP increased NGF approximately 50% and 2-times at 3 and 10 µM, respectively (FIG. 15). No affect was observed at 1 µM, and 0.3 µM was inconclusive due to an n=1 (FIG. 16).

5) RPP (SEQ ID NO: 12) was assessed in an LDH cytotoxicity assay conducted on ex vivo cultured whole DRG neurons (L5, from male SD rats). RPP showed no toxicity at 0, 1, 3, or 10 µM (FIG. 17). As expected, the positive control (2% triton) was neurotoxic, as demonstrated by an increase of 90,000 RLU.

6) We will assess the ability of RPP (SEQ ID NOS: 1 and 15 through 17) or RPP$_V$ (SEQ ID NOS: 18 through 117) peptide fused to a CPP (SEQ ID NOS: 118 through 137 and 140 through 159) to induce NTF expression and stimulate regeneration in both motor and sensory ex vivo nerve models through the respective use of spinal cord and isolated dorsal root ganglion (DRG) explants[147]. Both models are used extensively to study neuroprotective and trophic properties of growth factors[148]. A 10 mm segment of intact DRG will be extracted (from 6 rats) from both sides of the spinal column (L4-L6) and cultured (FIGS. 21 & 22)[149,150]. The remaining spinal column material will be preserved for motor-neuron linked spinal cord slice cultures. These spinal columns will be sectioned transversely at 300 µm intervals with a microtome and the slices will be transferred to culture inserts with semipermeable membranes and allowed to acclimatize in culture conditions for a week[149,150]. The culture inserts with week-old organotypic spinal cord slices, having a stable population of surviving motor neurons, will then be transferred to 6-well plate for an additional 7 days in culture.

Both ex vivo explant cultures will be maintained for 2 weeks in neurobasal/B27 medium to allow extensive elongation of neuronal processes[147]. To induce a physical injury, a glass Pasteur pipette will be used to create a scratch through the elaborated neuronal processes 6 mm from the perimeter of the DRG ganglia and from the gray-white matter junction of the ventral spinal cord slice. The ex vivo cultures will be treated with RPP (SEQ ID NOS: 1 and 15 through 17) or RPP$_V$ (SEQ ID NOS: 18 through 117) peptide fused to a CPP (SEQ ID NOS: 118 through 137 and 140 through 159) (0, 1, 3, or 10 µM) starting 24 hours post-injury.

The regenerative capacity of injured neurites (motor and sensory) will be determined by monitoring cell viability and measuring axonal outgrowth. Cell viability will be assessed 7-dpt by labeling live and dead cells respectively with calcein-AM and ethidium homodimer-1. Neurite extension, an indicator of neuron regeneration, will be measured at 1, 4, and 7-dpt. Gray-scaled micrographs of the scratch region will be acquired with a Zeiss AxioObserver microscope coupled to a monochrome digital camera[151]. The number, length, and total area of regenerated sprouts within the scratch region will be analyzed with ImageJ[152].

NGF exerts much of its functional activity through its receptor, the TrkA receptor in the DRG[153], while PTN has been found to cause increased axonal outgrowth primarily in motor neurons[150,154]. BDNF and NTF-3 are present in both motor and sensory neurons. We will quantify the gene expression and protein levels of NTFs with qRT-PCR and WB[139,146]. Tissue from each ex vivo system harvested at 1, 4, and 7-dpi and RNA and protein lysates isolated. A two-way ANOVA analysis, followed by a Tukey's post hoc test, will be performed to make comparisons between control and RPP (SEQ ID NOS: 1 and 15 through 17) or RPP$_V$ (SEQ ID NOS: 18 through 117) peptide fused to a CPP (SEQ ID NOS: 118 through 137 and 140 through 159) dosing groups for indicated time points. Means of populations will be reported as mean±SD, with a p-value of 0.05 or less considered statistically significant. Statistical analysis will be performed using SAS software (SAS Institute, Cary NC).

7) RPP (SEQ ID NOS: 1 and 15 through 17) or RPP$_V$ (SEQ ID NOS: 18 through 117) peptide fused to a CPP (SEQ ID NOS: 118 through 137 and 140 through 159) will be assessed for the ability to improve regeneration and functional recovery after sciatic nerve defect in vivo in 100 rats. We have demonstrated that RPP accumulates in the nuclei of the sciatic nerve neurons in the spinal cord 48 hours after RPP was injected at the sciatic nerve injury site (FIG. 4). RPP (SEQ ID NOS: 1 and 15 through 17) or RPP$_V$ (SEQ ID NOS: 18 through 117) peptide fused to a CPP (SEQ ID NOS: 118 through 137 and 140 through 159) will be administered intravenously (IV), which will allow us to test a higher maximum feasible dose (MFD) as compared to intramuscular (IM) or subcutaneous (SC) administration. Administration by IV also avoids first-pass metabolism associated with oral and intraperitoneal (IP) administration. Dosing concentrations for the regeneration and functional recovery study will be based on the findings of a one-month single IV dose range-finding toxicity and toxicokinetic study in Sprague-Dawley rats. The dose range-finding toxicity study will be initiated upon completion after completion of 1). Briefly, the study will use four dosing levels up to 1000 mg/kg or max tolerated dose or MFD, as recommended by FDA guidance (M3(R2), 2009). The number of animals allocated per group will be as follows: Main Study: 10/sex/group; TK: 3/sex/control group and 9/sex/dosing group. Animals will be assessed for body weight, food consumption, clinical chemistry, hematology, urinalysis, organ weights, histopathology (8 core tissues), and toxicokinetics.

In the regeneration and functional recovery study, Sprague-Dawley rats will be administered RPP (SEQ ID NOS: 1 and 15 through 17) or RPP$_V$ (SEQ ID NOS: 18 through 117) peptide fused to a CPP (SEQ ID NOS: 118 through 137 and 140 through 159) weekly, by IV using a long-term venous catheter[155], for 6-weeks in 3 dosing groups (TBD)+control (10/sex/group). All animals will be anesthetized, prior to exposing the sciatic nerve[156] and removing a 0.7 cm section to create an approximately 1 cm segmental defect following retraction of the nerve stumps[157]. The nerve will be repaired using the decellularized nerve graft. The surgical incision will then be closed, and the nerve will be allowed to regenerate for 6 weeks. Only the dosing groups will be given RPP (SEQ ID NOS: 1 and 15 through 17) or RPP$_V$ (SEQ ID NOS: 18 through 117) peptide fused to a CPP (SEQ ID NOS: 118 through 137 and 140 through 159). During the 6-week period, we will evaluate functional recovery and tolerance to RPP (SEQ ID NOS: 1 and 15 through 17) or RPP$_V$ (SEQ ID NOS: 18 through 117) peptide fused to a CPP (SEQ ID NOS: 118 through 137 and 140 through 159) dosing. Each week the rats will be weighed, temperature recorded, and toe-spreading reflex assay (to determine the maximum footprint width of the injured leg testing motor nerve function) will be performed[156]. Walking track analysis (Digigait) will be performed every 2 weeks, and electrophysiological studies[158] will be conducted. Briefly, electrophysiology testing will be performed on the rat sciatic nerve. Electrical stimuli are applied using single-pulse shocks (1 mA, 0.1 ms) to the native sciatic nerve trunk at the point 5 mm proximal to the graft suturing point. Compound muscle action potentials (CMAPs) are recorded on the gastrocnemius belly from IV to 12V or until a supramaximal CMAP is reached. Normal CMAPs from the un-operated contralateral side of sciatic nerve are also recorded for comparison. The recovery rate will be determined by the ratio of injured hindlimb's CMAP to contralateral normal hindlimb's CMAP[159,160].

At the end of week 6, the sciatic nerve as well as the ventral horn (VH) of the spinal cord and DRG associated with the L4 to L6 nerve roots will be collected[161,162]. Nerve regeneration will be evaluated histologically. The proximal and distal ends and the center of the grafts will be prepared for transmission electron microscopy (TEM) through the cross section to evaluate myelination along the graft[163,164]. Briefly, ultrathin sections of ~70 nm will be cut from the nerve using an ultramicrotome, then stained with uranyl acetate and lead citrate. 10-15 fields from random sections will be selected for analysis and the number, and the size of myelinated fibers will be quantified. Mean fiber density will be calculated as previously described[73]. In addition to TEM, more sections from the same nerve will be prepared for IHC to visualize β-tubulin III in order to measure the direct growth of the axons, S100 to measure the penetration and growth of Schwann cells into the graft, von Willebrand factor to assess for angiogenesis and capillary infiltration of the healing nerve, and Luxol blue staining[165,166] to measure myelin formation within the graft. The ventral horns and DRG will be assess for RPP (SEQ ID NOS: 1 and 15 through 17) or RPP$_V$ (SEQ ID NOS: 18 through 117) peptide fused to a CPP (SEQ ID NOS: 118 through 137 and 140 through 159) associated changes within the cell bodies of the motor and sensory nerves that were injured. Images of the stained tissues will be taken with a light microscope and quantification of intensity and area fraction of the positive reactions in anatomically matched tissues will be performed using the ImageJ software (https://imagej.nih.gov/ij), to compare nerve regeneration rates between the groups[165]. DRG neurons of the injured nerve will be counted and compared to the contralateral uninjured DRG as previously described[167]. NTFs (BDNF, NGF, PTN, and NTF-3), CTDSP1 and REST will be examined via qPCR and WB.

PREDICTED RESULT & ALTERNATIVE STRATEGY. We expect that mesenchymal progenitor cells (MPCs) treated with RPP (SEQ ID NOS: 1 and 15 through 17) or RPP$_V$ (SEQ ID NOS: 18 through 117) peptide fused to a CPP (SEQ ID NOS: 118 through 137 and 140 through 159)+ neuroinductive media (− retinoic acid, RA) will increase the expression of neurotrophic factors (NTFs) and decrease the levels of REST, compared to neuroinductive media—RA, but similar to neuroinductive media+RA. We expect that the ex vivo models treated with RPP (SEQ ID NOS: 1 and 15 through 17) or RPP$_V$ (SEQ ID NOS: 18 through 117) peptide fused to a CPP (SEQ ID NOS: 118 through 137 and 140 through 159) will show an increase in neurite outgrowth in comparison to the no treatment group due to decreased REST levels. It is possible that the regenerative effects of RPP (SEQ ID NOS: 1 and 15 through 17) or RPP$_V$ (SEQ ID NOS: 18 through 117) peptide fused to a CPP (SEQ ID NOS: 118 through 137 and 140 through 159) may not be pronounced in the absence of support cells, which can secrete neurotrophic factors in vivo following neuronal injury. An alternative experiment will include the co-culture of neuro-supportive cells (e.g., Schwann cells and mesenchymal stem cells) with the dorsal root ganglion (DRG) and spinal cord explants, enriched with motor and sensory neurons, prior to injury and the subsequent RPP (SEQ ID NOS: 1 and 15 through 17) or RPP$_V$ (SEQ ID NOS: 18 through 117) peptide fused to a CPP (SEQ ID NOS: 118 through 137 and 140 through 159) treatment. Successively we will analyze the ability of the RPP (SEQ ID NOS: 1 and 15 through 17) or RPPv (SEQ ID NOS: 18 through 117) peptide fused to a CPP (SEQ ID NOS: 118 through 137 and 140 through 159) to help the regeneration of the severed nerve in a rat model. We expect that the rats treated with RPP (SEQ ID NOS: 1 and 15 through 17) or RPP$_V$ (SEQ ID NOS: 18 through 117) peptide fused to a CPP (SEQ ID NOS: 118 through 137 and 140 through 159) will have improved recovery as compared to control rats as determined by histological, electrophysiological, and functional assessments. We also expect RPP (SEQ ID NOS: 1 and 15 through 17) or RPP$_V$ (SEQ ID NOS: 18 through 117) peptide fused to a CPP (SEQ ID NOS: 118 through 137 and 140 through 159) to increase NTFs expression and decrease REST protein levels. If we do not observe signs of recovery and removal of the REST blockade, we will increase the local concentration of RPP (SEQ ID NOS: 1 and 15 through 17) or RPP$_V$ (SEQ ID NOS: 18 through 117) peptide fused to a CPP (SEQ ID NOS: 118 through 137 and 140 through 159) by direct injection to the target site (i.e., graft site or intrathecal).

Materials and Methods

Cell Culture. MPC harvesting, culturing, and neurotrophic induction have been previously described[168]. Briefly, MPCs are plated in pre-induction media, for 2 days, then augmented with all-trans-retinoic acid (RA) for 1 day, followed by 7 days in the neuroinductive media. The neuroinductive media will be changed every third day. On day 7-post induction, REST and NTFs levels will be assessed.

qRT-PCR. Methods described in Example 10.

Western Blot Analysis. Whole-cell lysates were prepared following the procedures in Ballas et. al., 2001[19]. Western blots will be performed by standard procedures using anti-REST-C[64], anti-NTFs (using commercially available antibodies), anti-GAPDH (abeam [6C5]), and anti-IgG conjugated to infrared dyes (Thermo Fisher), and analyzed on an Odyssey infrared fluorescence imager (LiCor).

Test Article Identification. RPP (SEQ ID NOS: 1 and 15 through 17) or RPP$_V$ (SEQ ID NOS: 18 through 117) peptide fused to a CPP (SEQ ID NOS: 118 through 137 and 140 through 159), Purity. ≥95%

Preparation of Dose Formulation. In bulk every 4 days.

Dose Formulation Assay and Stability. Dose formulations will be assessed for stability and concentration on Day 1 and 7 in the first week of the study. The acceptable concentration range is ±10% of nominal.

Vertebrate Animals. Male and female adult Sprague-Dawley rats, (approximately 250-300 g males, 150-200 g females) will be used to determine the efficacy of the RPP (SEQ ID NOS: 1 and 15 through 17) or RPP$_V$ (SEQ ID NOS: 18 through 117) peptide fused to a CPP (SEQ ID NOS: 118 through 137 and 140 through 159) in improving recovery from PNI. The studies will require 100 rats, 8-11 weeks old. Rats will be obtained from Charles River Laboratories.

Description of Procedures

Surgery: Rats will be anesthetized with isofluorane (4% induction, 3% maintenance) prior to all surgical procedures. In 2) organotypic spinal cord cultures will be prepared from the lumbar spinal cord of postnatal-day-8 rats (Sprague Dawley) using techniques as described previously (Rothstein et al., 1993; Corse et al., 1999). Briefly, rats will be quickly sacrificed, and the lumbosacral spinal cord will be removed and placed in Gey's balanced salt solution (Gibco) containing glucose (6.4 mg/L). In a laminar flow hood using sterile technique, the meninges will be carefully removed under magnification, and the lumbar spinal nerve roots will be transected. The cord will be placed on Aclar film and sectioned at 300 µm intervals from L2 to L5 with a McIlwain tissue chopper. Individual cord sections will be carefully transferred, using the Gey's balanced salt/glucose solution, to Millicell-CM (Millipore) permeable membranes in 6-well culture plates. Five cord sections will be placed on each membrane. Each well contained 1 mL of medium consisting of 50% minimal essential medium plus 25 mM Hepes; 25% Hanks balanced salt solution with D-glucose (25.6 mg/L); 25% heat-inactivated horse serum; and 2 mM L-glutamine. Cultures will be maintained at 37° C. under 5% CO2 in a humidified incubator for a week with medium being changed every 3 days. After a week, the slices will be transferred to another 6-well culture plates and allowed to stabilize and extend neurites for another 7 days in culture prior to any treatments.

In 3) we will expose the sciatic nerve[117] (FIGS. 21 & 22) and remove a 0.7 cm section to create an approximately 1 cm segmental defect following retraction of the nerve stumps (Hems and Glasby, 1993). The nerve will be repaired using the decellularized nerve graft. The surgical incision will then be closed, and the nerve will be allowed to regenerate for 6 weeks. Group one (control) will undergo approximately 1 cm sciatic nerve resection and will be grafted with a 1 cm decellularized allograft nerve. Group two through five will undergo a 1 cm sciatic nerve resection, grafted with a 1 cm decellularized allograft and given weekly IV injections of RPP (SEQ ID NOS: 1 and 15 through 17) or RPP$_V$ (SEQ ID NOS: 18 through 117) peptide fused to a CPP (SEQ ID NOS: 118 through 137 and 140 through 159) at drug concentrations to be determined from the dose range-finding study. All animals will be sacrificed at week 6.

Behavioral Assessments: We will monitor the animals for up to 6 weeks to evaluate functional recovery and tolerance to peptide treatment. Each week the rats will be weighed, temperature recorded and toe-spreading reflex assay (to determine the maximum footprint width of the injured leg testing motor nerve function) will be performed[117]. Walking track analysis will be performed every 2 weeks. and Electrophysiological studies will be conducted prior to sacrifice at 6 weeks.

Electrophysiology Assessments: Electrophysiology testing will be performed following previous methods[158]. In brief, the rat sciatic nerve is re-exposed and electrical stimuli (single-pulse shocks, 1 mA, 0.1 ms) are applied to the native sciatic nerve trunk at the point 5 mm proximal to the graft suturing point. CMAPs are recorded on the gastrocnemius belly from IV to 12V or until a supramaximal CMAP is reached. Normal CMAPs from the un-operated contralateral side of sciatic nerve are also recorded for comparison. Grass Tech S88X Stimulator (Astro-Med Inc.) is used for the test and PolyVIWE16 data acquisition software (Astro-Med, Inc.) is used for recording. Recovery rate is the ratio of injured hindlimb's CMAP to contralateral normal hindlimb's CMAP of a rat[158].

Sacrifice: Rats will be sacrificed at 6 weeks post injury. After sacrifice, we will use histology to evaluate axon growth through the graft, remyelination, MPC cell activity at the site of injury, anterior horn cell and DRG activity and vascularization of the regenerating nerve. We will harvest the gastrocnemius and tibialis anterior muscle of each rat after sacrifice to assess gross weight to quantify atrophy.

Justification: After PNI, there is a complex interplay between cells and molecules in the vasculature, the immune system and all of the cells endogenous to the peripheral nervous system. We do not completely understand the sequence nor the interactions between the different cells, signaling molecules, cell—cell interactions and circuitry that occurs after traumatic injury, so it is impossible to model it in vitro at the current time. Additionally, the RPP (SEQ ID NOS: 1 and 15 through 17) or RPP$_V$ (SEQ ID NOS: 18 through 117) peptide fused to a CPP (SEQ ID NOS: 118 through 137 and 140 through 159) that is the subject of investigation in this proposal may impact neural precursor cells, adult neurons as well as other cell types, and so it is critical to evaluate it in vivo in the context of PNI. The FDA also requires in vivo proof of efficacy before allowing IND status for a biologic, so this provides further justification for the in vivo nature of these experiments. Rats are used because of a significant body of behavioral research after PNI has indicated their reliability in these types of experiments. Thus, there is an extensive literature that provides a detailed framework for design and execution of experiments. Rats are more intelligent than mice, and are larger, enabling a greater ability to discern changes in functional recovery after injury. Rat physiology has more similarities to humans than the mouse, allowing for better translational relevance of experimental data. Further, the REST pathway we are targeting is conserved in Rats.

Minimization of Pain and Distress: Rats will be anesthetized with isoflurane (3-4%) for the segmental peripheral nerve defect. Following surgery animals will be allowed to recover on a heat pad until mobile. Rats will be administered acetaminophen (6 mg/ml in drinking water) for 2 days after the surgery, and additionally if signs of pain or distress are observed. Rats will be observed daily by both laboratory and veterinary staff, and animals deemed to be in distress will be treated or euthanized according to veterinary recommendations.

Euthanasia: The euthanasia used is consistent with the recommendations of the American Veterinary Medical Association Guidelines for the euthanasia of animals.

Example 14—RPP (SEQ ID NOS: 1 and 15 Through 17) or RPP$_V$ (SEQ ID NOS: 18 Through 117) Peptide Fused to a CPP (SEQ ID NOS: 118 Through 137 and 140 Through 159) can be Used for the Prevention and Treatment of Chronic Pain Completed Assessments:
The activation of REST after nerve injury results in decreased expression of several genes required for normal excitability of sensory neurons, including the potassium channels K$_V$4.3 (Kcnd3) and K$_V$7.2 (Kcnq2), the sodium channel Nav1.8 (Scn10a), and the mu opioid receptor Oprm1[60,72-74]. The basis for blocking REST to alleviate chronic pain are published studies using mouse and rat peripheral nerve injury (PNI) models[60,72-74].

1) Real-time quantitative reverse transcription PCR (qRT-PCR) analysis showed that NBFL cells dosed with 1 μM linear (SEQ ID NO: 4) or cyclic (SEQ ID NO: 2) RPP for 16 or 48 hours, evoke an increase in K$_V$4.3 mRNA expression (FIG. 9, C and Table 16 below).

TABLE 16

| Kv4.3 response to 1 μM RPP in FIG. 9 | | |
|---|---|---|
| | Increase | |
| RPP | 16 h | 48 h |
| Linear | 5× | 5× |
| Cyclic | NA | 25× |

NA = Not assessed

4) RPP (SEQ ID NO: 12; 0 (water), 1, 3, or 10 μM) was incubated for 48 hours in an ex vivo culture of whole DRGs (L5, from male SD rats) and assessed for its potential to induce expression of chronic pain associated genes K$_V$4.3, K$_V$7.2, Nav1.8, and OPRM1 (FIG. 14). RPP increased K$_V$4.3 expression 2-times at 10 μM, compared to control; increased K$_V$7.2 express 7.5- and 9-times at 3 and 10 μM, respectively; increased Nav1.8 expression 2.9- and 4.8-times at 3 and 10 μM, respectively; increased OPRM1 expression at 3 and 10 μM respectively (FIG. 14). RPP sequence ID numbers 13 and 14 were assessed at 3 μM after a 48 hour dosing period in an ex vivo culture of whole DRGs (L5, from male SD rats) and assessed for Nav1.8. Sequence 13 and 14 increased Nav1.8 expression 6- and 13-times, respectively, compared to control (FIG. 15).

5) RPP (SEQ ID NO:12) was not neurotoxic in a LDH assay conducted on ex vivo cultured whole DRGs neurons (L5, from male SD rats). RPP did not increase RLU levels compared to control. As expected the positive control (2% triton) increased RLU 90,000-times (FIG. 17).

Planned Assessments

Aim 1: Determine the Pharmacokinetics, Distribution, and Dosing of RPP (SEQ ID NOS: 1 and 15 Through 17) or RPP$_V$ (SEQ ID NOS: 18 Through 117) Peptide Fused to a CPP (SEQ ID NOS: 118 Through 137 and 140 Through 159)

SUBAIM 1.1 Development and validation of liquid chromatography-tandem mass spectrometry (LC-MS/MS) methods for detecting RPP (SEQ ID NOS: 1 and 15 through 17) or RPP$_V$ (SEQ ID NOS: 18 through 117) peptide fused to a CPP (SEQ ID NOS: 118 through 137 and 140 through 159), (in a range between 10 and 10,000 ng/mL) in rat and monkey blood plasma, CSF, and tissue.

SUBAIM 1.2. To determine the route of administration in the in vivo animal studies and the clinic, an exploratory pharmacokinetics (PK) study in SD rats will be conducted. Blood plasma samples will be collected after IV, SC, or PO administration of 1000 mg/kg RPP (SEQ ID NOS: 1 and 15 through 17) or RPP$_V$ (SEQ ID NOS: 18 through 117) peptide fused to a CPP (SEQ ID NOS: 118 through 137 and 140 through 159) at 5 min, 30 min, 4 h, 8 h, 24 h, and 48 h (2/sex/time point) and assessed for peak drug concentration ($C_{max}$), area under the curve (AUC), and half-life ($t_{1/2}$). To assess RPP (SEQ ID NOS: 1 and 15 through 17) or $RPP_V$ (SEQ ID NOS: 18 through 117) peptide fused to a CPP (SEQ ID NOS: 118 through 137 and 140 through 159), penetration to the central and peripheral nervous system, target tissues (CSF, brain, lumbar spinal cord and dorsal root ganglia (DRG)) will also be collected at euthanasia and measured for drug concentrations. RPP (SEQ ID NOS: 1 and 15 through 17) or $RPP_V$ (SEQ ID NOS: 18 through 117) peptide fused to a CPP (SEQ ID NOS: 118 through 137 and 140 through 159), will be detected using validated LS-MS/MS methods (SUBAIM 1.1)

SUBAIM 1.3. To determine dosing in the rat efficacy study (Aim 2), a single dose range-finding study in SD rat using the optimal route of administration identified in SUB-AIM 1.1 will be conducted. Four dose levels+vehicle control (3/sex/group) will be selected, based on the PK data from SUBAIM 1.1. The high dose (HD) should identify the limit dose (maximum feasible dose (MFD)), maximum tolerated dose (MTD), and/or saturation of exposure). The lower doses will be spaced in ⅓ increments. Animals will be assessed daily for survival and clinical signs (abnormalities and signs of pain or distress). Blood will be collected post dose at 6 time points selected based on the PK data from SUBAIM 1.1 and assessed for $C_{max}$, AUC, and $t_{1/2}$. Tissues that will be assessed for gene changes in the efficacy study (DRGs, lumbar spinal cord, brain) will be collected at euthanasia and assessed for RPP (SEQ ID NOS: 1 and 15 through 17) or $RPP_V$ (SEQ ID NOS: 18 through 117) peptide fused to a CPP (SEQ ID NOS: 118 through 137 and 140 through 159), concentration.

Aim 2: Assessing the Effect of RPP (SEQ ID NOS: 1 and 15 Through 17) or $RPP_V$ (SEQ ID NOS: 18 Through 117) Peptide Fused to a CPP (SEQ ID NOS: 118 through 137 and 140 through 159) on Chronic Pain.

We have demonstrated that RPP accumulates in the nuclei of rat motoneurons in the lumbar (L4-L6) spinal cord 48 hours after administration at the site of sciatic nerve transection (FIG. 4). To assess the effects of our drug on pain, we will use the preclinical SNI model using the sciatic nerve. SNI is a well-established animal model for neuropathic pain that produces robust and prolonged changes in thermal sensitivities, peripheral and central morphine analgesia, and c-fiber hypoesthesia[74]. Furthermore, SNI has previously been shown by us and others to induce expression of REST and its target genes implicated in chronic pain (FIG. 18 and Table 12, respectively)[60,72-74]. Additionally, we observed increased CTDSP1 levels, as we predicted (FIG. 18).

Efficacy of RPP (SEQ ID NOS: 1 and 15 through 17) or $RPP_V$ (SEQ ID NOS: 18 through 117) peptide fused to a CPP (SEQ ID NOS: 118 through 137 and 140 through 159) to decrease chronic pain will be done in Phase 1 and durability of the pain reduction will be determined in Phase 2. The SNI sciatic nerve rat model will be used to test if RPP (SEQ ID NOS: 1 and 15 through 17) or $RPP_V$ (SEQ ID NOS: 18 through 117) peptide fused to a CPP (SEQ ID NOS: 118 through 137 and 140 through 159), decreases chronic neuropathic pain. Administration of RPP (SEQ ID NOS: 1 and 15 through 17) or $RPP_V$ (SEQ ID NOS: 18 through 117) peptide fused to a CPP (SEQ ID NOS: 118 through 137 and 140 through 159), or vehicle or a standard of care drug used to treat neuropathic pain, oxycodone will be done. The experimental procedure for phase 1 is summarized in Table 17 below:

TABLE 17

| SNI and Sham Surgery Groups | | Rat # | Euthanasia Day Post-Start of rpp dosing | Assessment |
|---|---|---|---|---|
| 1 | rpp LD | 12 SNI | 14 | All rats behavior testing |
| | | 12 Sham | | 8 rats morphological analysis (4 SNI/4 sham) |
| | | | | 16 rats qPCR analysis (4 SNI/4 sham) |
| | | 12 SNI | 28 | All rats behavior testing |
| | | 12 Sham | | 8 rats morphological analysis (4 SNI/4 sham) |
| | | | | 16 rats qPCR analysis (4 SNI/4 sham) |
| 2 | rpp MD | 12 SNI | 14 | All rats behavior testing |
| | | 12 Sham | | 8 rats morphological analysis (4 SNI/4 sham) |
| | | | | 16 rats qPCR analysis (4 SNI/4 sham) |
| | | 12 SNI | 28 | All rats behavior testing |
| | | 12 Sham | | 8 rats morphological analysis (4 SNI/4 sham) |
| | | | | 16 rats qPCR analysis (4 SNI/4 sham) |
| 3 | rpp HD | 12 SNI | 14 | All rats behavior testing |
| | | 12 Sham | | 8 rats morphological analysis (4 SNI/4 sham) |
| | | | | 16 rats qPCR analysis (4 SNI/4 sham) |
| | | 12 SNI | 28 | All rats behavior testing |
| | | 12 Sham | | 8 rats morphological analysis (4 SNI/4 sham) |
| | | | | 16 rats qPCR analysis (4 SNI/4 sham) |
| 4 | Oxycodone | 12 SNI | 14 | All rats behavior testing |
| | | 12 Sham | | 8 rats morphological analysis (4 SNI/4 sham) |
| | | | | 16 rats qPCR analysis (4 SNI/4 sham) |
| | | 12 SNI | 28 | All rats behavior testing |
| | | 12 Sham | | 8 rats morphological analysis (4 SNI/4 sham) |
| | | | | 16 rats qPCR analysis (4 SNI/4 sham) |
| 5 | Vehicle | 12 SNI | 14 | All rats behavior testing |
| | | 12 Sham | | 8 rats morphological analysis (4 SNI/4 sham) |
| | | | | 16 rats qPCR analysis (4 SNI/4 sham) |
| | | 12 SNI | 28 | All rats behavior testing |
| | | 12 Sham | | 8 rats morphological analysis (4 SNI/4 sham) |
| | | | | 16 rats qPCR analysis (4 SNI/4 sham) |

A total of 312 2-month old SD rats (equal numbers of males and females) will be needed for this aim. A sample size of 12 rats per group will have 80% power to detect a difference of 1.20 standard deviations in pain assessments. Power analysis is based on a t-test for independent samples with a 5%, 2-sided significance level. For the efficacy study, the rats will be randomly assigned to the experimental groups (n=12/group) designated into the table on the right. Rats from each of the ten randomized groups will be examined with stimulus evoked and non-stimulus evoked behavior tests, morphological, immuno-histochemical analysis, quantitative RT-PCR (qRT-PCR) analysis, and WB analysis. At euthanasia, blood will be drawn at 2 time points (14 and 28 days) post-start of drug delivery and assessed for standard PK parameters. The DRG and brain will be extracted to determine Oprm1, Nav1.8, $K_V4.3$, and $K_V7.2$ levels. In addition, tissue will be collected for LC-MS/MS analysis to determine rpp concentration.

Surgery: SNI or sham surgery (surgery which exposes the nerve branches without nerve injury) will be performed as described previously[169]. Briefly, the rats will be anesthetized and the common peroneal and tibial nerves ligated. A 2-4 mm segment of each nerve distal to the ligation will be cut and removed, leaving the third branch of the sciatic nerve, the sural nerve intact. The sural nerve is spared to produce an increased response to noxious and non-noxious stimuli in the ipsilateral innervated region beginning at 4-days post-injury, stabilizing at 7 days and maintained up to 6 months. 7-days post injury is the accepted time point for development of chronic neuropathic pain and is translationally relevant.

Drug/Vehicle: Administration will begin on day 5 post-surgery. For RPP (SEQ ID NOS: 1 and 15 through 17) or $RPP_V$ (SEQ ID NOS: 18 through 117) peptide fused to a CPP (SEQ ID NOS: 118 through 137 and 140 through 159), the route, frequency, and drug concentrations to be tested will be based on the PK studies in Specific Aim 1. For oxycodone, the route of administration and efficacious drug exposure in the rat that approximates efficacious exposure in the humans is known: (oxycodone at a dose of 0.56 mg/kg and 0.2 mL vehicle)[170].

Behavior Tests: The effects on pain transmission and motor function will be assessed one day prior to surgery and every other day beginning on day 4 post-surgery. Both stimulus evoked and non-stimulus evoked behavior tests will be used to determine the functional effectiveness of the RPP (SEQ ID NOS: 1 and 15 through 17) or $RPP_V$ (SEQ ID NOS: 18 through 117) peptide fused to a CPP (SEQ ID NOS: 118 through 137 and 140 through 159) compared to oxycodone and vehicle. In recent years concerns over the translatability of some stimulus evoked behavior tests has led to the increasing use of stimulus evoked, non-stimulus evoked, and operant or voluntary behavior tests. For this proposal we will use the most widely used and translatable stimulus evoked behavior tests: the electronic Von Frey and heat hyperalgesia tests, a non-stimulus evoked gait analysis, and a place escape/avoidance paradigm to measure the aversive state of pain[171]. Recent studies have indicated the value in including gait analysis to detect subtle improvements and deteriorations in animal models[172]. The rat handlers and assessors performing the behaviors tests will be blinded to which experimental/control group the rats were randomly assigned. Each animal will have a unique animal number. A secret color code will be used to designate control and experimental groups. Only after analysis will this code be revealed.

Stimulus Evoked Behavior Tests: Hypersensitivity to mechanical stimulation: An electronic von Frey (Bioseb, Chaville, France) consisting of a hand-held force transducer fitted with a plastic tip will be used to test the mechanical withdrawal threshold of the left and right hind paws. The plastic tip of the force transducer will be applied to the medial plantar surface of the paw for testing the saphenous nerve and to the lateral plantar surface of the paw to test the sciatic (peroneal nerve).

Heat hyperalgesia will be measured based on a published method that we modified to use a laser as the heat source[173]. An 808 nm wavelength laser will be used as the heat source (2 W output power, the beam diameter on the skin=3 mm) and will be applied to the relevant dermatome are for the nerve being tested. The small beam size allows the involved dermatomes to be specifically targeted. For the sciatic nerve and saphenous nerves, limb withdrawal latency induced by thermal stimulation will be recorded with a cutoff point of 10 seconds.

Non-Stimulus Evoked Behavior Test: Gait Analysis: Sciatic nerve motor function will be assessed using the Digigait and Sciatic Nerve Index[172]. Briefly, utilizing the Digigait equipment available in the Rodent Behavioral Core, which has been characterized and optimized by our laboratory, sciatic nerve function will be determined pre-injury and on post-surgical days 7, 14 and 28. Rats will be placed on the motorized treadmill within the Digigait holder and a speed of 20 cm/sec set for recording of all animals. The Sciatic Nerve Index program will be used to analyze the function of the affected hind limb.

Place Escape/Avoidance: This procedure is designed to test the hypothesis that rats will avoid the environment that is associated with mechanical stimulation to the hyperalgesic area. It has been reported that a sensitivity to change in escape/avoidance behavior occurs in injured rats after treatment with analgesics (Baastrup et al 2010)[174]. The cerebral-dependent place escape/avoidance paradigm test has been described by LaBuda and Fuchs (2000)[171] and depends on escape/avoidance learning to a novel aversive environment. The animals will be tested only once 3 to 5 weeks post-injury by the same trained investigator. Testing will be done in the USU Rat Behavior Core. The animals will be allowed to habituate to ambient light and noise conditions in the test room for a minimum of 1 hour. For this test, the rats will have free access between the 'non-aversive' dark and 'aversive' light side of an enclosed chamber with a mesh floor which is readily accessible by a von Frey filament from below. Either the injured or non-injured hind paw will be routinely stimulated if the rat is in the dark or light area, respectively. A mechanical stimulus (von Frey filament) that is adequate to elicit a withdrawal response on the injured paw will be applied every 15 sec to the lateral plantar surface of one of the hind paws of the animal, depending on the location of the animal during that time, for a period of 30 min. Escape/avoidance behavior will be defined as a shift from the dark to the light area. The percentage of time spent in the white side of the box and the number of crossings between the black and white sides will be recorded. The cumulated time in the white side and the total number of crossings will be used as an indication of escape/avoidance learning.

Euthanasia: For morphological and immunohistochemical analysis, the rats will be anesthetized with ketamine/xylazine (80 to 100 mg/kg+10 mg/kg, i.p., 21 gauge needle) and perfused transcardially with 300 ml phosphate buffered saline (pH 7.4) followed by 300 ml of 4% paraformaldehyde in 0.1 M phosphate buffer. After perfusion, nerves, DRG and spinal cord will be dissected, post-fixed for 24 hours in 4% paraformaldehyde and cryoprotected for 24 hours in 30% sucrose. The tissue samples will be cut into 10 µm sections using a cryostat (Leica CM3050 S, Leica Biosystems, Wetzlar, Germany).

Histology: After euthanasia and nerve sampling, sections will be stained with Hematoxylin and Eosin. The expression levels and distribution of the REST-target genes Oprm1, Nav1.8, $K_V4.3$, and $K_V7.2$ will be assessed by immunofluorescence.

Gene Expression Analysis: For gene expression analysis of the sciatic nerve and its associated DRG and spinal cord segments, REST-target genes Oprm1, Nav1.8, $K_V4.3$, and $K_V7.2$ and control genes (Hprt, Gapd, Rn18s) will be assessed by qRT-PCR.

Protein Expression Analysis: Protein expression analysis of the sciatic nerve associated DRGs, will be assessed by SDS-PAGE immunoblotting of Oprm1, Nav1.8, $K_V4.3$, and $K_V7.2$. GAPDH will be used as loading control.

Statistical Approach: For behavior data, results will be presented as mean±standard error of the mean (SEM). A 2 factor ANOVA will be used to assess groups of animals based on time post-treatment. The Bonferroni-Holm method will be used to adjust for multiple comparisons. Two-tailed statistical significance will be established as P<0.05. For immunohistochemical analysis, Two-way ANOVA will be used to compare means for interaction effects as well as effect of group and time. For qRT-PCR, values will be reported as mean f standard error of the mean (SEM). Statistically significant drug effects on the gene expression will be determined by one-way analysis of variance (ANOVA) with Tukey's multiple comparison test.

The experimental procedure for Phase 2 is outlined in Table 18 below:

that after the drug administration period (14 or 28 days) the rats will be monitored and behaviorally assessed for pain response and motor function every other day for 30 days. The rats will be euthanized on day 30. A total of 72 2-month old, SD rats (equal numbers of males and females) will be needed for this study. A sample size of 12 rats per group will have 80% power to detect a difference of 1.20 standard deviations in pain assessments. Power analysis is based on a t-test for independent samples with a 5%, 2-sided significance level. The rats will be randomly assigned to the experimental groups designated in the table on the right. Rats from each of the ten randomized groups will be examined with stimulus evoked and non-stimulus evoked behavior tests, morphological, immuno-histochemical analysis, quantitative RT-PCR (qRT-PCR) analysis, and WB analysis.

Aim 3. Toxicology and Safety Pharmacology Assessments of RPP (SEQ ID NOS: 1 and 15 Through 17) or $RPP_V$ (SEQ ID NOS: 18 Through 117) Peptide Fused to a CPP (SEQ ID NOS: 118 Through 137 and 140 Through 159).

To support first-in-human dosing, we will assess in vitro cardiac and genetic toxicity and in vivo toxicology, safety pharmacology, and toxicokinetics of RPP (SEQ ID NOS: 1 and 15 through 17) or $RPP_V$ (SEQ ID NOS: 18 through 117) peptide fused to a CPP (SEQ ID NOS: 118 through 137 and 140 through 159) in two species, as recommended by FDA guidances M3(R2), S213, S6(R1), S7A, and S7B[175-179]. In both species, the route of administration will be selected based on the results of the PK assessment in AIM 1.

SUBAIM 3.1. Single dose range-finding study in monkey: Four dose levels+vehicle control will be assessed in 3 monkeys/sex/group. The HD should identify the MTD, MFD, and/or saturation of exposure. The lower doses will be spaced in ⅓ increments. Blood will be collected at 6 time

TABLE 18

| SNI and Sham Surgery Groups | | Rat # | Euthanasia Day Post-Start of rpp dosing | Assessment |
|---|---|---|---|---|
| 1 | rpp (TBD) | 12 SNI | 14 | All rats behavior testing |
| | | 12 Sham | | 8 rats morphological analysis (4 SNI/4 sham) |
| | | | | 16 rats qPCR analysis (4 SNI/4 sham) |
| | | 12 SNI | 28 | All rats behavior testing |
| | | 12 Sham | | 8 rats morphological analysis (4 SNI/4 sham) |
| | | | | 16 rats qPCR analysis (4 SNI/4 sham) |
| 4 | Oxycodone | 12 SNI | 14 | All rats behavior testing |
| | | 12 Sham | | 8 rats morphological analysis (4 SNI/4 sham) |
| | | | | 16 rats qPCR analysis (4 SNI/4 sham) |
| | | 12 SNI | 28 | All rats behavior testing |
| | | 12 Sham | | 8 rats morphological analysis (4 SNI/4 sham) |
| | | | | 16 rats qPCR analysis (4 SNI/4 sham) |
| 5 | Vehicle | 12 SNI | 14 | All rats behavior testing |
| | | 12 Sham | | 8 rats morphological analysis (4 SNI/4 sham) |
| | | | | 16 rats qPCR analysis (4 SNI/4 sham) |
| | | 12 SNI | 28 | All rats behavior testing |
| | | 12 Sham | | 8 rats morphological analysis (4 SNI/4 sham) |
| | | | | 16 rats qPCR analysis (4 SNI/4 sham) |

In Phase 2, the durability of the pain reduction of RPP (SEQ ID NOS: 1 and 15 through 17) or $RPP_V$ (SEQ ID NOS: 18 through 117) peptide fused to a CPP (SEQ ID NOS: 118 through 137 and 140 through 159) will be examined. For this study, the RPP (SEQ ID NOS: 1 and 15 through 17) or $RPP_V$ (SEQ ID NOS: 18 through 117) peptide fused to a CPP (SEQ ID NOS: 118 through 137 and 140 through 159) dose (low, medium, or high) and the period of drug delivery (14 or 28 days) that was determined in Phase 1 to be most efficacious will be used. The same methodology described above for the Phase 1 efficacy study will be followed. The difference being points (TBD base on PK data collected in Aim 1) and assessed for $C_{max}$, AUC, and $t_{1/2}$. There will be daily assessments for survival and clinical signs.

SUBAIMs 3.2 & 3.3. Toxicology studies in rat (3.2) and monkey (3.3). The dosing period in both species will be 4 weeks, to support dosing in humans of the same duration+a 6-week recovery period, selected because of the high stability of rpp observed in the cellular assays[77]. There will be three dose levels+vehicle control. The high doses will be the maximum tolerated doses identified in the dose range-finding studies (rat AIM 1.2 and monkey Aim 3.1). The MD will be ⅓ lower than the HD, based on AUC in the range-finding studies. The LD will approximate the efficacious dose in the in vivo efficacy study (Aim 2). The dosing interval will be the $t_{1/2}$ of RPP (SEQ ID NOS: 1 and 15 through 17) or RPP$_V$ (SEQ ID NOS: 18 through 117) peptide fused to a CPP (SEQ ID NOS: 118 through 137 and 140 through 159) in each species. In the rat study, there will be 15/sex/group. 10/sex/group will be sacrificed at the end of the Dosing Period and 5/sex/vehicle will be sacrificed at the end of the Recovery Period. Additionally, 9/sex/rpp groups and 3/sex/vehicle group will be assigned to the toxicokinetic portion of the study. In the monkey study, all animals will be assessed for toxicology and TK (3/sex/group in the Main Study and 2/sex/group in the Recovery Period). The following toxicological parameters will be assessed in both species: clinical observations, body weight, food consumption, ophthalmoscopy (fundoscopy and slit lamp examinations), and a standard battery of clinical chemistry, organ weights, and histological parameters will be assessed. Monkeys will undergo assessments of respiratory (e.g. tidal volume and hemoglobin oxygen saturation) and cardiac electrocardiogram recordings measured using non-surgical telemetry functions[179], as recommended by FDA guidance S7A[179]. The cardiovascular assessment will occur, twice during the pre-treatment, after the first dose, and at the end of the Recovery Period (if needed). The recordings will be evaluated qualitatively by a consultant board certified cardiologist. All waveforms will be qualitatively evaluated to detect rhythm or conduction disturbances, including evaluations of PR and QRS intervals. Rats will be assessed for CNS functions using the modified Irwin's functional observational battery[179,180]. TK assessments ($C_{max}$, AUC, and $t_{1/2}$) from blood plasma will be made at 6 time points (determined by the rang-finding studies).

SUBAIM 3.4. In vitro hERG assay[177]. Inhibition of hERG channels is a common cause of long QT syndrome and is also correlated with arrhythmias that can lead to ventricular fibrillation and sudden cardiac death. To test whether RPP (SEQ ID NOS: 1 and 15 through 17) or $RPP_V$ (SEQ ID NOS: 18 through 117) peptide fused to a CPP (SEQ ID NOS: 118 through 137 and 140 through 159) inhibits hERG channel current, we will contract an electrophysiological evaluation on hERG channel current in CHO cells treated with a high concentration of RPP (SEQ ID NOS: 1 and 15 through 17) or $RPP_V$ (SEQ ID NOS: 18 through 117) peptide fused to a CPP (SEQ ID NOS: 118 through 137 and 140 through 159) (10 μM) or positive control (cisapride, 0.03 μM). Each cell will serve as its own positive control. Whole cell recordings will be conducted using conventional voltage clamp techniques.

SUBAIM 3.5. Genotoxicity. RPP (SEQ ID NOS: 1 and 15 through 17) or $RPP_V$ (SEQ ID NOS: 18 through 117) peptide fused to a CPP (SEQ ID NOS: 118 through 137 and 140 through 159) will be assessed in in vitro OECD compliant Ames and in vitro chromosomal aberration assays (S2B, November 1997)[176] to determine its genotoxic potential.

AIM 4. RPP (SEQ ID NOS: 1 and 15 through 17) or $RPP_V$ (SEQ ID NOS: 18 through 117) peptide fused to a CPP (SEQ ID NOS: 118 through 137 and 140 through 159) ABUSE POTENTIAL ASSESSMENT. Because opioid receptor gene expression is inhibited by REST, it is possible that RPP (SEQ ID NOS: 1 and 15 through 17) or $RPP_V$ (SEQ ID NOS: 18 through 117) peptide fused to a CPP (SEQ ID NOS: 118 through 137 and 140 through 159) could augment the effects of endogenous opioid receptor ligands such as endorphins[181,182]. Additionally, recent studies do show an increase in expression of REST in the DRG and the periaqueductal gray area (PAG) during conditions involving pain[183,184]. To determine if RPP (SEQ ID NOS: 1 and 15 through 17) or $RPP_V$ (SEQ ID NOS: 18 through 117) peptide fused to a CPP (SEQ ID NOS: 118 through 137 and 140 through 159) produces reward-seeking behavior we will evaluate its effects on rats using conditioned place preference (CPP), a widely used behavioral assay to test the rewarding properties of drugs[185-189]. CPP is a well-established method that has demonstrated morphine reward-seeking behavior in an SNI animal model.

First, RPP (SEQ ID NOS: 1 and 15 through 17) or $RPP_V$ (SEQ ID NOS: 18 through 117) peptide fused to a CPP (SEQ ID NOS: 118 through 137 and 140 through 159) will be administered (route TBD) to uninjured rats and then CPP will be performed. Oxycodone will be used in place of morphine as a positive control for consistency with Aim 2 and saline will be injected into separate rats as a negative control.

The apparatus consists of a three-compartment chamber: the two outer compartments are designed to have different characteristics (e.g. white vs. black walls), and the central compartment has no special characteristics. Each experiment consists of three phases. Phase I Pre-test (Day 1): After administration of saline, rats will be placed in the center compartment with gates open to provide access to both the other compartments. Rats will be monitored for 15 min to determine baseline preference by recording the time spent in each chamber. The mean spontaneous preference times for the compartments will be determined. Rats that spend more than 60% of the test time in any one chamber will be considered biased and will be removed from the experiment. Phase II Conditioning (Days 2-7): Rats will be administered vehicle or RPP (SEQ ID NOS: 1 and 15 through 17) or $RPP_V$ (SEQ ID NOS: 18 through 117) peptide fused to a CPP (SEQ ID NOS: 118 through 137 and 140 through 159), and then they will be randomly assigned/conditioned to receive RPP (SEQ ID NOS: 1 and 15 through 17) or $RPP_V$ (SEQ ID NOS: 18 through 117) peptide fused to a CPP (SEQ ID NOS: 118 through 137 and 140 through 159) in one compartment and vehicle in the other. The dose of RPP (SEQ ID NOS: 1 and 15 through 17) or $RPP_V$ (SEQ ID NOS: 18 through 117) peptide fused to a CPP (SEQ ID NOS: 118 through 137 and 140 through 159) used will be based on the concentration that produces measurable effects on mechanical and thermal hyperalgesia determined in AIM 2. Treatment compartment and the order of drug and vehicle administration will be counterbalanced for all groups to avoid biases. This phase consists of six consecutive conditioning sessions 30 min in length. Conditioning will also be done with oxycodone for a separate group. Phase III Test (Day 8): rats will be injected with saline and placed in the center of the CPP box and monitored for 15 min. The difference between the time spent in the drug-paired compartment during post-conditioning and that spent during pre-conditioning will be used to assess the degree of place conditioning elicited by RPP (SEQ ID NOS: 1 and 15 through 17) or $RPP_V$ (SEQ ID NOS: 18 through 117) peptide fused to a CPP (SEQ ID NOS: 118 through 137 and 140 through 159)[190].

RPP (SEQ ID NOS: 1 and 15 through 17) or $RPP_V$ (SEQ ID NOS: 18 through 117) peptide fused to a CPP (SEQ ID NOS: 118 through 137 and 140 through 159) will be assessed using 8-groups of 12 injured rats (SNI vs. SHAM, conditioning with oxycodone, RPP (SEQ ID NOS: 1 and 15 through 17) or $RPP_V$ (SEQ ID NOS: 18 through 117) peptide fused to a CPP (SEQ ID NOS: 118 through 137 and 140 through 159), and saline). A sample size of 12 rats per group will have 80% power to detect a difference of 1.20 standard deviations in pain assessments. Power analysis is based on a t-test for independent samples with a 5%, 2-sided significance level. The rats will be randomly assigned to the experimental groups. Rats will be assigned to undergo SNI or SHAM surgery randomly. The von Frey test will be performed one day before and 4 and 8-days post-injury to monitor the pain state. At 8-days post-injury the CPP test will be conducted as previously described. The research associate performing the behavior tests will be blinded to which experimental group/control group the rat was randomly assigned. Each animal will have a unique animal number. A secret color code will be used to designate control and experimental groups. Only after analysis will this code be revealed. Animals will be euthanized, and samples analyzed as described in AIM 2.

PREDICTED RESULTS & ALTERNATIVE STRATEGIES. We predict that the RPP (SEQ ID NOS: 1 and 15 through 17) or RPP$_V$ (SEQ ID NOS: 18 through 117) peptide fused to a CPP (SEQ ID NOS: 118 through 137 and 140 through 159) will reduce REST levels in injured neurons and restore proper expression of ion channels required for excitability. At the behavioral level, RPP (SEQ ID NOS: 1 and 15 through 17) or RPP$_V$ (SEQ ID NOS: 18 through 117) peptide fused to a CPP (SEQ ID NOS: 118 through 137 and 140 through 159) should return the stimulus or non-stimulus evoked behavior tests to baseline in SNI rats. Furthermore, given its mode of action, we do not expect RPP (SEQ ID NOS: 1 and 15 through 17) or RPP$_V$ (SEQ ID NOS: 18 through 117) peptide fused to a CPP (SEQ ID NOS: 118 through 137 and 140 through 159) to have addictive properties. However, if drug administration shows abuse potential, we will confirm this positive result with a progressive ratio (PR) schedule of reinforcement during RPP (SEQ ID NOS: 1 and 15 through 17) or RPP$_V$ (SEQ ID NOS: 18 through 117) peptide fused to a CPP (SEQ ID NOS: 118 through 137 and 140 through 159) administration.

Example 15—RPP (SEQ ID NOS: 1 and 15 Through 17) or RPP$_V$ (SEQ ID NOS: 18 Through 117) Peptide Fused to a CPP (SEQ ID NOS: 118 Through 137 and 140 Through 159) can be Used to Prevent Relapse of Glioblastoma Multiforme (GBM)

Assess the neurogenic and anti-oncogenic potency of RPP (SEQ ID NOS: 1 and 15 through 17) or RPP$_V$ (SEQ ID NOS: 18 through 117) peptide fused to a CPP (SEQ ID NOS: 118 through 137 and 140 through 159) on brain tumor initiating cells (BTICs) and in vivo. Test article (RPP (SEQ ID NOS: 1 and 15 through 17) or RPP$_V$ (SEQ ID NOS: 18 through 117) peptide fused to a CPP (SEQ ID NOS: 118 through 137 and 140 through 159) activity will be assessed in primary cultured BTICs derived from 10 grade IV GBM patients obtained at the Mayo Clinic using methods we have established[191-193]. Cells ($0.25 \times 10^4$) will be plated (3.8 cm2 TC dish) in media (250 μL) dosed with 5 μL vehicle or with 3 dose levels of test article at the optimal dose range (determined in the neuronal differentiation study described in Example 13) for 0, 2, 4, or 8 days (Main Study) and then allowed to recover after wash out of test article for 8 days (Recovery Period). Markers for pluripotency (Sox2 and Nestin), proliferation (Ki67), cell death (caspase 3), and differentiation (MAP2, neuron and GFAP, glia) will be monitored on Days 0, 2, 4, and 8 during the dosing period (Main Study) and on Days 10, 13, and 16 during the Recovery Period (3/TC wells/group for each day) by WB and RT-PCR.

Primary cultured BTICs derived from 10 grade IV GBM patients will be used in an intracranial xenograph tumorigenicity nude mouse model as described previously by us and others[191,192,194]. Briefly, cells ($5 \times 10^4$) will be suspended in 5 μL PBS (control) or PBS containing one of 3 TBD (based on BTIC neurogenic potency assay above) test article dose levels and delivered using an automated syringe pump with a guide-screw system[112,195]. The injection coordinates will be X:1.5; Y:1.34; Z: −3.5 targeting the mouse striatum; a highly reliable site for tumor engraftment[196]. Mice will be assayed for survival during weeks 4, 8, 16, and 20 using the Kaplan-Meier method[197] followed by postmortem histopathology to evaluate tumor size and invasiveness (H&E stain), cell death (TUNEL), and proliferation (anti-human nuclei) (3/sex/group for all procedures).

Statistical approach: Values will be reported as mean f standard error of the mean (SEM) or standard deviation (SD) as indicated. Statistical significance will be determined by applying appropriate parametric or non-parametric variations of the student's t test or one-way analysis of variance (ANOVA). Briefly, the ratio of total REST to phosphorylated REST at different control and drug candidate treatments will be statistically tested using the Kruskal-Wallis test. Differences in marker expression between BTICs control and drug candidate cultures and orthotopic xenografts will be statistically tested using the Tukey multiple comparison test. Differences in tumor size and invasiveness between mice injected with BTICs treated with control or test article will be statistically tested using the Mann-Whitney U test, and differences in survival will be statistically tested using the log-rank test and Cox proportion hazard test[198].

Predicted results: At every time point, we expect mice with xenografts of test article dosed BTICs to present tumor free or with smaller less invasive tumors, with more cell death (TUNEL), and less GBM proliferation (anti-human nuclei) as compared to control. Additionally, we expect increased survival time in mice injected with test article and BTICs compared to BTICs alone.

Materials and Methods

Test Systems

Cells. Primary cultured brain tumor initiating cells (BTICs) were derived from 10 grade IV GBM patients. The methods for extracting and propagating the BTICs have been previously described by Dr. Alfredo Quinones-Hinojosa and his research team[191-193].

Species/Strain. Nu/nu Harlan Sprague Dawley mice

Age: At study start: 6 weeks

Weight: At study start: Males: 20-30 g; Females: 18-35 g

Test Article Identification.

RPP (SEQ ID NOS: 1 and 15 through 17) or RPP$_V$ (SEQ ID NOS: 18 through 117) peptide fused to a CPP (SEQ ID NOS: 118 through 137 and 140 through 159)

Purity: ≥95% HPLC

Dose Formulation preparation and stability: RPP (SEQ ID NOS: 1 and 15 through 17) or RPP$_V$ (SEQ ID NOS: 18 through 117) peptide fused to a CPP (SEQ ID NOS: 118 through 137 and 140 through 159) and vehicle control will be prepared in bulk every week. Dose formulation concentrations will be assessed on at the beginning of every week. The acceptable concentration range is ±10% of nominal.

Vehicle: Water
Study Design
Neurogenic Potency of Test Article Study:

Dose: 3 test article dose levels+vehicle control. The test article doses will be determined based on the results of the neuronal differentiation study described in Example 11.

Administration: Doses will be administered every 2 days with media change.

Duration: Main study: 0, 2, 4, or 8 days; recovery period: 2, 5, or 8 days.

Number of replicates. 3 tissue culture (TC) wells per group.

Dosing volume. 5 μL

Parameters analyzed. Markers for pluripotency (Sox2 and Nestin), proliferation (Ki67), cell death (caspase 3), and differentiation (MAP2, neuron and GFAP, glia) will be monitored on Days 0, 2, 4, and 8 during the dosing period (Main study) and on Days 10, 13, and 16 during the recovery period (3/TC wells/group for each day) by WB and RT-PCR (Table 10).

TABLE 10

Assessment of neurogenic potency of test article on BTICs

| Test Article* | | No. of replicates (TC wells (3.8 cm$^2$)) | | | | | | |
|---|---|---|---|---|---|---|---|---|
| | | Main Study | | | | Recovery Period | | |
| Group No. | Dose | Day 0 | Day 2 | Day 4 | Day 8 | Day 10 | Day 13 | Day 16 |
| 1 | 0 | 3 | 3 | 3 | 3 | 3 | 3 | 3 |
| 2 | TBD | 3 | 3 | 3 | 3 | 3 | 3 | 3 |
| 3 | TBD | 3 | 3 | 3 | 3 | 3 | 3 | 3 |
| 4 | TBD | 3 | 3 | 3 | 3 | 3 | 3 | 3 |

*The test article will be RPP (SEQ ID NOS: 1 and 15 through 17) or RPPv (SEQ ID NOS: 18 through 117) peptide fused to a CPP (SEQ ID NOS: 118 through 137 and 140 through 159)

Anti-Oncogenic Potency of Test Article on BTICs in Mice:

Dose: 3 doses of test article+vehicle control. Test article doses will be based on the results of the neurogenic potency study.

Frequency of administration: Single dose

Route: Automated syringe pump with a guide-screw system[112,195]. The injection coordinates will be X:1.5; Y:1.34; Z:−3.5 targeting the mouse striatum; a highly reliable site for tumor engraftment[196].

Vehicle: Phosphate-buffered saline (PBS)

Number of animals. 3/sex/group

Dosing volume. 5 μL

Parameters analyzed. Mice will be assayed for survival during weeks 4, 8, 16, and 20 using the Kaplan-Meier method[197] followed by postmortem histopathology to evaluate tumor size and invasiveness (H&E stain), cell death (TUNEL), and proliferation (anti-human nuclei) (Table 11).

TABLE 11

Assessment of anti-oncogenic potency of test article on BTICs in mice

| Test Article* | | Injection Solution | | Mouse No. (M/F) Weeks | | | |
|---|---|---|---|---|---|---|---|
| Group No. | Dose | BTIC No. | PBS μL | 4 | 8 | 16 | 20 |
| 1 | 0 | 5 × 10$^4$ | 5 | 3/3 | 3/3 | 3/3 | 3/3 |
| 2 | TBD | 5 × 10$^4$ | 5 | 3/3 | 3/3 | 3/3 | 3/3 |
| 3 | TBD | 5 × 10$^4$ | 5 | 3/3 | 3/3 | 3/3 | 3/3 |
| 4 | TBD | 5 × 10$^4$ | 5 | 3/3 | 3/3 | 3/3 | 3/3 |

*RPP (SEQ ID NOS: 1 and 15 through 17) or RPPv (SEQ ID NOS: 18 through 117) peptide fused to a CPP (SEQ ID NOS: 118 through 137 and 140 through 159)

Environmental Conditions

Housing. 2 animals/cage, 12 hour light/dark cycle.

Diet. Ad libitum food and water.

Table 19 below shows the sequences for SEQ ID NOS: 1 through 324:

TABLE 19

| Sequence ID (SEQ ID NO) | Sequence | Name |
|---|---|---|
| 1 | TEDLEPPEPPLPKEN | — |
| 15 | EDLEPPEPPLPK | — |
| 16 | nekplppeppeldet | — |
| 17 | kplppeppelde | — |
| 18 | MCTEDLEPPEPPLPKENC | v1 |
| 19 | MCTEAPAPPEPALPKKKKNC | v2 |
| 20 | MCTEDLQPPTAVPQENC | v3 |
| 21 | MCTEAPAPPEPALPKKKKNC | v4 |
| 22 | MCTADLEPPEPRMEKKKVDC | v5 |
| 23 | MCTGDLQPPKTTVSKKDC | v6 |
| 24 | MCTEDLQSPKTTMTKENC | v7 |
| 25 | MCTEDLEPPEPPLPKEDC | v8 |

TABLE 19-continued

| Sequence ID (SEQ ID NO) | Sequence | Name |
|---|---|---|
| 26 | MCTEDQEQQEEQLPEENC | v9 |
| 27 | MCTADLKPPKTTMTKQNC | v10 |
| 28 | MCPGDLKQPEPPMPKEYC | v11 |
| 29 | MCTEDLEPPKATMTKKDC | V12 |
| 30 | MCTEDQERPPVTKEDC | v13 |
| 31 | MCIADPEPPEAQLPEGNC | v14 |
| 32 | MCTGVQEPPEATLPKKNC | v15 |
| 33 | MCSEAQEPPESRLPQVNC | v16 |
| 34 | MCTKHLEPPGPPLPQENC | v17 |
| 35 | MCTAAPEPPEPPVSKEYC | v18 |
| 36 | MCTEDLQLPKTTMTKEYC | v19 |
| 37 | MCSVDLQPPARLRPMVNC | v20 |
| 38 | MCTGDLQPPESRQPQVNC | v21 |
| 39 | MCTGDLQPPEAQVIEVNC | v22 |
| 40 | MCTEDLQPPEPQLPEVNC | v23 |
| 41 | MCTEDMEPRKTTMTKKYC | v25 |
| 42 | MCTEAPAPPEPALPKKKKKKNC | v26 |
| 43 | MCTEAPAPPEPALPKKKKKNC | v27 |
| 44 | MCTEDLQSPKTTMTKENC | v28 |
| 45 | MCTGDLKLPEPPMSKKKKKNC | v29 |
| 46 | MCTEDLQPPKTTMAEKYC | v30 |
| 47 | MCSEDPEPPKTTMTKKNC | v31 |
| 48 | MCTEDLKPPEASLPEENC | v32 |
| 49 | MCAGDLEQPEPPVAKKKKKNC | v33 |
| 50 | MCNGDLERPEPPVAKEYC | v34 |
| 51 | MCTEDLKPPEPPLPKENC | v35 |
| 52 | MCNEALEPPPLRKEHC | v36 |
| 53 | MCPEDLERPPLTKEHC | v37 |
| 54 | MCTEDLEPPERPLPREIC | v38 |
| 55 | MCAGDLKPPETTMSKKNC | v39 |
| 56 | MCTEDLQQPERSQPMESC | v40 |
| 57 | MCPEDLQPPEPALPEKKKKKIVVLALVVKSAVSVGVV | v41 |
| 58 | MCTEVLVPRTTSGKGRLWFWLWSQKGHPSASACGS | v42 |
| 59 | MCAEDLQPPPLLEAHCGSDSGRKKRRQC | v43 |
| 60 | MCTAAPEPPEPQLPQANC | v44 |
| 61 | MCPADLQQPETSLPEENC | v45 |
| 62 | MCSVDLQPPARLRPMVNC | v46 |
| 63 | MCTEALEPPEPPLTKENC | v47 |

TABLE 19-continued

| Sequence ID (SEQ ID NO) | Sequence | Name |
|---|---|---|
| 64 | MCTEAMEPPEPPLARESC | v48 |
| 65 | MCTADLQPPEASLPQQNC | v49 |
| 66 | MCTAAPEPPEPRLPEGNC | v50 |
| 67 | MCTKDLAPQAPPLLKENC | v51 |
| 68 | cnekplppeppeldetcm | v1$^{RI}$ |
| 69 | cnkkkkkplapeppapaetcm | v2$^{RI}$ |
| 70 | cneqpvatppqldetcm | v3$^{RI}$ |
| 71 | cnkkkkplapeppapaetcm | v4$^{RI}$ |
| 72 | cdkksvttkppqldgtcm | v5$^{RI}$ |
| 73 | cdkksvttkppqldgtcm | v6$^{RI}$ |
| 74 | cnektmttkpsqldetcm | v7$^{RI}$ |
| 75 | cdekplppeppeldetcm | v8$^{RI}$ |
| 76 | cneeplqeelleldetcm | v9$^{RI}$ |
| 77 | cnqktmttkppkldgpcm | v10$^{RI}$ |
| 78 | cyekpmppepqldgpcm | v11$^{RI}$ |
| 79 | cdekktmtakppeldetcm | v12$^{RI}$ |
| 80 | cdektvppreqdetcm | v13$^{RI}$ |
| 81 | cngeplqaeppepdaicm | v14$^{RI}$ |
| 82 | cnkkpltaeppeqvgtcm | v15$^{RI}$ |
| 83 | cnvqplppgppelhktcm | v16$^{RI}$ |
| 84 | cneqplppgppepaatcm | v17$^{RI}$ |
| 85 | cyeksvppeppepaatcm | v18$^{RI}$ |
| 86 | cyektmttkplqldetcm | v19$^{RI}$ |
| 87 | cnvmprlrappqldvscm | v20$^{RI}$ |
| 88 | cnvqpqrseppqldgtcm | v21$^{RI}$ |
| 89 | cnveivqaeppqldgtcm | v22$^{RI}$ |
| 90 | cnveplqpeppqldetcm | v23$^{RI}$ |
| 91 | cykktmttkppemdetcm | v25$^{RI}$ |
| 92 | cnkkkkkkpklapeppapaetcm | v26$^{RI}$ |
| 93 | cnkkkkkplapeppapaetcm | v27$^{RI}$ |
| 94 | cnektmttkpsqldetcm | v28$^{RI}$ |
| 95 | cnkkkkksmppepplkldgtcm | v29$^{RI}$ |
| 96 | cykeamttkppqldetcm | v30$^{RI}$ |
| 97 | cnkktmttkppepdescm | v31$^{RI}$ |
| 98 | cneeplsaeppkldetcm | v32$^{RI}$ |
| 99 | cnkkkkkavppepqeldgacm | v33$^{RI}$ |
| 100 | cyekavppepreldgncm | v34$^{RI}$ |

TABLE 19-continued

| Sequence ID (SEQ ID NO) | Sequence | Name |
|---|---|---|
| 101 | cnekplppeppkldetcm | v35$^{RI}$ |
| 102 | chekrlpppelaencm | v36$^{RI}$ |
| 103 | chektlppreldepcm | v37$^{RI}$ |
| 104 | cierplpreppeldetcm | v38$^{RI}$ |
| 105 | cnkksmtteppkldgacm | v39$^{RI}$ |
| 106 | csmpqsrepqqledetcm | v40$^{RI}$ |
| 107 | cvvgvsvaskvvlalvvikkkkkeplapeppqldepcm | v41$^{RI}$ |
| 108 | csgcasasphgkqswlwfwlrgkgsttrpvlvetcm | v42$^{RI}$ |
| 109 | cqrrkkrgsdsgchaellpppqldeacm | v43$^{RI}$ |
| 110 | cnaqplqpeppepaatcm | v44$^{RI}$ |
| 111 | cneeplstepqqldapcm | v45$^{RI}$ |
| 112 | cnvmprlrappqldvscm | v46$^{RI}$ |
| 113 | cnektlppeppelaetcm | v47$^{RI}$ |
| 114 | cseralppeppemaetcm | v48$^{RI}$ |
| 115 | cnqqplsaeppqldatcm | v49$^{RI}$ |
| 116 | cngeplrpeppepaatcm | v50$^{RI}$ |
| 117 | cnekllppaqpaldktcm | v51$^{RI}$ |
| 118 | GRKKRRQRRR | — |
| 119 | GDIMGEWGNEIFGAIAGFLGYGRKKRRQRRR | — |
| 120 | RRRRRRRR | — |
| 121 | KKKKKKKK | — |
| 122 | DIMGEWGNEIFGAIAGFLG | — |
| 123 | CHHHHHRKKRRQRRRRHHHHHC | — |
| 124 | CHHHHHRRRRRRRRRHHHHHC | — |
| 125 | FFLIPKGRRRRRRRRGC | — |
| 126 | FΦRRRR | — |
| 127 | RRWRRWRRRRWWRr | — |
| 128 | RWRRRRWRRWWRr | — |
| 129 | RRWRRWRRRRWWr | — |
| 130 | RRWRRWRRRr | — |
| 131 | RRWWRRWRr | — |
| 132 | RRWWRRWRRR | — |
| 133 | RRRRRRC$_{12}$RRWRRr | — |
| 134 | YALTSAISRIITHHHHHH | — |
| 135 | RRRRRC$_{14}$RRWWRR | — |
| 136 | RRC$_{14}$RRC$_{14}$RRRRR | — |
| 137 | RRC$_{14}$RRR | — |
| 138 | GS | — |

TABLE 19-continued

| Sequence ID (SEQ ID NO) | Sequence | Name |
|---|---|---|
| 139 | GSGS | — |
| 140 | rrrqrrkkrg | — |
| 141 | rrrqrrkkrgyglfgaiagfiengwegmgmidg | — |
| 142 | rrrrrrrr | — |
| 143 | kkkkkkkk | — |
| 144 | glfgaiagfiengwegmid | — |
| 145 | chhhhrrrrqrrkkrhhhhc | — |
| 146 | chhhhrrrrrrrrrhhhhc | — |
| 147 | cgrrrrrrrrgkpilffc | — |
| 148 | rrrrΦf | — |
| 149 | rrwrrrrwrrwwrr | — |
| 150 | rrwrrwrrrrwwr | — |
| 151 | rwwrrrrwrrwwrr | — |
| 152 | rrrrwrrwwrr | — |
| 153 | rrwrrwwrr | — |
| 154 | rrrwrrwwrr | — |
| 155 | rrrwwrrC$_{14}$rrrrrr | — |
| 156 | hhhhhhtiirsiastlay | — |
| 157 | rrwwrrC$_{14}$rrrrr | — |
| 158 | rrC$_{14}$rrC$_{14}$rrrrr | — |
| 159 | rrC$_{14}$rrr | — |
| 160 | sg | — |
| 161 | sgsg | — |
| 162 | ATGGATAGTAGTGCGGTGATCACACAAATCTCCAAGGAGGAAGCCCGTGGGCCGCTGCGGGGAAGGGTGATCAAAAATCGGCAGCTAGTCAAAAACCTCGCTCTCGTGGGATACTTCATTCGCTGTTTTGCTGCGTCTGCCGCGATGACGGAGAAGCATTGCCTGCGCATTCAGGGGCGCCTTTACTTGTTGAGGAAAATGGTGCAATTCCTAAACAAACTCCAGTACAATACTTACTGCCGGAGGCAAAGGCACAAGACAGTGATAAGATATGTGTAGTAATAGACTTAGATGAAACACTGGTACATTCGTCATTCAAACCTGTTAATAATGCGGATTTCATCATACCTGTAGAAATCGACGGGGTTGTCCATCAGGTTTACGTCCTGAAGCGGCCTCATGTAGATGAATTTTTACAGCGGATGGGCGAGTTATTTGAATGTGTGCTGTTTACAGCTAGTCTTGCCAAGTACGCGGATCCTGTCGCGGATTTGCTTGATAAGTGGGGTGCGTTTCGGGCGAGATTATTTCGCGAATCTTGCGTTTTTCACAGAGGGTAACTACGTGAAGGACCTTAGTCGTCTGGGTAGAGATCTTAGAAGAGTGCTGATCCTTGACAACAGCCCAGCCAGCTATGTCTTTCATCCGGATAACGCAGTACCCGTGGCGTCTTGGTTCGACAATATGTCGGACACGGAGCTGCATGACCTGTTGCCGTTCTTTGAGCAGTTGAGTCGCGTTGATGACGTTTACTCGGTTTTGCGTCAACCCCGTCCGGGATCTGGTTCTGGCTCTCACCATCACCATCACCACTAG | — |
| 163 | MDSSAVITQISKEEARGPLRGKGDQKSAASQKPRSRGILHSLFCCVCRDDGEALPAHSGAPLLVEENGAIPKQTPVQYLLPEAKAQDSDKICVVIDLDETLVHSSFKPVNNADFIIPVEIDGVVHQVYVLKRPHVDEFLQRMGELFECVLFTASLAKYADPVADLLDKWGAFRARLFRESCVFHRGNYVKDLSRLGRDLRRVLILDNSPASYVFHPDNAVPVASWFDNMSDTELHDLLPFFEQLSRVDDVYSVLRQPRPGSGSGSHHHHHH | — |

TABLE 19-continued

| Sequence ID (SEQ ID NO) | Sequence | Name |
|---|---|---|
| 164 | ATGTGTACCGAAGATCTGGAACCACCAGAACCACCACTGCCAAAGGAAAATTGTGGATCCGGTTCTGGCTCAGGTTCTTCCCCTATACTAGGTTATTGGAAAATTAAGGGCCTTGTGCAACCCACTCGACTTCTTTTGGAATATCTTGAAGAAAAATATGAAGAGCATTTGTATGAGCGCGATGAAGGTGATAAATGGCGAAACAAAAGTTTGAATTGGGTTTGGAGTTTCCCAATCTTCCTTATTATATTGATGGTGATGTTAAATTAACACAGTCTATGGCCATCATACGTTATATAGCTGACAAGCACAACATGTTGGGTGGTTGTCCAAAAGAGCGTGCAGAGATTTCAATGCTTGAAGGAGCGGTTTTGGATATTAGATACGGTGTTTCGAGAATTGCATATAGTAAAGACTTTGAAACTCTCAAAGTTGATTTTCTTAGCAAGCTACCTGAAATGCTGAAAATGTTCGAAGATCGTTTATGTCATAAAACATATTTAAATGGTGATCATGTAACCCATCCTGACTTCATGTTGTATGACGCTCTTGATGTTGTTTTATACATGGACCCAATGTGCCTGGATGCGTTCCCAAAATTAGTTTGTTTTAAAAAACGTATTGAAGCTATCCCACAAATTGATAAGTACTTGAAATCCAGCAAGTATATAGCATGGCCTTTGCAGGGCTGGCAAGCCACGTTTGGTGGTGGCGACCATCCTCCAAAATAA | — |
| 165 | MCTEDLEPPEPPLPKENCGSGSGSGSSPILGYWKIKGLVQPTRLLLEYLEEKYEEHLYERDEGDKWRNKKFELGLEFPPNLPYYIDGDVKLTQSMAIIRYIADKHNMLGGCPKERAEISMLEGAVLDIRYGVSRIAYSKDFETLKVDFLSKLPEMKMFEDRLCHKTYLNGDHVTHPDFMLYDALDVVLYMDPMCLDAFPKLVCFKKRIEAIPQIDKYLKSSKYIAWPLQGWQATFGGGDHPPK | — |
| 166 | AATAAAGCTTATGTGTACCGAAGATCTGGAACCACCAGAACCACCACTGCCAA | v1f |
| 167 | AATAGGATCCACAATTTTCCTTTGGCAGTGGTGGTTCTGGTGGTTCCA | v1r |
| 168 | AATAAAGCTTATGTGTACCGAAGCTCCGGCACCACCAGAACCAGCACTGCCAAAG | v2f |
| 169 | AATAGGATCCACAATTTTTTTTTTTTTCTTTGGCAGTGCTGGTTCTGGTGGTGC | v2r |
| 170 | AATAAAGCTTATGTGTACCGAAGATCTGCAACCACCAACAGCAGTGCCAC | v3f |
| 171 | AATAGGATCCACAATTTTCCTGTGGCACTGCTGTTGGTGGTTGCAGATCTTC | v3r |
| 172 | AATAAAGCTTATGTGTACCGAAGCTCCGGCACCACCAGAACCAGCACTGCCAAAG | v4f |
| 173 | AATAGGATCCACAATTTTTTTTTTCTTTGGCAGTGCTGGTTCTGGTGGTGC | v4r |
| 174 | ATGTGTACCGCAGATCTGGAACCACCAGAACCACGAATGGAA | v5f |
| 175 | AATAGGATCCACAATCTACCTTTTTTTTTCCATTCGTGGTTCTGGTGGTTCCA | v5r |
| 176 | AATAAAGCTTATGTGTACCGGAGATCTGCAACCACCAAAAACAACAGTGTCAA | v6f |
| 177 | AATAGGATCCACAATCTTTCTTTGACACTGTTGTTTTGGTGGTTGCAGA | v6r |
| 178 | AATAAAGCTTATGTGTACCGAAGATCTGCAATCACCAAAAACAACAATGACAA | v7f |
| 179 | AATAGGATCCACAATTTTCCTTTGTCATTGTTGTTTTGGTGATTGCAGA | v7r |
| 180 | AATAAAGCTTATGTGTACCGAAGATCTGGAACCACCAGAACCACCACTGCCAA | v8f |
| 181 | AATAGGATCCCACAATCTTCCTTTGGCAGTGGTGGTTCTGGTGGTTCCAGA | v8r |

TABLE 19-continued

| Sequence ID (SEQ ID NO) | Sequence | Name |
|---|---|---|
| 182 | AATAAAGCTTATGTGTACCGAAGATCAGGAACAACAAGAAGAACAACTG | v9f |
| 183 | AATAGGATCCACAATTTTCCTCTGGCAGTTGTTCTTCTTGTTGTTCCTGATC | v9r |
| 184 | AATAAAGCTTATGTGTACCGCAGATCTGAAACCACCAAAAACAACAATGACAA | v10f |
| 185 | AATAGGATCCACAATTTTGCTTTGTCATTGTTGTTTTGGTGGTTTCAGA | v10r |
| 186 | AATAAAGCTTATGTGTCCCGGAGATCTGAAACAACCAGAACCACCAATGCCAA | v11f |
| 187 | AATAGGATCCACAATATTCCTTTGGCATTGGTGGTTCTGGTTGTTTCAGA | v11r |
| 188 | AATAAAGCTTATGTGTACCGAAGATCTGGAACCACCAAAAGCAACAATGACAA | v12f |
| 189 | AATAGGATCCACAATCTTTCTTTGTCATTGTTGCTTTTGGTGGTTCCAGA | v12r |
| 190 | AATAAAGCTTATGTGTACCGAAGATCAGGAACGACCACCAGTGACAAAG | v13f |
| 191 | AATAGGATCCACAATCTTCCTTTGTCACTGGTGGTCGTTCCTGATCTTC | v13r |
| 192 | AATAAAGCTTATGTGTATCGCAGATCCGGAACCACCAGAAGCACAACTG | v14f |
| 193 | AATAGGATCCACAATTTCCCTCTGGCAGTTGTGCTTCTGGTGGTTCCGGATCTG | v14r |
| 194 | AATAAAGCTTATGTGTACCGGAGTTCAGGAACCACCAGAAGCAACACTG | v15f |
| 195 | AATAGGATCCACAATTTTTCTTTGGCAGTGTTGCTTCTGGTGGTTCCTGAAC | v15r |
| 196 | AATAAAGCTTATGTGTAGCGAAGCTCAGGAACCACCAGAATCACGACTG | v16f |
| 197 | AATAGGATCCACAATTTACCTGTGGCAGTCGTGATTCTGGTGGTTCCTGAG | v16r |
| 198 | AATAAAGCTTATGTGTACCAAACATCTGGAACCACCAGGACCACCATTGC | v17f |
| 199 | AATAGGATCCACAATTTTCCTGTGGCAATGGTGGTCCTGGTGGTTCCAGATG | v17r |
| 200 | AATAAAGCTTATGTGTACCGCAGCTCCGGAACCACCAGAACCACCAGTGT | v18f |
| 201 | AATAGGATCCACAATATTCCTTTGACACTGGTGGTTCTGGTGGTTCCGGAG | v18r |
| 202 | AATAAAGCTTATGTGTACCGAAGATCTGCAACTACCAAAAACAACAATGACA | v19f |
| 203 | AATAGGATCCACAATATTCCTTTGTCATTGTTGTTTTTGGTAGTTGCAGA | v19r |
| 204 | AATAAAGCTTATGTGTTCCGTAGATCTGCAACCACCAGCACGACTACGGCCAA | v20f |
| 205 | AATAGGATCCACAATTTACCATTGGCCGTAGTCGTGCTGGTGGTTGCAGAT | v20r |
| 206 | AATAAAGCTTATGTGTACCGGAGATCTGCAACCACCAGAATCACGACAGCCA | v21f |

TABLE 19-continued

| Sequence ID (SEQ ID NO) | Sequence | Name |
|---|---|---|
| 207 | AATAGGATCCACAATTTACCTGTGGCTGTCGTGATTCTGGTGGTTGCAGAT | v21r |
| 208 | AATAAAGCTTATGTGTACCGGAGATCTGCAACCACCAGAAGCACAAGTGA | v22f |
| 325 | AATAGGATCCACAATTTACCTGTGGCTGTCGTGATTCTGGTGGTTGCAGAT | v22r |
| 210 | AATAAAGCTTATGTGTACCGAAGATCTGCAACCACCAGAACCACAACTGCCA | v23f |
| 211 | AATAGGATCCACAATTTACCTCTGGCAGTTGTGGTTCTGGTGGTTGCAGAT | v23r |
| 212 | AATAAAGCTTATGTGTACCGAAGATATGGAACCACGAAAAACAACAATGA | v25f |
| 213 | AATAGGATCCACAATATTTCTTTGTCATTGTTGTTTTCGTGGTTCCATAT | v25r |
| 214 | AATAAAGCTTATGTGTACCGAAGCTCCGGCACCACCAGAACCAGCACTGCCAAAG | v26f |
| 215 | AATAGGATCCACAATTTTTTTTTTTTTTCTTTGGCAGTGCTGGTTCTGGTGGT | v26r |
| 216 | AATAAAGCTTATGTGTACCGAAGCTCCGGCACCACCAGAACCAGCACTGCCAAAG | v27f |
| 217 | AATAGGATCCACAATTTTTTTTTTTTCTTTGGCAGTGCTGGTTCTGGTGGTG | v27r |
| 218 | AATAAAGCTTATGTGTACCGAAGATCTGCAATCACCAAAAACAACAATG | v28f |
| 219 | AATAGGATCCACAATTTTCCTTTGTCATTGTTGTTTTGGTGATTGCAGA | v28r |
| 220 | AATAAAGCTTATGTGTACCGGAGATCTGAAACTACCAGAACCACCAATGTCAAAG | v29f |
| 221 | AATAGGATCCACAATTTTTTTTTTTTCTTTGACATTGGTGGTTCTGGTAG | v29r |
| 222 | AATAAAGCTTATGTGTACCGAAGATCTGCAACCACCAAAAACAACAATG | v30f |
| 223 | AATAGGATCCACAATATTTCTCTGCCATTGTTGTTTTGGTGGTTGCAGAT | v30r |
| 224 | AATAAAGCTTATGTGTAGCGAAGATCCGGAACCACCAAAAACAACAATGAC | v31f |
| 225 | AATAGGATCCACAATTTTTCTTTGTCATTGTTGTTTTGGTGGTTCCGGAT | v31r |
| 226 | AATAAAGCTTATGTGTACCGAAGATCTGAAACCACCAGAAGCATCACTGC | v32f |
| 227 | AATAGGATCCACAATTTTCCTCTGGCAGTGATGCTTCTGGTGGTTTCAGAT | v32r |
| 228 | AATAAAGCTTATGTGTGCCGGAGATCTGGAACAACCAGAACCACCAGTGGCAAA | v33f |
| 229 | AATAGGATCCACAATTTTTTTTTTTTCTTTGCCACTGGTGGTTCTGGTTGTTC | v33r |
| 230 | AATAAAGCTTATGTGTAACGGAGATCTGGAACGACCAGAACCACCAGTG | v34f |
| 231 | AATAGGATCCACAATATTCCTTTGCCACTGGTGGTTCTGGTCGTTCCAGAT | v34r |

TABLE 19-continued

| Sequence ID (SEQ ID NO) | Sequence | Name |
|---|---|---|
| 232 | AATAAAGCTTATGTGTACCGAAGATCTGAAACCACCAGAACC ACCACTGC | v35f |
| 233 | AATAGGATCCACAATTTTCCTTTGGCAGTGGTGGTTCTGGTGG TTTCAGAT | v35r |
| 234 | AATAAAGCTTATGTGTAACGAAGCTCTGGAACCACCACCACTG CGAAAG | v36f |
| 235 | AATAGGATCCACAATGTTCCTTTCGCAGTGGTGGTGGTTCCAG AGCTTC | v36r |
| 236 | AATAAAGCTTATGTGTCCCGAAGATCTGGAACGACCACCATTG ACAAAG | v37f |
| 237 | AATAGGATCCACAATGTTCCTTTGTCAATGGTGGTCGTTCCAG AT | v37r |
| 238 | AATAAAGCTTATGTGTACCGAAGATCTGGAACCACCAGAACG ACCACTGC | v38f |
| 239 | AATAGGATCCACAAATTTCCCTTGGCAGTGGTCGTTCTGGTGG TTCCAGA | v38r |
| 240 | AATAAAGCTTATGTGTGCCGGAGATCTGAAACCACCAGAAAC AACAATGTC | v39f |
| 241 | AATAGGATCCACAATTTTTCTTTGACATTGTTGTTTCTGGTGGT TTCAGA | v39r |
| 242 | AATAAAGCTTATGTGCACCGAAGATCTGCAACAACCAGAACG ATCACAGC | v40f |
| 243 | AATAGGATCCACAACTTTCCATTGGCTGTGATCGTTCTGGTTG TTGCAGA | v40r |
| 244 | AATAAAGCTTATGTGTCCCGAAGATCTGCAACCACCAGAACC AGCACTGCCAGAGAAAAA | v41f |
| 245 | AATAGGATCCGACCACGCCGACGCTGACGGCGCTTTTTACGAC CAGAGCCAGAACCACAA | v41r |
| 246 | ACCAGAACCAGCACTGCCAGAGAAAAAAAAAAAAAAAATTGT GGTTCTGGCTCTGGTCGT | v41 |
| 247 | AATAAAGCTTATGTGTACCGAAGTTCTGGTACCACGAACCACC AGTGGCAAAGGAAG | v42f |
| 248 | AATAGGATCCGGAGCCACACGCCGATGCTGACGGATGGCCTT TTTGCGACCAGAGCCAGAA | v42r |
| 249 | ACCACGAACCACCAGTGGCAAAGGAAGATTGTGGTTCTGGCT CTGGTCGCAAAAAGGCCA | v42 |
| 250 | AATAAAGCTTATGTGTGCCGAAGATCTGCAACCACCACCACTG CTAGAGGCA | v43f |
| 251 | AATAGGATCCACACTGACGGCGCTTTTTACGACCAGAGTCAGA ACCACAATGTGCCTCT | v43r |
| 252 | ATCTGCAACCACCACCACTGCTAGAGGCACATTGTGGTTCTGA CTCTGGTCGTAAAAAG | v43 |
| 253 | AATAAAGCTTATGTGTACCGCAGCTCCGGAACCACCAGAACC ACAACTG | v44f |
| 254 | AATAGGATCCACAATTTGCCTGTGGCAGTTGTGGTTCTGGTGG TTCCGGAG | v44r |
| 255 | AATAAAGCTTATGTGTCCCGCAGATCTGCAACAACCAGAAAC ATCACTG | v45f |
| 256 | AATAGGATCCACAATTTTCCTCTGGCAGTGATGTTTCTGGTTGT TGCAGAT | v45r |

TABLE 19-continued

| Sequence ID (SEQ ID NO) | Sequence | Name |
|---|---|---|
| 257 | AATAAAGCTTATGTGTTCCGTAGATCTGCAACCACCAGCACGACTACG | v46f |
| 258 | AATAGGATCCACAATTTACCATTGGCCGTAGTCGTGCTGGTGGTTGCAGAT | v46r |
| 259 | AATAAAGCTTATGTGCACCGAgGCTTTGGAACCACCAGAACCACCACTG | v47f |
| 260 | AATAGGATCCACAATTTTCCTTTGTCAGTGGTGGTTCTGGTGGTTCCAAAG | v47r |
| 261 | AATAAAGCTTATGTGTACCGAAGCTATGGAACCACCAGAACCACCACTG | v48f |
| 262 | AATAGGATCCACAACTTTCCCTTGCCAGTGGTGGTTCTGGTGGTTCCATAG | v48r |
| 263 | AATAAAGCTTATGTGTACCGCAGATCTGCAACCACCAGAAGCATCACTG | v49f |
| 264 | AATAGGATCCACAATTTTGCTGTGGCAGTGATGCTTCTGGTGGTTGCAGAT | v49r |
| 265 | AATAAAGCTTATGTGTACCGCAGCTCCGGAACCACCAGAACCACGACTGCCA | v50f |
| 266 | AATAGGATCCACAATTTCCCTCTGGCAGTCGTGGTTCTGGTGGTTCC | v50r |
| 267 | AATAAAGCTTATGTGTACCAAAGATTTGGCACCACAAGCACCACCATTGCT | v51f |
| 268 | AATAGGATCCACAATTTTCCTTTAGCAATGGTGGTGCTTGTGGTGCCAAA | v51r |
| 269 | AAATAAGCTTGTATATCTCCTTCTTAAAGTTAAACA | P12 |
| 270 | AATAACTCGAGAGATCCGGCTGCTAACAAAGC | P14 |
| 271 | ATAAGCTTTAATACGACTCACTATAGGGTTAACTTTAGTAAGGAGGACAGCTAA | P17 |
| 272 | GTGGTGATGGTGATGGTGACCTA | P19 |
| 273 | ATTATTCTCGAGTTAATAGCCGGTGCCGTGGTGATGGTGATGGTGACCTA | P20 |
| 274 | AAATACTCGAGTCGTTTTATCTGTTGTTTGTCGGT | P21 |
| 275 | AAATAAGCTTCTCTGAATGGCGGGAGTATGAAAA | P22 |
| 276 | CCGCGAATGGTGAGATTGAGAA | P23 |
| 277 | ACGCAAAAAGGCCATCCGTCAG | P24 |
| 278 | ATTATTCTCGAGTTAATAGCCGGTGCCTAAGCCGCTACCACCACGCCGACGCTGACGG | P28 |
| 279 | AAATAAGCTTATGGATAGTAGTGCGGTGATCA | P31 |
| 280 | ATTATTCTCGAGCTAGTGGTGATGGTGATGGT | P32 |
| 281 | AACTAAGCTTTTCCTCCTGTTAGCCCAAAAAAC | P33 |
| 282 | AATACTCGAGGCTGTTTTGGCGGATGAGAGAA | P34 |
| 283 | AAATCCATGGATAGTAGTGCGGTGATCA | P35 |
| 284 | AAATCATATGGATAGTAGTGCGGTGATCA | P36 |
| 285 | AATACTCGAGCTAGTGGTGATGGTGATGGTGAG | P37 |
| 286 | AATACTCGAGAGAGCCAGAACCAGATCCCGGA | P38 |

TABLE 19-continued

| Sequence ID (SEQ ID NO) | Sequence | Name |
|---|---|---|
| 287 | TAAGCCGCTACCACCACGCCGAC | P39 |
| 288 | GGTGCAATTCCTAAAACTCCAGTACAATACTTACTGC | P40 |
| 289 | GTATTGTACTGGAGTTTTAGGAATTGCACCATTTTCCTC | P41 |
| 290 | AATACTCGAGTTATTTTGGAGGATGGTCGCCACCA | P108 |
| 291 | AATAAAGCTTATGGGATCCGGTTCTGGCTCAGGTTCTTCC | P109 |
| 292 | NAANCANCANTGNCANAGNAANATTGTGGTTCTGGCTCTGGTCGTAAAA | 11F |
| 293 | GNACNACNACNGCNAANGGNAANTTGTGGTTCTGGCTCTGGTCGTAAAA | 12F |
| 294 | GNANCACNANTGCNANAGGNANATTGTGGTTCTGGCTCTGGTCGTAAAA | 13F |
| 295 | NAACNANCACNGNCAANGNAAANTTGTGGTTCTGGCTCTGGTCGTAAAA | 14F |
| 296 | GAANCANCANTGNCANAGNAANATTGTGGTTCTGGCTCTGGTCGTAAAA | 15F |
| 297 | GAACNACNACNGCNAANGGNAANTTGTGGTTCTGGCTCTGGTCGTAAAA | 16F |
| 298 | GAANCACNANTGCNANAGGNANATTGTGGTTCTGGCTCTGGTCGTAAAA | 17F |
| 299 | GAACNANCACNGNCAANGNAAANTTGTGGTTCTGGCTCTGGTCGTAAAA | 18F |
| 300 | GAANCANCACTGCCANAGNAAAATTGTGGTTCTGGCTCTGGTCGTAAAA | 19F |
| 301 | NAACCACCANTGNCAAAGGAANATTGTGGTTCTGGCTCTGGTCGTAAAA | 20F |
| 302 | GAANCACNACTGCCANAGGNAAATTGTGGTTCTGGCTCTGGTCGTAAAA | 21F |
| 303 | GNACCACCANTGCNAAAGGAANATTGTGGTTCTGGCTCTGGTCGTAAAA | 22F |
| 304 | TGNTGNTTNCANATNTTNGGNACACATTTAGCTGTCCTCCTTACTAAAGTT | 11R |
| 305 | TNGTNGTNCCNGANCTNCGNTACACATTTAGCTGTCCTCCTTACTAAAGTT | 12R |
| 306 | TGNTGNTTNCNGATNTNCGGNACACATTTAGCTGTCCTCCTTACTAAAGTT | 13R |
| 307 | TNGTNGTNCCANANCTTNGNTACACATTTAGCTGTCCTCCTTACTAAAGTT | 14R |
| 308 | TGNTGNTTCCANATNTTNGGNACACATTTAGCTGTCCTCCTTACTAAAGTT | 15R |
| 309 | TNGTNGTTCCNGANCTNCGNTACACATTTAGCTGTCCTCCTTACTAAAGTT | 16R |
| 310 | TGNTNGTTCCNGATNTNCGGNACACATTTAGCTGTCCTCCTTACTAAAGTT | 17R |
| 311 | TNGTGNTTCCANANCTTNGNTACACATTTAGCTGTCCTCCTTACTAAAGTT | 18R |
| 312 | TGGTGNTTNCAGATCTTNGGNACACATTTAGCTGTCCTCCTTACTAAAGTT | 19R |

TABLE 19-continued

| Sequence ID (SEQ ID NO) | Sequence | Name |
|---|---|---|
| 313 | TGNTGGTTCCANATNTTCGGTACACATTTAGCTGTCCTCCTTACTAAAGTT | 20R |
| 314 | TGGTNGTTNCAGATCTNCGGNACACATTTAGCTGTCCTCCTTACTAAAGTT | 21R |
| 315 | TGNTGGTTCCNGATNTTCGGTACACATTTAGCTGTCCTCCTTACTAAAGTT | 22R |
| 316 | CCTGCAGGTAATACGACTCACTATAGGGTTAACTTTAGTAAGGAGGACAGCTAAAAGCTTATGTGTACCGAAGATCTGGAACCACCAGAACCACCACTGCCAAAGGAAAATTGTGGATCCGGCTCTGGTCGTAAAAAGCGCCGTCAGCGTCGGCGTGGTGGCTCCGGTAGCTTAGGTCACCATCACCATCACCACGGCACCGGCTATTAACTCGAG | — |
| 317 | ATGTGTACCGAAGATCTGGAACCACCAGAACCACCACTGCCAAAGGAAAATTGTGGATCCGGCTCTGGTCGTAAAAAGCGCCGTCAGCGTCGGCGTGGTGGCTCCGGTAGCTTAGGTCACCATCACCATCACCACGGCACCGGCTATTAA | — |
| 318 | AAATCCTGCAGGTAATACGACTCACTATAGGGTTAAC | — |
| 319 | ATTATTCTCGAGTTAATAGCCGGTGCCGTGGTGATGGTGACCTA | — |
| 320 | TATACCCTGCAGGTAATACGACTCACTATAGGGTTAACTTTAGTAAGGAGGACAGCTAAAAGCTTATGTGTGAAGACGCCAAAAACATAAAGAAAGGCCCGGCGCCATTCTATCCGTGTGGATCCGGCTCTGGTCGTAAAAAGCGCCGTCAGCGTCGGCGTGGTGGCTCCGGTAGCTTAGGTCACCATCACCATCACCACGGCACCGGCTATTAACTCGAGAGATC | — |
| 321 | CCTGCAGGTAATACGACTCACTATAGGGTTAACTTTAGTAAGGAGGACAGCTAAAAGCTTATGTGTGAAGACGCCAAAAACATAAAGAAAGGCCCGGCGCCATTCTATCCGTGTGGATCCGGCTCTGGTCGTAAAAAGCGCCGTCAGCGTCGGCGTGGTGGCTCCGGTAGCTTAGGTCACCATCACCATCACCACGGCACCGGCTATTAACTCGAG | — |
| 322 | ATGTGTGAAGACGCCAAAAACATAAAGAAAGGCCCGGCGCCATTCTATCCGTGTGGATCCGGCTCTGGTCGTAAAAAGCGCCGTCAGCGTCGGCGTGGTGGCTCCGGTAGCTTAGGTCACCATCACCATCACCACGGCACCGGCTATTAA | — |
| 323 | AAATCCTGCAGGTAATACGACTCACTATAGGGTTAAC | — |
| 324 | ATTATTCTCGAGTTAATAGCCGGTGCCGTGGTGATGGTGACCTA | — |
| 2 | MCTEDLEPPEPPLPKENCGSGSGRKKRRQRRRGGSGSLGHHHHHHGTGY | — |
| 3 | MCEDAKNIKKGPAPFYPCGSGSGRKKRRQRRRGGSGSLGHHHHHHGTGY | Control |
| 4 | CAQKDYKDDDDKTEDLEPPEPPLPKENGRKKRRQRRRG | — |
| 5 | CTEDLEPPEPPLPKENSGDIMGEWGNEIFGAIAGFLGYGRKKRRQRRRG$^{cycli\ (head\ to\ tail)}$ | — |
| 6 | TEDLEPPEPPLPKENRRWWRRWRRRRWWRr | — |
| 7 | EDLEPPEPPLPKRWWRRRRWRRWWRr | — |
| 8 | AGDLEQPEPPVAKKKKKNRRWWRRWRr | — |
| 9 | rrrrwrrwwrrwrrnekplppeppeldet | — |
| 10 | TEDLEPPEPPLPKENrrrrwrrwwrrwrr | — |
| 11 | TEDLEPPEPPLPKENRRRRRRC$_{14}$RRWWRRr | — |
| 12 | rwwrrC$_{14}$rrrrrkplppeppelde$^{cyclic\ (head\ to\ tail)}$ | — |

TABLE 19-continued

| Sequence ID (SEQ ID NO) | Sequence | Name |
|---|---|---|
| 13 | rrC$_{14}$rrC$_{14}$rrrrrrkplppeppelde$^{cyclic\ (head\ to\ tail)}$ | — |
| 14 | rrC$_{14}$rrrkplppeppelde$^{cyclic\ (head\ to\ tail)}$ | - |

Lower case = D amino acids; C$_{14}$ = 2-aminotetradecanoic acid; Φ is L-2-naphthyl-alanine; N = any nucleotide Although certain presently preferred embodiments of the invention have been specifically described herein, it will be apparent to those skilled in the art to which the invention pertains that variations and modifications of the various embodiments shown and described herein may be made without departing from the spirit and scope of the invention.

REFERENCES (FOR SPECIFICATION, EXCEPT EXAMPLES)

1 Bruce, A. W. et al. Genome-wide analysis of repressor element 1 silencing transcription factor/neuron-restrictive silencing factor (REST/NRSF) target genes. Proc Natl Acad Sci USA 101, 10458-10463, doi:10.1073/pnas.04018271010401827101 [pii] (2004).
2 Nesti, E., Corson, G. M., McCleskey, M., Oyer, J. A. & Mandel, G. C-terminal domain small phosphatase 1 and MAP kinase reciprocally control REST stability and neuronal differentiation. Proc Natl Acad Sci USA 111, E3929-3936, doi:1414770111 [pii]10.1073/pnas.1414770111 (2014).
3 Nesti, E. METHODS AND COMPOSITIONS USEFUL IN MANIPULATING THE STABILITY OF RE1 SILENCING TRANSCRIPTION FACTOR. US, PTC patent (2014, 2015).
4 Nesti, E. Harnessing the master transcriptional repressor REST to reciprocally regulate neurogenesis. Neurogenesis 2, doi:10.1080/23262133.2015.1055419 (2015).
Calderone, A. et al. Ischemic insults derepress the gene silencer REST in neurons destined to die. J Neurosci 23, 2112-2121, doi:23/6/2112 [pii] (2003).
6 Kaneko, N., Hwang, J. Y., Gertner, M., Pontarelli, F. & Zukin, R. S. Casein kinase 1 suppresses activation of REST in insulted hippocampal neurons and halts ischemia-induced neuronal death. J Neurosci 34, 6030-6039, doi:34/17/6030 [pii]10.1523/JNEUROSCI.4045-13.2014 (2014).
7 Noh, K. M. et al. Repressor element-1 silencing transcription factor (REST)-dependent epigenetic remodeling is critical to ischemia-induced neuronal death. Proc Natl Acad Sci USA 109, E962-971, doi:1121568109 [pii] 10.1073/pnas.1121568109 (2012).
8 Abe, K. Therapeutic potential of neurotrophic factors and neural stem cells against ischemic brain injury. J Cereb Blood Flow Metab 20, 1393-1408, doi:10.1097/00004647-200010000-00001 (2000).
9 Kan Ding, P. K. G., and Ramon Diaz-Arrastia. in Translational Research in Traumatic Brain Injury (ed Grant G Laskowitz D) Ch. 14, (Taylor and Francis, 2016).
10 Pasquina, P., Kirtley, R. & Ling, G. Moderate-to-severe traumatic brain injury. Semin Neurol 34, 572-583, doi: 10.1055/s-0034-1396010 (2014).
11 Hwang, J. Y., Kaneko, N., Noh, K. M., Pontarelli, F. & Zukin, R. S. The gene silencing transcription factor REST represses miR-132 expression in hippocampal neurons destined to die. J Mol Biol 426, 3454-3466, doi:10.1016/j.jmb.2014.07.032 (2014).
12 McClelland, S. et al. The transcription factor NRSF contributes to epileptogenesis by selective repression of a subset of target genes. Elife 3, e01267 (2014).
13 Lu, T. et al. REST and stress resistance in ageing and Alzheimer's disease. Nature 507, 448-454, doi:nature13163 [pii]10.1038/nature13163 (2014).
14 Orta-Salazar, E. et al. REST/NRSF-induced changes of ChAT protein expression in the neocortex and hippocampus of the 3xTg-AD mouse model for Alzheimer's disease. Life sciences 116, 83-89, doi:10.1016/j.lfs.2014.09.013 (2014).
15 Sharp, D. J., Scott, G. & Leech, R. Network dysfunction after traumatic brain injury. Nat Rev Neurol 10, 156-166, doi:10.1038/nrneurol.2014.15 (2014).
16 Roopra, A., Dingledine, R. & Hsieh, J. Epigenetics and epilepsy. Epilepsia 53 Suppl 9, 2-10, doi:10.1111/epi.12030 (2012).
17 Bergsland, M., Covacu, R., Perez Estrada, C., Svensson, M. & Brundin, L. Nitric oxide-induced neuronal to glial lineage fate-change depends on NRSF/REST function in neural progenitor cells. Stem Cells 32, 2539-2549, doi: 10.1002/stem.1749 (2014).
18 Conaco, C., Otto, S., Han, J. J. & Mandel, G. Reciprocal actions of REST and a microRNA promote neuronal identity. Proc Natl Acad Sci USA 103, 2422-2427, doi: 0511041103 [pii]10.1073/pnas.0511041103 (2006).
19 Covey, M. V., Streb, J. W., Spektor, R. & Ballas, N. REST regulates the pool size of the different neural lineages by restricting the generation of neurons and oligodendrocytes from neural stem/progenitor cells. Development 139, 2878-2890, doi:dev.074765 [pii]10.1242/dev.074765 (2012).
Gao, Z. et al. The master negative regulator REST/NRSF controls adult neurogenesis by restraining the neurogenic program in quiescent stem cells. J Neurosci 31, 9772-9786, doi:31/26/9772 [pii]10.1523/JNEUROSCI.1604-11.2011 (2011).
21 Kohyama, J. et al. BMP-induced REST regulates the establishment and maintenance of astrocytic identity. J Cell Biol 189, 159-170, doi:jcb.200908048 [pii]10.1083/jcb.200908048 (2010).
22 Mandel, G. et al. Repressor element 1 silencing transcription factor (REST) controls radial migration and temporal neuronal specification during neocortical development. Proc Natl Acad Sci USA 108, 16789-16794, doi:1113486108 [pii]10.1073/pnas.1113486108 (2011).
23 Vincent, A. S., Roebuck-Spencer, T. M. & Cernich, A. Cognitive changes and dementia risk after traumatic brain injury: implications for aging military personnel. Alzheimers Dement 10, S174-187, doi:10.1016/j.jalz.2014.04.006 (2014).

24 Kirn, J. R. The relationship of neurogenesis and growth of brain regions to song learning. *Brain Lang* 115, 29-44, doi:S0093-934X(09)00135-7 [pii]10.1016/j.bandl. 2009.09.006 (2010).

25 Oomen, C. A., Bekinschtein, P., Kent, B. A., Saksida, L. M. & Bussey, T. J. Adult hippocampal neurogenesis and its role in cognition. *Wiley Interdiscip Rev Cogn Sci* 5, 573-587, doi:10.1002/wcs.1304 (2014).

26 Samuels, I. S. et al. Deletion of ERK2 mitogen-activated protein kinase identifies its key roles in cortical neurogenesis and cognitive function. *J Neurosci* 28, 6983-6995, doi:28/27/6983 [pii]10.1523/JNEUROSCI.0679-08.2008 (2008).

27 Shors, T. J. et al. Neurogenesis in the adult is involved in the formation of trace memories. *Nature* 410, 372-376, doi:10.1038/35066584 (2001).

28 Villeda, S. A. et al. The ageing systemic milieu negatively regulates neurogenesis and cognitive function. *Nature* 477, 90-94, doi:10.1038/nature10357 (2011).

29 Bird, C. M. & Burgess, N. The hippocampus supports recognition memory for familiar words but not unfamiliar faces. *Curr Biol* 18, 1932-1936, doi:10.1016/j.cub.2008.10.046 (2008).

T. J. Shors, G. M., A. Beylin, M. Zhao, T. Rydel, E. Gould. Neurogenesis in the adult is involved in the formation of trace memories. *Nature* 410, 372-376 (2001).

31 VanElzakker, M., Fevurly, R. D., Breindel, T. & Spencer, R. L. Environmental novelty is associated with a selective increase in Fos expression in the output elements of the hippocampal formation and the perirhinal cortex. *Learn Mem* 15, 899-908, doi:10.1101/lm. 1196508 (2008).

32 Thornton, G. K. & Woods, C. G. Primary microcephaly: do all roads lead to Rome?*Trends Genet* 25, 501-510, doi:10.1016/j.tig.2009.09.011 (2009).

33 Ghaziuddin, M., Zaccagnini, J., Tsai, L. & Elardo, S. Is megalencephaly specific to autism? *J Intellect Disabil Res* 43 (Pt 4), 279-282 (1999).

34 Kuhn, H. G., Cooper-Kuhn, C. M., Boekhoorn, K. & Lucassen, P. J. Changes in neurogenesis in dementia and Alzheimer mouse models: are they functionally relevant? *Eur Arch Psychiatry Clin Neurosci* 257, 281-289, doi:10.1007/s00406-007-0732-4 (2007).

Baker, M. Tumours spark stem-cell review. *Nature* 457, 941, doi:10.1038/457941a (2009).

36 Brederlau, A. et al. Transplantation of human embryonic stem cell-derived cells to a rat model of Parkinson's disease: effect of in vitro differentiation on graft survival and teratoma formation. *Stem Cells* 24, 1433-1440, doi: 2005-0393 [pii]10.1634/stemcells.2005-0393 (2006).

37 Burns, T. C., Verfaillie, C. M. & Low, W. C. Stem cells for ischemic brain injury: a critical review. *J Comp Neurol* 515, 125-144, doi:10.1002/cne.22038 (2009).

38 Carlson, A. P., Schermer, C. R. & Lu, S. W. Retrospective evaluation of anemia and transfusion in traumatic brain injury. *J Trauma* 61, 567-571, doi:10.1097/01.ta.0000231768.44727.a200005373-200609000-00007 [pii] (2006).

39 Carmeliet, P. & Storkebaum, E. Vascular and neuronal effects of VEGF in the nervous system: implications for neurological disorders. *Semin Cell Dev Biol* 13, 39-53, doi:10.1006/scdb.2001.0290S1084952101902903 [pii] (2002).

Choe, Y., Kozlova, A., Graf, D. & Pleasure, S. J. Bone morphogenic protein signaling is a major determinant of dentate development. *J Neurosci* 33, 6766-6775, doi:33/16/6766 [pii]10.1523/JNEUROSCI.0128-13.2013 (2013).

41 Erdo, F. et al. Host-dependent tumorigenesis of embryonic stem cell transplantation in experimental stroke. *J Cereb Blood Flow Metab* 23, 780-785, doi:10.1097/01.WCB.0000071886.63724.FB (2003).

42 Greig, N. H. et al. Incretin mimetics as pharmacologic tools to elucidate and as a new drug strategy to treat traumatic brain injury. *Alzheimers Dement* 10, S62-75, doi:S1552-5260(13)02925-7 [pii]10.1016/j.jalz.2013.12.011 (2014).

43 Kaplan, G. B., Vasterling, J. J. & Vedak, P. C. Brain-derived neurotrophic factor in traumatic brain injury, post-traumatic stress disorder, and their comorbid conditions: role in pathogenesis and treatment. *Behav Pharmacol* 21, 427-437, doi:10.1097/FBP.0b013e32833d8bc9 (2010).

44 Knoepfler, P. S. Deconstructing stem cell tumorigenicity: a roadmap to safe regenerative medicine. *Stem Cells* 27, 1050-1056, doi:10.1002/stem.37 (2009).

Luca Longhia, Elisa R. Zaniera, Nicolas Royob, Nino Stocchettia, Tracy K. McIntosha. Stem cell transplantation as a therapeutic strategy for traumatic brain injury. *Transplant Immunology* 15, 134-148 (2005).

46 Robertson, C. S. et al. Effect of erythropoietin and transfusion threshold on neurological recovery after traumatic brain injury: a randomized clinical trial. *JAMA* 312, 36-47, doi:1884575 [pii]10.1001/jama.2014.6490 (2014).

47 Salim, A. et al. Role of anemia in traumatic brain injury. *J Am Coll Surg* 207, 398-406, doi:S1072-7515(08)00322-0 [pii]10.1016/j.jamcollsurg.2008.03.013 (2008).

48 Deng, W., Aimone, J. B. & Gage, F. H. New neurons and new memories: how does adult hippocampal neurogenesis affect learning and memory? *Nat Rev Neurosci* 11, 339-350, doi:nrn2822 [pii]10.1038/nrn2822 (2010).

49 Goldman, S. A. & Nottebohm, F. Neuronal production, migration, and differentiation in a vocal control nucleus of the adult female canary brain. *Proc Natl Acad Sci USA* 80, 2390-2394 (1983).

50 Gould, E., Beylin, A., Tanapat, P., Reeves, A. & Shors, T. J. Learning enhances adult neurogenesis in the hippocampal formation. *Nat Neurosci* 2, 260-265, doi:10.1038/6365 (1999).

51 Kim, J. R. & Nottebohm, F. Direct evidence for loss and replacement of projection neurons in adult canary brain. *J Neurosci* 13, 1654-1663 (1993).

52 Mu, Y. & Gage, F. H. Adult hippocampal neurogenesis and its role in Alzheimer's disease. *Mol Neurodegener* 6, 85, doi:1750-1326-6-85 [pii]10.1186/1750-1326-6-85 (2011).

53 Pytte, C. L., Gerson, M., Miller, J. & Kirn, J. R. Increasing stereotypy in adult zebra finch song correlates with a declining rate of adult neurogenesis. *Dev Neurobiol* 67, 1699-1720, doi:10.1002/dneu.20520 (2007).

54 Scharff, C., Kirn, J. R., Grossman, M., Macklis, J. D. & Nottebohm, F. Targeted neuronal death affects neuronal replacement and vocal behavior in adult songbirds. *Neuron* 25, 481-492, doi:S0896-6273(00)80910-1 [pii] (2000).

55 Seib, D. R. et al. Loss of Dickkopf-1 restores neurogenesis in old age and counteracts cognitive decline. *Cell Stem Cell* 12, 204-214, doi:S1934-5909(12)00644-3 [pii] 10.1016/j.stem.2012.11.010 (2013).

56 Deister, C. & Schmidt, C. E. Optimizing neurotrophic factor combinations for neurite outgrowth. *J Neural Eng* 3, 172-179, doi:10.1088/1741-2560/3/2/011 (2006).

57 Zhao, Y. et al. Brain REST/NRSF Is Not Only a Silent Repressor but Also an Active Protector. *Mol Neurobiol* 54, 541-550, doi:10.1007/s12035-015-9658-4 (2017).

58 Uchida, H., Ma, L. & Ueda, H. Epigenetic Gene Silencing Underlies C-Fiber Dysfunctions in Neuropathic Pain. *Journal of Neuroscience* 30, 4806-4814, doi:10.1523/JNEUROSCI.5541-09.2010 (2010).

59 Rose, K. et al. Transcriptional repression of the M channel subunit $K_v7.2$ in chronic nerve injury. *Pain* 152, 742-754, doi:10.1016/j.pain.2010.12.028 (2011).

60 Costigan, M. et al. Multiple chronic pain states are associated with a common amino acid-changing allele in KCNS1. *Brain* 133, 2519-2527, doi:10.1093/brain/awq195 (2010).

61 Ueda, H. et al. A mimetic of the mSin3-binding helix of NRSF/REST ameliorates abnormal pain behavior in chronic pain models. *Bioorg Med Chem Lett* 27, 4705-4709, doi:10.1016/j.bmcl.2017.09.006 (2017).

62 Zhang, J., Chen, S. R., Chen, H. & Pan, H. L. RE1-silencing transcription factor controls the acute-to-chronic neuropathic pain transition and Chrm2 receptor gene expression in primary sensory neurons. *J Biol Chem* 293, 19078-19091, doi:10.1074/jbc.RA118.005846 (2018).

63 Banerjee, P. N., Filippi, D. & Allen Hauser, W. The descriptive epidemiology of epilepsy—a review. *Epilepsy Res* 85, 31-45, doi:10.1016/j.eplepsyres.2009.03.003 (2009).

64 Mucha, M. et al. Transcriptional control of KCNQ channel genes and the regulation of neuronal excitability. *J Neurosci* 30, 13235-13245, doi:10.1523/JNEUROSCI.1981-10.2010 (2010).

65 Escayg, A. et al. Mutations of SCN1A, encoding a neuronal sodium channel, in two families with GEFS+2. *Nat Genet* 24, 343-345, doi:10.1038/74159 (2000).

66 Martin, D. et al. REST represses a subset of the pancreatic endocrine differentiation program. *Dev Biol* 405, 316-327, doi:10.1016/j.ydbio.2015.07.002 (2015).

67 Abderrahmani, A. et al. Neuronal traits are required for glucose-induced insulin secretion. *FEBS Lett* 565, 133-138, doi:10.1016/j.febslet.2004.04.002 (2004).

68 Martin, D. et al. Functional significance of repressor element 1 silencing transcription factor (REST) target genes in pancreatic beta cells. *Diabetologia* 51, 1429-1439, doi:10.1007/s00125-008-0984-1 (2008).

69 Rigamonti, D. et al. Loss of huntingtin function complemented by small molecules acting as repressor element 1/neuron restrictive silencer element silencer modulators. *J Biol Chem* 282, 24554-24562, doi:10.1074/jbc.M609885200 (2007).

70 Sipione, S. et al. Early transcriptional profiles in huntingtin-inducible striatal cells by microarray analyses. *Hum Mol Genet* 25, 210, doi:10.1093/hmg/ddv416 (2016).

71 Zuccato, C. et al. Huntingtin interacts with REST/NRSF to modulate the transcription of NRSE-controlled neuronal genes. *Nat Genet* 35, 76-83, doi:10.1038/ng1219 (2003).

72 Bao, S. et al. Targeting cancer stem cells through L1CAM suppresses glioma growth. *Cancer Res* 68, 6043-6048, doi:10.1158/0008-5472.CAN-08-1079 (2008).

73 Jackson, M., Hassiotou, F. & Nowak, A. Glioblastoma stem-like cells: at the root of tumor recurrence and a therapeutic target. *Carcinogenesis* 36, 177-185, doi:10.1093/carcin/bgu243 (2015).

74 Liu, G. et al. Analysis of gene expression and chemoresistance of CD133+ cancer stem cells in glioblastoma. *Mol Cancer* 5, 67, doi:10.1186/1476-4598-5-67 (2006).

75 Persano, L., Rampazzo, E., Basso, G. & Viola, G. Glioblastoma cancer stem cells: role of the microenvironment and therapeutic targeting. *Biochem Pharmacol* 85, 612-622, doi:10.1016/j.bcp.2012.10.001 (2013).

76 Conti, L. et al. REST controls self-renewal and tumorigenic competence of human glioblastoma cells. *PLoS One* 7, e38486, doi:10.1371/journal.pone.0038486 (2012).

77 Kamal, M. M. et al. REST regulates oncogenic properties of glioblastoma stem cells. *Stem Cells* 30, 405-414, doi:10.1002/stem.1020 (2012).

78 Wagoner, M. P. & Roopra, A. A REST derived gene signature stratifies glioblastomas into chemotherapy resistant and responsive disease. *BMC Genomics* 13, 686, doi:10.1186/1471-2164-13-686 (2012).

79 Taylor, P. et al. REST is a novel prognostic factor and therapeutic target for medulloblastoma. *Mol Cancer Ther* 11, 1713-1723, doi:10.1158/1535-7163.MCT-11-0990 (2012).

80 Jin, H. et al. Identification of RE1-Silencing Transcription Factor as a Promoter of Metastasis in Pancreatic Cancer. *Front Oncol* 9, 291, doi:10.3389/fonc.2019.00291 (2019).

REFERENCES (FOR EXAMPLES ONLY)

1 Bruce, A. W. et al. Genome-wide analysis of repressor element 1 silencing transcription factor/neuron-restrictive silencing factor (REST/NRSF) target genes. *Proc Natl Acad Sci USA* 101, 10458-10463, doi:10.1073/pnas.04018271010401827101 [pii] (2004).

2 Nesti, E., Corson, G. M., McCleskey, M., Oyer, J. A. & Mandel, G. C-terminal domain small phosphatase 1 and MAP kinase reciprocally control REST stability and neuronal differentiation. *Proc Natl Acad Sci USA* 111, E3929-3936, doi:1414770111 [pii]10.1073/pnas.1414770111 (2014).

3 Nesti, E. METHODS AND COMPOSITIONS USEFUL IN MANIPULATING THE STABILITY OF RE1 SILENCING TRANSCRIPTION FACTOR. US, PTC patent (2014, 2015).

4 Nesti, E. Harnessing the master transcriptional repressor REST to reciprocally regulate neurogenesis. *Neurogenesis* 2, doi:10.1080/23262133.2015.1055419 (2015).

Arranz-Gibert, P. et al. Immunosilencing peptides by stereochemical inversion and sequence reversal: retro-D-peptides. *Sci Rep* 8, 6446, doi:10.1038/s41598-018-24517-6 (2018).

6 Hall, E. D., Bryant, Y. D., Cho, W. & Sullivan, P. G. Evolution of post-traumatic neurodegeneration after controlled cortical impact traumatic brain injury in mice and rats as assessed by the de Olmos silver and fluorojade staining methods. *J Neurotrauma* 25, 235-247, doi:10.1089/neu.2007.0383 (2008).

7 Calderone, A. et al. Ischemic insults derepress the gene silencer REST in neurons destined to die. *J Neurosci* 23, 2112-2121, doi:23/6/2112 [pii] (2003).

8 Kaneko, N., Hwang, J. Y., Gertner, M., Pontarelli, F. & Zukin, R. S. Casein kinase 1 suppresses activation of REST in insulted hippocampal neurons and halts ischemia-induced neuronal death. *J Neurosci* 34, 6030-6039, doi:34/17/6030 [pii]10.1523/JNEUROSCI.4045-13.2014 (2014).

9 Noh, K. M. et al. Repressor element-1 silencing transcription factor (REST)-dependent epigenetic remodeling is critical to ischemia-induced neuronal death. *Proc Natl Acad Sci USA* 109, E962-971, doi:1121568109 [pii] 10.1073/pnas.1121568109 (2012).

Abe, K. Therapeutic potential of neurotrophic factors and neural stem cells against ischemic brain injury. *J Cereb*

*Blood Flow Metab* 20, 1393-1408, doi:10.1097/00004647-200010000-00001 (2000).

11 Kan Ding, P. K. G., and Ramon Diaz-Arrastia. in *Translational Research in Traumatic Brain Injury* (ed Grant G Laskowitz D) Ch. 14, (Taylor and Francis, 2016).

12 Pasquina, P., Kirtley, R. & Ling, G. Moderate-to-severe traumatic brain injury. *Semin Neurol* 34, 572-583, doi: 10.1055/s-0034-1396010 (2014).

13 Hwang, J. Y., Kaneko, N., Noh, K. M., Pontarelli, F. & Zukin, R. S. The gene silencing transcription factor REST represses miR-132 expression in hippocampal neurons destined to die. *J Mol Biol* 426, 3454-3466, doi:10.1016/j.jmb.2014.07.032 (2014).

14 McClelland, S. et al. The transcription factor NRSF contributes to epileptogenesis by selective repression of a subset of target genes. *Elife* 3, e01267 (2014).

15 Lu, T. et al. REST and stress resistance in ageing and Alzheimer's disease. *Nature* 507, 448-454, doi:nature13163 [pii]10.1038/nature13163 (2014).

16 Orta-Salazar, E. et al. REST/NRSF-induced changes of ChAT protein expression in the neocortex and hippocampus of the 3xTg-AD mouse model for Alzheimer's disease. *Life sciences* 116, 83-89, doi:10.1016/j.lfs.2014.09.013 (2014).

17 Sharp, D. J., Scott, G. & Leech, R. Network dysfunction after traumatic brain injury. *Nat Rev Neurol* 10, 156-166, doi:10.1038/nrneurol.2014.15 (2014).

18 Roopra, A., Dingledine, R. & Hsieh, J. Epigenetics and epilepsy. *Epilepsia* 53 Suppl 9, 2-10, doi:10.1111/epi.12030 (2012).

19 Bergsland, M., Covacu, R., Perez Estrada, C., Svensson, M. & Brundin, L. Nitric oxide-induced neuronal to glial lineage fate-change depends on NRSF/REST function in neural progenitor cells. *Stem Cells* 32, 2539-2549, doi: 10.1002/stem.1749 (2014).

Conaco, C., Otto, S., Han, J. J. & Mandel, G. Reciprocal actions of REST and a microRNA promote neuronal identity. *Proc Natl Acad Sci USA* 103, 2422-2427, doi: 0511041103 [pii]10.1073/pnas.0511041103 (2006).

21 Covey, M. V., Streb, J. W., Spektor, R. & Ballas, N. REST regulates the pool size of the different neural lineages by restricting the generation of neurons and oligodendrocytes from neural stem/progenitor cells. *Development* 139, 2878-2890, doi:dev.074765 [pii]10.1242/dev.074765 (2012).

22 Gao, Z. et al. The master negative regulator REST/NRSF controls adult neurogenesis by restraining the neurogenic program in quiescent stem cells. *J Neurosci* 31, 9772-9786, doi:31/26/9772 [pii]10.1523/JNEUROSCI.1604-11.2011 (2011).

23 Kohyama, J. et al. BMP-induced REST regulates the establishment and maintenance of astrocytic identity. *J Cell Biol* 189, 159-170, doi:jcb.200908048 [pii]10.1083/jcb.200908048 (2010).

24 Mandel, G. et al. Repressor element 1 silencing transcription factor (REST) controls radial migration and temporal neuronal specification during neocortical development. *Proc Natl Acad Sci USA* 108, 16789-16794, doi:1113486108 [pii]10.1073/pnas.1113486108 (2011).

Vincent, A. S., Roebuck-Spencer, T. M. & Cernich, A. Cognitive changes and dementia risk after traumatic brain injury: implications for aging military personnel. *Alzheimers Dement* 10, S174-187, doi:10.1016/j.jalz.2014.04.006 (2014).

26 Kim, J. R. The relationship of neurogenesis and growth of brain regions to song learning. *Brain Lang* 115, 29-44, doi:S0093-934X(09)00135-7 [pii]10.1016/j.bandl.2009.09.006 (2010).

27 Oomen, C. A., Bekinschtein, P., Kent, B. A., Saksida, L. M. & Bussey, T. J. Adult hippocampal neurogenesis and its role in cognition. *Wiley Interdiscip Rev Cogn Sci* 5, 573-587, doi:10.1002/wcs.1304 (2014).

28 Samuels, I. S. et al. Deletion of ERK2 mitogen-activated protein kinase identifies its key roles in cortical neurogenesis and cognitive function. *J Neurosci* 28, 6983-6995, doi:28/27/6983 [pii]10.1523/JNEUROSCI.0679-08.2008 (2008).

29 Shors, T. J. et al. Neurogenesis in the adult is involved in the formation of trace memories. *Nature* 410, 372-376, doi: 10.1038/35066584 (2001).

Villeda, S. A. et al. The ageing systemic milieu negatively regulates neurogenesis and cognitive function. *Nature* 477, 90-94, doi:10.1038/nature10357 (2011).

31 Bird, C. M. & Burgess, N. The hippocampus supports recognition memory for familiar words but not unfamiliar faces. *Curr Biol* 18, 1932-1936, doi:10.1016/j.cub.2008.10.046 (2008).

32 T. J. Shors, G. M., A. Beylin, M. Zhao, T. Rydel, E. Gould. Neurogenesis in the adult is involved in the formation of trace memories. *Nature* 410, 372-376 (2001).

33 VanElzakker, M., Fevurly, R. D., Breindel, T. & Spencer, R. L. Environmental novelty is associated with a selective increase in Fos expression in the output elements of the hippocampal formation and the perirhinal cortex. *Learn Mem* 15, 899-908, doi:10.1101/lm.1196508 (2008).

34 Thornton, G. K. & Woods, C. G. Primary microcephaly: do all roads lead to Rome? *Trends Genet* 25, 501-510, doi: 10.1016/j.tig.2009.09.011 (2009).

Ghaziuddin, M., Zaccagnini, J., Tsai, L. & Elardo, S. Is megalencephaly specific to autism?*J Intellect Disabil Res* 43 (Pt 4), 279-282 (1999).

36 Kuhn, H. G., Cooper-Kuhn, C. M., Boekhoorn, K. & Lucassen, P. J. Changes in neurogenesis in dementia and Alzheimer mouse models: are they functionally relevant? *Eur Arch Psychiatry Clin Neurosci* 257, 281-289, doi: 10.1007/s00406-007-0732-4 (2007).

37 Baker, M. Tumours spark stem-cell review. *Nature* 457, 941, doi:10.1038/457941a (2009).

38 Brederlau, A. et al. Transplantation of human embryonic stem cell-derived cells to a rat model of Parkinson's disease: effect of in vitro differentiation on graft survival and teratoma formation. *Stem Cells* 24, 1433-1440, doi: 2005-0393 [pii] 10.1634/stemcells.2005-0393 (2006).

39 Burns, T. C., Verfaillie, C. M. & Low, W. C. Stem cells for ischemic brain injury: a critical review. *J Comp Neurol* 515, 125-144, doi: 10.1002/cne.22038 (2009).

40 Carlson, A. P., Schermer, C. R. & Lu, S. W. Retrospective evaluation of anemia and transfusion in traumatic brain injury. *J Trauma* 61, 567-571, doi:10.1097/01.ta.0000231768.44727.a200005373-200609000-00007 [pii] (2006).

41 Carmeliet, P. & Storkebaum, E. Vascular and neuronal effects of VEGF in the nervous system: implications for neurological disorders. *Semin Cell Dev Biol* 13, 39-53, doi:10.1006/scdb.2001.0290510849521019029 03 [pii] (2002).

42 Choe, Y., Kozlova, A., Graf, D. & Pleasure, S. J. Bone morphogenic protein signaling is a major determinant of dentate development. *J Neurosci* 33, 6766-6775, doi:33/16/6766 [pii]10.1523/JNEUROSCI.0128-13.2013 (2013).
43 Erdo, F. et al. Host-dependent tumorigenesis of embryonic stem cell transplantation in experimental stroke. *J Cereb Blood Flow Metab* 23, 780-785, doi:10.1097/01.WCB.0000071886.63724.FB (2003).
44 Greig, N. H. et al. Incretin mimetics as pharmacologic tools to elucidate and as a new drug strategy to treat traumatic brain injury. *Alzheimers Dement* 10, S62-75, doi:S1552-5260(13)02925-7 [pii]10.1016/j.jalz.2013.12.011 (2014).
Kaplan, G. B., Vasterling, J. J. & Vedak, P. C. Brain-derived neurotrophic factor in traumatic brain injury, post-traumatic stress disorder, and their comorbid conditions: role in pathogenesis and treatment. *Behav Pharmacol* 21, 427-437, doi:10.1097/FBP.0b013e32833d8bc9 (2010).
46 Knoepfler, P. S. Deconstructing stem cell tumorigenicity: a roadmap to safe regenerative medicine. *Stem Cells* 27, 1050-1056, doi:10.1002/stem.37 (2009).
47 Luca Longhia, Elisa R. Zaniera, Nicolas Royob, Nino Stocchettia, Tracy K. McIntosha. Stem cell transplantation as a therapeutic strategy for traumatic brain injury. *Transplant Immunology* 15, 134-148 (2005).
48 Robertson, C. S. et al. Effect of erythropoietin and transfusion threshold on neurological recovery after traumatic brain injury: a randomized clinical trial. *JAMA* 312, 36-47, doi:1884575 [pii]10.1001/jama.2014.6490 (2014).
49 Salim, A. et al. Role of anemia in traumatic brain injury. *J Am Coll Surg* 207, 398-406, doi:S1072-7515(08)00322-0 [pii]10.1016/j.jamcollsurg.2008.03.013 (2008).
50 Deng, W., Aimone, J. B. & Gage, F. H. New neurons and new memories: how does adult hippocampal neurogenesis affect learning and memory? *Nat Rev Neurosci* 11, 339-350, doi:nrn2822 [pii]10.1038/nrn2822 (2010).
51 Goldman, S. A. & Nottebohm, F. Neuronal production, migration, and differentiation in a vocal control nucleus of the adult female canary brain. *Proc Natl Acad Sci USA* 80, 2390-2394 (1983).
52 Gould, E., Beylin, A., Tanapat, P., Reeves, A. & Shors, T. J. Learning enhances adult neurogenesis in the hippocampal formation. *Nat Neurosci* 2, 260-265, doi:10.1038/6365 (1999).
53 Kim, J. R. & Nottebohm, F. Direct evidence for loss and replacement of projection neurons in adult canary brain. *J Neurosci* 13, 1654-1663 (1993).
54 Mu, Y. & Gage, F. H. Adult hippocampal neurogenesis and its role in Alzheimer's disease. *Mol Neurodegener* 6, 85, doi:1750-1326-6-85 [pii]10.1186/1750-1326-6-85 (2011).
55 Pytte, C. L., Gerson, M., Miller, J. & Kim, J. R. Increasing stereotypy in adult zebra finch song correlates with a declining rate of adult neurogenesis. *Dev Neurobiol* 67, 1699-1720, doi:10.1002/dneu.20520 (2007).
56 Scharff, C., Kim, J. R., Grossman, M., Macklis, J. D. & Nottebohm, F. Targeted neuronal death affects neuronal replacement and vocal behavior in adult songbirds. *Neuron* 25, 481-492, doi:S0896-6273(00)80910-1 [pii] (2000).
57 Seib, D. R. et al. Loss of Dickkopf-1 restores neurogenesis in old age and counteracts cognitive decline. *Cell Stem Cell* 12, 204-214, doi:S1934-5909(12)00644-3 [pii] 10.1016/j.stem.2012.11.010 (2013).
58 Deister, C. & Schmidt, C. E. Optimizing neurotrophic factor combinations for neurite outgrowth. *J Neural Eng* 3, 172-179, doi: 10.1088/1741-2560/3/2/011 (2006).
59 Zhao, Y. et al. Brain REST/NRSF Is Not Only a Silent Repressor but Also an Active Protector. *Mol Neurobiol* 54, 541-550, doi:10.1007/s12035-015-9658-4 (2017).
60 Uchida, H., Ma, L. & Ueda, H. Epigenetic Gene Silencing Underlies C-Fiber Dysfunctions in Neuropathic Pain. *Journal of Neuroscience* 30, 4806-4814, doi:10.1523/JNEUROSCI.5541-09.2010 (2010).
61 Alvarado, S. et al. Peripheral nerve injury is accompanied by chronic transcriptome-wide changes in the mouse prefrontal cortex. *Mol Pain* 9, 21, doi:10.1186/1744-8069-9-21 (2013).
62 Hammer, P. et al. mRNA-seq with agnostic splice site discovery for nervous system transcriptomics tested in chronic pain. *Genome Res* 20, 847-860, doi:10.1101/gr.101204.109 (2010).
63 Willis, D. E., Wang, M., Brown, E., Fones, L. & Cave, J. W. Selective repression of gene expression in neuropathic pain by the neuron-restrictive silencing factor/repressor element-1 silencing transcription (NRSF/REST). *Neuroscience Letters* 625, 20-25, doi:10.1016/j.neulet.2015.12.003 (2016).
64 Ballas, N., Grunseich, C., Lu, D. D., Speh, J. C. & Mandel, G. REST and its corepressors mediate plasticity of neuronal gene chromatin throughout neurogenesis. *Cell* 121, 645-657, doi:S0092-8674(05)00285-0 [pii]10.1016/j.cell.2005.03.013 (2005).
65 Chong, J. A. et al. REST: a mammalian silencer protein that restricts sodium channel gene expression to neurons. *Cell* 80, 949-957, doi:0092-8674(95)90298-8 [pii] (1995).
66 Mortazavi, A., Leeper Thompson, E. C., Garcia, S. T., Myers, R. M. & Wold, B. Comparative genomics modeling of the NRSF/REST repressor network: from single conserved sites to genome-wide repertoire. *Genome Res* 16, 1208-1221, doi:gr.4997306 [pii]10.1101/gr.4997306 (2006).
67 Otto, S. J. et al. A new binding motif for the transcriptional repressor REST uncovers large gene networks devoted to neuronal functions. *J Neurosci* 27, 6729-6739, doi:27/25/6729 [pii]10.1523/JNEUROSCI.0091-07.2007 (2007).
68 Schoenherr, C. J. & Anderson, D. J. Silencing is golden: negative regulation in the control of neuronal gene transcription. *Curr Opin Neurobiol* 5, 566-571, doi:0959-4388(95)80060-3 [pii] (1995).
69 Schoenherr, C. J., Paquette, A. J. & Anderson, D. J. Identification of potential target genes for the neuron-restrictive silencer factor. *Proc Natl Acad Sci USA* 93, 9881-9886 (1996).
70 Rose, K. et al. Transcriptional repression of the M channel subunit $K_v7.2$ in chronic nerve injury. *Pain* 152, 742-754, doi:10.1016/j.pain.2010.12.028 (2011).
71 Costigan, M. et al. Multiple chronic pain states are associated with a common amino acid-changing allele in KCNS1. *Brain* 133, 2519-2527, doi:10.1093/brain/awq195 (2010).
72 Zhang, F. et al. Repressor element 1-silencing transcription factor drives the development of chronic pain states. *Pain*, doi:10.1097/j.pain.0000000000001633 (2019).
73 Zhang, J., Chen, S. R., Chen, H. & Pan, H. L. RE1-silencing transcription factor controls the acute-to-chronic neuropathic pain transition and Chrm2 receptor gene expression in primary sensory neurons. *J Biol Chem* 293, 19078-19091, doi: 10.1074/jbc.RA118.005846 (2018).
74 Ueda, H. et al. A mimetic of the mSin3-binding helix of NRSF/REST ameliorates abnormal pain behavior in 75 Uchida, H., Sasaki, K., Ma, L. & Ueda, H. Neuron-restrictive silencer factor causes epigenetic silencing of $K_v4.3$ gene after peripheral nerve injury. *Neuroscience* 166, 1-4, doi:10.1016/j.neuroscience.2009.12.021 (2010).

76 Gervasi N M., D. A., Clark D M., Dingle M, Pisarchik A V., Nesti L J. C-terminal domain small phosphatase 1 (CTDSP1) regulates growth factor expression and axonal regeneration. *Journal of Translational Medicine* Manuscripted submitted for publication. (2020).

77 Nesti, E., Pisarchik, A. COMPOSITIONS AND METHODS FOR DEREPRESSING RE1 SILENCING TRANSCRIPTION FACTOR TARGET GENES. USA patent (2019).

78 Cole, L. A., Kurscheid, S., Nekrasov, M., Domaschenz, R., Dennis, J. H., Tremethick, D. J. Redefining the nucleosomal architecture of active and inactive promoters in the context of cellular plasticity and cancer. *Nature Communications* revision returned (2020).

79 Ren, Y., Vera, D. L., Hughes, K. A. & Dennis, J. H. Stimulation of the *Drosophila* immune system alters genome-wide nucleosome occupancy. *Genom Data* 3, 146-147, doi:10.1016/j.gdata.2015.01.001 (2015).

80 Sexton, B. S. et al. The spring-loaded genome: nucleosome redistributions are widespread, transient, and DNA-directed. *Genome Res* 24, 251-259, doi:10.1101/gr.160150.113 (2014).

81 Sexton, B. S. et al. Hierarchical regulation of the genome: global changes in nucleosome organization potentiate genome response. *Oncotarget* 7, 6460-6475, doi: 10.18632/oncotarget.6841 (2016).

82 Lunyak, V. V. & Rosenfeld, M. G. No rest for REST: REST/NRSF regulation of neurogenesis. *Cell* 121, 499-501, doi:10.1016/j.cell.2005.05.003 (2005).

83 Dirks, P. B. Making a commitment: neurons refuse cancer's advances. *Nat Neurosci* 22, 507-508, doi: 10.1038/s41593-019-0373-8 (2019).

84 Kaspar, A. A. & Reichert, J. M. Future directions for peptide therapeutics development. *Drug Discov Today* 18, 807-817, doi:10.1016/j.drudis.2013.05.011 (2013).

85 Hamzeh-Mivehroud, M., Alizadeh, A. A., Morris, M. B., Bret Church, W. & Dastmalchi, S. Phage display as a technology delivering on the promise of peptide drug discovery. *Drug Discovery Today* 18, 1144-1157, doi: 10.1016/j.drudis.2013.09.001 (2013).

86 Hoekstra, E., Peppelenbosch, M. P. & Fuhler, G. M. Meeting report europhosphatase 2015: Phosphatases as drug targets in cancer. *Cancer Research* 76, 193-196, doi:10.1158/0008-5472.CAN-15-2091 (2016).

87 Shi, Y. Serine/Threonine Phosphatases: Mechanism through Structure. *Cell* 139, 468-484, doi:10.1016/j.cell.2009.10.006 (2009).

88 Sussman, F., Villaverde, M. C., L. Dominguez, J. & Danielson, U. H. On the Active Site Protonation State in Aspartic Proteases: Implications for Drug Design. *Current Pharmaceutical Design*, Volume 19, Number 23 19, 4257-4275, doi:10.1002/(SICI)1520-667X(1998)10: 1<19:AID-MCS3>3.0.CO;2-1 (2013).

89 Anobom, C. D. et al. From structure to catalysis: Recent developments in the biotechnological applications of lipases. *BioMed Research International* 2014, doi: 10.1155/2014/684506 (2014).

90 Blundell, T. L., Jhoti, H. & Abell, C. High-Throughput Crystallography for Lead Discovery in Drug Design. *Nature Reviews Drug Discovery* 1, 45-54, doi:10.1038/nrd706 (2002).

91 Weir, M. R. Renin inhibitors: novel agents for renoprotection or a better angiotensin receptor blocker for blood pressure lowering? *Current opinion in nephrology and hypertension* 16, 416-421, doi:10.1097/MNH.0b013e328209fe00 (2007).

92 Yeo, M. et al. Small CTD phosphatases function in silencing neuronal gene expression. *Science* 307, 596-600, doi:307/5709/596 [pii]10.1126/science.1100801 (2005).

93 Fulda, S., Wick, W., Weller, M. & Debatin, K. M. Smac agonists sensitize for Apo2L/TRAIL- or anticancer drug-induced apoptosis and induce regression of malignant glioma in vivo. *Nature Medicine* 8, 808-815, doi:10.1038/nm735 (2002).

94 Noguchi, H. et al. A new cell-permeable peptide allows successful allogeneic islet transplantation in mice. *Nature Medicine* 10, 305-309, doi: 10.1038/nm994 (2004).

95 Pooga, M. et al. Cellular translocation of proteins by transportan. *The FASEB journal: official publication of the Federation of American Societies for Experimental Biology* 15, 1451-1453, doi:10.1096/fj.00-0780fje (2001).

96 Schwarze, S. R., Ho, A., Vocero-Akbani, A. & Dowdy, S. F. In vivo protein transduction: delivery of a biologically active protein into the mouse. *Science* (New York, N. Y.) 285, 1569-1572, doi:10.1126/science.285.5433.1569 (1999).

97 Yeo, M., Lin, P. S., Dahmus, M. E. & Gill, G. N. A Novel RNA Polymerase II C-terminal Domain Phosphatase That Preferentially Dephosphorylates Serine 5. *Journal of Biological Chemistry* 278, 26078-26085, doi: 10.1074/jbc.M301791200 (2003).

98 Banerjee, P. N., Filippi, D. & Allen Hauser, W. The descriptive epidemiology of epilepsy—a review. *Epilepsy Res* 85, 31-45, doi:10.1016/j.eplepsyres.2009.03.003 (2009).

99 Mucha, M. et al. Transcriptional control of KCNQ channel genes and the regulation of neuronal excitability. *J Neurosci* 30, 13235-13245, doi:10.1523/JNEUROSCI.1981-10.2010 (2010).

100 Escayg, A. et al. Mutations of SCN1A, encoding a neuronal sodium channel, in two families with GEFS+2. *Nat Genet* 24, 343-345, doi:10.1038/74159 (2000).

101 Martin, D. et al. REST represses a subset of the pancreatic endocrine differentiation program. *Dev Biol* 405, 316-327, doi:10.1016/j.ydbio.2015.07.002 (2015).

102 Abderrahmani, A. et al. Neuronal traits are required for glucose-induced insulin secretion. *FEBS Lett* 565, 133-138, doi:10.1016/j.febslet.2004.04.002 (2004).

103 Martin, D. et al. Functional significance of repressor element 1 silencing transcription factor (REST) target genes in pancreatic beta cells. *Diabetologia* 51, 1429-1439, doi:10.1007/s00125-008-0984-1 (2008).

104 Rigamonti, D. et al. Loss of huntingtin function complemented by small molecules acting as repressor element 1/neuron restrictive silencer element silencer modulators. *J Biol Chem* 282, 24554-24562, doi:10.1074/jbc.M609885200 (2007).

105 Sipione, S. et al. Early transcriptional profiles in huntingtin-inducible striatal cells by microarray analyses. *Hum Mol Genet* 25, 210, doi:10.1093/hmg/ddv416 (2016).

106 Zuccato, C. et al. Huntingtin interacts with REST/NRSF to modulate the transcription of NRSE-controlled neuronal genes. *Nat Genet* 35, 76-83, doi:10.1038/ng1219 (2003).

107 Bao, S. et al. Targeting cancer stem cells through L1CAM suppresses glioma growth. *Cancer Res* 68, 6043-6048, doi: 10.1158/0008-5472.CAN-08-1079 (2008).

108 Jackson, M., Hassiotou, F. & Nowak, A. Glioblastoma stem-like cells: at the root of tumor recurrence and a therapeutic target. *Carcinogenesis* 36, 177-185, doi: 10.1093/carcin/bgu243 (2015).

109 Liu, G. et al. Analysis of gene expression and chemoresistance of CD133+ cancer stem cells in glioblastoma. *Mol Cancer* 5, 67, doi:10.1186/1476-4598-5-67 (2006).

110 Persano, L., Rampazzo, E., Basso, G. & Viola, G. Glioblastoma cancer stem cells: role of the microenvironment and therapeutic targeting. *Biochem Pharmacol* 85, 612-622, doi:10.1016/j.bcp.2012.10.001 (2013).

111 Conti, L. et al. REST controls self-renewal and tumorigenic competence of human glioblastoma cells. *PLoS One* 7, e38486, doi:10.1371/journal.pone.0038486 (2012).

112 Kamal, M. M. et al. REST regulates oncogenic properties of glioblastoma stem cells. *Stem Cells* 30, 405-414, doi:10.1002/stem.1020 (2012).

113 Wagoner, M. P. & Roopra, A. A REST derived gene signature stratifies glioblastomas into chemotherapy resistant and responsive disease. *BMC Genomics* 13, 686, doi:10.1186/1471-2164-13-686 (2012).

114 Taylor, P. et al. REST is a novel prognostic factor and therapeutic target for medulloblastoma. *Mol Cancer Ther* 11, 1713-1723, doi:10.1158/1535-7163.MCT-11-0990 (2012).

115 Jin, H. et al. Identification of RE1-Silencing Transcription Factor as a Promoter of Metastasis in Pancreatic Cancer. *Front Oncol* 9, 291, doi:10.3389/fonc.2019.00291 (2019).

116 Jackson, W. M. et al. Mesenchymal progenitor cells derived from traumatized human muscle. *J Tissue Eng Regen Med* 3, 129-138, doi: 10.1002/term.149 (2009).

117 Schmitz, H. C. & Beer, G. M. The toe-spreading reflex of the rabbit revisited—functional evaluation of complete peroneal nerve lesions. *Lab Anim* 35, 340-345, doi: 10.1258/0023677011911930 (2001).

118 Hems, T. E. & Glasby, M. A. The limit of graft length in the experimental use of muscle grafts for nerve repair. *J Hand Surg Br* 18, 165-170 (1993).

119 Ballas, N. et al. Regulation of neuronal traits by a novel transcriptional complex. *Neuron* 31, 353-365, doi: 10.1016/s0896-6273(01)00371-3 (2001).

120 Symes, A. J. et al. Ciliary neurotrophic factor coordinately activates transcription of neuropeptide genes in a neuroblastoma cell line. *Proc Natl Acad Sci USA* 90, 572-576, doi:10.1073/pnas.90.2.572 (1993).

121 Chou, B. K. et al. Efficient human iPS cell derivation by a non-integrating plasmid from blood cells with unique epigenetic and gene expression signatures. *Cell Res* 21, 518-529, doi:10.1038/cr.2011.12 (2011).

122 Swistowski, A. et al. Xeno-free defined conditions for culture of human embryonic stem cells, neural stem cells and dopaminergic neurons derived from them. *PLoS One* 4, e6233, doi:10.1371/journal.pone.0006233 (2009).

123 Yan, Y. et al. Efficient and rapid derivation of primitive neural stem cells and generation of brain subtype neurons from human pluripotent stem cells. *Stem Cells Transl Med* 2, 862-870, doi: 10.5966/sctm.2013-0080 (2013).

124 Efthymiou, A. et al. Functional screening assays with neurons generated from pluripotent stem cell-derived neural stem cells. *J Biomol Screen* 19, 32-43, doi:10.1177/1087057113501869 (2014).

125 Malik, N. et al. Compounds with species and cell type specific toxicity identified in a 2000 compound drug screen of neural stem cells and rat mixed cortical neurons. *Neurotoxicology* 45, 192-200, doi:10.1016/j.neuro.2014.10.007 (2014).

126 Pei, Y. et al. Comparative neurotoxicity screening in human iPSC-derived neural stem cells, neurons and astrocytes. *Brain Res* 1638, 57-73, doi:10.1016/j.brainres.2015.07.048 (2016).

127 Lischka, F. W. et al. Neonatal mouse cortical but not isogenic human astrocyte feeder layers enhance the functional maturation of induced pluripotent stem cell-derived neurons in culture. *Glia* 66, 725-748, doi:10.1002/glia.23278 (2018).

128 Papapetrou, E. P. & Schambach, A. Gene Insertion Into Genomic Safe Harbors for Human Gene Therapy. *Mol Ther* 24, 678-684, doi:10.1038/mt.2016.38 (2016).

129 He, R. et al. Recombinant luciferase-expressing human cytomegalovirus (CMV) for evaluation of CMV inhibitors. *Virol J* 8, 40, doi:10.1186/1743-422X-8-40 (2011).

130 Jacqmain, J., Nudi, E. T., Fluharty, S. & Smith, J. S. Pre and post-injury environmental enrichment effects functional recovery following medial frontal cortical contusion injury in rats. *Behav Brain Res* 275, 201-211, doi: 10.1016/j.bbr.2014.08.056 (2014).

131 Monaco, C. M. et al. Environmental enrichment promotes robust functional and histological benefits in female rats after controlled cortical impact injury. *Exp Neurol* 247, 410-418, doi:10.1016/j.expneurol.2013.01.007 (2013).

132 Shear, D. A. et al. Nicotinamide Treatment in Traumatic Brain Injury: Operation Brain Trauma Therapy. *J Neurotrauma* 33, 523-537, doi:10.1089/neu.2015.4115 (2016).

133 Wagner, A. K., Postal, B. A., Darrah, S. D., Chen, X. & Khan, A. S. Deficits in novelty exploration after controlled cortical impact. *J Neurotrauma* 24, 1308-1320, doi:10.1089/neu.2007.0274 (2007).

134 Zhang, J., Groff, R. F. & Dayawansa, S. Imipramine treatment increases cell proliferation following fluid percussion brain injury in rats. *Neurol Res* 35, 247-254, doi:10.1179/1743132813Y.0000000164 (2013).

135 Xiong, Y. et al. Histological and functional outcomes after traumatic brain injury in mice null for the erythropoietin receptor in the central nervous system. *Brain Res* 1230, 247-257, doi:10.1016/j.brainres.2008.06.127 (2008).

136 Susarla, B. T., Villapol, S., Yi, J. H., Geller, H. M. & Symes, A. J. Temporal patterns of cortical proliferation of glial cell populations after traumatic brain injury in mice. *ASN Neuro* 6, 159-170, doi:10.1042/AN20130034 (2014).

137 Xiong, Y. et al. Role of gender in outcome after traumatic brain injury and therapeutic effect of erythropoietin in mice. *Brain Res* 1185, 301-312, doi:10.1016/j.brainres.2007.09.052 (2007).

138 Choi, S. H., Woodlee, M. T., Hong, J. J. & Schallert, T. A simple modification of the water maze test to enhance daily detection of spatial memory in rats and mice. *J Neurosci Methods* 156, 182-193, doi:10.1016/j.jneumeth.2006.03.002 (2006).

139 Omura, T. et al. Different expressions of BDNF, NT3, and NT4 in muscle and nerve after various types of peripheral nerve injuries. *J Peripher Nerv Syst* 10, 293-300, doi:10.1111/j.1085-9489.2005.10307.x (2005).

140 Zhang, J. Y., Luo, X. G., Xian, C. J., Liu, Z. H. & Zhou, X. F. Endogenous BDNF is required for myelination and 141 regeneration of injured sciatic nerve in rodents. *Eur J Neurosci* 12, 4171-4180 (2000).
141 Zhao, Y. et al. Brain REST/NRSF Is Not Only a Silent Repressor but Also an Active Protector. *Molecular Neurobiology* 54, 541-550, doi:10.1007/s12035-015-9658-4 (2017).
142 Charbord, J. et al. High throughput screening for inhibitors of REST in neural derivatives of human embryonic stem cells reveals a chemical compound that promotes expression of neuronal genes. *Stem Cells* 31, 1816-1828, doi:10.1002/stem.1430 (2013).
143 Nesti, L. J. et al. Differentiation potential of multipotent progenitor cells derived from war-traumatized muscle tissue. *J Bone Joint Surg Am* 90, 2390-2398, doi:10.2106/JBJS.H.00049 (2008).
144 Bulken-Hoover, J. D. et al. Inducible expression of neurotrophic factors by mesenchymal progenitor cells derived from traumatically injured human muscle. *Mol Biotechnol* 51, 128-136, doi:10.1007/s12033-011-9445-z (2012).
145 Mosmann, T. Rapid colorimetric assay for cellular growth and survival: application to proliferation and cytotoxicity assays. *J Immunol Methods* 65, 55-63, doi:10.1016/0022-1759(83)90303-4 (1983).
146 Chan, J. R., Cosgaya, J. M., Wu, Y. J. & Shooter, E. M. Neurotrophins are key mediators of the myelination program in the peripheral nervous system. *Proc Natl Acad Sci USA* 98, 14661-14668, doi:10.1073/pnas.251543398 (2001).
147 Leung, J. Y. et al. Metallothionein promotes regenerative axonal sprouting of dorsal root ganglion neurons after physical axotomy. *Cell Mol Life Sci* 69, 809-817, doi:10.1007/s00018-011-0790-7 (2012).
148 Rothstein, J. D., Jin, L., Dykes-Hoberg, M. & Kuncl, R. W. Chronic inhibition of glutamate uptake produces a model of slow neurotoxicity. *Proc Natl Acad Sci USA* 90, 6591-6595 (1993).
149 Corse, A. M. et al. Preclinical testing of neuroprotective neurotrophic factors in a model of chronic motor neuron degeneration. *Neurobiol Dis* 6, 335-346, doi:10.1006/nbdi.1999.0253 (1999).
150 Mi, R., Chen, W. & Hoke, A. Pleiotrophin is a neurotrophic factor for spinal motor neurons. *Proc Natl Acad Sci USA* 104, 4664-4669, doi:10.1073/pnas.0603243104 (2007).
151 Cargnin, F. et al. An RNA binding protein promotes axonal integrity in peripheral neurons by destabilizing REST. *J Neurosci* 34, 16650-16661, doi:10.1523/JNEUROSCI.1650-14.2014 (2014).
152 Rueden, C. T. et al. ImageJ2: ImageJ for the next generation of scientific image data. *BMC Bioinformatics* 18, 529-529, doi: 10.1186/s12859-017-1934-z (2017).
153 Woolf, C. J. Phenotypic modification of primary sensory neurons: the role of nerve growth factor in the production of persistent pain. *Philos Trans R Soc Lond B Biol Sci* 351, 441-448, doi:10.1098/rstb.1996.0040 (1996).
154 Fremin, C. et al. ERK2 but not ERK1 plays a key role in hepatocyte replication: an RNAi-mediated ERK2 knockdown approach in wild-type and ERK1 null hepatocytes. *Hepatology* 45, 1035-1045, doi:10.1002/hep.21551 (2007).
155 River, C. Sergical Services, <https://www.criver.com/sites/default/files/resources/VascularCatheterSurgeryOptionsInfor inationSheet.pdf> (2018).
156 Beer, S. a. The toe-spreading reflex of the rabbit revisited—functional evaluation of complete peroneal nerve lesions. *Laboratory Animals* 35, 340-345 (2001).
157 Glasby, M. A. & Hems, T. E. Repairing spinal roots after brachial plexus injuries. *Paraplegia* 33, 359-361, doi:10.1038/sc.1995.80 (1995).
158 Jin, J. et al. Functional motor recovery after peripheral nerve repair with an aligned nanofiber tubular conduit in a rat model. *Regen Med* 7, 799-806, doi:10.2217/rme.12.87 (2012).
159 Han, D., Lu, J., Xu, L. & Xu, J. Comparison of two electrophysiological methods for the assessment of progress in a rat model of nerve repair. *International Journal of Clinical and Experimental Medicine* 8, 2392-2398 (2015).
160 Yekta, A. et al. Perineural dexmedetomidine effects on sciatic nerve in rat. *Brazilian Journal of Anesthesiology (English Edition)* 67, 57-66, doi:10.1016/j.bjane.2015.08.012 (2017).
161 Rigaud, M. et al. Species and strain differences in rodent sciatic nerve anatomy: implications for studies of neuropathic pain. *Pain* 136, 188-201, doi:10.1016/j.pain.2008.01.016 (2008).
162 Sleigh, J. N., Weir, G. A. & Schiavo, G. A simple, step-by-step dissection protocol for the rapid isolation of mouse dorsal root ganglia. *BMC Res Notes* 9, 82, doi:10.1186/s13104-016-1915-8 (2016).
163 Ronchi, G. et al. Discrepancies in quantitative assessment of normal and regenerated peripheral nerve fibers between light and electron microscopy. *J Peripher Nerv Syst* 19, 224-233, doi:10.111/jns.12090 (2014).
164 Varejao, A. S. et al. Functional and morphological assessment of a standardized rat sciatic nerve crush injury with a non-serrated clamp. *J Neurotrauma* 21, 1652-1670, doi:10.1089/neu.2004.21.1652 (2004).
165 Carriel, V., Garzon, I., Alaminos, M. & Cornelissen, M. Histological assessment in peripheral nerve tissue engineering. *Neural Regen Res* 9, 1657-1660, doi:10.4103/1673-5374.141798 (2014).
166 Hazari, A., Wiberg, M., Johansson-Ruden, G., Green, C. & Terenghi, G. A resorbable nerve conduit as an alternative to nerve autograft in nerve gap repair. *Br J Plast Surg* 52, 653-657, doi:10.1054/bjps.1999.3184 (1999).
167 Shi, T. J. et al. Effect of peripheral nerve injury on dorsal root ganglion neurons in the C57 BL/6J mouse: marked changes both in cell numbers and neuropeptide expression. *Neuroscience* 105, 249-263 (2001).
168 Jackson, W. M. et al. Mesenchymal progenitor cells derived from traumatized muscle enhance neurite growth. *J Tissue Eng Regen Med* 7, 443-451, doi:10.1002/term.539 (2013).
169 Kobiela Ketz A, B. K., Grunberg N E, Kasper C E, Osborne L, Pryor B, Tosini N L, Wu X, Anders J J. Characterization of macrophage/microglial activation and effect of photobiomodulation in the spared nerve injury model of neuropathic pain. *Pain Medicine* 5, 932-946, doi:10.1093/pm/pnw144 (2016).
170 Whiteside, G. T., Adedoyin A, Leventhal L. Predictive validity of animal pain models? A comparison of the pharmacokinetic-pharmacodynamic relationship for pain drugs in rats and humans. *Neuropharm,* 767-775, doi:10.1016/j.neuropharm.2008.01.001 (2008).
171 LaBuda, C. J. & Fuchs, P. N. A behavioral test paradigm to measure the aversive quality of inflammatory and neuropathic pain in rats. *Exp Neurol* 163, 490-494, doi:10.1006/exnr.2000.7395 (2000).
172 Xu, Y. et al. Gait Assessment of Pain and Analgesics: Comparison of the DigiGait and CatWalk Gait Imaging Systems. *Neurosci Bull* 35, 401-418, doi:10.1007/s12264-018-00331-y (2019).

173 Hargreaves, K., Dubner, R., Brown, F., Flores, C. & Joris, J. A new and sensitive method for measuring thermal nociception in cutaneous hyperalgesia. *Pain* 32, 77-88, doi: 10.1016/0304-3959(88)90026-7 (1988).

174 Baastrup, C., Jensen, T. S. & Finnerup, N. B. Pregabalin attenuates place escape/avoidance behavior in a rat model of spinal cord injury. *Brain Res* 1370, 129-135, doi: 10.1016/j.brainres.2010.11.008 (2011).

175 FDA. *Guidance for industry* (ed CDER; CBER) (FDA, https://www.fda.gov/downloads/Drugs/GuidanceCompli- anceRegulatoryInformation/Guidances/UCM074957.pdf, 1997).

176 FDA. S2B *Genotoxicity: A Standard Battery for Genotoxicity Testing of Pharmaceuticals*, <https://www.fda.gov/media/71971/download> (1997).

177 FDA. *S7B Nonclinical Evaluation of the Potential for Delayed Ventricular Repolarization (QT Interval Prolongation) by Human Pharmaceuticals*, <https://www.fda.gov/media/72043/download> (2005).

178 FDA. (ed CDER; CBER) (FDA, https://www.fda.gov/downloads/drugs/guidances/ucm073246.pdf, 2010).

179 FDA. (ed CDER; CBER) (FDA, https://www.fda.gov/downloads/drugs/guidances/ucm074959.pdf, July 2001).

180 Irwin, S. Comprehensive observational assessment: Ia. A systematic, quantitative procedure for assessing the behavioral and physiologic state of the mouse. *Psychopharmacologia* 13, 222-257 (1968).

181 Morrone, L., Scuteri, D., Rombola, L., Mizoguchi, H. & Bagetta, G. Opioids Resistance in Chronic Pain Management. *Current Neuropharmacology* 15, 444-456, doi: 10.2174/1570159X14666161101092822 (2017).

182 Ploj, K., Roman, E. & Nylander, I. Long-term effects of short and long periods of maternal separation on brain opioid peptide levels in male Wistar rats. *Neuropeptides* 37, 149-156, doi:10.1016/S0143-4179(03)00043-X (2003).

183 Zhu, C. et al. Neuron-restrictive silencer factor-mediated downregulation of p-opioid receptor contributes to the reduced morphine analgesia in bone cancer pain. *PAIN* 158, 879-890, doi:10.1097/j.pain.0000000000000848 (2017).

184 Lu, C. e. et al. Neuron-restrictive silencer factor in periaqueductal gray contributes to remifentanil-induced postoperative hyperalgesia via repression of the mu- opioid receptor. *Journal of the Neurological Sciences* 352, 48-52, doi:10.1016/j.jns.2015.03.018 (2015).

185 Schwartz, A. S. & Marchok, P. L. Depression of morphine-seeking behaviour by dopamine inhibition. *Nature* 248, 257-258 (1974).

186 Spyraki, C., Fibiger, H. C. & Phillips, A. G. Attenuation of heroin reward in rats by disruption of the mesolimbic dopamine system. *Psychopharmacology* 79, 278-283 (1983).

187 Phillips, A. G. & LePiane, F. G. Reinforcing effects of morphine microinjection into the ventral tegmental area. *Pharmacology, biochemistry, and behavior* 12, 965-968 (1980).

188 Phillips, A. G., LePiane, F. G. & Fibiger, H. C. Dopaminergic mediation of reward produced by direct injection of enkephalin into the ventral tegmental area of the rat. *Life sciences* 33, 2505-2511 (1983).

189 Prus A J, J. J., Rosecrans J A. in *Methods of Behavior Analysis in Neuroscience* (ed Buccafusco J J) Ch. 4, (CRC Press/Taylor & Francis, 2009).

190 Carr, K. D., Bak, T. H., Simon, E. J. & Portoghese, P. S. Effects of the selective kappa opioid antagonist, nor-binaltorphimine, on electrically-elicited feeding in the rat. *Life sciences* 45, 1787-1792 (1989).

191 Galli, R. et al. Isolation and characterization of tumorigenic, stem-like neural precursors from human glioblastoma. *Cancer Res* 64, 7011-7021, doi:10.1158/0008-5472.CAN-04-1364 (2004).

192 Garzon-Muvdi, T. et al. Regulation of brain tumor dispersal by NKCC1 through a novel role in focal adhesion regulation. *PLoS Biol* 10, e1001320, doi:10.1371/journal.pbio.1001320 (2012).

193 Guerrero-Cazares, H., Chaichana, K. L. & Quinones-Hinojosa, A. Neurosphere culture and human organotypic model to evaluate brain tumor stem cells. *Methods Mol Biol* 568, 73-83, doi: 10.1007/978-1-59745-280-9_6 (2009).

194 Tilghman, J. et al. Regulation of Glioblastoma Tumor-Propagating Cells by the Integrin Partner Tetraspanin CD151. *Neoplasia* 18, 185-198, doi:10.1016/j.neo.2016.02.003 (2016).

195 Lal, S. et al. An implantable guide-screw system for brain tumor studies in small animals. *J Neurosurg* 92, 326-333, doi:10.3171/jns.2000.92.2.0326 (2000).

196 Manton, C. A. et al. Induction of cell death by the novel proteasome inhibitor marizomib in glioblastoma in vitro and in vivo. *Sci Rep* 6, 18953, doi:10.1038/srep18953 (2016).

197 Kaplan, E. L. M., P. Nonparametric estimation from incomplete observations. *Journal of the American Statistical Association* 53, 457-481, doi:10.2307/2281868 (1958).

198 Marubini E, V. M. C. *Estimation of Survival Probabilities. Analysing survival data from clinical trials and observational studies.* 41-81 (John Wiley and Sons, 1995).

What is claimed is:

1. An isolate peptide comprising an amino acid sequence, wherein the amino acid sequence is selected from the group consisting of SEQ ID NOS: 1, 15-17, 18, 22, 25, 31, 35, 60, 63, 64, 66, 68, 75, 81, 85, 110, 113, 114, and 116.

2. The peptide of claim 1, wherein the amino acid sequence is a fusion peptide.

3. The peptide of claim 2, wherein the amino acid sequence is fused to a cell penetrating peptide or an endosomal release sequence.

4. The peptide of claim 3, wherein the cell penetrating peptide or the endosomal release sequence is selected from the group consisting of SEQ ID NOS: 118-137 or 140-159.

5. The peptide of claim 3, wherein a linker connects the amino acid sequence to the cell penetrating peptide or the endosomal release sequence.

6. The peptide of claim 5, wherein the linker is selected from the group consisting of SEQ ID NOS: 138, 139, 160, and 161.

7. The peptide of claim 3, wherein the cell penetrating peptide or the endosomal release sequence is fused to the amino acid sequence at an N- or a C-terminus.

8. A pharmaceutical composition comprising the peptide of claim 1.

9. The composition of claim 8, wherein the peptide is contained in an oral solution, a caplet, a capsule, an injectable, an infusible, a suppository, a lozenge, a tablet, a cream, a salve, or an inhalant.

10. The composition of claim 8, further comprising an excipient.

11. An isolate peptide comprising an amino acid sequence, wherein the amino acid sequence is a cyclized fusion peptide selected from the group consisting of SEQ ID NOS: 2, 5, 12, 13 and 14.

12. The peptide of claim 11, wherein the amino acid sequence is fused to a cell penetrating peptide or an endosomal release sequence.

13. The peptide of claim 12, wherein the cell penetrating peptide or the endosomal release sequence is fused to the amino acid sequence at an N- or a C-terminus.

14. A pharmaceutical composition comprising the peptide of claim 11.

15. The composition of claim 14, wherein the peptide is contained in an oral solution, a caplet, a capsule, an injectable, an infusible, a suppository, a lozenge, a tablet, a cream, a salve, or an inhalant.

16. The composition of claim 14, further comprising an excipient.

17. An isolate peptide comprising an amino acid sequence, wherein the amino acid sequence is a fusion peptide selected from the group consisting of SEQ ID NOS: 2 and 4-14.

18. A pharmaceutical composition comprising the peptide of claim 17.

19. The composition of claim 18, wherein the peptide is contained in an oral solution, a caplet, a capsule, an injectable, an infusible, a suppository, a lozenge, a tablet, a cream, a salve, or an inhalant.

20. The composition of claim 18, further comprising an excipient.

* * * * *